United States Patent [19]
Bott et al.

[11] Patent Number: 5,801,038
[45] Date of Patent: *Sep. 1, 1998

[54] MODIFIED SUBTILISINS HAVING AMINO ACID ALTERATIONS

[75] Inventors: Richard Ray Bott, Burlingame; Robert Mark Caldwell, San Francisco; Brian C. Cunningham, Piedmont; David Aaron Estell, Mountain View; Scott Douglas Power, San Bruno; James Allen Wells, San Mateo, all of Calif.

[73] Assignee: Genencor International Inc., Palo Alto, Calif.

[ * ] Notice: The term of this patent shall not extend beyond the expiration date of Pat. No. RE. 34,606.

[21] Appl. No.: 485,827

[22] Filed: Jun. 7, 1995

Related U.S. Application Data

[62] Division of Ser. No. 212,291, Mar. 14, 1994, which is a continuation of Ser. No. 898,382, Jun. 9, 1992, abandoned, which is a continuation of Ser. No. 747,459, Aug. 12, 1991, abandoned, which is a continuation of Ser. No. 540,868, Jun. 14, 1990, abandoned, which is a continuation of Ser. No. 35,652, Apr. 5, 1987, abandoned, which is a continuation-in-part of Ser. No. 858,594, Apr. 30, 1986, abandoned, which is a continuation-in-part of Ser. No. 614,612, May 29, 1984, Pat. No. 4,760,025, which is a continuation-in-part of Ser. No. 614,615, May 29, 1984, abandoned, which is a continuation-in-part of Ser. No. 614,617, May 29, 1984, abandoned, which is a continuation-in-part of Ser. No. 614,491, May 29, 1984, abandoned.

[51] Int. Cl.$^6$ ............... C11D 7/42; C12N 9/52; C12N 9/56; C12N 15/75
[52] U.S. Cl. ............ 435/221; 435/69.1; 435/172.3; 435/220; 435/222; 435/252.31; 435/320.1; 510/300; 536/23.2; 935/14; 935/29; 935/74
[58] Field of Search .................. 435/220, 221, 435/222, 69.1, 252.3, 252.31, 320.1, 172.3; 536/23.2; 510/300

[56] References Cited

U.S. PATENT DOCUMENTS

| Re. 34,606 | 5/1994 | Estell et al. ........................ 435/222 |
| 4,002,572 | 1/1977 | te Nijenhuis ........................ 510/306 |
| 4,458,066 | 7/1984 | Caruthers et al. ................... 536/25.43 |
| 4,543,329 | 9/1985 | Daum et al. ........................ 435/69.1 |
| 4,760,025 | 7/1988 | Estell et al. ........................ 510/392 |

FOREIGN PATENT DOCUMENTS

WO 8503949  9/1985  WIPO.

OTHER PUBLICATIONS

Pahler, A., et al., The EMBO Journal, vol. 3, "Three-dimensional structure of fungal proteinase K reveals similarity to bacterial subtilisin", pp. 1311–1314, 1984.

Meloun, B., et al., FEBS Letters, vol. 183, "Complete primary structure of thermitase from Thermoactinomyces vulgaris and its structural features related to the subtilisin–type proteinases", pp. 195–199, 1985.

(List continued on next page.)

*Primary Examiner*—Robert A. Wax
*Assistant Examiner*—William W. Moore
*Attorney, Agent, or Firm*—Flehr Hohbach Test Albritton & Herbert LLP; Richard F. Trecartin; Robin M. Silva

[57] ABSTRACT

Novel carbonyl hydrolase mutants derived from the amino acid sequence of naturally-occurring or recombinant non-human carbonyl hydrolases and DNA sequences encoding the same. The mutant carbonyl hydrolases, in general, are obtained by in vitro modification of a precursor DNA sequence encoding the naturally-occurring or recombinant carbonyl hydrolase to encode the substitution, insertion or deletion of one or more amino acids in the amino acid sequence of a precursor carbonyl hydrolase. Such mutants have one or more properties which are different than the same property of the precursor hydrolase.

16 Claims, 42 Drawing Sheets

OTHER PUBLICATIONS

Rastetter, W.H., "Enzyme engineering: applications and promise." *Trends Biotechnol.*, 1:80–84 (1983).

Winter, G., et al., "Redesigning enzyme structure by site-directed mutagenesis: tyrosyl tRNA synthetase and ATP binding." *Nature*, 299:756–758 (1982).

Wallace, B.R., et al., "Oligonucleotide directed mutagenesis of the human β-globin gene: a general method for producing specific point mutations in cloned DNA." *Nucleic Acids Res.*, 9:3647–3656 (1981).

Shortle, D., et al., "Gap misrepair mutagenesis: Efficient site-directed induction of transition, transversion, and frameshift mutations in vitro." *Proc. Natl. Acad. Sci. USA.*, 79:1588–1592 (1982).

Wells, J.A., "Cloning, sequencing, and secretion of *Bacillus amyloliquefaciens* subtilisin in *Bacillus subtilis*," *Nucleic Acids Res.*, 11:8913:8926 (1985).

Vasantha, N., et al., "Genes for Alkaline Protease and Neutral Protease from *Bacillus amyloliquefaciens* Contain a Large Open Reading Frame Between the Regions Coding for Signal Sequence and Mature Protein." *J. Bacteriol.*, 159:811–819 (1984).

Jacobs, M., et al., "Cloning, sequencing and expression of subtilisin Carlsberg from *Bacillus licheniformis*." *Nucleic Acids Res.*, 13: 8913–8926 (1985).

Stahl, M.L., et al., "Replacement of the *Bacillus subtilis* Subtilisin Structural Gene with and In Vitro-Derived Deletion Mutation." *J. Bacteriol.*, 158:411–418 (1984).

Svendsen, I., "Chemical Modifications of the Subtilisins with Special Reference to the Binding of Large Substrates. A Review." *Carlsberg Res. Commun.*, 41:237–291 (1976).

Smith, E.L., "The Complete Sequence; Comparison with Subtilisin BPN; Evolutionary Relationships." *J. Biol. Chem.*, 243:2184–2191 (1968).

Kurihara, M., et al., "Isolation and Sequence of the Chymotryptic Peptides and the Complete Amino Acid Sequence." *J. Biol. Chem.*, 247:5619–5631 (1972).

Svendsen, I., et al., "Complete Amino Acid Sequence of Alkaline Mesentericopeptidase: A subtilisin isolate from a strain of *Bacillus mesentericus*." *FEBS*, 196:228–232 (1986).

Wright, C.S., "Structure of Subtilisin BPN' at 2.5 A Resolution" *Nature*, 221:235–242 (1969).

Grantham, R., "Amino Acid Difference Formula to Help Explain Protein Evolution." *Science*, 185:962–964 (1974).

Stauffer, C.E., et al., "The Effect on Subtilisin Activity of Oxidizing a Methionine Residue." *J. Biol. Chem.* 244:5333–5338 (1969).

Jaye, M., et al., "Isolation of a human anti-haemophilic factor IX cDNA clone using a unique 52-base synthetic oligonucleotide probe deduced from the amino acid sequence of bovine factor IX." *Nucleic Acids Res.*, 11;2325–2335 (1983).

Cantor, C.R., et al. "Biophysical Chemistry: Part I: The conformation of biological macromolecules." W.H. Freeman and Company, San Francisco, pp. 3–154, 253–309 (1980).

Robertus, J.D., et al., "An X-Ray Crystallographic Study of the Binding of Peptide Chloromethyl Ketone INhibitors to Subtilisin BPN'," *Biochemistry*, 11:2439–2449 (1972).

Ricchelli, F., et al., "Effects of pH and Urea on the Conformational Properties of Subtilisin DY," *Biochemical J.*, 207:201–205 (1982).

Mattoccia, E., et al., "Mutation in the A Block of the Yeast tRNA$^{Leu}$+is 3 Gene that Allows Transcription but Abolishes Splicing and 5'-End Maturation." *Cell*, 32:67–76 (1983).

Inouye, S., et al., "Role of positive charge on the amino--terminal region of the signal peptide in protein secretion across the membrane." *Proc. Natl. Acad. Sci. USA* 79:3438–3441 (1982).

Inouye, S., et al., "Effects of Mutations at Glycine Residues in the Hydrophobic Region of the *Escherichia coli* Prolipoprotein Signal Peptide on the Secretion across the Membrane." *J. Biol. Chem.*, 259:3729–3733 (1984).

Carter, P., et al., "Improved Oligonucleotide Site-Directed Mutagenesis Using M13 Vectors." *Nucleic Acids Res.*, 13:4431–4443 (1985).

Baughman, G., et al., "Translational regulation of the L11 ribosomal protein operon of *Escherichia coli*: Analysis of the mRNA target site using olignucleotide-directed mutagenesis." *Proc. Natl. Acad. Sci. USA*, 81:5389–5393 (1984).

Carter, P. J., et al., "The Use of Double Mutants to Detect Structural Changes in the Active Site of the Tyrosyl-tRNA Synthetase (Bacillus stearothermophilus)." *Cell*, 33:835–840 (1984).

Stroud, R.M., *Sci. Amer.*, 131:74–88 (1974).

Kraut, J., *Ann. Rev. Biochem.*, 46:331–358 (1977).

Markland, F.S., et al., *The Enzymes*, ed. Boyer, P.D., Acad Press, New York, vol. III, pp. 561–608 (1971).

Nedkov, P., et al., *Hoppe–Seyler's Z. Physiol. Chem.*, 364:1537–1540 (1983).

Drenth, J., et al., *Eur. J. Biochem.*, 26, 177–181 (1972).

Robertus, J.D., et al., *Biochemistry*, 11:4293–4303 (1972).

Matthews, D.A., et al., *J. Biol. Chem.*, 250:7120–7126 (1975).

Poulos, T.L., et al., *J. Biol. Chem.*, 251:1097–1103 (1976).

Philipp, M., et al., *Mol. Cell. Biochem.*, 51:5–32 (1983).

Jencks, W.P., *Catalysis in Chemistry and Enzymology*, McGraw–Hill, pp. 321–436 (1969).

Fersht, A., *Enzyme Structure and Mechanism*, Freeman, San Francisco. pp. 226–287 (1977).

Kaiser, E.T., et al., *Ann. Rev. Biochem.*, 54:565–595 (1985).

Ulmer, K.M. *Science*, 219:666–671 (1983).

Wilkinson, A.J., et al., *Biochemistry*, 22:3581–3586 (1983).

Wilkinson, A.H., et al., *Nature*, 307:187–188 (1984).

Perry, L.J., et al., *Science*, 226:555–557 (1984).

Villafranca, D.E., et al., *Science*, 222:782–788 (1983).

Carter, P.J., et al., *Cell*, 38:835–840 (1984).

Craik, C.S., et al., *Science*, 228:291–297 (1985).

Polgar, L. and Sajgo, M., *Biochem. Biophy. Acta.*, 667:351–354 (1981).

Paterson, A. and Clarke, P.H., *J. Gen. Micro.* 114:65–85 (1979).

Uehara, H., et al., *J. Bacteriology*, 139:583–590 (1979).

Kerjan, P., et al., *Eur. J. Biochem.*, 98:353–362 (1979).

Wells, et al., *Nucleic Acids Res.*, 11:7911–7923 (1983).

Thomas, et al., *Nature*, 318:37–38 (1985).

Gardell, et al., *Nature*, 317:551–555 (1985).

Vasantha, et al., *J. Bacteriol.*, 165:837–842 (1986).

Zaghloul, et al., *J. Bacteriol.*, 164:550–555 (1985).

Carter, et al., *Science*, 237:394–399 (1987).

Wells, et al., *Cold Spring Harbor Symposia on Quantitative Biology*, LII:647–652 (1987).

Toney et al., *Science*, 243:1485–1488 (1989).

Iverson, et al., *Science*, 243:1184–1188 (1989).

Wells, J.A., et al., "Designing Substrate Specificity by Protein Engineering of Electrostatic Interactions." *Proc. Nat. Acad. Sci. USA*, 84:1219–1223 (1987).

Estell, D.A., et al., "Probing Steric and Hydrophobic Effects on Enzyme–Substrate Interactions by Protein Engineering." *Science*, 233:659–633 (1986).

Wells, J.A., et al., "Protein Engineering of Subtilisin." *Protein Engineering*, pp. 279–287 (1987).

Abrahmsen, L., et al., "Engineering Subtilisin and Its Substrates for Efficient Ligation of Peptide Bonds in Aqueous Solution." *Biochemistry*, 30:4151–4159 (1991).

Markland, F.S., *Carlsberg Res. Comm.*, 41:237–291 (1976).

Polgar, et al., *Adv. Enzymol.*, 33:381–400 (1970).

Ottesen, et al., *Meth Enzymol.*, XIX:199–215 (1970).

Watson, J.D., in *Molecular Biology of the Gene*, 3rd Edition. Benjamin/Cummings Publ. Co., Inc. Menlo Park, CA pp. 313 (1987).

Singleton, et al., *Dictionary of Microbiology and Molecular Biology*, Second Edition. John Wiley & Sons. Chichester. p. 741 (1987).

Wells, et al., Subtilisin: An Enzyme Designed to be Engineered, in Proteins: *Form and Function* (Bradshaw et al., eds.). Elsevier Trends Journals, Cambridge, UK, pp. 45–57 (1990).

Allinger, et al., in *Organic Chemistry*, Worth Publishers, New York, NY p. 757 (1971).

```
                                                                              80                                     Ser Ala 90
       70  Gly Thr Val Ala Ala Leu Asn Asn Ser Ile Gly Val Leu Gly Val Ala Pro Ser Ala Ser Leu Tyr Ala Val Lys
624    GGC ACA GTT GCG GCT CTT AAT AAC TCA ATC GGT GTA TTA GGC GTT GCG CCA AGC GCA TCA CTT TAC GCT GTA AAA

Asp Ala 100                                       110                                    Ala Asn Asn Met
       Val Leu Gly Ala Asp Gly Ser Gly Gln Tyr Ser Trp Ile Ile Asn Gly Ile Glu Trp Ala Ile Ala Asn Asn Met
699    GTT CTC GGT GCT GAC GGT TCC GGC CAA TAC AGC TGG ATC ATT AAC GGA ATC GAG TGG GCG ATC GCA AAC AAT ATG

120             Ser                     130                                 140
       Asp Val Ile Asn Met Ser Leu Gly Ser Ser Gly Pro Ser Ala Ala Leu Lys Ala Ala Val Asp Lys Ala Val Ala
774    GAC GTT ATT AAC ATG AGC CTC GGC TCT TCT GGG CCT TCT GCT GCC TTA AAA GCG GCA GTT GAT AAA GCC GTT GCA

Ser Thr 160
       Ser Gly Val Val Val Val Ala Ala Ala Ser Thr Ser Ser Asn Gln Arg Ala Ser Thr Val Gly Tyr Pro Gly
849    TCC GGC GTC GTC GTA GTC GCA GCG GCT ACT TCC AGC AAC CAA AGA GCA AGC ACA GTG GGC TAC CCT GGT 170                                       180                                        190
       Lys Tyr Pro Ser Val Ile Ala Val Gly Ala Val Asp Ser Ser Asn Gln Arg Ala Ser Phe Ser Ser Val Gly Pro
924    AAA TAC CCT TCT GTC ATT GCA GTT GGC GCT GTT GAC AGC AGC AGC AAC CAA AGA GCA TCT TTC TCA AGC GTA GGA CCT 200                                       210
       Glu Leu Asp Val Met Ala Pro Gly Val Ser Ile Gln Ser Thr Leu Pro Gly Asn Lys Tyr Gly Ala Tyr Asn Gly
999    GAG CTT GAT GTC ATG GCA CCT GGC GTC TCT ATC CAA AGC ACG CTT CCT GGA AAC AAA TAC GGG GCG TAC AAC GGG 220                                       230                                       240
       Thr Ser Met Ala Ser Pro His Val Ala Gly Ala Ala Ala Leu Ile Leu Ser Lys His Pro Asn Trp Thr Asn Thr
1074   ACG TCA ATG GCA TCT CCG CAC GTT GCC GGA GCG GCT GCT TTG ATT CTT TCT AAG CAC CCG AAC TGG ACA AAC ACT 250                                         260
       Gln Val Arg Ser Ser Leu Glu Asn Thr Thr Lys Leu Gly Asp Ser Phe Tyr Tyr Gly Lys Gly Leu Ile Asn
1149   CAA GTC CGC AGC AGT TTA GAA AAC ACC ACA AAA CTT GGT GAT TCT TTC TAC TAT GGA AAA GGG CTG ATC AAC 270             275                           TERM
       Val Gln Ala Ala Ala Gln OC
1224   GTA CAG GCG GCA GCT CAG TAA       AACATAAAAACCGGCCTTGGCCCCGCCGGTTTTTATTATTTTCTTCCTCCGCATGTTCAATCCGCTCC

1316   ATAATCGACGGATGGCTCCCTCTGAAATTTTAACGAGAAACGGCGGGTTGACCGGCCAAGTCCCGTAACGGCCAAGTCCTGAAAGCTCAATCGCCG

1416   CTTCCCGGTTTCCGGTCAGCTCAATGCCGTAACGGTCGGCGGCGTTTCCTGATACCGGGAGACGGCATTCGTAATCGGATC
```

FIG. 1B

Homology of Bacillus proteases

1. Bacillus amyloliquifaciens
2. Bacillus subtilis var. I168
3. Bacillus licheniformis (carlsbergensis)

| Pos | 121 | 122 | 123 | 124 | 125 | 126 | 127 | 128 | 129 | 130 | 131 | 132 | 133 | 134 | 135 | 136 | 137 | 138 | 139 | 140 |
|---|---|---|---|---|---|---|---|---|---|---|---|---|---|---|---|---|---|---|---|---|
| 1 | V | I | N | M | S | L | G | G | P | S | G | S | A | A | L | K | A | A | V | D |
| 2 | V | I | N | M | S | L | G | G | P | T | G | S | T | A | L | K | T | V | V | D |
| 3 | V | I | N | M | S | L | G | G | A | S | G | S | T | A | M | K | Q | A | V | D |

| Pos | 141 | 142 | 143 | 144 | 145 | 146 | 147 | 148 | 149 | 150 | 151 | 152 | 153 | 154 | 155 | 156 | 157 | 158 | 159 | 160 |
|---|---|---|---|---|---|---|---|---|---|---|---|---|---|---|---|---|---|---|---|---|
| 1 | K | A | V | A | S | G | V | V | V | V | A | A | A | G | N | E | G | T | S | G |
| 2 | K | A | V | S | S | G | I | V | V | A | A | A | A | G | N | E | G | S | S | G |
| 3 | N | A | Y | A | R | G | V | V | V | V | A | A | A | G | N | S | G | N | S | G |

| Pos | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|
| 1 | S | S | S | T | V | G | Y | P | G | K | Y | P | S | V | I | A | V | G | A | V |
| 2 | S | T | S | T | V | G | Y | P | A | K | Y | P | S | T | I | A | V | G | A | V |
| 3 | S | T | N | T | I | G | Y | P | A | K | Y | D | S | V | I | A | V | G | A | V |

| Pos | 181 | 182 | 183 | 184 | 185 | 186 | 187 | 188 | 189 | 190 | 191 | 192 | 193 | 194 | 195 | 196 | 197 | 198 | 199 | 200 |
|---|---|---|---|---|---|---|---|---|---|---|---|---|---|---|---|---|---|---|---|---|
| 1 | D | S | S | N | Q | R | A | S | F | S | S | V | G | P | E | L | D | V | M | A |
| 2 | N | S | S | N | Q | R | A | S | F | S | S | A | G | S | E | L | D | V | M | A |
| 3 | D | S | N | S | N | R | A | S | F | S | V | V | G | A | E | L | E | V | M | A |

| Pos | 201 | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|---|
| 1 | P | G | V | S | I | Q | S | T | L | P | G | N | K | Y | G | A | Y | N | G | T |
| 2 | P | G | V | S | I | Q | S | T | L | P | G | N | T | Y | G | A | Y | N | G | T |
| 3 | P | G | A | G | V | Y | S | T | Y | P | T | N | T | Y | A | T | L | N | G | T |

| Pos | 221 | 222 | 223 | 224 | 225 | 226 | 227 | 228 | 229 | 230 | 231 | 232 | 233 | 234 | 235 | 236 | 237 | 238 | 239 | 240 |
|---|---|---|---|---|---|---|---|---|---|---|---|---|---|---|---|---|---|---|---|---|
| 1 | S | M | A | S | P | H | V | A | G | A | A | L | I | L | S | K | H | P | N | |
| 2 | S | M | M | A | T | P | H | V | A | G | A | A | L | I | L | S | K | H | P | N |
| 3 | S | M | A | S | P | H | V | A | G | A | A | L | I | L | S | K | H | P | N | |

| Pos | 241 | 242 | 243 | 244 | 245 | 246 | 247 | 248 | 249 | 250 | 251 | 252 | 253 | 254 | 255 | 256 | 257 | 258 | 259 | 260 |
|---|---|---|---|---|---|---|---|---|---|---|---|---|---|---|---|---|---|---|---|---|
| 1 | W | T | N | T | Q | V | R | S | S | L | E | N | T | T | T | K | L | G | D | S |
| 2 | W | T | N | A | Q | V | R | D | R | L | E | S | T | A | T | K | Y | L | G | S |
| 3 | L | S | A | S | Q | V | R | N | R | L | S | S | T | A | T | Y | L | L | N | S |

| Pos | 261 | 262 | 263 | 264 | 265 | 266 | 267 | 268 | 269 | 270 | 271 | 272 | 273 | 274 | 275 |
|---|---|---|---|---|---|---|---|---|---|---|---|---|---|---|---|
| 1 | F | Y | Y | G | K | G | L | I | N | V | Q | A | A | A | Q |
| 2 | F | Y | Y | G | K | G | L | I | N | V | Q | E | A | A | A | 
| 3 | F | Y | Y | G | K | G | L | I | N | V | E | A | A | A | Q |

FIG. 5A-2

ALIGNMENT OF B.AMYLOLIQUIFACIENS SUBTILISIN AND THERMITASE
1. B.amyloliquifaciens subtilisin
2. thermitase

TOTALLY CONSERVED RESIDUES IN SUBTILISINS

1. Codon number:
2. Wild type amino acid sequence:
```
              43               45
   Lys-Val-Ala-Gly-Gly-Ala-Ser-Met-Val-Pro-Ser
```

3. Wild type DNA sequence:
```
5'-AAG-GTA-GCA-GGA-GGC-GCC-AGC-ATG-GTT-CCT-TCT
   TTC-CAT-CGT-CCT-CCG-CGG-TCG-TAC-CAA-GGA-AGA-5'
```

4. pΔ50:
```
5'-AAG-GCC-T-------GC-ATG+GTA-CCT-TCT
   TTC-CGG-A-------CG-TAC-CAT-GGA-AGA-5'
        StuI              KpnI
```

5. pΔ50 cut with StuI/KpnI:
```
5'-AAG-G            * pCT-TCT
   TTC-Cp             CAT-GGA-AGA-5'
```

6. Cut pΔ50 ligated with cassettes:
```
5'-AAG-GTA-GCA-GGC-GGA-GCC-AGC-ATG+GTA-CCT-TCT
   TCC-CAT-CGT-CCG-CCT-CGG-TCG-TAC-CAT-GGA-AGA-5'
```

7. Mutagenesis primer for pΔ50:
```
5'-CT-GAT-TTA-AAG-GCC-TGC-ATG-GTA-CCT-TCT-GA
```

8. Mutants made:  V45,P45,V45/P48,E46,E48,V48,C49,C50,F50

FIG. 10

```
1. Codon number:                    117           120           124   126                130

2. Wild type amino acid sequence:   Asn-Asn-Met-Asp-Val-Ile-Asn-Met-Ser-Leu-Gly-Gly-Pro-Ser 3. Wild type DNA sequence:          5'-AAC-AAT-ATG-GAC-GTT-ATT-AAC-ATG-AGC-CTC-GGC-GGA-CCT-TCT
                                       TTG-TTA-TAC-CTG-CAA-TAA-TTG-TAC-TCG-GAG-CCG-CCT-GGA-AGA-5'
                                                            ***                         *
4. pΔ124:                           5'-AAC-AAT-ATG-GAT-ATC----------C-GGG-GGC-CCT-TCT
                                       TTG-TTA-TAC-CTA-TAG----------G-CCC-CCG-GGA-AGA-5'
                                                  EcoRV                 ApaI
                                                     *                                  *
5. pΔ124 cut with EcoRV             5'-AAC-AAT-ATG-GAT                    pCT-TCT
   and ApaI                            TTG-TTA-TAC-CTAp                CCG-GGA-AGA-5'

***                            *
6. Cut pΔ124 ligated with           5'-AAC-AAT-ATG-GAT-GTT-ATT-AAC-ATG-AGC-CTC-GGC-GGC-CCT-TCT
   cassettes:                          TTG-TTA-TAC-CTA-CAA-TAA-TTG-TAC-TCG-GAG-CCG-CCG-GGA-AGA-5'

7. Mutagenesis primer               5'-AAC-AAT-ATG-GAT-ATC-C-GGG-GGC-CCT-TCT-GGT-TC-3'
   for pΔ124:

8. Mutants made:                    I124, L124 and C126
```

FIG. 11

```
                                                        166
Wild type amino acid sequence:    Thr Ser Gly Ser Ser Ser Thr Val Gly Tyr Pro Gly
     Codon:

1. Wild type DNA sequence:        5'-ACT TCC GGC AGC TCA AGC ACA GTG GGC TAC CCT GGT-3'
                                  3'-TGA AGG CCG TCG AGT TCG TGT CAC CCG ATG GGA CCA-5'

*                              *
2. p 166 DNA sequence:            5'-ACT TCC GGG AGC TCA A- - - - - - - -C CCG GGT-3'
                                  3'-TGA AGG CCC TCG AGT T                G GGC CCA-5'
                                              SacI                         XmaI

*                             *
3. p 166 cut with SacI and XmaI:  5'-ACT TCC GGG AGC T                   pCCG GGT-3'
                                  3'-TGA AGG CCC TCG AGT TCG TGT CAC CCG    CA-5'

*           ***
4. Cut p 166 ligated with         5'-ACT TCC GGG AGC TCA AGC ACA GTG NNN TAC CCG GGT-3'
   duplex DNA cassette pools:     3'-TGA AGG CCC TCG AGT TCG TGT CAC NNN ATG GGC CCA-5'

MUTAGENESIS PRIMER 37MER

5'   AA GGC ACT TCC GGG AGC TCA ACC CGG GTA AA  TAC CCT  3'
```

FIG. 13

Gly-169 CASSETTE MUTAGENESIS

```
Codon:                              162                              169                173
Wild type amino acid sequence:      Ser Ser Thr Val Gly Tyr Pro Gly Lys Tyr Pro Ser 1. Wild type DNA sequence       5'  TCA AGC ACA GTG GGC TAC CCT GGT AAA TAC CCT TCT  3'
                                3'  AGT TCG TGT CAC CCG ATG GGA CCA TTT ATG GGA AGA  5'

*              *        *
2. p169 DNA sequence            5'  TCA AGC ACA GTC GGG TAC CCT-----GA TAT CCT TCT  3'
                                3'  AGT TCG TGT CAG CCC ATG GGA      CT ATA GGA AGA  5'
                                                       KpnI           EcoRV

*              *
3. p169 cut with KpnI and EcoRV: 5' TAC AGC ACA GTC GGG TAC                          3'
                                3'  AGT TCG TGT CAG CCC                              5'
                                                                         pAT CCT TCT  3'
                                                                         TA  GGA AGA  5'

*              *
4. Cut p169 ligated with        5'  TAC AGC ACA GTG GGG TAC CCT NNN AAA TAT CCT TGT  3'
   oligonucleotide pools        3'  AGT TCG TGT CAC CCC ATG GGA NNN TTT ATA GGA AGA  5'

Mutagenesis primer for p169     5'  AAG CAC AGT GGG GTA CCC TGA TAT CCT TCT GTC A    3'
```

1. Codon number: 100, 104, 105, 108
2. Wild type amino acid sequence: Gly-Ser-Gly-Gln-Tyr-Ser-Trp-Ile-Ile-
3. Wild type DNA sequence: 5'-GGT-TCC-GGC-CAA-TAC-AGC-TGG-ATC-ATT-3'
   Pvu II
4. Primer for Hind III insertion at 104:
   5'-GGT-TCC-GGC-CAA-GCTT-AGC-TGG-ATC-ATT-3'
   Hind III
5. Primers for 104 mutants:
   5'---T-TCC-GCC-CAA-NNN-AGC-TGG-ATC-----3'
6. Mutants made: A, M, L, S AND H104

FIG. 20

1. Codon number: 148, 150, 152, 155
2. Wild type amino acid sequence: Val-Val-Val-Ala-Ala-Ala-Gly-Asn-Glu
3. Wild type DNA sequence: 5'-GTA-GTC-GTT-GCG-GCA-GCC-GGT-AAC-GAA-3'
4. V152/P153:
   5'-GTA-GTC-GTT-GCG-GTA-CCC-GGT-AAC-GAA-3'
   Kpn I
5. S 152:
   5'-GTA-GTC-GTT-GCG-AGC-GCC-GGT-AAC-GAA-3'
6. G 152:
   5'-GTA-GTC-GTT-GCG-GGC-GCC-GGT-AAC-GAA-3'

FIG. 22

1. Codon number:
2. Wild type amino acid sequence:
```
            211                     215        217        220
            Gly-Asn-Lys-Tyr-Gly-Ala-Tyr-Asn-Gly-Thr-Ser-Met-Ala
```

3. Wild type DNA sequence:
```
5'-GGA-AAC-AAA-TAC-GGG-GCG-TAC-AAC-GGT-ACG-TCA-ATG-GCA
   CCT-TTG-TTT-ATG-CCC-CGC-ATG-TTG-CCA-TGC-AGT-TAC-CGT-5'
```

4. pΔ217:
```
                            *                      **
5'-GGA-AAC-AAA-TAC-GGC-GCC-TAC------GG-ATA-TCA-ATG-GCA
   CCT-TTG-TTT-ATG-CCG-CGG-ATG------CC-TAT-AGT-TAC-CGT-5'
                   Nar I                  Eco RV
```

5. pΔ217 cut with Nar I and Eco RI:
```
                            *                       pA-TCA-ATG-GCA
5'-GGA-AAC-AAA-TAC-GG                                T-AGT-TAC-CGT-5'
   CCT-TTG-TTT-ATG-CCG-CCG-Gp
```

6. Cut pΔ217 ligated with cassettes:
```
                            *         *    **
5'-GGA-AAC-AAA-TAC-GGC-GCG-NNN-AAC-GGT-ACA-TCA-ATG-GCA
   CCT-TTG-TTT-ATG-CCG-CGC-NNN-TTG-CCA-TGT-AGT-TAC-CGT-5'
```

7. Mutagenesis primer for pΔ217:
```
                                      * **
5'-GA-AAC-AAA-TAC-GGC-GCC-TAC-GGA-TAT-CAA-TGG-CAT-3'
```

8. Mutants made: All 19 at 217

1. Codon number:
2. Wild type amino acid sequence:
```
                91                              95                          100
                Tyr-Ala-Val-Lys-Val-Leu-Gly-Ala-Asp-Gly-Ser
```

3. Wild type DNA sequence:
```
5'-TAC-GCT-GTA-AAA-GTT-CTC-GGT-GCT-GAC-GGT-TCC
   ATG-CGA-CAT-TTT-CAA-GAG-CCA-CGA-CTG-CCA-AGG-5'
```

4. pΔ95:
```
                        *                       *
5'-TAC-GCG-T--------CTC-GCT-GCA-GAC-GGT-TCC
   ATG-CGC-A--------GAG-CGA-CGT-CTG-CCA-AGG-5'
        MluI                Pst I
```

5. pΔ95 cut with MluI and PstI
```
      *                                         *pGAC-GGT-TCC
5'-TA                                            A-CGT-CTG-CCA-AGG-5'
   ATG-CGCp
```

6. Cut pΔ95 ligated with cassettes:
```
             *                       *          *
5'-TAC-GCG-GTA-AAA-GTT-CTC-GGT-GCA-GAC-GGT-TCC
   ATG-CGC-CAT-TTT-CAA-GAG-CCA-CGT-CTG-CCA-AGG-5'
```

7. Mutagenesis primer for pΔ95:
```
              *                    *     *
5'-CA-TCA-CTT-TAC-GCG-T-CTC-GCT-GCA-GAC-GGT-TCC
```

8. Mutants made: C94, C95, D96

FIG. 25

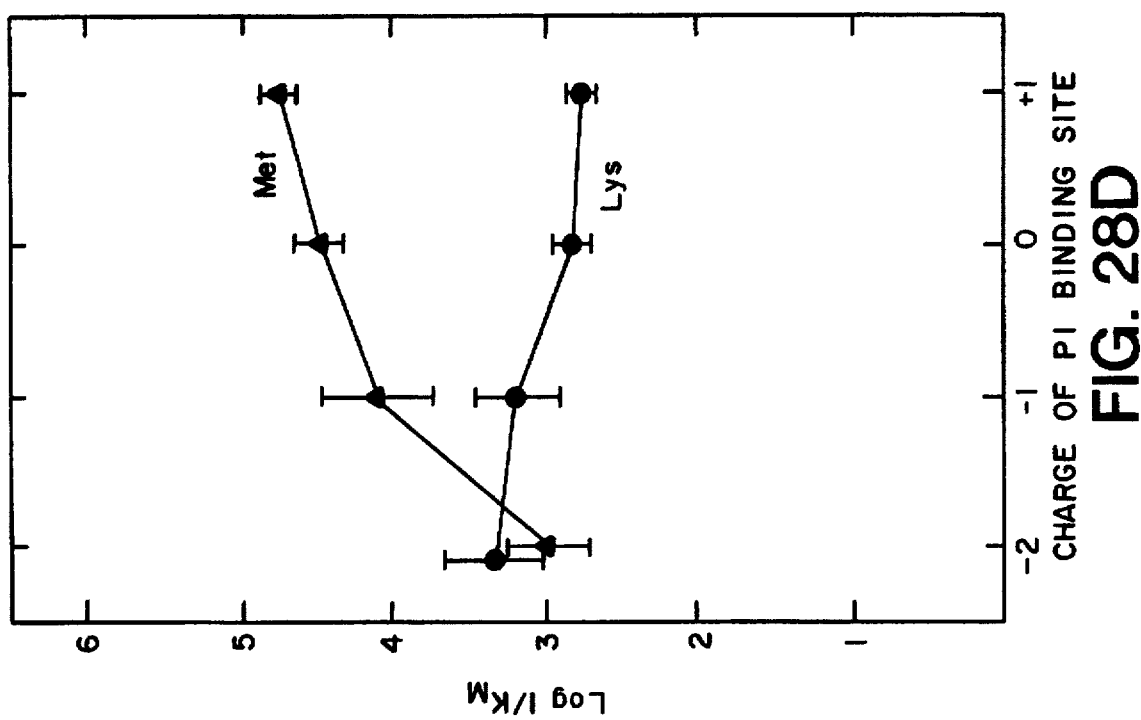
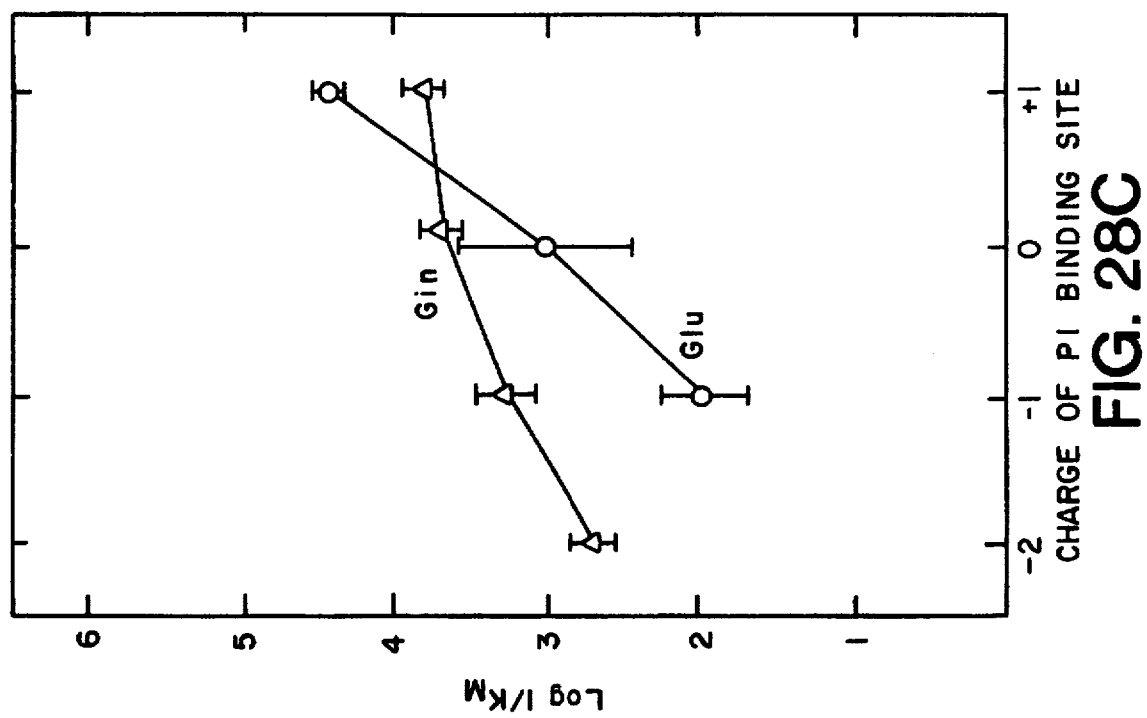

FIG. 35A

```
                          195                    200                      206
W.T A.A.:                 Glu Leu Asp Val Met Ala Pro Gly Val Ser Ile Gln
W.T.DNA:                  GAG CTT GAT GTC ATG GCA CCT GGC GTA TCT ATC CAA
                          CTC GAA CTA CAG TAC CGT GGA CCG CAT AGA TAG GTT pΔ222 DNA:                GAG CTT GAT GTC ATG GCA CCT GGC GTA TCT ATC CAA
                          CTC GAA CTA CAG TAC CGT GGA CCG CAT AGA TAG GTT
                                    *  **

A 197 DNA:                GAG CTC GCA CGT CAG TAC CGT GGA CCG CAT AGA TAG GTT
                          CTC GAG CGT GCA GTC ATG GCA CCT GGC GTA TCT ATC CAA
                              SstI

Fragments from            GAG-CT
pΔ222 and A197            Cp
cut w/ PstI, SstI:              * pΔ222,A197                GAG CTC GAT GTC ATG GCA CCT GGC GTA TCT ATC CAA
cut & ligated             CTC GAG CTA CAG TAC CGT GGA CCG CAT AGA TAG GTT
w/oligodeoxy-                 SstI
nucleotide pools:

207                    210                      218
W.T A.A.:                 Ser Thr Leu Pro Gly Asn Lys Tyr Gly Ala Tyr Asn
W.T.DNA:                  AGC ACG CTT CCT GGA AAC AAA TAC GGG GCG TAC AAC
                          TCG TGC GAA GGA CCT TTG TTT ATG CCC CGC ATG TTG pΔ222DNA:                 AGC ACG CTT CCT GGA AAC AAA TAC GGG GCG TAC AAC
                          TCG TGC GAA GGA CCT TTG TTT ATG CCC CGC ATG TTG

A197 DNA:                 AGC ACG CTT CCT GGA AAC AAA TAC GGG GCG TAC AAC
                          TCG TGC GAA GGA CCT TTG TTT ATG CCC CGC ATG TTG
                                          *          *
                                          *          *
                                          SmaI

Fragments from            AGC ACG CTT CCC GGG AAC AAA TAC GGG GCG TAC AAC
pΔ222 and A197            TCG TGC GAA GGG CCC TTG TTT ATG CCC CGC ATG TTG
cut w/PstI,SstI:
```

```
                          219 220                                        230
W.T A.A.:                 Gly Thr Ser Met Ala Ser Pro His Val Ala Gly Ala

W.T.DNA:                  GGT ACG TCA ATG GCA TCT CCG CAC GTT GCC GGA GCG-3'
                          CCA TGC AGT TAC CGT AGA GGC GTG CAA CGG CCT CGC-5'
                                  *                                * pΔ222DNA:                 GGT ACC TCA----------CG CAC GCT GCA GGA GCG-3'
                          CCA TGG AGT----------GC GTG CGA CGT CCT CGC-5'
                              Kpnl                    Pstl A197 DNA:                 GGT ACG TCA ATG GCA TCT AGA GGC GTG CAA CGT CCT CGC-5'
                          CCA TGC AGT TAC CGT AGA GGC GTG CAA CGT CCT CGC-5'

Fragments from                                             pGGA GCG-3'
pΔ222 and A197                                          A  CGT CCT CGC-5'
cut w/PstI,SstI:                                                Pstl destroyed
                                     *                        * pΔ222,A197                GGT ACC TCA ATG GCA TCT CCG CAC GTT GCA GGA GCG-3'
cut & ligated             CCA TGG AGT TAC CGT AGA GGC GTG CAA CGT CCT CGC-5'
w/oligodeoxy-                  Kpnl                         Pstl
nucleotide pools:
```

FIG. 35B

Oligodeoxynucleotide pools synthesized with 2% contaminating nucleotides in each cycle to give ~15% of pool with 0 mutations, ~28% of pool with single mutations, and ~57% of pool with 2 or more mutations, according to the general formula $f = \frac{\mu^n}{n!} e^{-\mu}$.

MODIFIED SUBTILISINS HAVING AMINO ACID ALTERATIONS

This application is a Divisional of U.S. Ser. No. 08/212,291, filed Mar. 14, 1994, which is a Continuation of Ser. No. 07/898,382, filed Jun. 9, 1992, now abandoned, which is a Continuation application of Ser. No. 07/747,459, filed Aug. 12, 1991, now abandoned, which is a Continuation application of Ser. No. 07/540,868, filed Jun. 14, 1990, now abandoned, which is a Continuation application of Ser. No. 07/035,652, filed Apr. 5, 1987, now abandoned, which is a Continuation-in-Part application of Ser. No. 06/858,594, filed Apr. 30, 1986, now abandoned, which is a Continuation-in-Part application of the following: Ser. No. 06/614,612, filed May 29, 1984, which issued as U.S. Pat. No. 4,760,025, Ser. No. 06/614,615, filed May 29, 1984, now abandoned, Ser. No. 06/614,617, filed May 29, 1984, now abandoned, and Ser. No. 06/614,491, filed May 29, 1984, and now abandoned.

FIELD OF THE INVENTION

The present invention relates to novel carbonyl hydrolase mutants derived from the amino acid sequence of naturally-occurring or recombinant non-human carbonyl hydrolases and to DNA sequences encoding the same. Such mutant carbonyl hydrolases, in general, are obtained by in vitro modification of a precursor DNA sequence encoding the naturally-occurring or recombinant carbonyl hydrolase to encode the substitution, insertion or deletion of one or more amino acids in a precursor amino acid sequence.

BACKGROUND OF THE INVENTION

Serine proteases are a subgroup of carbonyl hydrolase. They comprise a diverse class of enzymes having a wide range of specificities and biological functions. Stroud, R. M. (1974) *Sci Amer.* 131, 74–88. Despite their functional diversity, the catalytic machinery of serine proteases has been approached by at least two genetically distinct familites of enzymes: the Bacillus subtilisins and the mammalian and homologous bacterial serine proteases (e.g., trypsin and *S. gresius* trypsin). These two families of serine proteases show remarkably similar mechanisms of catalysis. Kraut, J. (1977) *Ann. Rev. Biochem.* 46, 331–358. Furthermore, although the primary structure is unrelated, the tertiary structure of these two enzyme families bring together a conserved catalytic triad of amino acids consisting of serine, histidine and aspartate.

Subtilisin is a serine endoprotease (MW 27,500) which is secreted in large amounts from a wide variety of Bacillus species. The protein sequence of subtilisin has been determined from at least four different species of Bacillus. Markland, F. S., et al. (1971) in *The Enzymes*, ed. Boyer P. D., Acad Press, New York, Vol. III, pp. 561–608; Nedkov, P. et al. (1983) *Hoppe-Seyler's Z. Physiol. Chem.* 364, 1537–1540. The three-dimensional crystallographic structure of subtilisin BPN' (from *B. amyloliqoefaciens*) to 2.5 A resolution has also been reported. Wright, C. S., et al. (1969) *Nature* 221, 235–242; Drenth, J. et al. (1972) *Eur. J. Biochem.* 26, 177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972) *Biochemistry* 11, 2439–2449), product complexes (Robertus, J. D., et al. (1972) *Biochemistry* 11, 4293–4303), and transition state analogs (Matthews, D. A., et al (1975) *J. Biol. Chem.* 250, 7120–7126; Poulos, T. L., et al. (1976) *J. Biol. Chem.* 251, 1097–1103), which have been reported have also provided information regarding the active site and putative substrate binding cleft of subtilisin. In addition, a large number of kinetic and chemical modification studies have been reported for subtilisin (Philipp, M., et al. (1983) *Mol. Cell. Biochem.* 51, 5–32; Svendsen, I. B. (1976) *Carlsberg Res. Comm.* 41, 237–291; Markland, F. S. Id.) as well as at least one report wherein the side chain of methione at residue 222 of subtilisin was converted by hydrogen peroxide to methionine-sulfoxide (Stauffer, D. C., et al. (1965) *J. Biol. Chem.* 244, 5333–5338).

Substrate specificity is a ubiquitous feature of biological macromolecules that is determined by chemical forces including hydrogen bonding, electrostatic, hydrophobic and steric interactions. Jencks, W. P., in *Catalysis in Chemistry and Enzymology* (McGraw-Hill, 1969) pp. 321–436; Fersht, A., in *Enzyme Structure and Mechanism* (Freeman, San Francisco, 1977) pp. 226–287. Substrate specificity studies of enzymes, however, have been limited to the traditional means of probing the relative importance of these binding forces. Although substrate analogs can be synthesized chemically, the production of modified enzyme analogs has been limited to chemically modified enzyme derivatives (Kaiser, E. T., et al. (1985) *Ann. Rev. Biochem.* 54, 565–595 or naturally occurring mutants. Kraut, J. (1977) *Ann. Rev. Biochem.* 46, 331–358.

The recent development of various in vitro techniques to manipulate the DNA sequences encoding naturally-occuring polypeptides as well as recent developments in the chemical synthesis of relatively short sequences of single and double stranded DNA has resulted in the speculation that such techniques can be used to modify enzymes to improve some functional property in a predictable way. Ulmer, K. M. (1983) *Science* 219, 666–671. The only working example disclosed therein, however, is the substitution of a single amino acid within the active site of tyrosyl-tRNA synthetase (Cys35→Ser) which lead to a reduction in enzymatic activity. See Winter, G., et al. (1982) *Nature* 299, 756–758; and Wilkinson, A. J., et al. (1983) *Biochemistry* 22, 3581–3586 (Cys35→Gly mutation also resulted in decreased activity).

When the same t-RNA synthetase was modified by substituting a different amino acid residue within the active site with two different amino acids, one of the mutants (Thr51→Ala) reportedly demonstrated a predicted moderate increase in kcat/Km whereas a second mutant (Thr51→Pro) demonstrated a massive increase in kcat/Km which could not be explained with certainty. Wilkinson, A. H., et al. (1984) *Nature* 307, 187–188.

Another reported example of a single substitution of an amino acid residue is the substitution of cysteine for isoleucine at the third residue of T4 lysozyme. Perry, L. J., et al. (1984) *Science* 226, 555–557. The resultant mutant lysozyme was mildly oxidized to form a disulfide bond between the new cysteine residue at position 3 and the native cysteine at position 97. This crosslinked mutant was initially described by the author as being enzymatically identical to, but more thermally stable than, the wild type enzyme. However, in a "Note Added in Proof", the author indicated that the enhanced stability observed was probably due to a chemical modification of cysteine at residue 54 since the mutant lysozyme with a free thiol at Cys54 has a thermal stability identical to the wild type lysozyme.

Similarly, a modified dehydrofolate reductase from *E. coli* has been reported to be modified by similar methods to introduce a cysteine which could be crosslinked with a naturally-occurring cysteine in the reductase. Villafranca, D. E., et al. (1983) *Science* 222, 782–788. The author indicates that this mutant is fully reactive in the reduced state but has significantly diminished activity in the oxidized state. In addition, two other substitutions of specific amino acid residues are reported which resulted in mutants which had diminished or no activity.

As set forth below, several laboratories have also reported the use of site directed mutagensis to produce the mutation of more than one amino acid residue within a polypeptide.

The amino-terminal region of the signal peptide of the prolipoprotein of the *E. coli* outer membrane was stated to be altered by the substitution or deletion of residues 2 and 3 to produce a charge change in that region of the polypeptide. Inoyye, S., et al. (1982) *Proc. Nat. Acad. Sci. USA* 79, 3438–3441. The same laboratory also reported the substitution and deletion of amino acid redisues 9 and 14 to determine the effects of such substitution on the hydrophobic region of the same signal sequence. Inouye, S., et al. (1984) *J. Biol. Chem.* 259, 3729–3733. In the case of mutants at residues 2 and 3 the authors state that the results obtained were consistant with the proposed loop model for explaining the functions of the signal sequence. However, as reported the mutations at residues 9 and 14 produced results indicating that the signal peptide has unexpeded flexibility in terms of the relationship between its primary structure and function in protein secretion.

Double mutants in the active site of tyrosyl-t-RNA synthetase have also been reported. Carter, P. J., et al. (1984) *Cell* 38, 835–840. In this report, the improved affinity of the previously described Thr51→Pro mutant for ATP was probed by producing a second mutation in the active site of the enzyme. One of the double mutants, Gly35/Pro51, reportedly demonstrated an unexpected result in that it bound ATP in the transition state better than was expected from the two single mutants. Moreover, the author warns, at least for one double mutant, that it is not readily predictable how one substitution alters the effect caused by the other substitution and that care must be taken in interpreting such substitutions.

A mutant is disclosed in U.S. Pat. No. 4,532,207, wherein a polyarginine tail was attached to the C-terminal residue of β-urogastrone by modifying the DNA sequence encoding the polypeptide. As disclosed, the polyarginine tail changed the electrophoretic mobility of the urogastrone-polyaginine hybrid permiting selective purification. The polyarginine was subsequently removed, according to the patentee, by a polyarginine specific exopeptidase to produce the purified urogastrone. Properly construed, this reference discloses hybrid polypeptides which do not constitute mutant polypeptides containing the substitution, insertion or deletion of one or more amino acids of a naturally occurring polypeptide.

Single and double mutants of rat pancreatic trypsin have also been reported. Craik, C. S., et al. (1985) *Science* 228, 291–297. As reported, glycine residues at positions 216 and 226 were replaced with alanine residues to produce three trypsin mutants (two single mutants and one double mutant). In the case of the single mutants, the authors stated expectation was to observe a differential effect on Km. They instead reported a change in specificity (kcat/Km) which was primarily the result of a decrease in kcat. In contrast, the double mutant reportedly demonstrated a differential increase in Km for lysyl and arginyl substrates as compared to wild type trypsin but had virtually no catalytic activity.

The references discussed above are provided solely for their disclosure prior to the filing date of the instant case, and nothing herein is to be construed as an admission that the inventors are not entitled to antedate such disclosure by virtue of prior invention or priority based on earlier filed applications.

Based on the above references, however, it is apparent that the modification of the amino acid sequence of wild type enzymes often results in the decrease or destruction of biological activity. Moreover, these references do not address the mutation of the particular carbonyl hydrolases disclosed herein.

Accordingly, it is an object herein to provide carbonyl hydrolase mutants which have at least one property which is different from the same property of the carbonyl hydrolase precursor from which the amino acid of said mutant is derived.

It is a further object to provide mutant DNA sequences encoding such carbonyl hydrolase mutants as well as expression vectors containing such mutant DNA sequences.

Still further, another object of the present invention is to provide host cells transformed with such vectors as well as host cells which are capable of expressing such mutants either intracellularly or extracellularly.

SUMMARY OF THE INVENTION

The invention includes carbonyl hydrolase mutants, preferably having at least one property which is substantially different from the same property of the precursor non-human carbonyl hydrolase from which the amino acid sequence of the mutant is derived. These properties include oxidative stability, substrate, specificity catalytic activity, thermal stability, alkaline stability, pH activity profile and resistance to proteolytic degradation. The precursor carbonyl hydrolase may be naturally occurring carbonyl hydrolases or recombinant carbonyl hydrolases. The amino acid sequence of the carbonyl hydrolase mutant is derived by the substitution, deletion or insertion of one or more amino acids of the precursor carbonyl hydrolase amino acid sequence.

The invention also includes mutant DNA sequences encoding such carbonyl hydrolase mutants. These mutant DNA sequences are derived from a precursor DNA sequence which encodes a naturally occurring or recombinant precursor carbonyl hydrolase. The mutant DNA sequence is derived by modifying the precursor DNA sequence to encode the substitution, deletion or insertion of one or more amino acids encoded by the precursor DNA sequence. These recombinant DNA sequences encode mutants having an amino acid sequence which does not exist in nature and at least one property which is substantially different from the same property of the precursor carbonyl hydrolase encoded by the precursor DNA sequence.

Further the invention includes expression vectors containing such mutant DNA sequences as well as host cells transformed with such vectors which are capable of expressing said carbonyl hydrolase mutants.

BRIEF DESCRIPTION OF THE DRAWINGS

FIGS. 1A and 1B shows the nucleotide sequence of the coding strand, correlated with the amino acid sequence of *B. amyloliquefaciens* subtilisin gene. Promoter (p) ribosome binding site (rbs) and termination (term) regions of the DNA sequence as well as sequences encoding the presequence (PRE) putative prosequence (PRO) and mature form (MAT) of the hydrolase are also shown.

FIG. 3A shows Lysine P-1 substrate bound to form a salt bridge with a Glu at position 156. FIG. 3B shows Lysine P-1 substrate bound to form a salt bridge with Glu at position 166.

FIGS. 5A-1, 5A-2, 5B-1, 5B-2 and 5C depict the amino acid sequence of subtilisin obtained from various sources. The residues directly beneath each residue of *B. amyloliquefaciens* subtilisin are equivalent residues which (1) can be mutated in a similar manner to that described for *B. amyloliquefaciens* subtilisin, or (2) can be used as a replacement amino acid residue in *B. amyloliquefaciens* subtilisin. FIG. 5C depicts conserved residues of *B. amyloliquefaciens* subtilisin when compared to other subtilisin sequences.

FIG. 10 depicts the construction of mutations between codons 45 and 50 of *B. amyloliquefaciens* subtilisin.

FIG. 11 depicts the construction of mutations between codons 122 and 127 of *B. amyloliquefaciens* subtilisin.

FIG. 13 depicts the construction of mutations at codon 166 of *B. amyloliquefaciens* subtilisin.

FIG. 15A shows position 166 mutant subtilisins containing non-branched alkyl and aromatic side-chain substitutions arranged in order of increasing molecular volume. FIG. 15B shows a series of mutant enzymes progressing through β- and γ-branched aliphatic side chain substitutions of increasing molecular volume.

FIG. 18 depicts the construction of mutations at codon 169 of *B. amyloliquefaciens* subtilisin.

FIG. 19 depicts the construction of mutations at codon 104 of *B. amyloliquefaciens* subtilisin.

FIG. 20 depicts the construction of mutations at codon 152 *B. amyloliquefaciens* subtilisin.

FIG. 22 depicts the construction of mutations at codon 217 for *B. amyloliquefaciens* subtilisin.

FIG. 25 depicts the constructing mutants at codons 94, 95 and 96.

FIGS. 35A and 35B depicts the oligodeoxynucleotides used for random cassette mutagenesis over residues 197 through 228.

DETAILED DESCRIPTION

Figure 1A:
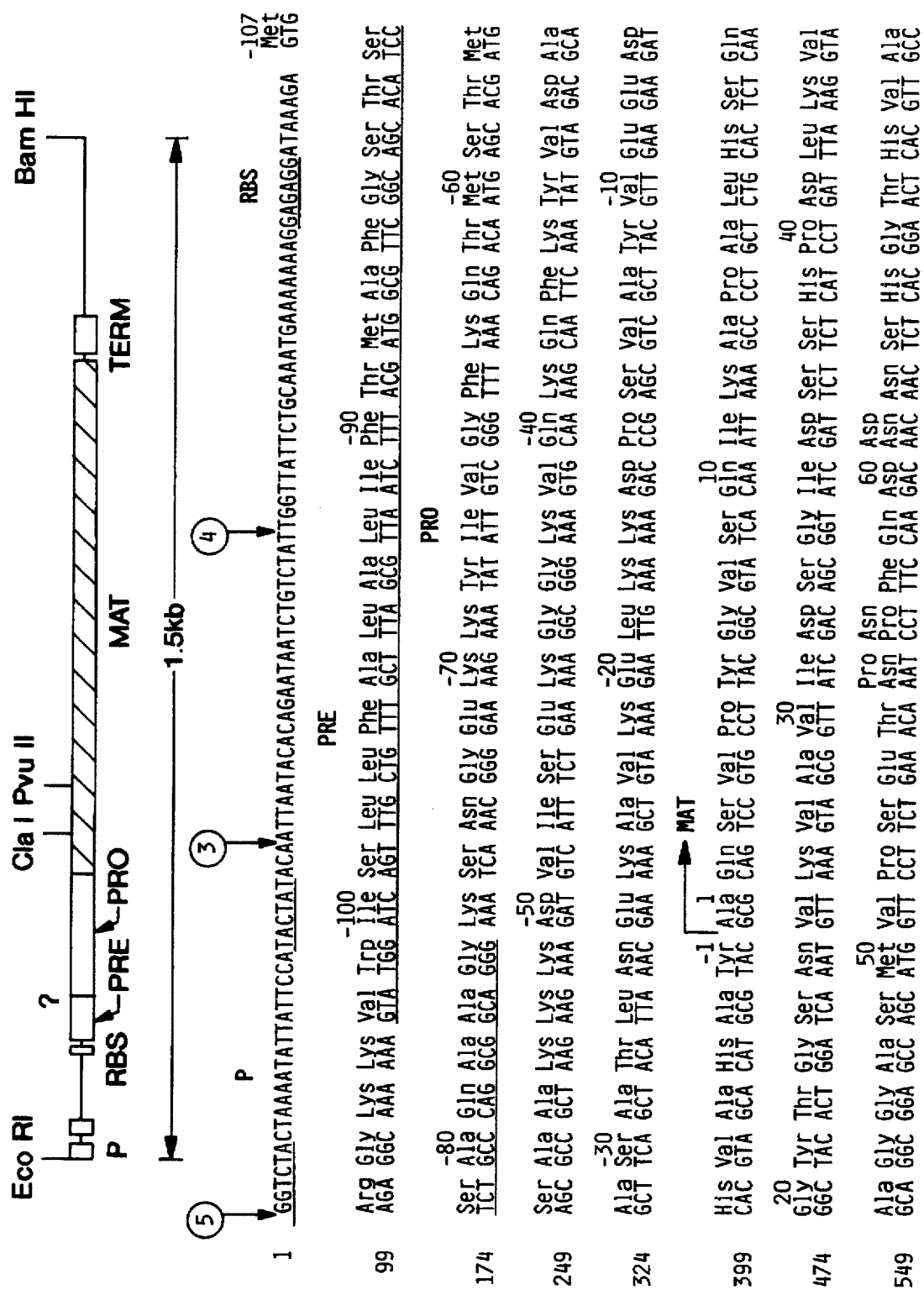

The inventors have discovered that various single and multiple in vitro mutations involving the substitution, deletion or insertion of one or more amino acids within a non-human carbonyl hydrolase amino acid sequence can confer advantageous properties to such mutants when compared to the non-mutated carbonyl hydrolase.

Specifically, *B. amyloliquefaciens* subtilisin, an alkaline bacterial protease, has been mutated by modifying the DNA encoding the subtilisin to encode the substitution of one or more amino acids at various amino acid residues within the mature form of the subtilisin molecule. These in vitro mutant subtilisins have at least one property which is different when compared to the same property of the precursor subtilisin. These modified properties fall into several categories including: oxidative stability, substrate specificity, thermal stability, alkaline stability, catalytic activity, pH activity profile, resistance to proteollytic degradation, Km, kcat and Km/kcat ratio.

Carbonyl hydrolases are enzymes which hydrolyze compounds containing

bonds in which X is oxygen or nitrogen. They include naturally-occurring carbonyl hydrolases and recombinant carbonyl hydrolases. Naturally occurring carbonyl hydrolases principally include hydrolases, e.g. lipases and peptide hydrolases, e.g. subtilisins or metalloproteases. Peptide hydrolases include α-aminoacylpeptide hydrolase, peptidylamino-acid hydrolase, acylamino hydrolase, serine carboxypeptidase, metallocarboxy-peptidase, thiol proteinase, carboxylproteinase and metalloproteinase. Serine, metallo, thiol and acid proteases are included, as well as endo and exo-proteases.

"Recombinant carbonyl hydrolase" refers to a carbonyl hydrolase in which the DNA sequence encoding the naturally occurring carbonyl hydrolase is modified to produce a mutant DNA sequence which encodes the substitution, insertion or deletion of one or more amino acids in the carbonyl hydrolase amino acid sequence. Suitable modification methods are disclosed herein and in EPO Publication No. 0130756 published Jan. 9, 1985.

Subtilisins are bacterial carbonyl hydrolases which generally act to cleave peptide bonds of proteins or peptides. As used herein, "subtilisin" means a naturally occurring subtilisin or a recombinant subtilisin. A series of naturally occurring subtilisins is known to be produced and often secreted by various bacterial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however is histidine-aspartate-serine. Thus, subtilisin herein refers to a serine protease having the catalytic triad of subtilisin related proteases.

"Recombinant subtilisin" refers to a subtilisin in which the DNA sequence encoding the subtilisin is modified to produce a mutant DNA sequence which encodes the substitution, deletion or insertion of one or more amino acids in the naturally occurring subtilisin amino acid sequence. Suitable methods to produce such modification include those disclosed herein and in EPO Publication No. 0130756. For example, the subtilisin multiple mutant herein containing the substitution of methionine at amino acid residues 50, 124 and 222 with phenylalanine, isoleucine and glutamine, respectively, can be considered to be derived from the recombinant subtilisin containing the substitution of glutamine at residue 222 (Gln222) disclosed in EPO Publication No. 0130756. The multiple mutant thus is produced by the substitution of phenylalanine for methionine at residue 50 and isoleucine for methionine at residue 124 in the Gln222 recombinant subtilisin.

"Non-human carbonyl hydrolases" and their genes may be obtained from many procaryotic and eucaryotic organisms. Suitable examples of procaryotic organisms include gram negative organisms such as E. coli or pseudomonas and gram positive bacteria such as micrococcus or bacillus. Examples of eucaryotic organisms from which carbonyl hydrolase and their genes may be obtained include yeast such as S. cerevisiae, fungi such as Aspergillus sp., and non-human mammalian sources such as, for example, Bovine sp. from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, non-human carbonyl hydrolase as used herein has a functional definition which refers to carbonyl hydrolases which are associated, directly or indirectly, with procaryotic and non-human eucaryotic sources.

A "carbonyl hydrolase mutant" has an amino acid sequence which is derived from the amino acid sequence of a non-human "precursor carbonyl hydrolase". The precursor carbonyl hydrolases include naturally-occuring carbonyl hydrolases and recombinant carbonyl hydrolases. The amino acid sequence of the carbonyl hydrolase mutant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor carbonyl hydrolase rathern than manipulation of the precursor carbonyl hydrolase per se. Suitable methods for such manipulation of the precursor DNA sequence include methods disclosed herein and in EPO Publication No. 0130756.

Specific residues of B. amyloliquefaciens subtilisin are identified for substitution, insertion or deletion. These amino acid position numbers refer to those assigned to the B. amyloliquefaciens subtilisin sequence presented in FIG. 1. The invention, however, is not limited to the mutation of this particular subtilisin but extends to precursor carbonyl hydrolases containing amino acid residues which are "equivalent" to the particular identified residues in B. amyloliquefaciens subtilisin.

A residue (amino acid) of a precursor carbonyl hydrolase is equivalent to a residue of B. amyloliquefaciens subtilisin if it is either homologous (i.e., corresponding in position in either primary or tertiary structure) or analagous to a specific residue or portion of that residue in B. amyloliquefaciens subtilisin (i.e., having the same or similar functional capacity to combine, react, or interact chemically).

Figure 5A-1:
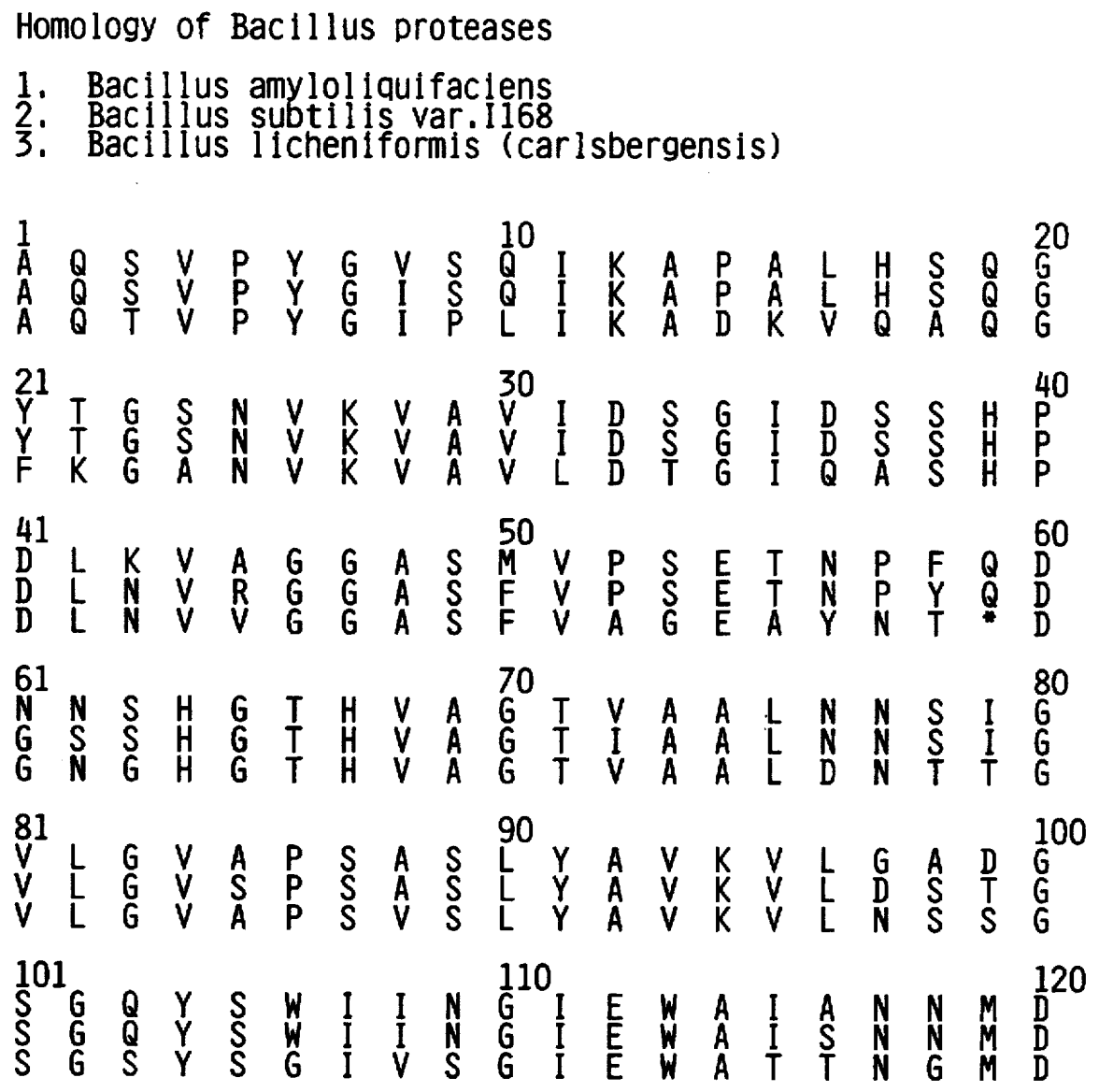
Figure 5C:
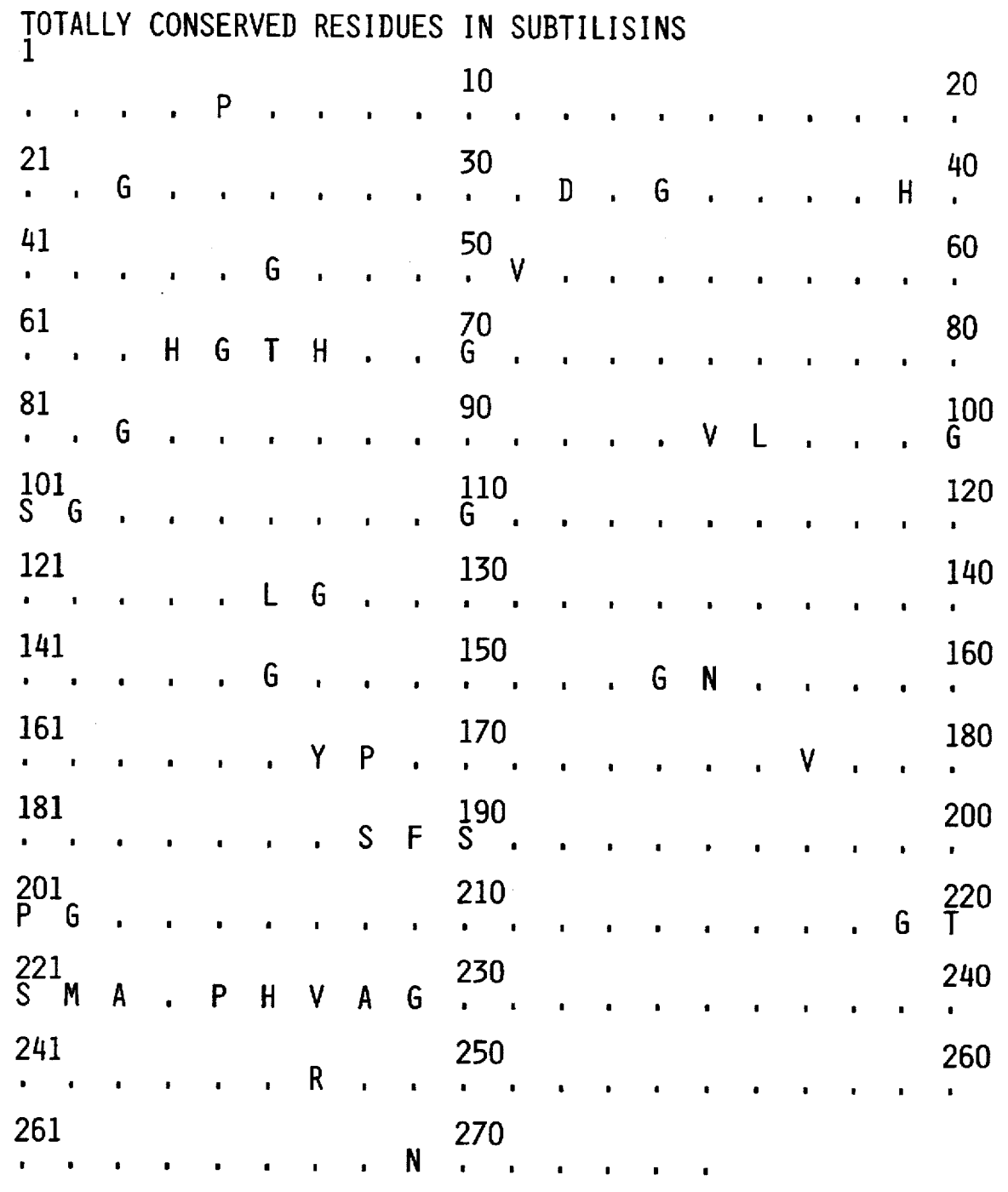

In order to establish homology to primary structure, the amino acid sequence of a precursor carbonyl hydrolase is directly comparted to the B. amyloliquefaciens subtilisin primary sequence and particularly to a set of residues known to be invariant in all subtilisins for which sequence is known (FIG. 5C). After aligning the conserved residues, allowing for necessary insertions and deletions in order to maintain alignment (i.e., avoiding the elimination of conserved residues through arbitrary deletion and insertion), the residues equivalent to particular amino acids in the primary sequence of B. amyloliquefaciens subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

Figure 2:
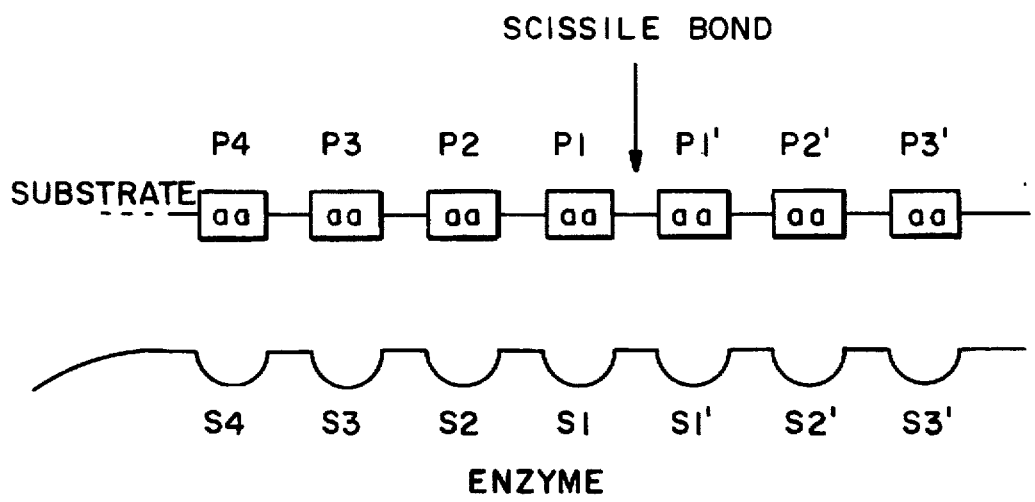
FIG. 2 is a schematic diagram showing the substrate binding cleft of subtilisin together with substrate.

For example, in FIGS. 5A-1 and 5A-2 the amino acid sequence of subtilisin from B. amyloliquefaciens B. subtilisin var. I168 and B. lichenformis (carlsbergensis) are aligned to provide the maximum amount of homology between amino acid sequences. A comparison of these sequences shows that there are a number of conserved residues contained in each sequence. These residues are identified in FIG. 5C.

These conserved residues thus may be used to define the corresponding equivalent amino acid residues of *B. amyloliquefaciens* subtilisin in other carbonyl hydrolases such as thermitase derived from Thermoactinomyces. These two particular sequences are aligned in FIG. 5B to produce the maximum homology of conserved residues. As can be seen there are a number of insertions and deletions in the thermitase sequence as compared to *B. amyloliquefaciens* subtilisin. Thus, the equivalent amino acid of Tyr217 in *B. amyloliquefaciens* subtilisin in thermitase is the particular lysine shown beneath Tyr217.

In FIG. 5A, the equivalent amino acid at position 217 in *B. amyloliquefaciens* subtilisin is Tyr. Likewise, in *B. subtilis* subtilisin position 217 is also occupied by Tyr but in *B. licheniformis* position 217 is occupied by Leu.

Thus, these particular residues in thermitase, and subtilisin from *B. subtilisin* and *B. licheniformis* may be substituted by a different amino acid to produce a mutant carbonyl hydrolase since they are equivalent in primary structure to Tyr217 in *B. amyloliquefaciens* subtilisin. Equivalent amino acids of course are not limited to those for Tyr217 but extend to any residue which is equivalent to a residue in *B. amyloliquefaciens* whether such residues are conserved or not.

Equivalent residues homologous at the level of tertiary structure for a precursor carbonyl hydrolase whose tertiary structure has been determined by x-ray crystallography, are defined as those for which the atomic coordinates of 2 or more of the main chain atoms of a particular amino acid residue of the precursor carbonyl hydrolase and *B. amyloliquefaciens* subtilisin (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *B. amyloliquefaciens* subtilisin the best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *B. amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *B. amyloliquefaciens* subtilisin as described herein. Further, they are those residues of the precursor carbonyl hydrolase (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *B. amyloliquefaciens* subtilisin. The three dimensional structures would be aligned as outlined above.

Some of the residues identified for substitution, insertion or deletion are conserved residues whereas others are not. In the case of residues which are not conserved, the replacement of one or more amino acids is limited to substitutions which produce a mutant which has an amino acid sequence that does not correspond to one found in nature. In the case of conserved residues, such replacements should not result in a naturally occurring sequence. The carbonyl hydrolase mutants of the present invention include the mature forms of carbonyl hydrolase mutants as well as the pro- and preproforms of such hydrolase mutants. The prepro-forms are the preferred construction since this facilitates the expression, secretion and maturation of the carbonyl hydrolase mutants.

"Prosequence" refers to a sequence of amino acids bound to the N-terminal portion of the mature form of a carbonyl hydrolase which when removed results in the appearance of the "mature" form of the carbonyl hydrolase. Many proteolytic enzymes are found in nature as translational proenzyme products and, in the absence of post-translational processing, are expressed in this fashion. The preferred prosequence for producing carbonyl hydrolase mutants, specifically subtilisin mutants, is the putative prosequence of *B. amyloliquefaciens* subtilisin although other subtilisin prosequences may be used.

A "signal sequence" or "presequence" refers to any sequence of amino acids bound to the N-terminal portion of a carbonyl hydrolase or to the N-terminal portion of a prohydrolase which may participate in the secretion of the mature or pro forms of the hydrolase. This definition of signal sequence is a functional one, meant to include all those amino acid sequences, encoded by the N-terminal portion of the subtilisin gene or other secretable carbonyl hydrolases, which participate in the effectuation of the secretion of subtilisin or other carbonyl hydrolases under native conditions. The present invention utilizes such sequences to effect the secretion of the carbonyl hydrolase mutants as defined herein.

A "prepro" form of a carbonyl hydrolase mutant consists of the mature form of the hydrolase having a prosequence operably linked to the amino-terminus of the hydrolase and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in EPO Publication No. 0130756 to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in EPO Publicatin No. 0130756 and further described by Yang, M. Y., et al. (1984) *J. Bacteriol.* 160, 15–21. Such host cells are distinguishable from those disclosed in PCT Publication No. 03949 wherein enzymatically inactive mutants of intracellular proteases in *E. coli* are disclosed. Other host cells for expressing subtilisin include *Bacillus subtilis* I168 (EPO Publication No. 0130756).

Host cells are transformed or transfected with vectors constructed using recombinant DNA techniques. Such transformed host cells are capable of either replicating vectors encoding the carbonyl hydrolase mutants or expressing the desired carbonyl hydrolase mutant. In the case of vectors which encode the pre or prepro form of the carbonyl hydrolase mutant, such mutants, when expressed, are typically secreted from the host cell into the host cell medium.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor carbonyl hydrolase may be obtained in accord with the general methods described in EPO Publication No. 0130756. As can be seen from the examples disclosed therein, the methods generally comprise synthesizing labelled probes having putative sequences encoding regions of the hydrolase of interest, preparing genomic libraries from organisims expressing the hydrolase, and screening the libraries for the gene of interest by hybridization to the probes. Positively hybridizing clones are then mapped and sequenced.

The cloned carbonyl hydrolase is then used to transform a host cell in order to express the hydrolase. The hydrolase gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosonal limitations. However, it is within the scope herein to integrate multiple copies of the hydrolase gene into host genome. This is facilitated by procaryotic and eucaryotic organisms which are particularly susceptible to homologous recombination.

Once the carbonyl hydrolase gene has been cloned, a number of modifications aruse of taken to enhance the use of the gene beyond synthesis of the naturally-occuring precursor carbonyl hydrolase. Such modifications include the production of recombinant carbonyl hydrolases as disclosed in EPO Publication No. 0130756 and the production of carbonyl hydrolase mutants described herein.

The following cassette mutagenesis method may be used to facilitate the construction and identification of the carbonyl hydrolase mutants of the present invention although other methods including site-directed mutagenesis may be used. First, the gene encoding the hydrolase is obtained and sequenced in whole or in part. Then the sequence is scanned for a point at which it is desired to make a mutation (deletion, insertion or substitution) of one or more amino acids in the expressed enzyme. The sequences flanking this point are evaluated for the presence of restriction sites for replacing a short segment of the gene with an oligonucleotide pool which when expressed will encode various mutants. Such restriction sites are preferably unique sites within the hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Mutation of the gene in order to change its sequence to conform to the desired sequence is accomplished by M13 primer extension in accord with generally known methods. Once the gene is cloned, the restriction sites flanking the sequence to be mutated are digested with the cognate restriction enzymes and a plurality of end termini-complementary oligonucleotide cassettes are ligated into the gene. The mutagenesis is enormously simplified by this method because all of the oligonucleotides can be synthesized so as to have the same restriction sites, and no synthetic linkers are necessary to create the restriction sites.

The number of commercially available restriction enzymes having sites not present in the gene of interest is generally large. A suitable DNA sequence computer search program simplifies the task of finding potential 5' and 3' convenient flanking sites. A primary constraint is that any mutation introduced in creation of the restriction site must be silent to the final construction amino acid coding sequence. For a candidate restriction site 5' to the target codon a sequence must exist in the gene which contains at least all the nucleotides but for one in the recognition sequence 5' to the cut of the candidate enzyme. For example, the blunt cutting enzyme SmaI (CCC/GGG) would be a 5' candidate if a nearby 5' sequence contained NCC, CNC, or CCN. Furthermore, if N needed to be altered to C this alteraiton must leave the amino acid coding sequence intact. In cases where a permanent silent mutation is necessary to introduce a restriction site one may want to avoid the introduction of a rarely used codon. A similar situation of SmaI would apply for 3' flanking sites except the sequence NGG, GNG, or GGN must exist. The criteria for locating candidate enzymes is most relaxed for blunt cutting enzymes and most stringent for 4 base overhang enzymes. In general many candidate sites are available. For the codon-221 target described herein a BalI site (TGG/CCA) would have been engineered in one base pair 5' from the KpnI site. A 3' EcoRV site (GAT/ATC) could have been employed 11 base pairs 5' to the PstI site. A cassette having termini ranging from a blunt end up to a four base-overhang will function without difficulty. In retrospect, this hypothetical EcoRV site would have significantly shortened the oligonucleotide cassette employed (9 and 13 base pairs) thus allowing greater purity and lower pool bias problems. Flanking sites should obviously be chosen which cannot themselves ligate so that ligation of the oligonucleotide cassette can be assured in a single orientation.

The mutant carbonyl hydrolases expressed upon transformation of suitable hosts are screened for enzymes exhibiting one or more properties which are substantially different from the properties of the precursor carbonyl hydrolases, e.g., changes in substrate specificity, oxidative stability, thermal stability, alkaline stability, resistance to proteolytic degradation, pH-activity profiles and the like.

The carbonyl hydrolase mutants of the present invention may also be generated by random mutagenesis. See for example the methods disclosed by Shortle, D., et al. (1985) *Genetics*, 110, 539; Shortle, D., et al. (1986) *Proteins: Structure, Function and Genetics*, 1, 81; Shortle, D. (1986) *J. Cell. Biochem*, 30, 281; Alber, T., et al. (1985) *Proc. Natl. Acad. of Sci.*, 82, 747; Matsumura, M., et al. (1985) *J. Biochem.*, 260, 15298; Liao, H., et al. (1986) *Proc. Natl. Acad. of Sci.*, 83 576; and the random mutagenesis method disclosed herein.

When combined with the alkaline stability screening procedure disclosed herein, mutants obtained by random mutagenesis were identified which demonstrated either increased or decreased alkaline or thermal stability.

A change in substrate specificity is defined as a difference between the kcat/Km ratio of the precursor carbonyl hydrolase and that of the hydrolase mutant. The kcat/Km ratio is a measure of catalytic efficiency. Carbonyl hydrolase mutants with increased or diminished kcat/Km ratios are described in the examples. Generally, the objective will be to secure a mutant having a greater (numerically large) kcat/Km ratio for a given substrate, thereby enabling the use of the enzyme to more efficiently act on a target substrate. A substantial change in kcat/Km ratio is preferably at least 2-fold increase or decrease. However, smaller increases or decreases in the ratio (e.g., at least 1.5-fold) are also considered substantial. An increase in kcat/Km ratio for one substrate may be accompanied by a reduction in kcat/Km ratio for another substrate. This is a shift in substrate specificity, and mutants exhibiting such shifts have utility where the precursor hydrolase is undesirable, e.g. to prevent undesired hydrolysis of a particular substrate in an admixture of substrates. Km and kcat are measured in accord with known procedures, as described in EPO Publication No. 0130756 or as described herein.

Oxidative stability is measured either by known procedures or by the methods described hereinafter. A substantial change in oxidative stability is evidenced by at least about 50% increase or decrease (preferably decrease) in the rate of loss of enzyme activity when exposed to various oxidizing conditions. Such oxidizing conditions are exposure to the organic oxidant diperdodecanoic acid (DPDA) under the conditions described in the examples.

Alkaline stability is measured either by known procedures or by the methods described herein. A substantial change in alkaline stability is evidenced by at least about a 5% or greater increase or decrease (preferably increase) in the half life of the enzymatic activity of a mutant when compared to the precursor carbonyl hydrolase. In the case of subtilisins, alkaline stability was measured as a function of autoproteolytic degradation of subtilisin at alkaline pH, e.g. for example, 0.1M sodium phosphate, pH 12 at 25° or 30° C.

Thermal stability is measured either by known procedures or by the methods described herein. A substantial change in thermal stability is evidenced by at least about a 5% or greater increase or decrease (preferably increase) in the half-life of the catalytic activity of a mutant when exposed to a relatively high temperature and neutral pH as compared to the precursor carbonyl hydrolase. In the case of subtilisins, thermal stability is measured by the autoproteolytic degradation of subtilisin at elevated temperatures and neutral pH, e.g., for example 2 mM calcium chloride, 50 mM MOPS pH 7.0 at 59° C.

The inventors have produced mutant subtilisins containing the substitution of the amino acid residues of *B. amyloliquefaciens* subtilisin shown in Table I. The wild type amino acid sequence and DNA sequence of *B. amyloliquefaciens* subtilisin is shown in FIG. 1.

TABLE I

| Residue | Replacement Amino Acid |
|---|---|
| Tyr21 | F |
| Thr22 | C |
| Ser24 | C |
| Asp32 | N Q S |
| Ser33 | A T |
| Asp36 | A G |
| Gly46 | V |
| Ala48 | E V R |
| Ser49 | C L |
| Met50 | C F V |
| Asn77 | D |
| Ser87 | C |
| Lys94 | C |
| Val95 | C |
| Tyr104 | A C D E F G H I K L M N P Q R S T V W |
| Ile107 | V |
| Gly110 | C R |
| Met124 | I L |
| Ala152 | G S |
| Asn155 | A D H Q T |
| Glu156 | Q S |
| Gly166 | A C D E F H I K L M N P Q R S T V W Y |
| Gly169 | A C D E F H I K L M N P Q R S T V W Y |
| Lys170 | E R |
| Tyr171 | F |
| Pro172 | E Q |
| Phe189 | A C D E G H I K L M N P Q R S T V W Y |
| Asp197 | R A |
| Met199 | I |
| Ser204 | C R L P |
| Lys213 | R T |
| Tyr217 | A C D E F G H I K L M N P Q R S T V W |
| Ser221 | A C |
| Met222 | A C D E F G H I K L N P Q R S T V W Y |

The different amino acids substituted are represented in Table I by the following single letter designations:

| Amino acid or residue thereof | 3-letter symbol | 1-letter symbol |
|---|---|---|
| Alanine | Ala | A |
| Glutamate | Glu | E |
| Glutamine | Gln | Q |
| Aspartate | Asp | D |
| Asparagine | Asn | N |
| Leucine | Leu | L |
| Glycine | Gly | G |
| Lysine | Lys | K |
| Serine | Ser | S |
| Valine | Val | V |
| Arginine | Arg | R |
| Threonine | Thr | T |
| Proline | Pro | P |
| Isoleucine | Ile | I |
| Methionine | Met | M |
| Phenylalanine | Phe | F |

-continued

| Amino acid or residue thereof | 3-letter symbol | 1-letter symbol |
|---|---|---|
| Tyrosine | Tyr | Y |
| Cysteine | Cys | C |
| Tryptophan | Trp | W |
| Histidine | His | H |

Except where otherwise indicated by context, wild-type amino acids are represented by the above three-letter symbols and replaced amino acids by the above single-letter symbols. Thus, if the methionine at residue 50 in *B. amyloliquefaciens* subtilisin is replaced by Phenylalanine, this mutation (mutant) may be designated Met50F or F50. Similar designations will be used for multiple mutants.

In addition to the amino acids used to replace the residues disclosed in Table I, other replacements of amino acids at the residues are expected to produce mutant subtilisins having useful properties. These residues and replacement amino acids are shown in Table II.

TABLE II

| Residue | Replacement Amino Acid(s) |
|---|---|
| Tyr-21 | L |
| Thr22 | K |
| Ser24 | A |
| Asp32 | |
| Ser33 | G |
| Gly46 | |
| Ala48 | |
| Ser49 | |
| Met50 | L K I V |
| Asn77 | D |
| Ser87 | N |
| Lys94 | R Q |
| Val95 | L I |
| Tyr104 | |
| Met124 | K A |
| Ala152 | C L I T M |
| Asn155 | |
| Glu156 | A T M L Y |
| Gly166 | |
| Gly169 | |
| Tyr171 | K R E Q |
| Pro172 | D N |
| Phe189 | |
| Tyr217 | |
| Ser221 | |
| Met222 | |

Each of the mutant subtilisins in Table I contain the replacement of a single residue of the *B. amyloliquefaciens* amino acid sequence. These particular residues were chosen to probe the influence of such substitutions on various properties of *B. amyloliquefacien* subtilisin.

Thus, the inventors have identified Met124 and Met222 as important residues which if substituted with another amino acid produce a mutant subtilisin with enhanced oxidative stability. For Met124, Leu and Ile are preferred replacement amino acids. Preferred amino acids for replacement of Met222 are disclosed in EPO Publication No. 0130756.

Various other specific residues have also been identified as being important with regard to substrate specificity. These residues include Tyr104, Ala152, Glu156, Gly166, Gly169, Phe189 and Tyr217 for which mutants containing the various replacement amino acids presented in Table I have already been made, as well as other residues presented below for which mutants have yet to be made.

The identification of these residues, including those yet to be mutated, is based on the inventors' high resolution crystal structure of *B. amyloliquefaciens* subtilisin to 1.8 Å (see Table III), their experience with in vitro mutagenesis of subtilisin and the literature on subtilisin. This work and the above referenced x-ray crystal structures of subtilisin containing covalently bound peptide inhibitors, product complexes and transition state analogs has helped in identifying an extended peptide binding cleft in subtilisin. This substrate binding cleft together with substrate is schematically diagramemed in FIG. 2, according to the nomenclature of Schechter, I., et al. (1967) *Biochem Bio. Res. Commun.* 27, 157. The scissile bond in the substrate is identified by an arrow. The P and P' designations refer to the amino acids which are positioned respectively toward the amino or carboxy terminus relative to the scissle bond. The S and S' designations refer to subsites in the substrate binding cleft of subtilisin which interact with the corresponding substrate amino acid residues.

| 1 | ALA N | 19.434 | 53.195 | −21.756 |
|---|---|---|---|---|
| 1 | ALA C | 18.731 | 50.885 | −21.324 |
| 1 | ALA CB | 21.099 | 51.518 | −21.183 |
| 2 | GLN CA | 17.219 | 49.008 | −21.434 |
| 2 | GLN D | 18.765 | 47.165 | −21.691 |
| 2 | GLN CG | 15.028 | 47.805 | −21.927 |
| 2 | GLN DE1 | 13.023 | 48.612 | −22.867 |
| 3 | SER N | 17.477 | 47.205 | −19.852 |
| 3 | SER C | 16.735 | 44.918 | −19.490 |
| 3 | SER CB | 18.588 | 45.838 | −18.069 |
| 4 | VAL N | 16.991 | 43.646 | −19.725 |
| 4 | VAL C | 16.129 | 41.934 | −18.290 |
| 4 | VAL CB | 16.008 | 41.622 | −20.833 |
| 4 | VAL CG2 | 16.037 | 42.266 | −22.186 |
| 5 | PRO CA | 15.384 | 41.415 | −16.027 |
| 5 | PRO D | 14.885 | 39.763 | −17.146 |
| 5 | PRO CG | 13.841 | 43.215 | −15.921 |
| 6 | TYR N | 16.363 | 39.240 | −15.487 |
| 6 | TYR C | 15.359 | 36.975 | −15.528 |
| 6 | TYR CB | 17.824 | 37.323 | −14.834 |
| 6 | TYR CD1 | 18.437 | 35.452 | −16.346 |
| 6 | TYR CE1 | 18.535 | 34.070 | −16.653 |
| 6 | TYR CZ | 18.222 | 33.154 | −15.628 |
| 7 | GLY N | 14.464 | 37.362 | −14.630 |
| 7 | GLY C | 12.400 | 36.535 | −15.670 |
| 8 | VAL N | 12.441 | 37.529 | −16.541 |
| 8 | VAL C | 12.363 | 36.433 | −18.735 |
| 8 | VAL CB | 11.765 | 38.900 | −18.567 |
| 8 | VAL CG2 | 10.991 | 39.919 | −17.733 |
| 9 | SER CA | 14.419 | 35.342 | −19.562 |
| 9 | SER B | 14.112 | 33.014 | −19.801 |
| 9 | SER DG | 16.162 | 36.747 | −20.358 |
| 10 | GLN CA | 13.964 | 32.636 | −16.876 |
| 10 | GLN D | 12.785 | 30.642 | −17.413 |
| 10 | GLN CG | 14.295 | 31.617 | −14.588 |
| 10 | GLN DE1 | 14.556 | 33.068 | −12.744 |
| 11 | ILE N | 11.625 | 32.575 | −17.670 |
| 11 | ILE C | 10.209 | 31.792 | −19.605 |
| 11 | ILE CB | 9.132 | 32.669 | −17.475 |
| 11 | ILE CG2 | 9.162 | 32.655 | −15.941 |
| 11 | IYS N | 11.272 | 32.185 | −20.277 |
| 12 | LYS C | 10.456 | 33.006 | −22.522 |
| 12 | LYS CB | 11.257 | 30.646 | −22.216 |
| 12 | LYS CI | 12.543 | 28.517 | −22.159 |
| 12 | LYS NZ | 14.476 | 27.680 | −20.935 |
| 13 | ALA CA | 9.325 | 35.198 | −22.631 |
| 13 | ALA O | 9.338 | 35.804 | −24.901 |
| 14 | PRO N | 11.332 | 35.950 | −23.893 |
| 14 | PRO C | 11.786 | 35.557 | −26.317 |
| 14 | PRO CB | 13.461 | 36.580 | −24.692 |
| 14 | PRO CD | 12.281 | 35.936 | −22.758 |
| 15 | ALA CA | 11.379 | 33.450 | −27.367 |
| 15 | ALA O | 10.008 | 33.710 | −29.278 |
| 16 | LEU N | 9.085 | 34.138 | −27.240 |
| 16 | LEU C | 7.912 | 35.925 | −28.521 |
| 16 | LEU CB | 6.746 | 34.623 | −26.698 |
| 16 | LEU CD1 | 5.001 | 33.234 | −27.809 |
| 17 | HIS N | 8.665 | 36.828 | −27.922 |

| | | | | | | | | | | |
|---|---|---|---|---|---|---|---|---|---|---|
| 17 | HIS C | 9.510 | 37.981 | −29.890 | | 21 | TYR CD2 | 3.650 | 34.794 | −31.397 |
| 17 | HIS CB | 9.708 | 39.100 | −27.652 | | 21 | TYR CE2 | 3.193 | 34.261 | −32.588 |
| 17 | HIS ND1 | 9.930 | 39.887 | −25.272 | | 21 | TYR OH | 1.501 | 34.241 | −34.250 |
| 17 | HIS CE1 | 9.226 | 39.914 | −24.144 | | 22 | THR CA | 4.262 | 40.527 | −27.129 |
| 18 | SER N | 10.443 | 37.033 | −30.022 | | 22 | THR D | 3.287 | 41.725 | −25.325 |
| 1 | ALA CA | 19.811 | 51.774 | −21.965 | | 22 | THR DG1 | 4.319 | 42.457 | −28.597 |
| 1 | ALA D | 18.376 | 51.197 | −20.175 | | 23 | GLY N | 1.939 | 40.285 | −26.453 |
| 2 | GLN N | 18.368 | 49.886 | −22.041 | | 23 | GLY C | −0.157 | 41.631 | −26.118 |
| 2 | GLN C | 17.875 | 47.706 | −20.992 | | 24 | SER N | −0.023 | 41.769 | −27.371 |
| 2 | GLN CB | 16.125 | 48.760 | −22.449 | | 24 | SER C | −2.383 | 42.626 | −27.864 |
| 2 | GLN CD | 13.912 | 47.762 | −22.930 | | 24 | SER CB | −0.734 | 43.120 | −29.520 |
| 2 | GLN NE2 | 14.115 | 46.917 | −23.926 | | 25 | ASN N | −3.059 | 43.692 | −27.515 |
| 3 | SER CA | 17.950 | 45.868 | −19.437 | | 25 | ASN C | −5.015 | 42.785 | −26.205 |
| 3 | SER O | 15.590 | 45.352 | −19.229 | | 25 | ASN CB | −4.165 | 43.227 | −28.700 |
| 3 | SER OG | 17.682 | 46.210 | −17.049 | | 25 | ASN DD1 | −4.965 | 43.767 | −31.083 |
| 4 | VAL CA | 15.946 | 42.619 | −19.639 | | 26 | VAL N | −4.177 | 42.449 | −25.292 |
| 4 | VAL O | 17.123 | 41.178 | −18.086 | | 26 | VAL C | −4.792 | 42.652 | −22.987 |
| 4 | VAL CG1 | 14.874 | 40.572 | −20.741 | | 26 | VAL CB | −3.714 | 40.503 | −23.821 |
| 5 | PRO N | 15.239 | 42.106 | −17.331 | | 26 | VAL CG2 | −3.598 | 39.576 | −25.018 |
| 5 | PRO C | 15.501 | 39.905 | −16.249 | | 27 | LYS CA | −6.133 | 43.524 | −21.175 |
| 5 | PRO CB | 14.150 | 41.880 | −15.263 | | 27 | LYS D | −6.405 | 41.873 | −19.413 |
| 5 | PRO CD | 14.004 | 42.986 | −17.417 | | 27 | LYS CG | −8.046 | 44.575 | −2.490 |
| 6 | TYR CA | 16.628 | 37.803 | −15.715 | | 27 | LYS CE | −10.304 | 45.497 | −23.137 |
| 6 | TYR D | 15.224 | 35.943 | −16.235 | | 28 | VAL N | −4.818 | 43.462 | −19.200 |
| 6 | TYR CG | 18.021 | 35.847 | −15.055 | | 28 | VAL C | −4.758 | 43.959 | −16.828 |
| 6 | TYR CD2 | 17.696 | 34.908 | −14.071 | | 28 | VAL CB | −2.926 | 42.666 | −17.932 |
| 6 | TYR CE2 | 17.815 | 33.539 | −14.379 | | 28 | VAL CG2 | −2.667 | 41.805 | −19.173 |
| 6 | TYR OH | 18.312 | 31.838 | −15.996 | | 29 | ALA CA | −5.747 | 44.330 | −14.639 |
| 7 | GLY CA | 13.211 | 36.640 | −14.376 | | 29 | ALA D | −4.666 | 42.845 | −13.104 |
| 7 | GLY D | 11.747 | 35.478 | −15.883 | | 30 | VAL N | −4.057 | 45.033 | −13.072 |
| 8 | VAL CA | 11.777 | 37.523 | −17.836 | | 30 | VAL C | −3.958 | 45.409 | −10.681 |
| 8 | VAL D | 11.639 | 35.716 | −19.670 | | 30 | VAL CB | −1.886 | 45.810 | −12.149 |
| 8 | VAL CG1 | 11.106 | 38.893 | −19.943 | | 30 | VAL CG2 | −1.053 | 45.236 | −13.307 |
| 9 | SER N | 13.661 | 36.318 | −18.775 | | 31 | ILE CA | −5.328 | 44.846 | −8.679 |
| 9 | SER C | 14.188 | 33.920 | −18.965 | | 31 | ILE D | −3.825 | 43.915 | −6.997 |
| 9 | SER CB | 15.926 | 35.632 | −19.505 | | 31 | ILE CG1 | −7.298 | 43.707 | −9.798 |
| 10 | GLN N | 14.115 | 33.887 | −17.662 | | 31 | ILE CD1 | −8.617 | 42.856 | −9.717 |
| 10 | GLN C | 12.687 | 31.887 | −17.277 | | 32 | ASP CA | −2.944 | 46.467 | −6.255 |
| 10 | GLN CB | 14.125 | 32.885 | −15.410 | | 32 | ASP D | −4.197 | 48.418 | −5.502 |
| 10 | GLN CD | 14.486 | 31.911 | −13.147 | | 32 | ASP CG | −0.483 | 45.702 | −6.273 |
| 10 | GLN NE2 | 14.552 | 30.960 | −12.251 | | 32 | ASP DD2 | −0.081 | 46.429 | −5.300 |
| 11 | ILE CA | 10.373 | 31.904 | −18.102 | | 33 | SER CA | −1.895 | 49.857 | −4.801 |
| 11 | ILE D | 9.173 | 31.333 | −20.180 | | 33 | SER D | −1.706 | 52.136 | −5.363 |
| 11 | ILE CG1 | 9.066 | 34.117 | −18.069 | | 33 | SER DG | 0.535 | 50.025 | −4.774 |
| 11 | ILE CD1 | 7.58 | 34.648 | −17.923 | | 34 | GLY CA | −2.255 | 51.728 | −8.165 |
| 12 | LYS CA | 11.388 | 32.119 | −21.722 | | 34 | GLY D | −0.144 | 50.831 | −8.761 |
| 12 | LYS D | 10.173 | 32.703 | −23.686 | | 35 | ILE CA | 0.208 | 52.438 | −10.995 |
| 12 | LYS CG | 12.283 | 29.830 | −21.423 | | 35 | ILE D | −0.327 | 54.538 | −11.744 |
| 12 | LYS CE | 13.023 | 27.467 | −21.166 | | 35 | ILE CG1 | −0.530 | 50.210 | −12.097 |
| 13 | ALA N | 10.109 | 34.138 | −21.991 | | 35 | ILE CD1 | −0.962 | 49.485 | −13.424 |
| 13 | ALA C | 10.026 | 35.716 | −23.863 | | 36 | ASP CA | 2.359 | 55.618 | −11.232 |
| 13 | ALA CB | 8.885 | 36.195 | −21.545 | | 18 | SER D | 10.547 | 36.112 | −33.534 |
| 14 | PRO CA | 11.985 | 36.430 | −25.220 | | 18 | SER DG | 13.321 | 36.450 | −30.399 |
| 14 | PRO O | 11.778 | 36.047 | −27.445 | | 19 | GLN CA | 8.082 | 34.962 | −32.878 |
| 14 | PRO CG | 13.328 | 36.978 | −23.221 | | 19 | GLN D | 6.297 | 35.972 | −34.219 |
| 15 | ALA N | 11.560 | 34.236 | −26.129 | | 19 | GLN CG | 7.975 | 32.602 | −31.823 |
| 15 | ALA C | 10.082 | 33.795 | −28.032 | | 19 | GLN DE1 | 5.719 | 31.833 | −31.444 |
| 15 | ALA CB | 11.552 | 31.969 | −27.062 | | 20 | GLY N | 7.205 | 37.223 | −32.587 |
| 16 | LEU CA | 7.791 | 34.558 | −27.828 | | 20 | GLY C | 5.181 | 38.492 | −31.880 |
| 16 | LEU D | 7.342 | 36.126 | −29.588 | | 21 | TYR N | 5.202 | 37.801 | −30.761 |
| 16 | LEU CG | 5.790 | 33.465 | −26.522 | | 21 | TYR C | 4.579 | 38.552 | −28.525 |
| 16 | LEU CD2 | 6.694 | 32.287 | −26.283 | | 21 | TYR CB | 3.498 | 36.431 | −29.443 |
| 17 | HIS CA | 8.890 | 38.151 | −28.530 | | 21 | TYR CD1 | 1.795 | 36.332 | −31.258 |
| 17 | HIS D | 9.107 | 38.622 | −30.856 | | 21 | TYR CE1 | 1.306 | 35.797 | −32.446 |
| 17 | HIS CG | 9.185 | 39.288 | −26.262 | | 21 | TYR CZ | 2.003 | 34.755 | −33.067 |
| 17 | HIS CD2 | 8.008 | 38.924 | −25.694 | | 22 | THR N | 3.902 | 39.680 | −28.288 |
| 17 | HIS NE2 | 8.079 | 39.328 | −24.381 | | 22 | THR C | 3.091 | 40.922 | −26.244 |
| 18 | SER CA | 11.109 | 36.739 | −31.322 | | 22 | THR CB | 5.133 | 41.759 | −27.611 |
| 18 | SER C | 10.159 | 36.123 | −32.353 | | 22 | THR CG2 | 6.476 | 41.323 | −28.229 |
| 18 | SER CB | 12.311 | 35.799 | −31.172 | | 23 | GLY CA | 0.809 | 40.600 | −25.542 |
| 19 | GLN N | 9.080 | 35.485 | −31.943 | | 23 | GLY D | −1.013 | 42.095 | −25.330 |
| 19 | GLN C | 7.142 | 36.111 | −33.303 | | 24 | SER CA | −0.897 | 42.957 | −28.012 |
| 19 | GLN CB | 7.221 | 33.849 | −32.280 | | 24 | SER D | −2.813 | 41.508 | −28.160 |
| 19 | GLN CD | 6.923 | 31.707 | −31.181 | | 24 | SER DG | 0.563 | 43.652 | −29.728 |
| 19 | GLN NE2 | 7.362 | 30.852 | −30.256 | | 25 | ASN CA | −4.519 | 43.687 | −27.393 |
| 20 | GLY CA | 6.369 | 38.387 | −32.859 | | 25 | ASN D | −6.233 | 42.668 | −26.190 |
| 20 | GLY D | 4.263 | 39.276 | −32.215 | | 25 | ASN CG | −4.960 | 44.170 | −29.885 |
| 21 | TYR CA | 4.118 | 37.831 | −29.763 | | 25 | ASN ND2 | −4.747 | 45.461 | −29.594 |
| 21 | TYR D | 5.422 | 38.074 | −27.756 | | 26 | VAL CA | −4.674 | 41.679 | −24.143 |
| 21 | TYR CG | 2.973 | 35.784 | −30.708 | | 26 | VAL D | −3.858 | 43.429 | −22.689 |

-continued

| | | | | |
|---|---|---|---|---|
| 26 | VAL CG1 | -4.160 | 39.802 | -22.548 |
| 27 | LYS N | -5.910 | 42.613 | -22.301 |
| 27 | LYS C | -5.815 | 42.872 | -19.841 |
| 27 | LYS CB | -7.590 | 43.981 | -21.149 |
| 27 | LYS CD | -9.321 | 45.302 | -22.020 |
| 27 | LYS NZ | -9.686 | 46.253 | -24.264 |
| 28 | VAL CA | -4.457 | 42.950 | -17.897 |
| 28 | VAL D | -4.209 | 45.095 | -16.817 |
| 28 | VAL CG1 | -2.466 | 42.105 | -16.589 |
| 29 | ALA N | -5.484 | 43.527 | -15.813 |
| 29 | ALA C | -4.750 | 44.010 | -13.553 |
| 29 | ALA CB | -7.172 | 44.107 | -14.101 |
| 30 | VAL CA | -3.146 | 44.962 | -11.910 |
| 30 | VAL D | -4.155 | 46.648 | -10.578 |
| 30 | VAL CG1 | -0.990 | 45.901 | -10.900 |
| 31 | ILE N | -4.514 | 44.515 | -9.877 |
| 31 | ILE C | -4.346 | 44.933 | -7.546 |
| 31 | ILE CB | -6.457 | 43.776 | -8.501 |
| 31 | ILE CG2 | -7.278 | 44.038 | -7.225 |
| 32 | ASP N | -4.044 | 46.193 | -7.227 |
| 32 | ASP C | -3.071 | 47.889 | -5.705 |
| 32 | ASP CB | -1.695 | 46.129 | -7.092 |
| 32 | ASP DD1 | 0.034 | 44.592 | -6.576 |
| 33 | SER N | -1.931 | 48.512 | -5.394 |
| 33 | SER C | -1.952 | 50.976 | -5.808 |
| 33 | SER CB | -0.621 | 49.922 | -3.939 |
| 34 | GLY N | -2.173 | 50.740 | -7.084 |
| 34 | GLY C | -1.035 | 51.648 | -9.057 |
| 35 | ILE N | -0.965 | 52.431 | -10.102 |
| 35 | ILE C | 0.568 | 53.919 | -11.263 |
| 35 | ILE CB | -0.042 | 51.694 | -12.367 |
| 35 | ILE CG2 | 1.149 | 51.741 | -13.362 |
| 36 | ASP N | 1.816 | 54.253 | -10.971 |
| 36 | ASP C | 2.281 | 55.956 | -12.702 |
| 36 | ASP D | 3.004 | 55.471 | -13.579 |
| 36 | ASP CG | 4.339 | 57.099 | -10.804 |
| 36 | ASP DD2 | 5.448 | 57.277 | -10.263 |
| 37 | SER CA | 1.183 | 57.221 | -14.512 |
| 37 | SER D | 2.545 | 58.303 | -16.151 |
| 37 | SER DG | -0.090 | 59.133 | -13.879 |
| 38 | SER CA | 4.261 | 59.505 | -14.487 |
| 38 | SER D | 6.543 | 59.251 | -15.285 |
| 38 | SER DG | 5.376 | 59.865 | -12.234 |
| 39 | HIS CA | 6.637 | 56.574 | -15.291 |
| 39 | HIS D | 5.738 | 55.878 | -17.419 |
| 39 | HIS CG | 8.014 | 54.600 | -14.456 |
| 39 | HIS NE2 | 8.769 | 54.345 | -13.389 |
| 40 | PRO CA | 7.988 | 56.697 | -18.831 |
| 40 | PRO D | 8.032 | 55.097 | -20.578 |
| 40 | PRO CG | 10.053 | 57.405 | -17.902 |
| 41 | ASP N | 8.481 | 54.328 | -18.485 |
| 41 | ASP DD1 | 10.325 | 51.395 | -20.429 |
| 41 | ASP CB | 9.799 | 52.239 | -18.224 |
| 41 | ASP C | 7.311 | 52.163 | -18.839 |
| 42 | LEU N | 6.185 | 52.803 | -18.558 |
| 42 | LEU C | 3.924 | 52.907 | -19.376 |
| 42 | LEU CB | 4.421 | 52.158 | -17.008 |
| 42 | LEU CD1 | 4.535 | 51.546 | -14.581 |
| 43 | LYS N | 3.018 | 52.135 | -19.946 |
| 43 | LYS C | 0.637 | 52.156 | -20.018 |
| 43 | LYS CB | 2.021 | 52.389 | -22.169 |
| 43 | LYS CD | 0.998 | 52.862 | -24.339 |
| 43 | LYS NZ | 0.337 | 51.757 | -26.218 |
| 44 | VAL CA | -1.407 | 52.839 | -18.765 |
| 44 | VAL D | -2.623 | 53.903 | -20.434 |
| 44 | VAL CG1 | -2.724 | 52.941 | -16.582 |
| 45 | ALA N | -3.494 | 51.951 | -19.871 |
| 45 | ALA C | -5.841 | 52.507 | -20.053 |
| 45 | ALA CB | -4.831 | 50.580 | -21.389 |
| 46 | GLY CA | -7.082 | 52.837 | -18.001 |
| 46 | GLY D | -5.938 | 52.006 | -16.035 |
| 47 | GLY CA | -8.014 | 52.246 | -14.388 |
| 47 | GLY D | -9.988 | 53.481 | -14.185 |
| 48 | ALA CA | -10.255 | 52.870 | -11.382 |
| 48 | ALA D | -9.066 | 51.720 | -9.725 |
| 49 | SER N | -10.149 | 53.547 | -9.037 |
| 49 | SER CB | -10.947 | 52.986 | -6.783 |
| 50 | MET N | -9.092 | 54.588 | -7.029 |
| 50 | MET C | -10.835 | 52.007 | -5.932 |
| 50 | MET CB | -11.463 | 51.962 | -3.561 |

-continued

| | | | | |
|---|---|---|---|---|
| 50 | MET SD | -12.012 | 50.018 | -4.996 |
| 51 | VAL N | -13.460 | 49.889 | -7.256 |
| 51 | VAL C | -10.427 | 52.760 | -3.422 |
| 51 | VAL CB | -8.443 | 53.155 | -2.000 |
| 51 | VAL CG2 | -7.764 | 51.815 | -2.305 |
| 52 | PRO CA | -12.372 | 55.933 | -0.821 |
| 52 | PRO D | -11.771 | 58.220 | -0.925 |
| 52 | PRO CG | -13.583 | 54.103 | 0.085 |
| 53 | SER N | -10.442 | 56.906 | 0.299 |
| 53 | SER C | -8.420 | 58.245 | -0.326 |
| 53 | SER CB | -9.004 | 57.707 | 2.069 |
| 54 | GLU N | -8.254 | 57.523 | -1.393 |
| 54 | GLU C | -7.767 | 57.303 | -3.785 |
| 54 | GLU CB | -6.134 | 56.599 | -2.154 |
| 54 | GLU CD | -4.066 | 56.062 | -0.970 |
| 36 | ASP CB | 3.712 | 55.720 | -10.514 |
| 36 | ASP DD1 | 3.755 | 57.974 | -11.429 |
| 37 | SER N | 1.304 | 56.822 | -13.111 |
| 37 | SER C | 2.371 | 58.095 | -14.949 |
| 37 | SER CB | -0.093 | 58.049 | -14.788 |
| 38 | SER N | 3.163 | 58.614 | -14.001 |
| 38 | SER C | 5.466 | 58.705 | -14.992 |
| 38 | SER CB | 4.742 | 60.435 | -13.398 |
| 39 | HIS N | 5.454 | 57.390 | -14.892 |
| 39 | HIS C | 6.681 | 56.401 | -16.718 |
| 39 | HIS CB | 6.637 | 55.203 | -14.515 |
| 39 | HIS ND1 | 8.195 | 54.356 | -15.561 |
| 39 | HIS CE1 | 9.970 | 53.930 | -15.130 |
| 40 | PRO N | 7.807 | 56.836 | -17.381 |
| 40 | PRO C | 8.156 | 55.280 | -19.357 |
| 40 | PRG CB | 9.247 | 57.533 | -19.161 |
| 40 | PRG CD | 8.988 | 57.452 | -16.776 |
| 41 | ASP DD2 | 11.148 | 50.399 | -18.668 |
| 41 | ASP CG | 10.473 | 51.307 | -19.211 |
| 41 | ASP CA | 8.645 | 52.959 | -18.966 |
| 41 | ASP D | 7.396 | 50.947 | -18.977 |
| 42 | LEU CA | 4.892 | 52.147 | -18.466 |
| 42 | LEU D | 3.993 | 54.163 | -19.490 |
| 42 | LEU CG | 5.182 | 51.363 | -15.946 |
| 42 | LEU CD2 | 5.273 | 49.871 | -16.350 |
| 43 | LYS CA | 1.893 | 52.685 | -20.721 |
| 43 | LYS D | 0.504 | 50.920 | -19.820 |
| 43 | LYS CG | 0.685 | 52.436 | -22.910 |
| 43 | LYS CE | -0.180 | 52.584 | -25.260 |
| 44 | VAL N | -0.191 | 53.035 | -19.490 |
| 44 | VAL C | -2.571 | 52.887 | -19.731 |
| 44 | VAL CB | -1.480 | 53.351 | -11.383 |
| 44 | VAL CG2 | -0.197 | 53.194 | -16.553 |
| 45 | ALA CA | -4.619 | 51.977 | -20.810 |
| 45 | ALA D | -6.703 | 53.085 | -20.703 |
| 46 | GLY N | -5.910 | 52.356 | -18.768 |
| 46 | GLY C | -6.987 | 52.443 | -16.538 |
| 47 | GLY N | -8.092 | 52.658 | -15.193 |
| 47 | GLY C | -9.179 | 52.757 | -13.572 |
| 48 | ALA N | -9.221 | 52.446 | -12.330 |
| 48 | ALA C | -9.790 | 52.675 | -9.968 |
| 48 | ALA CB | -11.558 | 52.100 | -11.617 |
| 49 | SER CA | -9.752 | 53.355 | -7.652 |
| 49 | SER D | -11.972 | 53.677 | -6.908 |
| 49 | SER DG | -8.879 | 54.255 | -5.650 |
| 50 | MET CA | -11.852 | 51.549 | -4.974 |
| 50 | MET D | -11.997 | 51.398 | -2.515 |
| 50 | MET CG | -11.912 | 49.463 | -6.389 |
| 50 | MET CE | -12.808 | 50.111 | -8.903 |
| 51 | VAL CA | -9.968 | 53.170 | -2.067 |
| 51 | VAL D | -10.237 | 55.437 | -2.682 |
| 51 | VAL CG1 | -7.892 | 53.579 | -0.631 |
| 52 | PRO N | -11.621 | 54.693 | -1.056 |
| 52 | PRO C | -11.490 | 51.123 | -0.440 |
| 52 | PRO CB | -13.400 | 55.594 | 0.244 |
| 52 | PRO CD | -12.164 | 53.620 | -0.175 |
| 53 | SER CA | -9.538 | 57.982 | 0.682 |
| 53 | SER D | -7.679 | 59.224 | -0.038 |
| 53 | SER DG | -8.256 | 56.521 | 2.127 |
| 54 | GLU CA | -7.204 | 57.648 | -2.421 |
| 54 | GLU D | -7.533 | 56.243 | -4.379 |
| 54 | GLU CG | -5.289 | 56.959 | -0.927 |
| 54 | GLU DE1 | -3.545 | 55.694 | -1.968 |
| 54 | GLU DE2 | -3.900 | 55.777 | 0.271 |
| 55 | THR CA | -9.433 | 5B.121 | -5.441 |

-continued

| | | | | |
|---|---|---|---|---|
| 55 | THR D | −9.433 | 57.919 | −7.810 |
| 55 | THR DG1 | −9.885 | 60.510 | −5.418 |
| 56 | ASN N | −7.482 | 58.403 | −6.877 |
| 56 | ASN DD1 | −5.075 | 58.967 | −10.331 |
| 56 | ASN CB | −5.898 | 59.694 | −6.208 |
| 56 | ASN C | −6.012 | 57.094 | −8.305 |
| 57 | PRO N | −6.362 | 56.261 | −9.258 |
| 57 | PRO CD | −7.384 | 56.433 | −10.272 |
| 57 | PRO CA | −5.679 | 54.961 | −9.332 |
| 57 | PRO D | −3.509 | 54.128 | −9.945 |
| 58 | PHE CA | −2.141 | 56.577 | −11.222 |
| 58 | PHE D | −0.635 | 57.497 | −10.680 |
| 58 | PHE CG | −3.983 | 56.968 | −13.357 |
| 58 | PHE CD2 | −5.211 | 57.630 | −13.459 |
| 58 | PHE CE2 | −6.194 | 57.095 | −14.276 |
| 59 | GLN N | −2.044 | 57.119 | −8.990 |
| 59 | GLN C | −0.807 | 56.403 | −7.000 |
| 59 | GLN CB | −1.862 | 58.668 | −7.089 |
| 59 | GLN CD | −1.790 | 60.151 | −5.150 |
| 59 | GLN NE2 | −2.959 | 59.685 | −4.742 |
| 60 | ASP CA | 0.851 | 54.792 | −6.304 |
| 60 | ASP D | 2.821 | 55.550 | −5.231 |
| 60 | ASP CG | 2.077 | 52.538 | −6.380 |
| 60 | ASP DD2 | 2.915 | 51.841 | −7.030 |
| 61 | ASN ND2 | −1.364 | 57.741 | −2.347 |
| 61 | ASN CG | −0.040 | 57.670 | −2.399 |
| 61 | ASN CA | 1.557 | 55.734 | −2.700 |
| 61 | ASN D | 2.933 | 54.862 | −0.902 |
| 62 | ASN CA | 2.877 | 52.348 | −1.709 |
| 62 | ASN D | 4.951 | 51.313 | −1.770 |
| 62 | ASN CG | 2.371 | 50.103 | −0.697 |
| 62 | ASN ND2 | 2.622 | 50.208 | 0.601 |
| 63 | SER CA | 5.189 | 51.696 | −4.709 |
| 63 | SER D | 5.593 | 49.790 | −6.269 |
| 63 | SER DG | 6.811 | 50.698 | −3.418 |
| 64 | HIS CA | 3.994 | 48.059 | −4.935 |
| 64 | HIS D | 3.861 | 46.974 | −7.108 |
| 64 | HIS CG | 3.144 | 46.021 | −3.726 |
| 64 | HIS CD2 | 4.054 | 45.194 | −3.135 |
| 64 | HIS NE2 | 3.556 | 43.920 | −3.368 |
| 65 | GLY CA | 1.552 | 48.264 | −7.830 |
| 65 | GLY D | 2.230 | 48.078 | −10.134 |
| 66 | THR CA | 4.064 | 50.117 | −9.954 |
| 66 | THR D | 5.333 | 48.789 | −11.461 |
| 66 | THR DG1 | 3.637 | 52.425 | −9.406 |
| 67 | HIS N | 5.685 | 48.443 | −9.274 |
| 67 | HIS C | 6.091 | 46.141 | −10.143 |
| 67 | HIS CB | 7.300 | 47.071 | −8.064 |
| 67 | HIS ND1 | 8.590 | 44.907 | −8.276 |
| 67 | HIS CE1 | 9.857 | 44.491 | −8.299 |
| 68 | VAL W | 4.892 | 45.749 | −9.731 |
| 68 | VAL C | 3.856 | 44.860 | −11.740 |
| 68 | VAL CB | 2.939 | 44.252 | −9.386 |
| 68 | VAL CG2 | 3.319 | 43.705 | −8.000 |
| 69 | ALA CA | 3.037 | 46.468 | −13.429 |
| 69 | ALA D | 4.028 | 45.913 | −15.565 |
| 70 | GLY N | 5.340 | 46.782 | −13.914 |
| 70 | GLY C | 7.046 | 45.370 | −15.021 |
| 71 | THR N | 6.820 | 44.431 | −14.138 |
| 71 | THR C | 6.224 | 42.506 | −15.543 |
| 71 | THR CB | 7.119 | 42.070 | −13.191 |
| 55 | THR N | −8.571 | 58.251 | −4.249 |
| 55 | THR C | −8.164 | 58.139 | −6.779 |
| 55 | THR CS | −10.586 | 59.200 | −5.303 |
| 55 | THR CG2 | −11.432 | 59.143 | −4.017 |
| 56 | ASN ND2 | −4.930 | 61.179 | −9.881 |
| 56 | ASN CG | −5.273 | 59.925 | −9.555 |
| 56 | ASN CA | −6.762 | 58.425 | −8.200 |
| 56 | ASN D | −5.104 | 56.866 | −7.470 |
| 57 | PRO CG | −7.123 | 55.257 | −11.177 |
| 57 | PRO CB | −6.644 | 54.178 | −10.235 |
| 57 | PRO C | −4.301 | 55.082 | −9.966 |
| 58 | PHE N | −3.998 | 56.262 | −10.491 |
| 58 | PHE C | −1.712 | 57.129 | −10.253 |
| 58 | PHE CB | −2.943 | 57.502 | −12.423 |
| 58 | PHE CD1 | −3.756 | 55.780 | −14.059 |
| 58 | PHE CE1 | −4.722 | 55.255 | −14.928 |
| 58 | PHE C2 | −5.949 | 55.939 | −15.051 |
| 59 | GLN CA | −1.172 | 57.583 | −7.934 |
| 59 | GLN D | −1.639 | 56.083 | −6.115 |
| 59 | GLN CG | −0.942 | 59.261 | −6.034 |
| 59 | GLN DE1 | −1.404 | 61.288 | −4.836 |
| 60 | ASP N | 0.410 | 55.895 | −7.211 |
| 60 | ASP C | 1.631 | 55.267 | −5.090 |
| 60 | ASP CB | 1.596 | 53.744 | −7.188 |
| 60 | ASP DD1 | 1.746 | 52.337 | −5.190 |
| 61 | ASN N | 0.959 | 55.265 | −3.950 |
| 61 | ASN DD1 | 0.666 | 58.566 | −2.875 |
| 61 | ASN CB | 0.531 | 56.401 | −1.784 |
| 61 | ASN C | 2.291 | 54.632 | −1.940 |
| 62 | ASN N | 2.210 | 53.434 | −2.468 |
| 62 | ASN C | 4.124 | 51.893 | −2.479 |
| 62 | ASN CB | 1.783 | 51.319 | −1.421 |
| 62 | ASN DD1 | 2.633 | 49.077 | −1.343 |
| 63 | SER N | 4.152 | 52.104 | −3.761 |
| 63 | SER C | 5.071 | 50.256 | −5.209 |
| 63 | SER CB | 6.523 | 51.958 | −4.012 |
| 64 | HIS N | 4.202 | 49.475 | −4.639 |
| 64 | HIS C | 3.366 | 41.759 | −6.261 |
| 64 | HIS CB | 3.184 | 41.501 | −3.747 |
| 64 | HIS ND1 | 2.107 | 45.247 | −4.241 |
| 64 | HIS CE1 | 2.416 | 43.966 | −4.054 |
| 65 | GLY N | 2.287 | 48.428 | −6.587 |
| 65 | GLY C | 2.392 | 48.636 | −9.037 |
| 66 | THR N | 3.233 | 49.659 | −8.832 |
| 66 | THR C | 5.089 | 49.009 | −10.291 |
| 66 | THR CB | 4.744 | 51.511 | −9.667 |
| 66 | THR CG2 | 5.536 | 52.078 | −10.849 |
| 67 | HIS CA | 6.103 | 47.361 | −9.458 |
| 67 | HIS D | 6.649 | 45.638 | −11.150 |
| 67 | HIS CG | 8.595 | 46.275 | −8.148 |
| 67 | HIS CD2 | 9.904 | 46.678 | −8.076 |
| 67 | HIS N52 | 10.678 | 45.514 | −8.186 |
| 68 | VAL CA | 4.142 | 44.607 | −10.266 |
| 68 | VAL D | 4.114 | 43.942 | −12.535 |
| 68 | VAL CG1 | 1.960 | 43.260 | −10.020 |
| 69 | ALA N | 3.373 | 46.049 | −12.113 |
| 69 | ALA C | 4.193 | 46.390 | −14.411 |
| 69 | ALA CB | 2.332 | 47.851 | −13.386 |
| 70 | GLY CA | 6.595 | 46.805 | −14.670 |
| 70 | GLY D | 7.604 | 45.154 | −16.119 |
| 71 | THR CA | 7.177 | 43.019 | −14.446 |
| 71 | THR D | 6.602 | 41.828 | −16.495 |
| 71 | THR DG1 | 8.191 | 42.592 | −12.390 |
| 71 | THR CG2 | 7.274 | 40.583 | −13.596 |
| 72 | VAL CA | 3.976 | 42.491 | −16.484 |
| 72 | VAL D | 4.341 | 42.380 | −18.860 |
| 72 | VAL CG1 | 1.512 | 42.480 | −17.170 |
| 73 | ALA N | 4.504 | 44.417 | −17.880 |
| 73 | ALA C | 5.433 | 46.333 | −19.355 |
| 73 | ALA CB | 3.107 | 45.441 | −19.433 |
| 74 | ALA CA | 7.470 | 47.591 | −18.859 |
| 74 | ALA D | 7.959 | 46.640 | −21.054 |
| 75 | LEU N | 7.650 | 48.784 | −21.039 |
| 75 | LEU C | 9.192 | 48.568 | −22.966 |
| 75 | LEU CB | 7.548 | 50.471 | −22.809 |
| 75 | LEU CD1 | 6.079 | 52.436 | −22.300 |
| 76 | ASN N | 9.147 | 48.103 | −24.169 |
| 76 | ASN DD1 | 10.950 | 45.840 | −24.928 |
| 76 | ASN CB | 10.010 | 46.651 | −25.908 |
| 76 | ASN C | 10.783 | 49.048 | −25.643 |
| 77 | ASN N | 11.804 | 49.664 | −25.071 |
| 77 | ASN C | 13.707 | 51.029 | −25.348 |
| 77 | ASN CB | 11.335 | 52.076 | −25.117 |
| 77 | ASN DD1 | 12.032 | 51.346 | −22.917 |
| 78 | SER N | 14.125 | 52.267 | −25.164 |
| 78 | SER C | 15.810 | 52.742 | −23.436 |
| 78 | SER CB | 15.905 | 53.941 | −25.587 |
| 79 | ILE N | 14.858 | 52.565 | −22.529 |
| 79 | ILE C | 14.617 | 51.683 | −20.230 |
| 79 | ILE CB | 14.471 | 54.174 | −20.697 |
| 79 | ILE CG2 | 14.997 | 55.320 | −21.612 |
| 80 | GLY N | 14.995 | 51.768 | −18.981 |
| 80 | GLY C | 14.612 | 49.448 | −18.219 |
| 81 | VAL N | 13.513 | 48.766 | −11.980 |
| 81 | VAL C | 12.511 | 46.919 | −19.217 |
| 81 | VAL CB | 13.001 | 46.755 | −16.677 |
| 81 | VAL CG2 | 11.638 | 47.261 | −16.231 |
| 82 | LEU CA | 11.312 | 45.020 | −20.256 |
| 82 | LEU D | 10.858 | 43.356 | −18.600 |

| | | | | |
|---|---|---|---|---|
| 82 | LEU CG | 11.430 | 43.568 | −22.366 |
| 82 | LEU CD2 | 12.359 | 42.675 | −23.192 |
| 83 | GLY CA | 8.133 | 43.321 | −19.114 |
| 83 | GLY D | 8.546 | 41.822 | −21.026 |
| 84 | VAL CA | 6.973 | 39.807 | −19.888 |
| 84 | VAL D | 6.424 | 39.472 | −22.194 |
| 84 | VAL CG1 | 5.680 | 37.677 | −19.557 |
| 85 | ALA N | 5.156 | 40.926 | −21.024 |
| 85 | ALA C | 4.213 | 42.683 | −22.396 |
| 85 | ALA CB | 2.746 | 40.663 | −21.748 |
| 86 | PRO CA | 5.413 | 44.635 | −23.205 |
| 86 | PRO D | 4.291 | 46.605 | −23.849 |
| 86 | PRO CG | 7.030 | 43.468 | −24.546 |
| 87 | SER N | 3.548 | 44.676 | −24.769 |
| 87 | SER C | 1.103 | 45.132 | −24.897 |
| 87 | SER CB | 2.401 | 44.777 | −26.927 |
| 88 | ALA N | 1.017 | 44.564 | −23.742 |
| 88 | ALA CA | −0.213 | 44.353 | −23.084 |
| 88 | ALA D | −0.174 | 46.717 | −22.435 |
| 89 | SER DG | −4.146 | 47.102 | −24.280 |
| 89 | SER CA | −3.001 | 46.867 | −22.227 |
| 89 | SER D | −3.793 | 45.864 | −20.209 |
| 90 | LEU CA | −2.378 | 47.667 | −18.593 |
| 90 | LEU D | −3.582 | 49.604 | −18.215 |
| 90 | LEU CG | −0.233 | 47.851 | −17.174 |
| 90 | LEU CD2 | 1.160 | 48.524 | −17.047 |
| 91 | TYR CA | −5.258 | 48.678 | −16.137 |
| 72 | VAL N | 4.930 | −42.887 | −15.427 |
| 72 | VAL C | 4.312 | 43.084 | −17.831 |
| 72 | VAL CB | 2.516 | 42.867 | −16.085 |
| 72 | VAL CG2 | 2.142 | 42.327 | −14.723 |
| 73 | ALA CA | 4.587 | 45.091 | −19.167 |
| 73 | ALA D | 5.062 | 47.188 | −20.216 |
| 74 | ALA N | 6.544 | 46.429 | −18.635 |
| 74 | ALA C | 7.740 | 47.648 | −20.342 |
| 74 | ALA CB | 8.653 | 47.446 | −17.925 |
| 75 | LEU CA | 7.812 | 49.968 | −22.456 |
| 75 | LEU D | 10.162 | 48.750 | −22.253 |
| 75 | LEU CG | 6.123 | 50.913 | −22.379 |
| 75 | LEU CD2 | 5.096 | 50.442 | −23.405 |
| 76 | ASN ND2 | 12.385 | 46.432 | −26.304 |
| 76 | ASN CG | 11.195 | 46.274 | −26.802 |
| 76 | ASN CA | 10.359 | 47.738 | −24.938 |
| 76 | ASN D | 10.157 | 49.479 | −26.619 |
| 77 | ASN CA | 12.220 | 50.957 | −25.681 |
| 77 | ASN D | 14.364 | 49.979 | −25.313 |
| 77 | ASN CG | 11.250 | 52.027 | −23.616 |
| 77 | ASN ND2 | 10.294 | 52.741 | −23.025 |
| 78 | SER CA | 15.513 | 52.614 | −24.906 |
| 78 | SER D | 16.982 | 53.071 | −23.164 |
| 78 | SER DG | 15.926 | 53.870 | −26.999 |
| 79 | ILE CA | 15.155 | 52.784 | −21.120 |
| 79 | ILE D | 13.843 | 50.841 | −20.679 |
| 79 | ILE CG1 | 12.945 | 54.032 | −20.814 |
| 79 | ILE CD1 | 12.335 | 55.176 | −20.155 |
| 80 | GLY CA | 14.476 | 50.940 | −17.913 |
| 80 | GLY D | 15.719 | 48.994 | −18.544 |
| 81 | VAL CA | 13.411 | 47.286 | −18.061 |
| 81 | VAL D | 12.260 | 47.739 | −20.117 |
| 81 | VAL CG1 | 14.030 | 47.084 | −15.573 |
| 82 | LEU N | 12.126 | 45.645 | −19.216 |
| 82 | LEU C | 10.390 | 44.028 | −19.510 |
| 82 | LEU CB | 12.206 | 44.219 | −21.229 |
| 82 | LEU CD2 | 10.796 | 44.657 | −23.223 |
| 83 | GLY N | 9.131 | 44.180 | −19.816 |
| 83 | GLY C | 8.027 | 42.011 | −19.925 |
| 84 | VAL N | 7.272 | 41.112 | −19.283 |
| 84 | VAL C | 6.164 | 40.030 | −21.140 |
| 84 | VAL CB | 6.256 | 38.920 | −18.841 |
| 84 | VAL CG2 | 7.190 | 38.507 | −17.705 |
| 85 | ALA CA | 4.217 | 41.194 | −22.158 |
| 85 | ALA D | 3.260 | 43.401 | −22.030 |
| 86 | PRO N | 5.240 | 43.186 | −23.059 |
| 86 | PRO C | 4.321 | 45.371 | −23.947 |
| 86 | PRO CB | 6.822 | 44.784 | −23.813 |
| 86 | PRO CD | 6.377 | 42.440 | −23.636 |
| 87 | SER CA | 2.489 | 45.324 | −25.529 |
| 87 | SER D | 0.162 | 45.513 | −25.619 |
| 87 | SER DG | 3.591 | 45.143 | −27.583 |
| 88 | ALA CB | −0.163 | 43.510 | −21.828 |
| 88 | ALA C | −0.898 | 45.717 | −22.690 |
| 89 | SER N | −2.219 | 45.691 | −22.678 |
| 89 | SER CB | −4.343 | 46.903 | −22.899 |
| 89 | SER C | −3.136 | 46.780 | −20.727 |
| 90 | LEU N | −2.446 | 47.656 | −20.037 |
| 90 | LEU C | −3.483 | 48.430 | −17.864 |
| 90 | LEU CB | −0.951 | 48.273 | −18.426 |
| 90 | LEU CD1 | −0.028 | 46.341 | −17.219 |
| 91 | TYR N | −4.264 | 47.944 | −16.938 |
| 91 | TYR C | −4.813 | 48.750 | −14.685 |
| 91 | TYR D | −4.496 | 47.749 | −14.02 |
| 91 | TYR CG | −7.094 | 48.237 | −17.741 |
| 91 | TYR CD2 | −7.971 | 49.275 | −18.149 |
| 91 | TYR CE2 | −8.315 | 49.421 | −19.492 |
| 91 | TYR DH | −8.172 | 48.752 | −21.764 |
| 92 | ALA CA | 4.549 | 50.199 | −12.707 |
| 92 | ALA D | −6.723 | 5D.898 | −12.050 |
| 93 | VAL N | −5.959 | 48.993 | −11.129 |
| 93 | VAL C | −6.708 | 49.014 | −8.899 |
| 93 | VAL CB | −7.957 | 47.555 | −10.611 |
| 93 | VAL CG2 | −8.195 | 47.370 | −12.072 |
| 94 | LYS CA | −6.378 | 50.464 | −6.999 |
| 94 | LYS D | −8.458 | 50.480 | −5.783 |
| 94 | LYS CG | −5.394 | 52.320 | −5.461 |
| 94 | LYS CE | −4.399 | 54.208 | −4.199 |
| 95 | VAL N | −6.909 | 49.071 | −5.026 |
| 95 | VAL C | −6.919 | 48.499 | −2.568 |
| 95 | VAL CB | −8.104 | 47.030 | −4.319 |
| 95 | VAL CG2 | −6.900 | 46.100 | −4.332 |
| 96 | LEU CA | −4.782 | 49.103 | −1.486 |
| 96 | LEU D | −3.942 | 51.121 | −2.336 |
| 96 | LEU CG | −3.593 | 46.799 | −2.072 |
| 96 | LEU CD2 | −4.489 | 46.082 | −1.045 |
| 97 | GLY CA | −3.890 | 52.307 | 0.287 |
| 97 | GLY D | −1.619 | 51.463 | 0.165 |
| 98 | ALA CB | −0.428 | 55.478 | 1.510 |
| 98 | ALA C | 0.188 | 53.118 | 1.917 |
| 99 | ASP N | −0.504 | 52.573 | 2.912 |
| 99 | ASP DD1 | −2.730 | 50.902 | 4.003 |
| 99 | ASP CB | −0.648 | 51.603 | 5.175 |
| 99 | ASP C | 0.146 | 50.165 | 3.320 |
| 100 | GLY N | −0.424 | 49.883 | 2.168 |
| 100 | GLY C | −1.520 | 47.651 | 2.002 |
| 101 | SER N | −2.342 | 43.128 | 2.908 |
| 101 | SER C | −4.759 | 47.894 | 2.532 |
| 101 | SER CB | −3.716 | 47.447 | 4.817 |
| 102 | GLY N | −5.821 | 47.092 | 2.577 |
| 102 | GLY C | −8.166 | 46.536 | 2.528 |
| 103 | GLN N | −9.377 | 47.058 | 2.498 |
| 103 | GLN C | −10.963 | 45.232 | 2.022 |
| 103 | GLN CB | −11.671 | 47.307 | 3.274 |
| 103 | GLN CD | −12.360 | 49.104 | 4.915 |
| 103 | GLN NE2 | −13.419 | 49.197 | 4.112 |
| 104 | TYR CA | −12.068 | 43.126 | 1.508 |
| 104 | TYR D | −12.939 | 43.276 | −0.687 |
| 104 | TYR CG | −11.629 | 40.829 | 2.472 |
| 104 | TYR CD2 | −10.379 | 40.959 | 1.860 |
| 104 | TYR CE2 | −9.352 | 40.057 | 2.171 |
| 104 | TYR OH | −8.481 | 38.191 | 3.324 |
| 105 | SER CA | −14.877 | 45.166 | −0.034 |
| 105 | SER D | −14.759 | 45.935 | −2.258 |
| 105 | SER OG | −15.209 | 47.039 | 1.450 |
| 106 | TRP CA | −12.421 | 47.391 | −1.948 |
| 106 | TRP D | −12.021 | 46.648 | −4.245 |
| 106 | TRP CG | −11.645 | 49.111 | −0.206 |
| 106 | TRP CD2 | −10.658 | 49.812 | 0.581 |
| 106 | TRP CE2 | −11.359 | 50.573 | 1.561 |
| 106 | TRP CZ2 | −10.671 | 51.318 | 2.500 |
| 106 | TRP CH2 | −9.293 | 51.291 | 2.455 |
| 107 | ILE CA | −10.765 | 44.250 | −3.325 |
| 107 | ILE D | −11.695 | 43.474 | −5.398 |
| 107 | ILE CG1 | −8.634 | 43.784 | −1.936 |
| 107 | ILE CD1 | −3.253 | 42.999 | −0.627 |
| 91 | TYR CB | −6.686 | 48.093 | −16.314 |
| 91 | TYR CD1 | −6.595 | 47.415 | −18.755 |
| 91 | TYR CE1 | −6.905 | 47.572 | −20.090 |
| 91 | TYR C2 | −7.794 | 48.582 | −20.463 |
| 92 | ALA N | −4.895 | 49.958 | −14.104 |
| 92 | ALA C | −5.823 | 50.033 | −11.903 |
| 92 | ALA CB | −3.997 | 51.621 | −12.488 |

| | | | | | | | | | |
|---|---|---|---|---|---|---|---|---|---|
| 93 | VAL CA | −7.183 | 48.854 | −10.325 | | 113 | TRP CZ3 | −10.610 | 47.899 | −14.879 |
| 93 | VAL D | −6.181 | 47.993 | −8.372 | | 114 | ALA N | −13.089 | 44.801 | −12.832 |
| 93 | VAL CG1 | −9.213 | 47.488 | −9.725 | | 114 | ALA C | −13.199 | 43.179 | −14.152 |
| 94 | LYS N | −6.907 | 50.217 | −8.327 | | 114 | ALA C | −11.299 | 43.192 | −13.140 |
| 94 | LYS C | −7.331 | 49.985 | −5.894 | | 115 | ILE CA | −15.070 | 41.640 | −14.897 |
| 94 | LYS CB | −6.051 | 51.976 | −6.818 | | 115 | ILE D | −16.077 | 42.225 | −17.070 |
| 94 | LYS CD | −4.868 | 53.785 | −5.582 | | 115 | ILE CG1 | −15.218 | 39.836 | −13.043 |
| 94 | LYS NZ | −3.735 | 55.544 | −4.387 | | 115 | ILE CD1 | −16.004 | 39.411 | −11.743 |
| 95 | VAL CA | −7.646 | 48.457 | −3.920 | | 116 | ALA CA | −17.390 | 44.440 | −16.050 |
| 95 | VAL D | −1.425 | 48.156 | −1.501 | | 116 | ALA D | −17.323 | 45.255 | −18.343 |
| 95 | VAL CG1 | −8.868 | 46.852 | −5.619 | | 117 | ASN N | −15.423 | 45.390 | −17.122 |
| 96 | LEU N | −5.676 | 48.974 | −2.604 | | 117 | ASN C | −13.821 | 44.974 | −19.034 |
| 96 | LEU C | −4.331 | 50.559 | −1.321 | | 117 | ASN CB | −13.615 | 46.958 | −17.426 |
| 96 | LEU CB | −3.509 | 48.241 | −1.573 | | 117 | ASN DD1 | −14.565 | 49.082 | −17.773 |
| 96 | LEU CD1 | −2.207 | 46.184 | −2.163 | | 118 | ASN N | −14.223 | 43.725 | −18.967 |
| 97 | GLY N | −4.326 | 50.975 | −0.086 | | 118 | ASN C | −12.240 | 42.444 | −19.843 |
| 97 | GLY C | −2.363 | 52.437 | 0.385 | | 118 | ASN CB | −14.247 | 42.863 | −21.219 |
| 98 | ALA N | −1.954 | 53.648 | 0.758 | | 118 | ASN DD1 | −16.510 | 42.321 | −20.759 |
| 98 | ALA CA | −0.563 | 54.068 | 0.965 | | 119 | MET N | −11.686 | 42.500 | −18.675 |
| 98 | ALA D | 1.393 | 52.921 | 1.663 | | 119 | MET C | −10.025 | 40.734 | −18.928 |
| 99 | ASP DD2 | −2.631 | 51.042 | 6.151 | | 119 | MET CB | −9.810 | 42.461 | −17.055 |
| 99 | ASP CG | −2.083 | 51.131 | 5.040 | | 119 | MET SD | −8.788 | 44.943 | −17.526 |
| 99 | ASP CA | 0.101 | 51.610 | 3.855 | | 120 | ASP N | −8.904 | 40.437 | −19.584 |
| 99 | ASP D | 0.735 | 49.313 | 4.029 | | 120 | ASP C | −7.822 | 38.390 | −18.856 |
| 100 | GLY CA | −0.343 | 48.521 | 1.615 | | 120 | ASP CB | −7.555 | 39.156 | −21.236 |
| 100 | GLY D | −1.649 | 46.512 | 1.479 | | 120 | ASP DD1 | −7.801 | 40.706 | −23.084 |
| 101 | SER CA | −3.542 | 47.388 | 3.315 | | 121 | VAL N | −7.021 | 39.117 | −18.115 |
| 101 | SER D | −4.758 | 48.972 | 1.907 | | 121 | VAL C | −6.296 | 39.534 | −15.786 |
| 101 | SER DG | −4.411 | 48.634 | 5.209 | | 121 | VAL CB | −4.755 | 38.587 | −17.496 |
| 102 | GLY CA | −7.077 | 47.422 | 1.896 | | 121 | VAL CG2 | −4.707 | 37.916 | −18.846 |
| 102 | GLY D | −7.888 | 45.431 | 3.030 | | 122 | ILE CA | −6.248 | 39.799 | −13.397 |
| 103 | GLN CA | −10.535 | 46.291 | 3.020 | | 122 | ILE D | −4.829 | 38.012 | −12.469 |
| 103 | GLN D | −10.779 | 45.482 | 0.817 | | 122 | ILE CG1 | −8.686 | 40.392 | −13.063 |
| 103 | GLN CG | −11.368 | 48.005 | 4.586 | | 122 | ILE CD1 | −9.976 | 39.788 | −12.383 |
| 103 | GLN DE1 | −12.159 | 49.816 | 5.902 | | 123 | ASN CA | −3.145 | 39.854 | −11.232 |
| 104 | TYR N | −11.611 | 44.141 | 2.451 | | 123 | ASN D | −3.708 | 41.631 | −9.833 |
| 104 | TYR C | −13.031 | 43.690 | 0.473 | | 123 | ASN CG | −0.692 | 40.048 | −10.777 |
| 104 | TYR CB | −12.697 | 41.866 | 2.143 | | 123 | ASN ND2 | −0.346 | 40.747 | −9.120 |
| 104 | TYR CD1 | −11.819 | 39.789 | 3.377 | | 124 | MET CA | −3.650 | 39.973 | −7.438 |
| 104 | TYR CE1 | −10.805 | 38.885 | 3.707 | | 108 | ILE C | −14.639 | 43.694 | −5.386 |
| 104 | TYR CZ | −9.564 | 39.022 | 3.081 | | 108 | ILE CB | −15.246 | 42.265 | −3.320 |
| 105 | SER N | −13.909 | 44.572 | 0.903 | | 108 | ILE CG2 | −16.568 | 42.024 | −4.095 |
| 105 | SER C | −14.172 | 45.920 | −1.159 | | 109 | ASN N | −14.751 | 44.958 | −4.981 |
| 105 | SER CB | −15.880 | 46.121 | 0.601 | | 109 | ASN C | −14.232 | 46.067 | −7.084 |
| 106 | TRP N | −13.079 | 46.625 | −0.834 | | 109 | ASN CB | −15.280 | 47.359 | −5.207 |
| 106 | TRP C | −11.895 | 46.436 | −3.012 | | 109 | ASN DD1 | −17.455 | 46.695 | −4.646 |
| 106 | TRP CB | −11.321 | 48.254 | −1.355 | | 110 | GLY N | −12.951 | 45.908 | −6.774 |
| 106 | TRP CD1 | −12.862 | 49.524 | 0.264 | | 110 | GLY C | −12.108 | 44.712 | −8.812 |
| 106 | TRP CE1 | −12.691 | 50.358 | 1.360 | | 111 | ILE N | −12.379 | 43.539 | −8.246 |
| 106 | TRP CE3 | −9.275 | 49.852 | 0.576 | | 111 | ILE C | −13.859 | 42.560 | −9.942 |
| 106 | TRP CZ3 | −8.568 | 50.563 | 1.525 | | 111 | ILE CB | −12.734 | 40.948 | −8.364 |
| 107 | ILE N | −11.339 | 45.330 | −2.481 | | 111 | ILE CG2 | −13.122 | 39.791 | −9.347 |
| 107 | ILE C | −11.855 | 43.594 | −4.190 | | 112 | GLU N | −14.893 | 43.075 | −9.280 |
| 107 | ILE CB | −9.944 | 43.183 | −2.523 | | 112 | GLU C | −15.872 | 44.347 | −11.171 |
| 107 | ILE CG2 | −9.944 | 43.183 | −3.381 | | 112 | GLU CB | −17.229 | 43.899 | −9.141 |
| 103 | ILE N | −12.994 | 43.292 | −3.577 | | 112 | GLU CD | −18.724 | 41.824 | −8.685 |
| 108 | ILE CA | −14.116 | 42.722 | −4.32 | | 112 | GLU DE2 | −19.123 | 41.928 | −9.866 |
| 108 | ILE D | −14.894 | 43.329 | −6.552 | | 113 | TRP CA | −14.756 | 46.400 | −12.000 |
| 108 | ILE CG1 | −14.726 | 41.077 | −2.482 | | 113 | TRP D | −14.319 | 45.932 | −14.332 |
| 105 | ILE CD1 | −15.452 | 40.845 | −1.131 | | 113 | TRP CG | −13.486 | 48.556 | −12.481 |
| 109 | ASN CA | −15.204 | 46.018 | −5.916 | | 113 | TRP CD2 | −12.441 | 48.552 | −13.463 |
| 109 | ASN G | −14.660 | 46.272 | −8.235 | | 113 | TRP CE2 | −12.545 | 49.761 | −14.215 |
| 109 | ASN CG | −16.528 | 47.486 | −4.353 | | 113 | TRP CZ2 | −11.696 | 50.045 | −15.274 |
| 109 | ASN ND2 | −16.633 | 48.447 | −3.442 | | 113 | TRP CH2 | −10.752 | 49.074 | −15.603 |
| 110 | GLY CA | −11.952 | 45.917 | −7.865 | | 114 | ALA CA | −12.333 | 44.065 | −13.874 |
| 110 | GLY D | −11.929 | 44.929 | −10.034 | | 114 | ALA D | −12.963 | 43.074 | −15.978 |
| 111 | ILE CA | −12.603 | 42.334 | −9.099 | | 115 | ILE N | −14.174 | 42.540 | −14.119 |
| 111 | ILE D | −13.921 | 42.384 | −11.148 | | 115 | ILE C | −15.928 | 42.485 | −15.856 |
| 111 | ILE CG1 | −11.421 | 40.501 | −7.655 | | 115 | ILE CB | −16.000 | 40.840 | −13.922 |
| 111 | ILE CD1 | −11.588 | 39.706 | −6.336 | | 115 | ILE CG2 | −17.151 | 40.168 | −14.755 |
| 112 | GLU CA | −16.118 | 43.376 | −10.046 | | 116 | ALA N | −16.534 | 43.527 | −15.267 |
| 112 | GLU D | −16.467 | 44.130 | −12.246 | | 116 | ALA C | −16.706 | 45.069 | −17.278 |
| 112 | GLU CG | −17.847 | 42.917 | −8.135 | | 116 | ALA CB | −18.011 | 45.510 | −15.151 |
| 112 | GLU DE1 | −19.041 | 40.866 | −8.016 | | 117 | ASN CA | −14.553 | 45.967 | −18.139 |
| 113 | TRP N | −15.094 | 45.403 | −10.971 | | 117 | ASN D | −12.991 | 45.436 | −19.820 |
| 113 | TRP C | −14.076 | 45.663 | −13.140 | | 117 | ASN CG | −14.400 | 48.177 | −16.939 |
| 113 | TRP CB | −13.882 | 47.553 | −11.434 | | 117 | ASN ND2 | −14.931 | 48.249 | −15.136 |
| 113 | TRP CD1 | −14.148 | 49.736 | −12.681 | | 118 | ASN CA | −13.760 | 42.642 | −19.832 |
| 113 | TRP NE1 | −13.597 | 50.443 | −13.723 | | 118 | ASN D | −11.617 | 42.309 | −20.932 |
| 113 | TRP CE3 | −11.451 | 47.645 | −13.809 | | 118 | ASN CG | −15.737 | 43.060 | −21.395 |

| | | | | |
|---|---|---|---|---|
| 118 | ASN ND2 | −16.136 | 44.096 | −22.133 |
| 119 | MET CA | −10.232 | 42.222 | −18.478 |
| 119 | MET D | −10.888 | 39.838 | −18.759 |
| 119 | MET CG | −9.880 | 43.883 | −16.502 |
| 119 | MET CE | −9.982 | 46.061 | −18.263 |
| 120 | ASP CA | −8.480 | 39.118 | −20.030 |
| 120 | ASP D | −8.038 | 37.189 | −18.690 |
| 120 | ASP CG | −8.237 | 39.730 | −22.454 |
| 120 | ASP DD2 | −9.327 | 39.135 | −22.739 |
| 121 | VAL CA | −6.226 | 38.601 | −16.974 |
| 121 | VAL D | −6.284 | 40.788 | −15.909 |
| 121 | VAL CG1 | −3.758 | 38.176 | −16.427 |
| 122 | ILE N | −6.318 | 38.978 | −14.590 |
| 122 | ILE C | −5.020 | 39.262 | −12.627 |
| 122 | ILE CB | −7.476 | 39.604 | −12.466 |
| 122 | ILE CG2 | −7.221 | 39.883 | −10.954 |
| 123 | ASN N | −4.263 | 40.222 | −12.110 |
| 123 | ASN C | −3.502 | 40.404 | −9.861 |
| 123 | ASN CB | −1.828 | 40.478 | −11.691 |
| 123 | ASN DD1 | −0.063 | 36.990 | −11.018 |
| 124 | MET N | −3.458 | 39.604 | −8.832 |
| 124 | MET C | −2.423 | 39.603 | −6.614 |
| 124 | MET N | −3.453 | 39.604 | −8.832 |
| 124 | MET C | −2.423 | 39.603 | −6.614 |
| 124 | MET D | −2.306 | 38.508 | −6.09 |
| 124 | MET CG | −6.158 | 40.082 | −7.471 |
| 124 | MET CE | −7.940 | 38.095 | −7.542 |
| 125 | SER CA | −0.193 | 40.287 | −5.769 |
| 125 | SER DG | 0.235 | 41.617 | −3.805 |
| 126 | LEU CG | 1.444 | 40.496 | −7.575 |
| 126 | LEU CA | −1.842 | 40.347 | −2.386 |
| 126 | LEU D | −2.844 | 38.136 | −2.529 |
| 126 | LEU CG | −3.988 | 41.447 | −3.333 |
| 126 | LEU CD2 | −4.179 | 42.760 | −4.073 |
| 127 | GLY CA | −3.035 | 37.871 | 0.193 |
| 127 | GLY D | −2.446 | 39.030 | 2.220 |
| 128 | GLY CA | −4.475 | 37.496 | 3.642 |
| 128 | GLY D | −4.903 | 35.158 | 3.276 |
| 129 | PRO CA | −4.671 | 34.525 | 5.998 |
| 129 | PRO D | −6.338 | 32.887 | 6.305 |
| 129 | PRO CG | −4.419 | 36.116 | 7.727 |
| 130 | SER N | −7.051 | 35.015 | 5.912 |
| 130 | SER C | −9.218 | 34.884 | 4.726 |
| 130 | SER CB | −9.069 | 35.351 | 7.216 |
| 131 | GLY N | −10.083 | 33.967 | 4.349 |
| 131 | GLY C | −12.205 | 34.713 | 3.542 |
| 132 | SER N | −13.040 | 35.058 | 2.594 |
| 132 | SER C | −15.289 | 34.805 | 1.936 |
| 132 | SER CB | −14.590 | 36.927 | 3.145 |
| 133 | ALA N | −16.547 | 34.588 | 2.294 |
| 133 | ALA C | −17.630 | 34.965 | 0.097 |
| 133 | ALA CB | −18.866 | 33.828 | 1.996 |
| 134 | ALA CA | −17.872 | 37.259 | −0.792 |
| 134 | ALA D | −16.781 | 37.585 | −2.869 |
| 135 | LEU N | −15.478 | 37.229 | −1.046 |
| 135 | LEU C | −14.158 | 36.005 | −2.705 |
| 135 | LEU CB | −13.036 | 37.328 | −0.798 |
| 135 | LEU CD1 | −11.460 | 38.415 | −2.292 |
| 136 | LYS N | −14.509 | 34.825 | −2.173 |
| 136 | LYS C | −15.544 | 33.739 | −4.150 |
| 136 | LYS CB | −14.903 | 32.341 | −2.186 |
| 136 | LYS CD | −15.083 | 29.892 | −2.134 |
| 136 | LYS NZ | −15.308 | 25.411 | −4.160 |
| 137 | ALA CA | −17.795 | 34.416 | −4.883 |
| 137 | ALA D | −17.705 | 35.049 | −7.208 |
| 138 | ALA N | −16.529 | 36.301 | −5.729 |
| 138 | ALA C | −14.903 | 36.696 | −7.557 |
| 138 | ALA CB | −15.522 | 36.567 | −5.934 |
| 139 | VAL CA | −12.946 | 35.291 | −7.837 |
| 139 | VAL D | −13.208 | 34.070 | −9.877 |
| 139 | VAL CG1 | −10.919 | 33.856 | −7.866 |
| 140 | ASP N | −14.593 | 33.536 | −8.122 |
| 140 | ASP C | −16.023 | 33.131 | −10.064 |
| 140 | ASP CB | −16.149 | 31.549 | −8.138 |
| 140 | ASP DD1 | −14.178 | 30.403 | −7.202 |
| 141 | LYS N | −16.658 | 34.263 | −9.820 |
| 141 | LYS C | −16.373 | 35.415 | −11.946 |
| 141 | LYS CB | −18.039 | 36.275 | −10.325 |
| 141 | LYS CO | −19.586 | 38.187 | −10.536 |
| 141 | LYS N2 | −21.138 | 40.037 | −10.275 |
| 142 | ALA CA | −14.173 | 36.192 | −12.614 |
| 142 | ALA D | −13.770 | 35.169 | −14.755 |
| 143 | VAL N | −13.582 | 33.856 | −12.832 |
| 143 | VAL C | −14.346 | 32.233 | −14.496 |
| 143 | VAL CB | −12.551 | 31.673 | −12.714 |
| 143 | VAL CG2 | −11.305 | 32.195 | −12.014 |
| 144 | ALA CA | −16.744 | 31.534 | −14.641 |
| 124 | MET CB | −4.943 | 39.387 | −6.890 |
| 124 | MET SD | −7.585 | 39.472 | −6.450 |
| 125 | SER N | −1.454 | 40.496 | −6.502 |
| 125 | SER C | −0.422 | 40.712 | −4.326 |
| 125 | SER CB | 1.021 | 41.027 | −6.328 |
| 126 | LEU N | −1.433 | 40.075 | −3.775 |
| 126 | LEU C | −2.438 | 39.056 | −1.807 |
| 126 | LEU CB | −2.791 | 41.568 | −2.410 |
| 126 | LEU CD1 | −5.278 | 41.131 | −2.578 |
| 127 | GLY N | −2.522 | 39.082 | −0.481 |
| 127 | GLY C | −3.176 | 38.180 | 1.682 |
| 128 | GLY N | −4.121 | 37.443 | 2.222 |
| 128 | GLY C | −4.644 | 36.038 | 4.104 |
| 129 | PRO N | −4.519 | 35.857 | 5.402 |
| 129 | PRO C | −6.116 | 34.086 | 6.082 |
| 129 | PRO CB | −4.060 | 34.684 | 7.384 |
| 129 | PRO CD | −4.239 | 36.870 | 6.418 |
| 130 | SER CA | −8.470 | 34.611 | 6.023 |
| 130 | SER D | −8.949 | 35.881 | 4.029 |
| 130 | SER DG | −8.723 | 34.626 | 8.403 |
| 131 | GLY CA | −10.824 | 34.229 | 3.074 |
| 131 | GLY D | −12.495 | 34.722 | 4.751 |
| 132 | SER CA | −14.407 | 35.433 | 3.011 |
| 132 | SER D | −14.799 | 34.586 | 0.824 |
| 132 | SER DG | −14.693 | 37.539 | 1.875 |
| 133 | ALA CA | −17.507 | 34.057 | 1.324 |
| 133 | ALA D | −17.743 | 34.437 | −1.014 |
| 134 | ALA N | −17.683 | 36.288 | 0.294 |
| 134 | ALA C | −16.635 | 37.369 | −1.674 |
| 134 | ALA CB | −18.263 | 38.600 | −0.187 |
| 135 | LEU CA | −14.197 | 37.244 | −1.804 |
| 135 | LEU D | −13.794 | 36.020 | −3.890 |
| 135 | LEU CG | −11.693 | 37.130 | −1.508 |
| 135 | LEU CD2 | −10.582 | 36.807 | −0.519 |
| 136 | LYS CA | −14.543 | 33.597 | −30.13 |
| 136 | LYS D | −15.279 | 33.431 | −5.305 |
| 136 | LYS CG | −14.743 | 31.067 | −1.043 |
| 136 | LYS CE | −15.743 | 28.707 | −2.778 |
| 137 | ALA N | −16.744 | 34.260 | −3.847 |
| 137 | ALA C | −17.338 | 35.303 | −6.045 |
| 137 | ALA CB | −19.094 | 34.941 | −4.263 |
| 138 | ALA CA | −16.001 | 37.311 | −6.685 |
| 138 | ALA D | −14.985 | 36.843 | −8.762 |
| 139 | VAL N | −13.950 | 35.959 | −7.027 |
| 139 | VAL C | −13.623 | 34.228 | −8.720 |
| 139 | VAL CB | −11.830 | 34.671 | −6.968 |
| 139 | VAL CG2 | −11.078 | 35.780 | −6.253 |
| 140 | ASP CA | −15.274 | 32.496 | −8.929 |
| 140 | ASP D | −15.274 | 32.496 | −8.929 |
| 140 | ASP CG | −16.080 | 32.579 | −11.190 |
| 140 | ASP CG | −15.388 | 30.640 | −7.186 |
| 141 | LYS CA | −16.139 | 30.132 | −6.329 |
| 141 | LYS D | −17.373 | 35.006 | −10.868 |
| 141 | LYS CG | −16.700 | 35.248 | −13.111 |
| 141 | LYS CE | −18.884 | 37.056 | −11.306 |
| 142 | ALA N | −15.167 | 35.848 | −11.566 |
| 142 | ALA C | −13.818 | 35.010 | −13.521 |
| 142 | ALA CB | −12.870 | 36.697 | −11.948 |
| 143 | VAL CA | −13.168 | 32.705 | −13.650 |
| 143 | VAL D | −14.140 | 31.886 | −15.639 |
| 143 | VAL CG1 | −12.300 | 30.370 | −13.461 |
| 144 | ALA N | −15.531 | 32.238 | −13.875 |
| 144 | ALA C | −16.928 | 32.681 | −15.861 |
| 144 | ALA D | −17.380 | 32.263 | −16.959 |
| 145 | SER N | −16.507 | 33.948 | −15.706 |
| 145 | SER C | −15.609 | 34.773 | −17.829 |
| 145 | SER CB | −17.016 | 36.376 | −16.414 |
| 146 | GLY N | −14.577 | 33.986 | −17.565 |
| 146 | GLY C | −12.273 | 34.4941 | −18.385 |
| 147 | VAL N | −12.150 | 35.162 | −17.254 |
| 147 | VAL C | −9.850 | 34.836 | −16.323 |
| 147 | VAL CB | −11.152 | 36.977 | −15.889 |
| 147 | VAL CG2 | −12.340 | 37.915 | −16.230 |

| | | | | | | | | | | |
|---|---|---|---|---|---|---|---|---|---|---|
| 148 | VAL CA | −7.482 | 34.230 | −16.008 | | 154 | GLY N | 1.827 | 33.693 | −1.244 |
| 148 | VAL D | −6.840 | 36.133 | −14.750 | | 154 | GLY C | 3.519 | 34.069 | 0.550 |
| 148 | VAL CG1 | −5.079 | −3.403 | −16.281 | | 155 | ASN N | 3.958 | 34.788 | 1.568 |
| 149 | VAL N | −7.258 | 34.355 | −13.531 | 5 | 155 | ASN C | 5.399 | 34.258 | 3.462 |
| 149 | VAL C | −5.700 | 34.385 | −11.613 | | 155 | ASN CB | 6.008 | 36.158 | 1.904 |
| 149 | VAL CB | −8.224 | 34.890 | −11.315 | | 155 | ASN DD1 | 6.123 | 36.065 | −0.534 |
| 149 | VAL CG2 | −9.456 | 35.386 | −12.096 | | 156 | GLU N | 4.711 | 33.168 | 3.675 |
| 150 | VAL CA | −3.393 | 34.987 | −10.901 | | 156 | GLU C | 5.522 | 31.328 | 5.183 |
| 150 | VAL D | −3.592 | 36.778 | −9.400 | | 156 | GLU CB | 3.205 | 31.980 | 5.100 |
| 150 | VAL CG1 | −0.973 | 34.633 | −11.461 | 10 | 156 | GLU CD | 2.394 | 33.951 | 6.270 |
| 151 | ALA N | −2.568 | 34.946 | −8.595 | | 156 | GLU DE2 | 3.106 | 34.456 | 7.146 |
| 151 | ALA C | −1.080 | 35.036 | −6.657 | | 157 | GLY CA | 7.306 | 29.917 | 4.387 |
| 151 | ALA CB | −3.577 | 35.390 | −6.307 | | 157 | GLY D | 5.416 | 28.346 | 4.009 |
| 152 | ALA CA | 0.714 | 35.438 | −5.112 | | 158 | THR CG2 | 8.079 | 25.396 | 3.850 |
| 152 | ALA D | −0.728 | 34.466 | −3.467 | | 158 | THR C5 | 7.564 | 25.346 | 5.296 |
| 153 | ALA N | 1.125 | 33.302 | −3.912 | 15 | 158 | THR C | 6.100 | 26.480 | 7.157 |
| 153 | ALA C | 0.931 | 32.725 | −1.511 | | 159 | SER N | 5.338 | 25.441 | 7.497 |
| 153 | ALA CB | 1.750 | 31.038 | −3.195 | | 159 | SER CB | 3.673 | 26.105 | 9.212 |
| 154 | GLY CA | 2.043 | 34.211 | 2.125 | | 159 | SER C | 4.494 | 23.720 | 8.944 |
| 154 | GLY D | 4.189 | 33.267 | −0.118 | | 160 | GLY N | 5.574 | 22.967 | 8.835 |
| 155 | ASN CA | 5.344 | 34.787 | 2.037 | | 160 | GLY C | 4.576 | 21.045 | 7.738 |
| 155 | ASN D | 6.101 | 34.829 | 4.295 | | 161 | SER N | 3.525 | 20.310 | 8.116 |
| 155 | ASN CG | 5.890 | 36.702 | 0.500 | 20 | 161 | SER C | 1.477 | 20.708 | 6.786 |
| 155 | ASN ND2 | 5.454 | 37.965 | 0.352 | | 161 | SER CB | 2.344 | 18.293 | 7.271 |
| 156 | GLU CA | 4.633 | 32.537 | 4.970 | | 162 | SER N | 1.303 | 21.841 | 7.459 |
| 156 | GLU D | 5.374 | 30.637 | 6.222 | | 162 | SER C | 0.430 | 23.552 | 5.848 |
| 156 | GLU CG | 2.491 | 32.442 | 6.368 | | 162 | SER CB | −0.213 | 23.666 | 8.242 |
| 156 | GLU DE1 | 1.744 | 34.322 | 5.312 | | 163 | SER N | −0.679 | 23.921 | 5.197 |
| 157 | GLY N | 6.389 | 31.057 | 4.227 | 25 | 163 | SER C | −0.441 | 26.177 | 4.513 |
| 157 | GLY C | 6.503 | 28.622 | 4.553 | | 163 | SER CB | −1.890 | 24.642 | 3.211 |
| 158 | THR N | 7.147 | 27.793 | 5.293 | | 164 | THR N | 0.387 | 26.952 | 3.852 |
| 158 | THR DG1 | 8.707 | 21.487 | 6.217 | | 164 | THR C | 0.185 | 29.286 | 3.194 |
| 158 | THR CA | 6.552 | 26.487 | 5.702 | | 164 | THR CB | 2.095 | 28.518 | 4.818 |
| 158 | THR D | 6.479 | 27.335 | 7.977 | | 164 | THR CG2 | 2.397 | 27.610 | 6.001 |
| 159 | SER DG | 3.141 | 25.904 | 10.525 | 30 | 165 | VAL CA | −0.959 | 29.542 | 1.010 |
| 159 | SER CA | 4.835 | 25.210 | 8.855 | | 165 | VAL D | −2.929 | 30.132 | 2.280 |
| 159 | SER D | 3.339 | 23.281 | 9.030 | | 165 | VAL CB | −1.339 | 28.624 | −0.161 |
| 160 | GLY CA | 5.434 | 21.504 | 8.895 | | 165 | VAL CG2 | −0.210 | 27.716 | −0.699 |
| 160 | GLY D | 4.808 | 21.326 | 6.555 | | 166 | GLY CA | −2.945 | 32.778 | 1.626 |
| 161 | SER CA | 2.654 | 19.777 | 7.054 | | 166 | GLY D | −4.124 | 32.106 | −0.396 |
| 161 | SER D | 0.696 | 20.347 | 5.869 | 35 | 167 | TYR CA | −6.223 | 34.046 | 0.113 |
| 161 | SER DG | 1.854 | 18.028 | 8.585 | | 167 | TYR D | −5.474 | 36.283 | 0.084 |
| 162 | SER CA | 0.167 | 22.725 | 7.113 | | 167 | TYR CG | −7.791 | 32.984 | 1.709 |
| 162 | SER D | 1.533 | 23.840 | 5.394 | | 167 | TYR CD2 | −8.710 | 32.116 | 1.133 |
| 162 | SER DG | 0.184 | 23.091 | 9.480 | | 167 | TYR CE2 | −9.068 | 30.955 | 1.809 |
| 163 | SER CA | −0.611 | 24.750 | 3.990 | | 167 | TYR DK | −6.880 | 29.481 | 3.658 |
| 163 | SER D | −1.078 | 26.548 | 5.504 | 40 | 168 | PRO CG | −6.943 | 36.376 | −3.938 |
| 163 | SER DG | −1.992 | 25.718 | 2.331 | | 168 | PRO CB | −7.964 | 35.344 | −3.505 |
| 164 | THR CA | 0.609 | 28.340 | 4.312 | | 168 | PRO C | −6.398 | 33.336 | −3.270 |
| 164 | THR D | 0.485 | 30.502 | 3.278 | | 169 | GLY N | −5.086 | 33.193 | −3.189 |
| 164 | THR DG1 | 2.894 | 28.282 | 3.692 | | 169 | GLY C | −4.937 | 30.702 | −3.470 |
| 165 | VAL N | −0.513 | 28.742 | 2.190 | | 170 | LYS N | −5.402 | 30.579 | −2.255 |
| 165 | VAL C | −2.028 | 30.545 | 1.497 | | 170 | LYS C | −7.055 | 28.773 | −2.516 |
| 144 | ALA CB | −17.942 | 31.968 | −13.700 | 45 | 170 | LYS CB | −6.246 | 29.294 | −0.286 |
| 145 | SER CA | −16.682 | 34.917 | −16.786 | | 170 | LYS CD | −6.250 | 28.289 | 2.031 |
| 145 | SER D | −15.910 | 35.321 | −18.893 | | 170 | LYS CZ | −4.259 | 27.463 | 3.215 |
| 145 | SER DG | −15.882 | 36.955 | −15.849 | | 171 | TYR CA | −9.012 | 29.043 | −3.859 |
| 146 | GLY CA | −13.619 | 33.799 | −18.675 | | 171 | TYR D | −7.760 | 28.714 | −5.928 |
| 146 | GLY D | −11.420 | 34.386 | −19.266 | | 171 | TYR CG | −10.497 | 30.984 | −3.047 |
| 147 | VAL CA | −10.874 | 35.856 | −16.912 | 50 | 171 | TYR CD2 | −10.456 | 32.374 | −3.026 |
| 147 | VAL D | −10.171 | 33.991 | −15.486 | | 171 | TYR CE3 | −10.941 | 33.088 | −1.936 |
| 147 | VAL CG1 | −8.896 | 37.803 | −15.570 | | 171 | TYR DH | −12.008 | 33.119 | 0.170 |
| 148 | VAL N | −8.583 | 35.018 | −16.603 | | 172 | PRO CA | −9.093 | 26.417 | −6.596 |
| 148 | VAL C | −7.157 | 34.907 | −14.701 | | 172 | PRO D | −8.525 | 26.784 | −8.881 |
| 148 | VAL CB | −6.273 | 34.126 | −16.950 | | 172 | PRO CG | −10.600 | 25.271 | −5.096 |
| 148 | VAL CG2 | −6.590 | 33.432 | −18.262 | 55 | 173 | SER N | −10.097 | 28.167 | −8.019 |
| 149 | VAL CA | −6.987 | 34.965 | −12.249 | | 173 | SER C | −9.025 | 29.773 | −9.595 |
| 149 | VAL D3 | −5.624 | 33.173 | −11.439 | | 173 | SER CB | −11.528 | 29.623 | −9.481 |
| 149 | VAL CG1 | −7.893 | 35.619 | −10.009 | | 174 | VAL N | −8.162 | 29.944 | −8.614 |
| 150 | VAL N | −4.732 | 35.301 | −11.404 | | 174 | VAL C | −5.754 | 30.131 | −9.068 |
| 150 | VAL C | −3.157 | 35.625 | −9.559 | | 174 | VAL CB | −6.899 | 31.775 | −7.596 |
| 150 | VAL CB | −2.274 | 35.305 | −11.951 | | 174 | VAL CG2 | −6.220 | 32.503 | −7.323 |
| 150 | VAL CG2 | −2.675 | 34.843 | −13.301 | 60 | 175 | ILE CA | −3.569 | 30.156 | −10.024 |
| 151 | ALA CA | −2.361 | 35.582 | −7.287 | | 175 | ILE D | −2.450 | 31.958 | −8.955 |
| 151 | ALA D | −0.618 | 33.889 | −6.904 | | 175 | ILE CG1 | −3.857 | 29.978 | −12.524 |
| 152 | ALA N | −0.490 | 35.907 | −5.822 | | 175 | ILE CD1 | −3.692 | 30.529 | −13.946 |
| 152 | ALA C | 0.304 | 34.320 | −4.158 | | 176 | ALA CA | −1.335 | 30.517 | −6.870 |
| 152 | ALA CB | 1.266 | 36.607 | −4.294 | | 176 | ALA D | 0.453 | 29.215 | −7.838 |
| 153 | ALA CA | 0.840 | 32.250 | −2.943 | 65 | 177 | VAL N | 0.864 | 31.410 | −7.180 |
| 153 | ALA D | 0.317 | 32.192 | −0.599 | | 177 | VAL C | 3.225 | 31.693 | −6.473 |

| | | | | | | | | | | |
|---|---|---|---|---|---|---|---|---|---|---|
| 177 | VAL CB | 2.439 | 32.607 | −8.755 | | 183 | SER C | 17.581 | 27.614 | −9.547 |
| 177 | VAL CG2 | 1.374 | 32.552 | −9.845 | | 183 | SER CB | 19.256 | 28.323 | −8.007 |
| 178 | GLY CA | 5.168 | 30.703 | −5.339 | | 183 | SER DG | 20.589 | 28.615 | −8.251 |
| 178 | GLY D | 6.499 | 31.435 | −7.286 | | 184 | ASN CA | 15.144 | 27.317 | −9.580 |
| 179 | ALA CA | 8.715 | 32.037 | −5.859 | | 184 | ASN D | 14.138 | 25.759 | −8.097 |
| 179 | ALA C | 10.198 | 30.481 | −4.719 | | 184 | ASN CG | 14.990 | 26.998 | −12.076 |
| 180 | VAL N | 10.659 | 31.162 | −6.885 | | 184 | ASN ND2 | 15.352 | 26.210 | −13.076 |
| 180 | VAL C | 13.048 | 31.585 | −7.171 | | 185 | GLN CA | 15.276 | 26.646 | −5.835 |
| 180 | VAL CB | 12.075 | 29.514 | −8.166 | | 185 | GLN D | 14.159 | 28.726 | −5.385 |
| 180 | VAL CG2 | 11.675 | 30.129 | −9.500 | | 185 | GLN CG | 16.539 | 26.242 | −3.614 |
| 181 | ASP CA | 15.451 | 32.108 | −7.039 | | 185 | GLN DE1 | 18.864 | 25.799 | −4.061 |
| 181 | ASP D | 15.339 | 31.090 | −3.292 | | 186 | ARG N | 13.278 | 26.958 | −4.448 |
| 181 | ASP CG | 17.120 | 30.534 | −5.971 | | 186 | ARG C | 12.780 | 28.782 | −2.866 |
| 181 | ASP DD2 | 17.680 | 30.256 | −4.887 | | 186 | ARG CB | 11.215 | 26.843 | −3.116 |
| 182 | SER CA | 17.622 | 32.214 | −10.191 | | 186 | ARG CD | 9.497 | 26.337 | −1.465 |
| 182 | SER D | 18.365 | 30.452 | −11.670 | | 186 | ARG CZ | 9.961 | 26.879 | 1.059 |
| 182 | SER DG | 18.016 | 34.561 | −10.475 | | 186 | ARG NH2 | 10.966 | 26.321 | 1.783 |
| 183 | SER CA | 18.716 | 28.645 | −9.444 | | 187 | ALA CA | 12.728 | 31.064 | −1.895 |
| 183 | SER D | 17.859 | 26.415 | −9.397 | | 187 | ALA D | 11.158 | 30.043 | −0.387 |
| 165 | VAL CG1 | −1.947 | 29.357 | −1.374 | | 188 | SER N | 13.051 | 30.770 | 0.549 |
| 166 | GLY N | −1.910 | 31.821 | 1.129 | | 188 | SER C | 11.356 | 30.847 | 2.412 |
| 166 | GLY C | −4.098 | 32.859 | 0.617 | | 188 | SER CB | 13.767 | 30.456 | 2.938 |
| 167 | TYR N | −5.054 | 33.730 | 0.970 | | 189 | PHE N | 10.943 | 32.010 | 1.974 |
| 167 | TYR C | −5.993 | 35.389 | −0.606 | | 189 | PHE C | 8.499 | 32.198 | 1.609 |
| 167 | TYR CB | −7.464 | 34.252 | 0.964 | | 189 | PHE CB | 9.787 | 34.217 | 2.243 |
| 167 | TYR CD1 | −7.208 | 32.703 | 2.947 | | 189 | PHE CD1 | 9.147 | 34.830 | −0.121 |
| 167 | TYR CE1 | −7.567 | 31.528 | 3.615 | | 189 | PHE CE1 | 9.483 | 35.187 | −1.411 |
| 167 | TYR CA | −8.486 | 30.671 | 3.046 | | 189 | PHE CZ | 10.786 | 35.586 | −1.725 |
| 168 | PRO N | −6.380 | 35.499 | −1.850 | | 190 | SER CA | 7.626 | 31.096 | −0.391 |
| 168 | PRO CD | −6.273 | 36.752 | −2.624 | | 190 | SER D | 7.034 | 29.083 | 0.866 |
| 168 | PRO CA | −7.134 | 34.457 | −2.560 | | 190 | SER DG | 7.136 | 30.337 | −2.618 |
| 168 | PRO D | −7.097 | 32.520 | −3.912 | | 191 | SER CA | 4.341 | 29.686 | 0.987 |
| 169 | GLY CA | −4.446 | 32.077 | −3.927 | | 191 | SER D | 4.543 | 28.268 | −0.995 |
| 169 | GLY D | −4.880 | 29.733 | −4.249 | | 191 | SER DG | 2.729 | 31.285 | 1.954 |
| 170 | LYS CA | −5.856 | 29.263 | −1.745 | | 192 | VAL CA | 3.629 | 25.932 | 0.391 |
| 170 | LYS D | −7.308 | 27.554 | −2.524 | | 192 | VAL D | 1.559 | 25.698 | 1.598 |
| 170 | LYS CG | −5.795 | 28.106 | 0.585 | | 192 | VAL CG1 | 6.144 | 25.727 | 0.722 |
| 170 | LYS CE | −5.731 | 27.271 | 3.029 | | 193 | GLY N | 1.938 | 24.172 | 0.047 |
| 171 | TYR N | −7.838 | 29.616 | −3.148 | | 193 | GLY C | 0.081 | 23.029 | −0.901 |
| 171 | TYR C | −8.603 | 28.309 | −5.113 | | 194 | PRO N | −1.023 | 22.289 | −0.722 |
| 171 | TYR CB | −9.962 | 30.224 | −4.242 | | 194 | PRO C | −2.237 | 22.605 | −2.914 |
| 171 | TYR CD1 | −11.060 | 30.303 | −1.982 | | 194 | PRO CB | −2.769 | 20.783 | −1.210 |
| 171 | TYR CE1 | −11.520 | 31.003 | −0.867 | | 194 | PRO CD | −1.633 | 21.954 | 0.578 |
| 171 | TYR CZ | −11.528 | 32.398 | −0.886 | | 195 | GLU CA | −3.145 | 24.850 | −3.252 |
| 172 | PRO N | −9.297 | 27.204 | −5.374 | | 195 | GLU D | −2.516 | 26.398 | −4.936 |
| 172 | PRO C | −9.233 | 27.156 | −7.909 | | 195 | GLU CG | −4.942 | 25.134 | −1.435 |
| 172 | PRO CB | −10.167 | 25.329 | −6.513 | | 195 | GLU DE1 | −3.110 | 24.960 | 0.165 |
| 172 | PRO CD | −10.364 | 26.669 | −4.514 | | 196 | LEU N | −0.829 | 25.264 | −3.870 |
| 173 | SER CA | −10.220 | 28.818 | −9.330 | | 196 | LEU C | 0.228 | 25.376 | −6.059 |
| 173 | SER D | −8.966 | 30.233 | −10.742 | | 196 | LEU CB | 1.540 | 25.739 | −3.854 |
| 173 | SER DG | −11.595 | 30.546 | −8.406 | | 196 | LEU CD1 | 2.739 | 27.716 | −4.639 |
| 174 | VAL CA | −7.053 | 30.891 | −8.85 | | 197 | ASP N | 0.140 | 26.208 | −7.093 |
| 174 | VAL D | −5.612 | 29.152 | −8.344 | | 197 | ASP C | 1.307 | 25.738 | −9.293 |
| 174 | VAL CG1 | −5.796 | 32.837 | −8.617 | | 197 | ASP CB | −1.067 | 26.598 | −9.191 |
| 175 | ILE N | −4.911 | 30.729 | −9.885 | | 197 | ASP DD1 | −2.807 | 25.155 | 8.354 |
| 175 | ILE C | −2.714 | 30.736 | −8.894 | | 198 | VAL N | 2.013 | 26.889 | −9.344 |
| 175 | ILE CB | −2.953 | 30.524 | −11.419 | | 198 | VAL C | 4.157 | 27.950 | −9.514 |
| 175 | ILE CG2 | −1.451 | 30.089 | −11.512 | | 198 | VAL CB | 2.894 | 27.476 | −11.637 |
| 176 | ALA N | −2.220 | 30.028 | −7.925 | | 198 | VAL CG2 | 2.337 | 28.919 | −11.484 |
| 176 | ALA C | 0.120 | 30.301 | −7.310 | | 199 | MET CA | 6.439 | 28.802 | −9.498 |
| 176 | ALA CB | −1.639 | 29.838 | −5.541 | | 199 | MET D | 6.696 | 29.518 | −11.793 |
| 177 | VAL CA | 2.261 | 31.534 | −7.656 | | 199 | MET CG | 7.365 | 26.849 | −8.139 |
| 177 | VAL D | 3.178 | 32.657 | −5.721 | | 199 | MET CE | 8.227 | 27.755 | −5.587 |
| 177 | VAL CG1 | 3.842 | 32.667 | −9.392 | | 200 | ALA CA | 7.991 | 31.929 | −11.055 |
| 178 | GLY N | 4.077 | 30.654 | −6.358 | | 200 | ALA D | 9.127 | 32.524 | −9.060 |
| 178 | GLY C | 6.446 | 31.233 | −6.074 | | 184 | ASN N | 16.373 | 28.094 | −9.602 |
| 179 | ALA N | 7.512 | 31.447 | −5.287 | | 184 | ASN C | 14.931 | 26.720 | −8.197 |
| 179 | ALA C | 9.939 | 31.099 | −5.779 | | 184 | ASN CB | 15.014 | 26.341 | −10.722 |
| 179 | ALA CB | 9.025 | 33.251 | −4.973 | | 184 | ASN DD1 | 14.700 | 28.184 | −12.277 |
| 180 | VAL CA | 11.970 | 30.482 | −6.981 | | 185 | GLN N | 15.542 | 27.247 | −7.159 |
| 180 | VAL D | 12.712 | 32.491 | −7.627 | | 185 | GLN C | 14.200 | 27.494 | −5.203 |
| 180 | VAL CG1 | 11.271 | 28.251 | −7.855 | | 185 | GLN CB | 16.599 | 26.568 | −5.101 |
| 181 | ASP N | 14.267 | 31.203 | −6.800 | | 185 | GLN DC | 18.011 | 26.102 | −3.206 |
| 181 | ASP C | 15.942 | 31.804 | −8.462 | | 185 | GLN NE2 | 18.266 | 26.386 | 1.934 |
| 181 | ASP CB | 16.446 | 31.921 | −5.914 | | 186 | ARG CA | 12.185 | 27.774 | −3.841 |
| 181 | ASP DD1 | 17.105 | 29.785 | −6.972 | | 186 | ARG D | 13.698 | 28.384 | −2.093 |
| 182 | SER N | 17.087 | 32.386 | −8.847 | | 186 | ARG CG | 10.214 | 27.471 | −2.161 |
| 182 | SER C | 18.153 | 30.817 | −10.494 | | 186 | ARG NE | 9.866 | 26.333 | −0.117 |
| 182 | SER CB | 18.678 | 33.313 | −10.464 | | 186 | ARG NH1 | 9.367 | 27.880 | 1.658 |
| 183 | SER N | 18.258 | 30.042 | −9.423 | | 187 | ALA N | 12.294 | 30.009 | −2.853 |

-continued

| | | | | |
|---|---|---|---|---|
| 187 | ALA C | 12.262 | 30.604 | −0.517 |
| 187 | ALA CB | 12.144 | 32.402 | −2.344 |
| 188 | SER CA | 12.671 | 30.286 | 1.868 |
| 188 | SER D | 10.740 | 30.111 | 3.212 |
| 188 | SER DG | 14.137 | 31.826 | 2.841 |
| 189 | PHE CA | 9.697 | 32.688 | 2.418 |
| 189 | PHE D | 7.389 | 32.556 | 2.011 |
| 189 | PHE CG | 10.117 | 34.696 | 0.867 |
| 189 | PHE CD2 | 11.415 | 35.116 | 0.567 |
| 189 | PHE CE2 | 11.769 | 35.545 | −1.701 |
| 190 | SER N | 8.703 | 31.526 | 0.499 |
| 190 | SER C | 6.663 | 30.162 | 0.328 |
| 190 | SER CB | 8.181 | 30.590 | −1.708 |
| 191 | SER N | 5.388 | 30.551 | 0.326 |
| 191 | SER C | 4.261 | 28.330 | 0.223 |
| 191 | SER CB | 3.015 | 30.411 | 0.911 |
| 192 | VAL N | 3.756 | 27.310 | 0.928 |
| 192 | VAL C | 2.254 | 25.291 | 0.686 |
| 192 | VAL CB | 4.781 | 25.127 | 1.088 |
| 192 | VAL CG2 | 4.617 | 25.104 | 2.592 |
| 193 | GLY CA | 0.629 | 23.564 | 0.410 |
| 193 | GLY D | 0.530 | 23.244 | −2.015 |
| 194 | PRO CA | −1.662 | 21.651 | −1.873 |
| 194 | PRO D | −2.403 | 22.244 | −4.085 |
| 194 | PRO CG | −2.311 | 20.622 | 0.213 |
| 195 | GLU N | −2.522 | 23.793 | −2.439 |
| 195 | GLU C | −2.095 | 25.631 | −4.058 |
| 195 | GLU CB | −4.043 | 25.786 | −2.470 |
| 195 | GLU CD | −4.315 | 24.860 | −0.100 |
| 195 | GLU DE2 | −5.138 | 24.520 | 0.785 |
| 196 | LEU CA | 0.241 | 25.929 | −4.664 |
| 196 | LEU D | 0.305 | 24.121 | −6.153 |
| 196 | LEU CG | 2.770 | 26.178 | −4.643 |
| 196 | LEU CD2 | 4.027 | 25.721 | −3.911 |
| 197 | ASP CA | 0.032 | 25.774 | −8.480 |
| 197 | ASP D | 1.655 | 24.734 | −9.914 |
| 197 | ASP CG | −2.406 | 26.351 | −8.549 |
| 197 | ASP DD2 | −3.035 | 27.327 | −8.088 |
| 198 | VAL CA | 3.206 | 26.970 | −10.209 |
| 198 | VAL D | 3.752 | 28.699 | −8.587 |
| 198 | VAL CG1 | 1.930 | 26.726 | −12.537 |
| 199 | MET N | 5.374 | 27.916 | −10.016 |
| 199 | MET C | 6.845 | 29.810 | −10.578 |
| 199 | MET CB | 7.660 | 27.970 | −9.077 |
| 199 | MET SD | 6.755 | 27.449 | −6.568 |
| 200 | ALA N | 7.426 | 30.942 | −10.103 |
| 200 | ALA C | 9.088 | 32.666 | −10.272 |
| 200 | ALA CB | 6.932 | 32.870 | −11.638 |
| 201 | PRO N | 9.927 | 33.455 | −10.95 |
| 201 | PRO C | 10.450 | 35.127 | −9.23 |
| 201 | PRO CB | 11.817 | 34.723 | −11.400 |
| 201 | PRO CD | 9.941 | 33.616 | −12.405 |
| 202 | GLY CA | 10.473 | 36.204 | −7.044 |
| 202 | GLY D | 11.352 | 37.124 | −4.979 |
| 203 | VAL CA | 13.948 | 36.929 | −5.716 |
| 203 | VAL D | 15.133 | 37.731 | −7.593 |
| 203 | VAL CG1 | 16.096 | 36.106 | −4.612 |
| 204 | SER N | 14.865 | 39.182 | −5.859 |
| 204 | SER C | 15.067 | 40.619 | −7.873 |
| 204 | SER CB | 17.087 | 39.976 | −6.326 |
| 205 | ILE N | 13.771 | 40.965 | −8.008 |
| 205 | ILE C | 13.207 | 42.749 | −9.478 |
| 205 | ILE CB | 11.532 | 40.833 | −9.144 |
| 205 | ILE CG2 | 10.899 | 41.281 | −10.467 |
| 206 | GLN N | 13.956 | 43.095 | −10.489 |
| 206 | GLN C | 13.002 | 44.978 | −11.630 |
| 206 | GLN CB | 15.455 | 44.708 | −11.740 |
| 206 | GLN CD | 17.285 | 45.145 | −10.007 |
| 206 | GLN NE2 | 16.556 | 46.260 | −9.857 |
| 207 | SER CA | 11.217 | 46.571 | −11.987 |
| 207 | SER D | 11.919 | 48.657 | −11.004 |
| 207 | SER DG | 8.993 | 46.056 | −12.613 |
| 208 | THR CG2 | 9.171 | 50.339 | −14.754 |
| 208 | THR CB | 8.620 | 50.415 | −13.357 |
| 208 | THR C | 9.197 | 50.488 | −10.803 |
| 209 | LEU N | 9.656 | 51.613 | −10.228 |
| 209 | LEU C | 8.673 | 53.610 | −9.262 |
| 209 | LEU CB | 10.335 | 52.192 | −7.958 |
| 209 | LEU CD1 | 11.968 | 51.114 | −6.472 |
| 210 | PRO N | 7.790 | 54.139 | −8.444 |
| 210 | PRO C | 8.383 | 56.573 | −8.639 |
| 210 | PRO CB | 6.302 | 55.733 | 7.517 |
| 210 | PRO CD | 7.193 | 53.491 | −7.271 |
| 211 | GLY CA | 9.069 | 58.765 | −9.410 |
| 211 | GLY D | 11.176 | 59.005 | −10.259 |
| 212 | ASN CA | 10.903 | 57.422 | −12.643 |
| 212 | ASN D | 13.188 | 57.181 | −12.420 |
| 212 | ASN CG | 11.803 | 58.185 | −14.814 |
| 212 | ASN ND2 | 12.273 | 59.159 | −15.576 |
| 213 | LYS CA | 12.810 | 54.946 | −10.537 |
| 213 | LYS D | 11.775 | 53.039 | −11.613 |
| 213 | LUS CG | 13.206 | 56.694 | −8.767 |
| 213 | LYS CE | 14.105 | 58.218 | −6.870 |
| 214 | TYR N | 13.681 | 52.703 | −10.444 |
| 214 | TYR C | 14.383 | 50.600 | −9.489 |
| 214 | TYR CB | 14.641 | 50.981 | −11.984 |
| 214 | TYR CD1 | 14.689 | 52.847 | −13.678 |
| 214 | TYR CE1 | 14.230 | 53.475 | −14.814 |
| 214 | TYR CZ | 13.204 | 52.895 | −15.550 |
| 215 | GLY N | 14.058 | 49.347 | −9.158 |
| 215 | GLY C | 14.130 | 47.325 | −7.749 |
| 216 | ALA N | 14.810 | 46.638 | −6.831 |
| 216 | ALA C | 13.682 | 44.922 | −5.512 |
| 216 | ALA CB | 15.715 | 44.354 | −6.887 |
| 217 | TYR CA | 11.964 | 43.488 | −4.440 |
| 217 | TYR D | 12.202 | 41.442 | −5.656 |
| 217 | TYR CG | 10.117 | 45.291 | −4.214 |
| 217 | TYR CD2 | 9.016 | 45.933 | −4.785 |
| 217 | TYR CE2 | 8.654 | 47.219 | −4.381 |
| 217 | TYR DH | 8.953 | 49.160 | −2.988 |
| 218 | ASN CA | 11.640 | 39.943 | −3.227 |
| 201 | PRO CA | 11.013 | 34.130 | −10.298 |
| 201 | PRO D | 9.579 | 35.907 | −9.682 |
| 201 | PRO CG | 11.392 | 34.040 | −12.678 |
| 202 | GLY N | 10.925 | 35.204 | −8.021 |
| 202 | GLY C | 11.580 | 36.658 | −6.115 |
| 203 | VAL N | 12.815 | 36.503 | −6.613 |
| 203 | VAL C | 14.706 | 38.017 | −6.469 |
| 203 | VAL CB | 14.814 | 35.688 | −5.351 |
| 203 | VAL CG2 | 14.079 | 34.741 | −4.378 |
| 204 | SER CA | 15.572 | 40.281 | −6.487 |
| 204 | SER D | 15.786 | 40.685 | −8.889 |
| 204 | SER DG | 17.752 | 41.186 | −6.672 |
| 205 | ILE CA | 13.069 | 41.234 | −9.225 |
| 205 | ILE D | 12.675 | 43.498 | −8.648 |
| 205 | ILE CG1 | 11.436 | 39.336 | −8.810 |
| 205 | ILE CD1 | 12.257 | 38.412 | −9.771 |
| 206 | GLN CA | 14.204 | 44.517 | −10.834 |
| 206 | GLN D | 12.669 | 44.318 | −12.621 |
| 206 | GLN CG | 16.684 | 44.163 | −10.980 |
| 206 | GLN DE1 | 18.328 | 44.936 | −9.353 |
| 207 | SER N | 12.359 | 46.064 | −11.214 |
| 207 | SER C | 11.089 | 48.093 | −11.749 |
| 207 | SER DB | 9.918 | 45.853 | −11.569 |
| 208 | THR N | 10.054 | 48.664 | −12.326 |
| 208 | THR DG1 | 7.570 | 49.414 | −13.144 |
| 208 | THR CA | 9.675 | 50.092 | −12.173 |
| 208 | THR D | 8.423 | 49.807 | −10.049 |
| 209 | LEU CA | 9.192 | 52.158 | −8.959 |
| 209 | LEU D | 9.140 | 54.227 | −10.222 |
| 209 | LEU CG | 10.804 | 50.816 | −8.416 |
| 209 | LEU CD1 | 9.607 | 50.282 | −6.649 |
| 210 | PRO CA | 7.273 | 55.517 | −8.649 |
| 210 | PRO D | 9.491 | 56.4445 | −8.104 |
| 210 | PRO CG | 6.004 | 54.379 | −6.944 |
| 211 | GLY N | 8.077 | 57.665 | −9.355 |
| 211 | GLY C | 10.094 | 58.454 | −10.490 |
| 212 | ASN N | 9.851 | 57.770 | −11.587 |
| 212 | ASN C | 12.059 | 56.753 | −12.056 |
| 212 | ASN CB | 11.224 | 58.595 | −13.499 |
| 212 | ASN DD1 | 11.853 | 57.054 | −15.323 |
| 213 | LYS N | 11.803 | 55.749 | −11.247 |
| 213 | LYS C | 12.668 | 53.459 | −10.866 |
| 213 | LYS CB | 12.769 | 55.241 | −9.059 |
| 213 | LYS CD | 13.246 | 57.030 | −7.312 |
| 213 | LYS NZ | 15.048 | 58.705 | −7.901 |
| 214 | TYR CA | 13.800 | 51.246 | −10.722 |
| 214 | TYR D | 15.211 | 51.253 | −8.817 |
| 214 | TYR CG | 14.130 | 51.621 | −13.246 |
| 214 | TYR DC2 | 13.129 | 51.065 | −14.014 |

| | | | | |
|---|---|---|---|---|
| 214 | TYR CE2 | 12.654 | 51.669 | −15.178 |
| 214 | TYR DH | 12.756 | 53.458 | −16.696 |
| 215 | GLY CA | 14.622 | 48.772 | −7.905 |
| 215 | GLY D | 13.249 | 46.917 | −8.521 |
| 216 | ALA CA | 14.454 | 45.203 | −6.781 |
| 216 | ALA D | 13.948 | 45.527 | −4.475 |
| 217 | TYR N | 12.758 | 43.952 | −5.575 |
| 217 | TYR C | 12.033 | 41.928 | −4.547 |
| 217 | TYR CB | 10.473 | 43.862 | −4.570 |
| 217 | TYR CD1 | 10.846 | 45.991 | −3.236 |
| 217 | TYR CE1 | 10.459 | 47.267 | −2.790 |
| 217 | TYR CZ | 9.358 | 47.882 | −3.391 |
| 218 | ASN N | 11.750 | 41.386 | −3.391 |
| 218 | ASN C | 10.204 | 39.636 | −2.749 |
| 218 | ASN D | 9.763 | 40.347 | −1.81 |
| 218 | ASN CG | 14.031 | 39.566 | −2.34 |
| 218 | ASN ND2 | 14.660 | 39.644 | −1.165 |
| 219 | GLY CA | 8.382 | 38.130 | −2.649 |
| 219 | GLY D | 7.873 | 37.500 | −4.876 |
| 220 | THR CA | 5.697 | 35.936 | −4.179 |
| 220 | THR D | 4.417 | 36.742 | −3.958 |
| 220 | THR DG1 | 4.136 | 35.543 | −2.451 |
| 221 | SER N | 4.738 | 38.238 | −4.303 |
| 221 | SER C | 4.760 | 39.641 | −6.383 |
| 221 | SER CB | 3.323 | 40.383 | −4.546 |
| 222 | MET N | 6.060 | 39.389 | −6.485 |
| 222 | MET SD | 7.768 | 41.533 | −4.993 |
| 222 | MET CB | 8.351 | 40.015 | −7.218 |
| 222 | MET C | 6.877 | 38.435 | −8.567 |
| 223 | ALA N | 6.554 | 37.246 | −8.041 |
| 223 | ALA C | 5.200 | 36.068 | −9.707 |
| 223 | ALA CB | 6.509 | 34.807 | −7.923 |
| 224 | SER CA | 2.758 | 36.488 | −9.700 |
| 224 | SER D | 2.145 | 36.593 | −12.057 |
| 224 | SER DG | 0.492 | 36.899 | −9.157 |
| 225 | PRO CA | 3.095 | 39.130 | −12.439 |
| 225 | PRO D | 3.406 | 38.650 | −14.804 |
| 225 | PRO CG | 4.411 | 40.402 | −10.764 |
| 226 | HIS N | 4.769 | 37.626 | −13.299 |
| 226 | HIS C | 4.418 | 35.947 | −15.061 |
| 226 | HIS CB | 6.608 | 36.046 | −13.765 |
| 226 | HIS ND1 | 8.048 | 37.488 | −12.170 |
| 226 | HIS CE1 | 9.270 | 38.052 | −12.236 |
| 227 | VAL N | 3.593 | 35.366 | −14.199 |
| 227 | VAL C | 1.479 | 35.197 | −15.421 |
| 227 | VAL CB | 2.103 | 33.444 | −13.619 |
| 227 | VAL CG2 | 3.204 | 32.665 | −12.891 |
| 228 | ALA CA | 0.011 | 37.109 | −15.517 |
| 228 | ALA D | −0.253 | 37.435 | −17.828 |
| 229 | GLY N | 1.791 | 38.028 | −16.941 |
| 229 | GLY C | 2.420 | 37.197 | −19.187 |
| 230 | ALA C | 2.711 | 35.988 | −18.646 |
| 230 | ALA C | 1.424 | 34.500 | −20.153 |
| 230 | ALA CB | 3.298 | 33.624 | −18.709 |
| 231 | ALA CA | −1.010 | 34.416 | −19.744 |
| 231 | ALA D | −1.909 | 35.056 | −21.852 |
| 232 | ALA N | −0.778 | 36.657 | −20.721 |
| 232 | ALA C | −0.281 | 37.284 | −23.078 |
| 232 | ALA CB | −0.742 | 39.121 | −21.377 |
| 233 | LEU CA | 1.617 | 36.293 | −24.209 |
| 233 | LEU D | 0.696 | 35.231 | −26.111 |
| 233 | LEU CG | 3.996 | 36.994 | −23.453 |
| 233 | LEU CD2 | 4.241 | 37.853 | −24.680 |
| 234 | ILE CD1 | 0.306 | 30.664 | −21.657 |
| 234 | ILE CB | −0.811 | 32.014 | −23.570 |
| 234 | ILE CA | −0.406 | 33.076 | −24.644 |
| 234 | ILE D | −1.883 | 33.144 | −26.544 |
| 235 | LEU CA | −3.596 | 35.028 | −25.423 |
| 235 | LEU D | −4.109 | 35.914 | −27.589 |
| 235 | LEU CG | −5.140 | 34.899 | −23.342 |
| 235 | LEU CD2 | −6.252 | 34.138 | −24.120 |
| 236 | SER CA | −1.764 | 37.237 | −27.986 |
| 236 | SER D | −1.746 | 36.634 | −30.290 |
| 236 | SER DG | 0.599 | 37.571 | −27.582 |
| 237 | LYS CA | −0.846 | 34.085 | −29.95 |
| 237 | LYS D | −2.378 | 32.951 | −31.44 |
| 237 | LYS CG | 0.677 | 32.240 | −30.71 |
| 218 | ASN CB | 12.553 | 39.340 | −2.154 |
| 218 | ASN DD1 | 14.612 | 39.709 | −3.422 |
| 219 | GLY N | 9.670 | 38.534 | −3.289 |
| 219 | GLY C | 7.570 | 37.384 | 3.681 |
| 220 | THR N | 6.561 | 36.638 | −3.205 |
| 220 | THR C | 4.879 | 37.044 | −4.864 |
| 220 | THR CB | 4.825 | 34.819 | −3.526 |
| 220 | THR CG2 | 5.704 | 33.696 | −2.900 |
| 221 | SER CA | 3.984 | 39.201 | −5.169 |
| 221 | SER D | 4.117 | 40.208 | −7.277 |
| 221 | SER DG | 3.435 | 40.282 | −3.149 |
| 222 | MET CE | 6.471 | 42.771 | −5.173 |
| 222 | MET CG | 8.506 | 41.399 | −6.602 |
| 222 | MET CA | 6.916 | 39.670 | −7.638 |
| 222 | MET D | 7.084 | 38.567 | −9.775 |
| 223 | ALA CA | 6.469 | 36.020 | −8.885 |
| 223 | ALA D | 5.133 | 35.948 | −10.929 |
| 224 | SER N | 4.076 | 36.360 | −9.038 |
| 224 | SER C | 2.661 | 37.161 | −11.039 |
| 224 | SER CB | 1.801 | 36.995 | −8.603 |
| 225 | PRO N | 3.156 | 38.411 | −11.159 |
| 225 | PRO C | 3.764 | 38.469 | −13.626 |
| 225 | PRO CB | 3.653 | 40.511 | −12.054 |
| 225 | PRO CD | 3.735 | 39.224 | −10.054 |
| 226 | HIS CA | 5.446 | 36.879 | −14.362 |
| 226 | HIS D | 4.425 | 35.809 | −16.293 |
| 226 | HIS CG | 7.814 | 36.859 | −13.358 |
| 226 | HIS CD2 | 8.883 | 37.118 | −14.167 |
| 226 | HIS CE2 | 9.771 | 37.866 | −13.443 |
| 227 | VAL CA | 2.583 | 34.388 | −14.727 |
| 227 | VAL D | 1.018 | 34.773 | −16.490 |
| 227 | VAL CG1 | 1.076 | 32.476 | −14.246 |
| 228 | ALA N | 1.003 | 36.242 | −14.814 |
| 228 | ALA C | 0.543 | 37.539 | −16.868 |
| 228 | ALA CB | −0.307 | 38.353 | −14.668 |
| 229 | GLY CA | 2.352 | 38.408 | −18.239 |
| 229 | GLY D | 2.189 | 37.375 | −20.384 |
| 230 | ALA CA | 2.794 | 34.801 | −19.546 |
| 230 | ALA D | 1.380 | 34.205 | −21.343 |
| 231 | ALA N | 0.385 | 34.623 | −19.328 |
| 231 | ALA C | −1.256 | 35.423 | −20.864 |
| 231 | ALA CB | −1.932 | 34.664 | −18.549 |
| 232 | ALA CA | −1.013 | 37.663 | −21.792 |
| 232 | ALA D | −0.841 | 37.501 | −24.187 |
| 233 | LEU N | 0.935 | 36.726 | −22.967 |
| 233 | LEY C | 0.821 | 35.169 | −24.880 |
| 233 | LEU CB | 3.063 | 35.877 | −23.907 |
| 233 | LEU CD1 | 5.259 | 36.342 | −22.921 |
| 234 | ILE N | 0.357 | 34.199 | −24.047 |
| 234 | ILE CG1 | 0.454 | 31.223 | −23.105 |
| 234 | ILE CG2 | −1.803 | 30.900 | −24.091 |
| 234 | ILE C | −1.621 | 33.597 | −25.434 |
| 235 | LEU N | −2.390 | 34.465 | −24.779 |
| 235 | LEU C | −3.258 | 35.843 | −26.672 |
| 235 | LEU CB | −4.432 | 35.765 | −24.378 |
| 235 | LEU CD1 | −5.652 | 35.683 | −22.145 |
| 236 | SER N | −2.094 | 36.438 | −26.798 |
| 236 | SER C | −1.491 | 36.292 | −29.144 |
| 236 | SER CB | −0.633 | 38.234 | −27.733 |
| 237 | LYS N | −1.046 | 35.067 | −28.882 |
| 237 | LYS C | −2.113 | 33.277 | −30.268 |
| 237 | LYS CB | 0.272 | 33.112 | −29.551 |
| 237 | LYS CD | 2.020 | 31.535 | −30.442 |
| 237 | LYS CE | 2.345 | 30.762 | −31.7 |
| 238 | HIS N | −2.951 | 32.989 | −29. |
| 238 | HIS C | −5.334 | 32.699 | −28.691 |
| 238 | HIS CB | −3.948 | 30.862 | −28.511 |
| 238 | HIS ND1 | −1.707 | 29.679 | −28.835 |
| 238 | HIS CE1 | −1.086 | 28.851 | −29.642 |
| 239 | PRO N | −5.848 | 33.917 | −29.365 |
| 239 | PRO C | −8.204 | 34.052 | −28.532 |
| 239 | PRO CB | −7.018 | 35.977 | −29.713 |
| 239 | PRO CD | −5.436 | 34.439 | −30.668 |
| 240 | ASN CA | −9.529 | 32.041 | −29.216 |
| 240 | ASN D | −10.540 | 30.610 | −27.576 |
| 240 | ASN CG | −7.971 | 30.827 | −30.889 |
| 240 | ASN ND2 | −7.670 | 29.509 | −30.986 |
| 241 | TRP CA | −8.304 | 30.124 | −26.120 |
| 241 | TRP D | −9.043 | 31.833 | −24.686 |
| 241 | TRP CG | −6.094 | 28.903 | −26.557 |
| 241 | TRP CD2 | −4.839 | 28.234 | −26.155 |
| 241 | TRP CE1 | −4.414 | 27.786 | −22.476 |
| 241 | TRP CZ2 | −3.195 | 26.786 | −27.174 |

| | | | | | | | | | |
|---|---|---|---|---|---|---|---|---|---|
| 241 | TRP CH2 | −2.470 | 26.873 | −26.005 | | 246 | VAL D | −2.705 | 28.227 | −19.361 |
| 242 | THR CA | −10.458 | 30.119 | −22.911 | | 246 | VAL CG1 | −3.544 | 31.272 | −20.027 |
| 242 | THR D | −8.335 | 29.674 | −21.937 | | 247 | ARG N | −4.767 | 28.240 | −18.462 |
| 242 | THR DG1 | −10.837 | 27.786 | −22.476 | | 247 | ARG C | −3.770 | 26.292 | −17.340 |
| 243 | ASN N | −9.946 | 30.659 | −20.611 | | 247 | ARG CB | 5.533 | 27.667 | −16.149 |
| 243 | ASN DD1 | −11.465 | 31.518 | −16.768 | | 247 | ARG CD | −6.056 | 27.179 | −13.793 |
| 243 | ASN CB | −9.708 | 31.530 | −18.332 | | 247 | ARG CZ | −5.893 | 26.866 | −11.315 |
| 243 | ASN C | −8.657 | 29.303 | −19.010 | | 247 | ARG NH2 | −5.177 | 26.428 | −10.270 |
| 244 | THR N | −9.564 | 28.362 | −19.283 | | 248 | SER CA | −4.039 | 24.131 | −18.426 |
| 244 | THR C | −8.133 | 26.393 | −19.802 | | 248 | SER D | −1.848 | 23.253 | −18.583 |
| 244 | THR CB | −10.665 | 26.098 | −19.494 | | 248 | SER DG | −6.146 | 23.090 | −18.532 |
| 244 | THR CG2 | −10.503 | 24.595 | −19.158 | | 249 | SER CA | −1.223 | 24.874 | −20.851 |
| 245 | GLN CA | −6.964 | 26.362 | −21.962 | | 249 | SER D | 1.026 | 24.705 | −20.049 |
| 245 | GLN D | −4.573 | 26.393 | −21.447 | | 249 | SER DG | −0.300 | 25.419 | −22.956 |
| 245 | GLN CG | −8.265 | 25.526 | −23.989 | | 250 | LEU CD2 | 1.824 | 29.814 | −18.222 |
| 245 | GLN DE1 | −9.306 | 26.769 | −25.727 | | 250 | LEU CG | 0.352 | 29.438 | −18.151 |
| 246 | VAL N | −5.697 | 28.304 | −21.218 | | 250 | LEU CA | 0.718 | 26.837 | −18.216 |
| 246 | VAL C | −3.936 | 28.462 | −19.467 | | 250 | LEU D | 2.283 | 25.421 | −17.032 |
| 246 | VAL CB | −4.779 | 30.555 | −20.621 | | 251 | GLU NE2 | −2.750 | 25.512 | −12.237 |
| 246 | VAL CG2 | −5.169 | 31.138 | −21.959 | | 251 | GLN CD | −2.345 | 24.550 | −13.034 |
| 247 | ARG CA | −4.380 | 27.714 | −17.168 | | 251 | GLN CB | −0.857 | 23.621 | −14.877 |
| 247 | ARG D | −2.705 | 25.985 | −16.764 | | 251 | GLN C | 0.959 | 22.664 | −16.361 |
| 247 | ARG CG | −4.987 | 27.095 | −14.852 | | 252 | ASN N | 0.633 | 22.394 | −17.390 |
| 247 | ARG NE | −5.440 | 26.757 | −12.546 | | 252 | ASN C | 2.394 | 21.359 | −18.991 |
| 247 | ARG NH1 | −7.064 | 27.484 | −11.210 | | 252 | ASN CB | 0.004 | 20.780 | −19.292 |
| 248 | SER N | −4.480 | 25.505 | −18.131 | | 252 | ASN DD1 | −0.836 | 19.355 | −17.502 |
| 248 | SER C | −2.657 | 24.086 | −19.073 | | 252 | ASN ND2 | −2.234 | 19.834 | −19.161 |
| 248 | SER CB | −5.034 | 23.408 | −19.372 | | 253 | THR CA | 4.256 | 22.717 | −19.713 |
| 249 | SER N | −2.500 | 24.853 | −20.136 | | 253 | THR D | 6.348 | 23.733 | −19.427 |
| 249 | SER C | −0.071 | 25.302 | −19.940 | | 253 | THR DG1 | 3.595 | 24.957 | −20.428 |
| 249 | SER CB | −1.369 | 25.758 | −22.068 | | 254 | THR N | 5.218 | 23.177 | −17.551 |
| 250 | LEU N | −0.289 | 26.333 | −19.160 | | 254 | THR C | 7.466 | 22.700 | −16.612 |
| 250 | LEU CD1 | −0.373 | 30.453 | −17.268 | | 254 | THR CB | 5.664 | 23.558 | −15.132 |
| 250 | LEU CB | 0.178 | 28.063 | −17.505 | | 254 | THR CG2 | 4.530 | 24.549 | −14.802 |
| 250 | LEU C | 1.092 | 25.694 | −17.265 | | 255 | THR CA | 9.771 | 22.594 | −15.817 |
| 251 | GLN N | 0.068 | 25.007 | −16.714 | | 255 | THR D | 9.439 | 22.786 | −13.474 |
| 251 | GLN DE1 | −2.819 | 23.424 | −12.935 | | 255 | THR DG1 | 11.082 | 23.709 | −17.321 |
| 251 | GLN CG | −1.218 | 24.814 | −13.994 | | 256 | LYS N | 9.606 | 20.702 | −14.314 |
| 251 | GLN CA | 0.381 | 23.941 | −15.745 | | 256 | LYS C | 10.522 | 20.333 | −12.063 |
| 251 | GLN D | 1.743 | 22.014 | −15.616 | | 256 | LYS CB | 9.024 | 18.590 | −13.249 |
| 252 | ASN CA | 1.082 | 21.206 | −18.282 | | 256 | LYS CD | 10.286 | 16.948 | −11.777 |
| 252 | ASN D | 2.809 | 20.442 | −19.768 | | 256 | LYS NZ | 9.243 | 14.869 | −11.054 |
| 252 | ASN CG | −1.036 | 19.926 | −18.571 | | 257 | LEU CA | 11.272 | 21.036 | −9.893 |
| 237 | LYS NZ | 3.525 | 29.848 | −31.596 | | 257 | LEU D | 12.096 | 20.565 | −7.732 |
| 238 | HIS CA | −4.168 | 32.163 | −29.379 | | 257 | LEU CG | 11.357 | 23.620 | −10.568 |
| 238 | HIS D | −5.713 | 32.584 | −27.562 | | 257 | LEU CD2 | 12.678 | 23.468 | −11.325 |
| 238 | HIS CG | −3.009 | 29.921 | −29.237 | | 258 | GLY CA | 10.602 | 18.793 | −6.879 |
| 238 | HIS CD2 | −3.137 | 29.258 | −30.394 | | 258 | GLY D | 8.283 | 18.956 | −7.202 |
| 238 | HIS NE2 | −1.948 | 28.600 | −30.599 | | 259 | ASP CA | 7.757 | 17.896 | −4.516 |
| 239 | PRO CA | −6.908 | 34.779 | −28.773 | | 259 | ASP D | 6.859 | 20.039 | −4.214 |
| 239 | PRO D | −8.949 | 34.519 | −27.662 | | 259 | ASP CG | 6.781 | 17.128 | −2.241 |
| 239 | PRO CG | −6.666 | 35.294 | −31.027 | | 259 | ASP DD2 | 7.098 | 16.299 | −1.321 |
| 240 | ASN N | −8.386 | 32.969 | −29.227 | | 260 | SER CA | 4.481 | 19.587 | −5.529 |
| 240 | ASN C | −9.508 | 31.180 | −27.980 | | 260 | SER D | 3.500 | 21.503 | −4.446 |
| 240 | ASN CB | −9.403 | 31.249 | −30.535 | | 260 | SER DG | 2.745 | 17.937 | −5.448 |
| 240 | ASN DD1 | −7.008 | 31.590 | −31.147 | | 261 | PHE CA | 3.831 | 20.468 | −1.885 |
| 241 | TRP N | −8.354 | 31.006 | −27.304 | | 261 | PHE D | 3.944 | 22.848 | −1.432 |
| 241 | TRP C | −9.106 | 30.638 | −24.936 | | 261 | PHE CG | 3.549 | 20.337 | 0.715 |
| 241 | TRP CB | −6.879 | 29.830 | −25.679 | | 261 | PHE CD2 | 4.401 | 21.060 | 1.558 |
| 241 | TRP CD1 | −6.338 | 28.433 | −27.818 | | 261 | PHE CE2 | 3.945 | 21.602 | 2.748 |
| 241 | TRP NE1 | −5.362 | 27.547 | −28.211 | | 262 | TYR N | 5.778 | 21.758 | −2.305 |
| 241 | TRP CE3 | −4.097 | 28.406 | −24.981 | | 262 | TYR C | 6.820 | 23.689 | −3.545 |
| 241 | TRP CZ3 | −2.912 | 27.667 | −24.943 | | 262 | TYR CB | 8.123 | 22.455 | −1.851 |
| 242 | THR N | −9.727 | 29.781 | −24.142 | | 262 | TYR CD1 | 8.084 | 20.484 | −0.364 |
| 242 | THR C | −9.469 | 30.176 | −21.747 | | 262 | TYR CE1 | 8.062 | 19.873 | 0.882 |
| 242 | THR CB | −11.579 | 29.032 | −22.675 | | 262 | TYR CZ | 8.069 | 20.672 | 2.018 |
| 242 | THR CG2 | −12.494 | 28.907 | −23.895 | | 263 | TYR N | 6.626 | 23.104 | −4.693 |
| 243 | ASN ND2 | −11.787 | 30.404 | −18.747 | | 263 | TYR C | 5.626 | 23.680 | −6.956 |
| 243 | ASN CG | −11.093 | 31.131 | −17.905 | | 263 | TYR CB | 7.928 | 22.768 | −6.681 |
| 243 | ASN CA | −9.053 | 30.731 | −19.444 | | 263 | TYR CD1 | 10.064 | 24.046 | −6.657 |
| 243 | ASN D | −7.593 | 29.136 | −18.440 | | 263 | TYR CE1 | 11.335 | 24.328 | −6.168 |
| 244 | THR CA | −9.381 | 26.934 | −19.059 | | 263 | TYR CZ | 11.838 | 23.618 | −5.106 |
| 244 | THR D | −7.324 | 25.757 | −19.111 | | 264 | GLY N | 4.471 | 23.161 | −6.516 |
| 244 | THR DG1 | −11.735 | 26.675 | −18.684 | | 264 | GLY C | 3.847 | 22.196 | −8.556 |
| 245 | GLN N | −8.082 | 26.716 | −21.073 | | 265 | LYS N | 3.436 | 22.477 | −9.754 |
| 245 | GLN C | −5.647 | 27.020 | −21.520 | | 265 | LYS C | 5.188 | 22.232 | −11.464 |
| 245 | GLN CB | −7.330 | 26.599 | −23.397 | | 265 | LYS CB | 2.755 | 22.071 | −12.044 |
| 245 | GLN CD | −8.493 | 25.873 | −25.428 | | 265 | LYS CD | 0.710 | 20.548 | −12.079 |
| 245 | GLN NE2 | −7.745 | 25.312 | −26.370 | | 265 | LYS CZ | −1.678 | 20.7557 | −12.489 |
| 246 | VAL CA | −4.477 | 29.040 | −20.770 | | 266 | GLY CA | 7.120 | 23.612 | −11.325 |

-continued

| | | | | |
|---|---|---|---|---|
| 266 | GLY D | 6.177 | 25.793 | −11.648 |
| 267 | LEU CA | 8.490 | 26.660 | −13.097 |
| 267 | LEU D | 7.953 | 25.909 | −15.298 |
| 267 | LEU CG | 10.432 | 28.060 | −14.058 |
| 267 | LEU CD2 | 11.924 | 27.921 | −14.327 |
| 268 | ILE CA | 6.406 | 28.035 | −15.944 |
| 268 | ILE D | 8.539 | 28.793 | −16.912 |
| 268 | ILE CG1 | 6.099 | 30.541 | −15.592 |
| 268 | ILE CD1 | 5.399 | 31.469 | −16.262 |
| 253 | THR N | 3.018 | 22.505 | −18.923 |
| 253 | THR C | 5.381 | 23.247 | −18.818 |
| 253 | THR CB | 4.086 | 23.672 | −20.952 |
| 253 | THR CG2 | 3.147 | 23.130 | −22.032 |
| 254 | THR CA | 6.216 | 23.612 | −16.588 |
| 254 | THR D | 7.402 | 21.580 | −17.095 |
| 254 | THR DG1 | 5.129 | 22.178 | −15.040 |
| 255 | THR N | 8.499 | 23.296 | −16.076 |
| 255 | THR C | 9.621 | 22.031 | −14.414 |
| 255 | THR CB | 11.080 | 23.455 | −15.897 |
| 255 | THR CG2 | 12.286 | 22.628 | −15.406 |
| 256 | LYS CA | 9.364 | 20.063 | −13.010 |
| 256 | LYS D | 11.662 | 20.274 | −12.592 |
| 256 | LYS CG | 9.018 | 17.805 | −11.921 |
| 256 | LYS CE | 10.212 | 15.940 | −10.623 |
| 257 | LEU N | 10.212 | 20.674 | −10.924 |
| 257 | LEU C | 11.250 | 20.232 | −8.614 |
| 257 | LEU CB | 11.187 | 22.547 | −9.522 |
| 257 | LEU CD1 | 11.245 | 25.003 | −9.921 |
| 258 | GLY N | 10.431 | 19.282 | −8.298 |
| 258 | GLY C | 9.168 | 18.703 | −6.373 |
| 259 | ASP N | 9.024 | 18.282 | −5.150 |
| 259 | ASP C | 6.659 | 18.941 | −4.709 |
| 259 | ASP CB | 7.996 | 17.540 | −3.053 |
| 259 | ASP DD1 | 5.611 | 17.527 | −2.354 |
| 260 | SER N | 5.560 | 18.610 | 5.312 |
| 260 | SER C | 4.046 | 20.362 | −4.289 |
| 260 | SER CB | 3.345 | 18.919 | −6.289 |
| 261 | PHE N | 4.241 | 19.778 | −3.112 |
| 261 | PHE C | 4.544 | 21.846 | −1.863 |
| 261 | PHE CB | 4.053 | 19.749 | −0.563 |
| 261 | PHE CD1 | 2.206 | 20.163 | 1.125 |
| 261 | PHE CE1 | 1.737 | 20.717 | 2.315 |
| 261 | PHE CZ | 2.605 | 21.465 | 3.114 |
| 262 | TYR CA | 6.688 | 22.914 | −2.251 |
| 262 | TYR D | 7.201 | 24.853 | −3.393 |
| 262 | TYR CG | 8.146 | 21.892 | −0.454 |
| 262 | TYR CD2 | 8.149 | 22.669 | 0.698 |
| 262 | TYR CE2 | 8.114 | 22.069 | 1.962 |
| 262 | TYR DH | 7.965 | 20.029 | 3.205 |
| 263 | TYR CA | 6.812 | 23.655 | −6.022 |
| 263 | TYR D | 5.781 | 24.117 | −8.111 |
| 263 | TYR CG | 9.279 | 23.035 | −6.068 |
| 263 | TYR CDZ | 9.800 | 22.342 | −4.995 |
| 263 | TRY CEZ | 11.062 | 22.640 | −4.491 |
| 263 | TYR DH | 12.065 | 23.949 | −4.597 |
| 264 | GLY CA | 3.301 | 23.064 | −7.412 |
| 264 | GLY D | 4.647 | 21.274 | −8.365 |
| 265 | LYS CA | 3.834 | 21.798 | −10.971 |
| 265 | LYS D | 5.684 | 21.563 | −11.305 |
| 265 | LYS CG | 1.490 | 21.563 | −11.305 |
| 265 | LYS CE | −0.692 | 20.496 | −11.391 |
| 266 | GLY N | 5.787 | 23.226 | −10.817 |
| 266 | GLY C | 7.155 | 25.052 | −11.818 |
| 267 | LEU N | 8.262 | 25.336 | −12.480 |
| 267 | LEU C | 7.804 | 26.771 | −14.437 |
| 267 | LEU CB | 10.010 | 26.855 | −13.214 |
| 267 | LEU CD1 | 10.096 | 29.331 | −13.250 |
| 268 | ILE N | 7.064 | 27.863 | −14.632 |
| 268 | ILE C | 7.426 | 28.246 | −17.065 |
| 268 | ILE CB | 5.369 | 29.210 | −15.899 |
| 268 | ILE CG2 | 4.243 | 28.925 | −14.867 |
| 269 | ASN N | 7.007 | 27.843 | −18.237 |
| 269 | ASN CA | 7.802 | 27.975 | −19. |
| 269 | ASN D | 5.965 | 27.760 | −20. |
| 269 | ASN CG | 9.161 | 26.806 | −21.210 |
| 269 | ASN ND2 | 10.011 | 25.796 | −21.472 |
| 270 | VAL CA | 5.863 | 30.418 | −21.614 |
| 270 | VAL D | 5.097 | 29.969 | −23.572 |
| 270 | VAL CG1 | 6.849 | 32.797 | −21.879 |
| 271 | GLN N | 7.325 | 29.701 | −23.352 |

-continued

| | | | | |
|---|---|---|---|---|
| 271 | GLN C | 6.869 | 27.934 | −25.031 |
| 271 | GLN CB | 9.104 | 29.220 | −24.964 |
| 271 | GLN CD | 10.901 | 28.585 | −26.582 |
| 271 | GLN NE1 | 11.702 | 28.553 | −25.510 |
| 272 | ALA CA | 6.224 | 25.712 | −24.240 |
| 272 | ALA D | 3.898 | 25.505 | −25.001 |
| 273 | ALA N | 4.247 | 26.661 | −23.135 |
| 273 | ALA C | 2.081 | 27.528 | −24.020 |
| 273 | ALA CB | 2.736 | 27.773 | −21.585 |
| 274 | ALA CB | 2.952 | 30.391 | −26.210 |
| 274 | ALA C | 1.730 | 28.367 | −27.090 |
| 275 | GLN N | 2.350 | 27.194 | −27.314 |
| 275 | GLN C | 2.147 | 27.261 | −29.777 |
| 275 | GLN DT | 1.193 | 27.361 | −30.590 |
| 275 | GLN CG | 0.501 | 24.664 | −27.447 |
| 275 | GLN DE1 | −1.376 | 23.895 | −28.729 |
| 269 | ASN C | 6.839 | 28.554 | −20.485 |
| 269 | ASN CB | 8.432 | 26.653 | −19.895 |
| 269 | ASN DD1 | 8.993 | 27.626 | −12.122 |
| 270 | VAL N | 6.908 | 29.868 | −20.724 |
| 270 | VAL C | 6.059 | 30.007 | −23.054 |
| 270 | VAL CB | 5.656 | 31.950 | −21.422 |
| 270 | VAL CG2 | 4.420 | 32.362 | −22.232 |
| 271 | GLN CA | 7.603 | 29.270 | −24.744 |
| 271 | GLN D | 6.213 | 27.806 | −26.091 |
| 271 | GLN CG | 9.406 | 28.618 | −26.338 |
| 271 | GLN DE1 | 11.369 | 28.579 | −27.718 |
| 272 | ALA N | 6.977 | 26.999 | −24.092 |
| 272 | ALA C | 4.701 | 25.958 | −24.164 |
| 272 | ALA CB | 6.743 | 24.742 | −23.172 |
| 273 | ALA CA | 2.840 | 26.921 | −22.859 |
| 273 | ALA D | 0.899 | 27.219 | −24.255 |
| 274 | ALA N | 2.755 | 28.404 | −24.762 |
| 274 | ALA CA | 2.109 | 29.144 | −25.847 |
| 274 | ALA D | 0.980 | 28.949 | −27.921 |
| 275 | GLN CA | 2.048 | 26.389 | −28.527 |
| 275 | GLN D | 3.260 | 27.807 | −29.916 |
| 275 | GLN CB | 0.666 | 25.734 | −28.520 |
| 275 | GLN CD | −0.823 | 23.936 | −27.631 |
| 275 | GLN NE2 | −1.373 | 23.411 | −26.538 |

The above structural studies together with the above referenced kinetic data and kinetic data presented herein indicate that the subsites in the binding cleft of subtilisin are capable of interacting with substrate amino acid residues from P-4 to P-2'.

Figure 3:
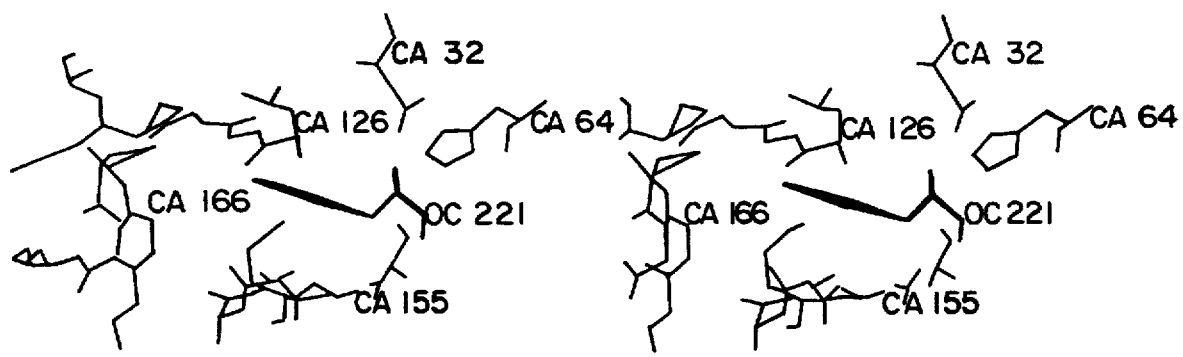
FIG. 3 is a stereo view of the S-1 binding subsite of *B. amyloliquefaciens* subtilisin showing a lysine P-1 substrate bound in the site in two different ways.

The most extensively studied of the above residues are Gly166, Gly169 and Ala152. There amino acids were identified as residues within the S-1 subsite. As seen in FIG. 3, which is a stereoview of the S-1 subsite, Gly166 and Gly169 occupy positions at the bottom of the S-1 subsite, whereas Ala152 occupies a position near the top of S-1, close to the catalytic Ser221.

All 19 amino acid substitutions of Gly166 and Gly169 have been made. As will be indicated in the examples which follow, the preferred replacement amino acids for Gly166 and/or Gly169 will depend on the specific amino acid occupying the P-1 position of a given substrate.

The only substitutions of Ala152 presently made and analyzed comprise the replacement of Ala152 with Gly and Ser. The results of these substitutions on P-1 specificity will be presented in the examples.

In addition to those residues specifically associated with specificity for the P-1 substrate amino acid, Tyr104 has been identified as being involved with P-4 specificity. Substitutions at Phe189 and Tyr217, however, are expected to respectively effect P-2' and P-1' specificity.

The catalytic activity of subtilisin has also been modified by single amino acid substitutions at Asn155.

Figure 4:
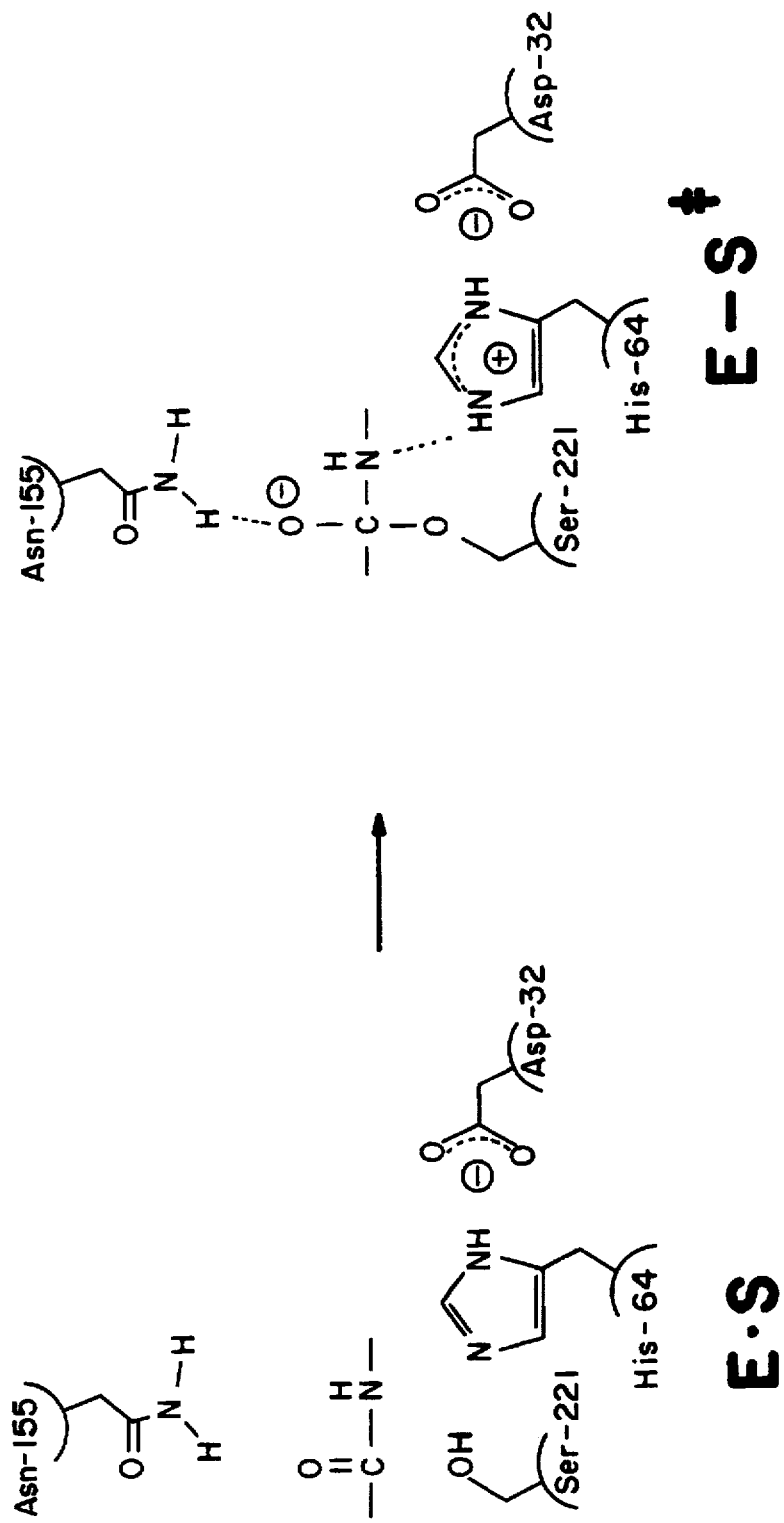
FIG. 4 is a schematic diagram of the active site of subtilisin Asp32, His64 and Ser221.

The catalytic triad of subtilisin is shown in FIG. 4. As can be seen, Ser221, His64 and Asp32 are positioned to facilitate nucleophilic attach by the serine hydroxylate on the carbonyl of the scissile peptide bond. Several hydrogen bonds may also help to stabilize the transition state complex for the tetrahedral substrate intermediate. One hydrogen bond is between aspartate and the positively charged histidine, ND1. Kossiakoff, A. A., et al. (1981) *Biochem.* 20, 6462–5474. A second hydrogen bond forms between the scissile amide nitrogen of the substrate and the (NE2) proton on the histidine. A third set of hydrogen bonds forms between the enzyme and the oxyanion that is produced from the carbonyl oxygen of the substrate. This latter set of hydrogen bonds is formed differently by the mammalian serine proteases and subtilisin. A fourth hydrogen bond appears to exist between the amide nitrogen of the peptide bond between P-1 and P-2 and the carbonyl oxygen of Ser125. Specifically, x-ray crystallographic studies of chymotrypsin (Henderson, R. (1970) *J. Mol. Biol.* 54, 341) indicate that two hydrogen bonds form between the substrate oxyanion and two main-chain amide protons from the enzyme (Gly193 and the catalytic Ser195). Crystallographic studies of subtilisin (Robertus, et al. (1972) *Biochem.* 11, 4293–4303; Matthews, et al. (1975) *J. Biol. Chem.* 250, 7120–7126; Poulos, et al. (1976) *J. Biol. Chem.* 250, 1097–1103) show that two hydrogen bonds are also formed with the oxyanion; one hydrogen bond donor is from the catalytic serine-221 main-chain amide while the other is from one of the NE2 protons of the asparagine-155 side chain. See FIG. 4.

Asn155 was substituted with Ala, Asp, His, Glu and Thr. These substitutions were made to investigate the the stabilization of the charged tetrahedral intermediate of the transition state complex by the potential hydrogen bond between the side chain of Asn155 and the oxyanion of the intermediate. These particular substitutions caused large decreases in substrate turnover, kcat (200 to 4,000 fold), marginal decreases in substrate binding Km (up to 7 fold), and a loss in transition state stabilization energy of 2.2 to 4.7 kcal/mol. The retention of Km and the drop in kcat will make these mutant enzymes useful as binding proteins for specific peptide sequences, the nature of which will be determined by the specificity of the precursor protease.

Various other amino acid residues have been identified which affect alkaline stability. In some cases, mutants having altered alkaline stability also have altered thermal stability.

In *B amyloliquefaciens* subtilisin residues Asp36, Ile107, Lys170, Ser204 and Lys213 have been identified as residues which upon substitution with a different amino acid alter the alkaline stability of the mutated enzyme as compared to the precursor enzyme. The substitution of Asp36 with Ala and the substitution of Lys170 with Glu each resulted in a mutant enzyme having a lower alkaline stability as compared to the wild type subtilisin. When Ile107 was substituted with Val, Ser204 substituted with Cys, Arg or Leu or Lys213 substituted with Arg, the mutant subtilisin had a greater alkaline stability as compared to the wild type subtilisin. However, the mutant Ser204P demonstrated a decrease in alkaline stability.

In addition, other residues, previously identified as being associated with the modification of other properties of subtilisin, also affect alkaline stability. These residues include Ser24, Met50, Glu156, Gly166, Gly169 and Tyr217. Specifically the following particular substitutions result in an increased alkaline stability: Ser24C, Met50F, Gly156Q or S, Gly166A, H, K, N or Q, Gly169S or A, and Tyr217F, K, R or L. The mutant Met50V, on the other hand, results in a decrease in the alkaline stability of the mutant subtilisin as compared to wild type subtilisin.

Other residues involved in alkaline stability based on the alkaline stability screen include the mutants of Table I for residues Asp197 and Met222.

Various other residues have been identified as being involved in thermal stability as determined by the thermal stability screen herein. These residues include the above identified residues which effect alkaline stability and Met299 and Tyr21. These latter two residues are also believed to be important for alkaline stability. Mutants at these residues include I199 and F21.

The amino acid sequence of *B. amyloliquefaciens* subtilisin has also been modified by substituting two or more amino acids of the wild-type sequence. Six categories of multiply substituted mutant subtilisin have been identified. The first two categories comprise thermally and oxidatively stable mutants. The next three other categories comprise mutants which combine the useful properties of any of several single mutations of *B. amyloliquefaciens* subtilisin. The last category comprises mutants which have modified alkaline and/or thermal stability.

The first category is double mutants in which two cysteine residues have been substituted at various amino acid residue positions within the subtilisin BPN' molecule. Formation of disulfide bridges between the two substituted cysteine residues results in mutant subtilisins with altered thermal stability and catalytic activity. These mutants include A21/C22/C87 and C24/C87 which will be described in more detail in Example 11.

The second category of multiple subtilisin mutants comprises mutants which are stable in the presence of various oxidizing agents such as hydrogen peroxide or peracids. Examples 1 and 2 describe these mutants which include F50/I124/Q222, F50/I124, F50/Q222, F50/L124/Q222, I124/Q222 and L124/Q222.

The third category of multiple subtilisin mutants comprises mutants with substitutions at position 222 combined with various substitutions at positions 166 or 169. These mutants, for example, combine the property of oxidative stability of the A222 mutation with the altered substrate specificity of the various 166 or 169 substitutions. Such multiple mutants include A166/A222, A166/C222, F166/C222, K166/A222, K166/C222, V166/A222 and V166/C222. The K166/A222 mutant subtilisin, for example, has a kcat/Km ratio which is approximately two times greater than that of the single A222 mutant subtilisin when compared using a substrate with phenylalanine as the P-1 amino acid. This category of multiple mutant is described in more detail in Example 12.

The fourth category of multiple mutants combines substitutions at position 156 (Glu to Q or S) with the substitution of Lys at position 166. Either of these single mutations improve enzyme performance upon substrates with glutamate as the P-1 amino acid. When these single mutations are combined, the resulting multiple enzyme mutants perform better than either precursor. See Example 9.

The fifth category of multiple mutants contain the substitution of up to four amino acids of the *B. amyloliquefaciens* subtilisin sequence. These mutants have specific properties which are virtually identicle to the properties of the subtilisin from *B. licheniformis*. The subtilisin from *B. licheniformis* differs from *B. amyloliquefaciens* subtilisin at 87 out of 275 amino acids. The multiple mutant F50/S156/A169/L217 was found to have similar substrate specificity and kinetics to the licheniformis enzyme. (See Example 13.) However, this is probably due to only three of the mutations (S156, A169 and L217) which are present in the substrate binding region of the enzyme. It is quite surprising that, by making only three changes out of the 87 different amino acids between the sequence of the two enzymes, the *B. amyloliquifaciens* enzyme was converted into an enzyme with properties similar to B. licheniformis enzyme. Other enzymes in this series include F50/Q156/N166/L217 and F50/S156/L217.

The sixth category of multiple mutants includes the combination of substitutions at position 107 (Ile to V) with the substitution of Lys at position 213 with Arg, and the combination of substitutions of position 204 (preferably Ser to C or L but also to all other amino acids) with the substituion of Lys at position 213 with R. Other multiple mutants which have altered alkaline stability include Q156/K166, Q156/N166, S156/K166, S156/N166 (previously identified as having altered substrate specificity), and F50/S156/A169/L217 (previously identified as a mutant of B. amyloliquifaciens subtilisin having properties similar to subtilisin from B. licheniformis). The mutant F50/V107/R213 was constructed based on the observed increase in alkaline stability for the single mutants F50, V107 and R213. It was determined that the V107/R213 mutant had an increased alkaline stability as compared to the wild type subtilisin. In this particular mutant, the increased alkaline stability was the result of the cumulative stability of each of the individual mutations. Similarly, the mutant F50/V107/R213 had an even greater alkaline stability as compared to the V107/R213 mutant indicating that the increase in the alkaline stability due to the F50 mutation was also cumulative.

Table IV summarizes the multiple mutants which have been made including those not mentioned above.

In addition, based in part on the above results, substitution at the following residues in subtilisin is expected to produce a multiple mutant having increased thermal and alkaline stability: Ser24, Met50, Ile107, Glu156, Gly166, Gly169, Ser204, Lys213, Gly215, and Tyr217.

TABLE IV

| Double Mutants | Triple, Quadruple or Other Multiple |
|---|---|
| C22/C87 | F50/I124/Q222 |
| C24/C87 | F50/L124/Q222 |
| V45/V48 | F50/L124/A222 |
| C49/C94 | A21/C22/C87 |
| C49/C95 | F50/S156/N166/L217 |
| C50/C95 | F50/Q156/N166/L217 |
| C50/C110 | F50/S156/A169/L217 |
| F50/I124 | F50/S156/L217 |
| F50/Q222 | F50/Q156/K166/L217 |
| I124/Q222 | F50/S156/K166/L217 |
| Q156/D166 | F50/Q156/K166/K217 |
| Q156/K166 | F50/S156/K166/K217 |
| Q156/N166 | F50/V107/R213 |
| S156/D166 | [S153/S156/A158/G159/S160/A161- |
| S156/K166 | 164/I165/S166/A169/R170] |
| S156/N166 | L204/R213 |
| S156/A169 | R213/204A, E, Q, D, N, G, K, |
| A166/A222 | V, R, T, P, I, M, F, Y, W |
| A166/C222 | or H |
| F166/A222 | V107/R213 |
| F166/C222 | |
| K166/A222 | |
| K166/C222 | |
| V166/A222 | |
| V166/C222 | |
| A169/A222 | |
| A169/A222 | |
| A169/C222 | |
| A21/C22 | |

In addition to the above identified amino acid residues, other amino acid residues of subtilisin are also considered to be important with regard to substrate specificity. These are the aforementioned residues which have yet to be mutated. Mutation of each of these residues is expected to produce changes in the substrate specificity of subtilisin. Moreover, multiple mutations among these residues and among the previously identified residues are also expected to produce subtilisin mutants having novel substrate specificity.

Particularly important residues are His67, Ile107, Leu126 and Leu135. Mutation of His67 should alter the S-1' subsite, thereby altering the specificity of the mutant for the P-1' substrate residue. Changes at this position could also affect the pH activity profile of the mutant. This residue was identified based on the inventor's substrate modeling from product inhibitor complexes.

Ile107 is involved in P-4 binding. Mutation at this position thus should alter specificity for the P-4 substrate residue. Ile107 was also identified by molecular modeling from product inhibitor complexes.

The S-2 binding site includes the Leu126 residue. Modification at this position should therefore affect P-2 specificity. Moreover, this residue is believed to be important to convert subtilisin to an amino peptidase. The pH activity profile should also be modified by appropriate substitution. These residues were identified from inspection of the refined model, the three dimensional structure from modeling studies. A longer side chain is expected to preclude binding of any side chain at the S-2 subsite. Therefore, binding would be restricted to subsites S-1, S-1', S-2', S-3' and cleavage would be forced to occur after the amino terminal peptide.

Leu135 is in the S-4 subsite and if mutated should alter substrate specificity for P-4 if mutated. This residue was identified by inspection of the three-dimensional structure and modeling based on the product inhibitor complex of F222.

In addition to these sites, specific amino acid residues within the segments 97-103, 126-129 and 213-215 are also believed to be important to substrate binding.

Segments 97-103 and 126-129 form an antiparallel beta sheet with the main chain of substrate residues P-4 through P-2. Mutating residues in those regions should affect the substrate orientation through main chain (enzyme)—main chain (substrate) interactions, since the main chain of these substrate residues do not interact with these particular residues within the S-4 through S-2 subsites.

Within the segment 97-103, Gly97 and Asp99 may be mutated to alter the position of residues 101-103 within the segment. Changes at these sites must be compatible, however. In B. amyloliquifaciens subtilisin Asp99 stabilizes a turn in the main chain tertiary folding that affects the direction of residues 101-103. B. licheniformis subtilisin Asp97, functions in an analogous manner.

In addition to Gly97 and Asp99, Ser101 interacts with Asp99 in B. amyliquefaciens subtilisin to stabilize the same main chain turn. Alterations at this residue should alter the 101-103 main chain direction.

Mutations at Glu103 are also expected to affect the 101-103 main chain direction.

The side chain of Gly102 interacts with the substrate P-3 amino acid. Side chains of substituted amino acids thus are expected to significantly affect specificity for the P-3 substrate amino acids.

All the amino acids within the 127-129 segment are considered important to substrate specificity. Gly 127 is positioned such that its side chain interacts with the S-1 and S-3 subsites. Altering this residue thus should alter the specificity for P-1 and P-3 residues of the substrate.

The side chain of Gly128 comprises a part of both the S-2 and S-4 subsites. Altered specificity for P-2 and P-4 therefore would be expected upon mutation. Moreover, such mutation may convert subtilisin into an amino peptidase for the same reasons substitutions of Leu126 would be expected to produce that result.

The Pro129 residue is likely to restrict the conformational freedom of the sequence 126-133, residues which may play a major role in determining P-1 specificity. Replacing Pro may introduce more flexibility thereby broadening the range of binding capabilities of such mutants.

The side chain of Lys213 is located within the S-3 subsite. All of the amino acids within the 213-215 segment are also considered to be important to substrate specificity. Accordingly, altered P-3 substrate specificity is expected upon mutation of this residue.

The Tyr214 residue does not interact with substrate but is positioned such that it could affect the conformation of the hair pin loop 204-217.

Finally, mutation of the Gly215 residue should affect the S-3' subsite, and thereby alter P-3' specificity.

In addition to the above substitutions of amino acids, the insertion or deletion of one or more amino acids within the external loop comprising residues 152-172 may also affect specificity. This is because these residues may play a role in the "secondary contact region" described in the model of streptomyces subtilisin inhibitor complexed with subtilisin. Hirono, et al. (1984) *J. Mol. Biol.* 178, 389–413. Thermitase K has a deletion in this region, which eliminates several of these "secondary contact" residues. In particular, deletion of residues 161 through 164 is expected to produce a mutant subtilisin having modified substrate specificity. In addition, a rearrangement in this area induced by the deletion should alter the position of many residues involved in substrate binding, predominantly at P-1. This, in turn, should affect overall activity against proteinaceous substrates.

The effect of deletion of residues 161 through 164 has been shown by comparing the activity of the wild type (WT) enzyme with a mutant enzyme containing this deletion as well as multiple substitutions (i.e., S153/S156/A158/G159/S160/Δ161–164/I165/S166/A169/R170). This produced the following results:

TABLE V

|  | kcat | Km | kcat/Km |
| --- | --- | --- | --- |
| WT | 50 | 1.4e-4 | 3.6e5 |
| Deletion mutant | 8 | 5.0e-6 | 1.6e6 |

The WT has a kcat 6 times greater than the deletion mutant but substrate binding is 28 fold tighter by the deletion mutant. The overall efficiency of the deletion mutant is thus 4.4 times higher than the WT enzyme.

All of these above identified residues which have yet to be substituted, deleted or inserted into are presented in Table VI.

TABLE VI

| Substitution/Insertion/Deletion Residues | |
| --- | --- |
| His67 | Ala152 |
| Leu126 | Ala153 |
| Leu135 | Gly154 |
| Gly97 | Asn155 |
| Asp99 | Gly156 |
| Ser101 | Gly157 |
| Gly102 | Gly160 |
| Glu103 | Thr158 |
| Leu126 | Ser159 |

TABLE VI-continued

| Substitution/Insertion/Deletion Residues | |
| --- | --- |
| Gly127 | Ser161 |
| Gly128 | Ser162 |
| Pro129 | Ser163 |
| Tyr214 | Thr164 |
| Gly215 | Val165 |
|  | Gly166 |
|  | Tyr167 |
|  | Pro168 |
|  | Gly169 |
|  | Lys170 |
|  | Tyr171 |
|  | Pro172 |

The mutants herein may be obtained as salts. It is clear that the ionization state of a protein will be dependent on the pH of the surrounding medium, if it is in solution, or of the solution from which it is prepared, if it is in solid form. Acidic proteins are commonly prepared as, for example, the ammonium, sodium, or potassium salts; basic proteins as the chlorides, sulfates, or phosphates. Accordingly, the present application includes both electrically neutral and salt forms of the designated carbonyl hydrolases, and the term carbonyl hydrolase referes to the organic structural backbone regardless of ionization state.

The carbonyl hydrolase mutants are particularly useful in the food processing and cleaning arts. The carbonyl hydrolases, including mutants, are produced by fermentation as described herein and recovered by suitable techniques. See for example K. Anstrup, 1974, *Industrial Aspects of Biochemistry*, ed. B. Spencer pp. 23–46. They are formulated with detergents or other surfactants in accord with methods known per se for use in industrial processes, especially laundry. In the latter case the enzymes are combined with detergents, builders, bleach and/or flourescent whitening agents as is known in the art for proteolytic enzymes. Suitable detergents include linear alkyl benzene sulfonates, alkyl ethoxylated sulfate, sulfated linear alcohol or ethoxylated linear alcohol. The compositions may be formulated in granular or liquid form. See for example U.S. Pat. Nos. 3,623,957; 4,404,128; 4,381,247; 4,404,115; 4,318,818; 4,261,868; 4,242,219; 4,142,999; 4,111,855; 4,011,169; 4,090,973; 3,985,686; 3,790,482; 3,749,671; 3,560,392; 3,558,498; and 3,557,002.

The following disclosure is intended to serve as a representation of embodiments herein, and should not be construed as limiting the scope of this application. These specific examples disclose the construction of certain of the above identified mutants. The construction of the other mutants, however, is apparent from the disclosure herein and that presented in EPO Publication No. 0130756.

Glossary of Experimental Manipulations

In order to simplify the Examples certain frequently occurring methods will be referenced by shorthand phrases.

Plasmids are designated by a small p proceeded and/or followed by capital letters and/or numbers. The starting plasmids herein are commercially available, are available on an unrestricted basis, or can be constructed from such available plasmids in accord with published procedures.

"Klenow treatment" refers to the process of filling a recessed 3' end of double stranded DNA with deoxyribonucleotides complementary to the nucleotides making up the protruding 5' end of the DNA strand or exonucleolytic removal of a protruding 3' end of a double stranded DNA fragment. This process is usually used to fill in a recessed end resulting from a restriction enzyme cleavage of DNA. This creates a blunt or flush end, as may be required for further ligations. Treatment with Klenow is accomplished by reacting (generally for 15 minutes at 15° C.) the appropriate complementary deoxyribonucleotides with the DNA to be filled in under the catalytic activity (usually 10 units) of the Klenow fragment of *E. coli* DNA polymerase I ("Klenow"). Klenow and the other reagents needed are commercially available. The procedure has been published extensively. See for example T. Maniatis, et al., 1982, *Molecular Cloning*, pp. 107–108.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA gragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis, et al., Id., pp. 133–134).

"Recovery" or "isolation" of a given fragment of DNA from a restriction digest means separation of the digest on 6 percent polyacrylamide gel electrophoresis, identification of the fragment of interest by molecular weight (using DNA fragments of known molecular weight as markers), removal of the gel section containing the desired fragment, and separation of the gel from DNA. This procedure is known generally. For example, see R. Lawn, et al., 1981, "Nucleic Acids Res." 9:6103–6114, and D. Goeddel, et al., 1980, "Nucleic Acids Res." 8:4057.

"Southern Analysis" is a method by which the presence of DNA sequences in a digest or DNA-containing composition is confirmed by hybridization to a known, labelled oligonucleotide or DNA fragment. For the purposes herein, Southern analysis shall mean separation of digests on 1 percent agarose and depurination as described by G. Wahl, et al., 1979, "Proc. Nat. Acad. Sci. U.S.A." 76:3683–3687, transfer to nitrocellulose by the method of E. Southern, 1975, "J. Mol. Biol." 98:503–517, and hybridization as described by T. Maniatis, et al., 1978, "cell" 15:687–701.

"Transformation" means introducing DNA into an organism so that the DNA is replicable, either as an extrachromosomal element or chromosomal integrant. Unless otherwise stated, the method used herein for transformation of *E. coli* is the $CaCl_2$ method of Mandel, et al., 1970, "J. Mol. Biol." 53:154, and for Bacillus, the method of Anagnostopolous, et al., 1961, "J. Bact." 81:741–746.

"Ligation" refers to the process of forming phosphodiester bonds between two double stranded nucleic acid fragments (T. Maniatis, et al., Id., p. 146). Unless otherwise stated, ligation was accomplished using known buffers and conditions with 10 units of T4 DNA ligase ("ligase") per 0.5 μg of approximately equimolar amounts of the DNA fragments to be ligated. Plasmids from the transformants were prepared, analyzed by restriction mapping and/or sequenced by the method of Messing, et al., 1981, "Nucleic Acids Res.", 9:309.

"Preparation" of DNA from transformants means isolating plasmid DNA from microbial culture. Unless otherwise stated, the alkaline/SDS method of Maniatis, et al., Id., p. 90, was used.

"Oligonucleotides" are short length single or double stranded polydeoxynucleotides which were chemically synthesized by the method of Crea, et al., 1980, "Nucleic Acids Res." 8:2331–2348 (except that mesitylene nitrotriazole was used as a condensing agent) and then purified on polyacrylamide gels.

All mutant plasmids were transformed (Anagnostopoulos, C., et al. (1961) *J. Bacteriol.* 81, 741–746) into BG2036 (Yang, M. (1984) *J. Bacteriol.* 160, 15–21) to express mutant subtilisins as described (Estell, D. A., et al. (1985) *J. Biol. Chem.* 260, 6518–6521).

All literature citations are expressly incorporated by reference.

The following is presented by way of example and is not to be construed as a limitation to the scope of the invention.

EXAMPLE 1

Identification of Peracid Oxidizable Residues of Subtilisin Q222 and L222

Figure 6A:
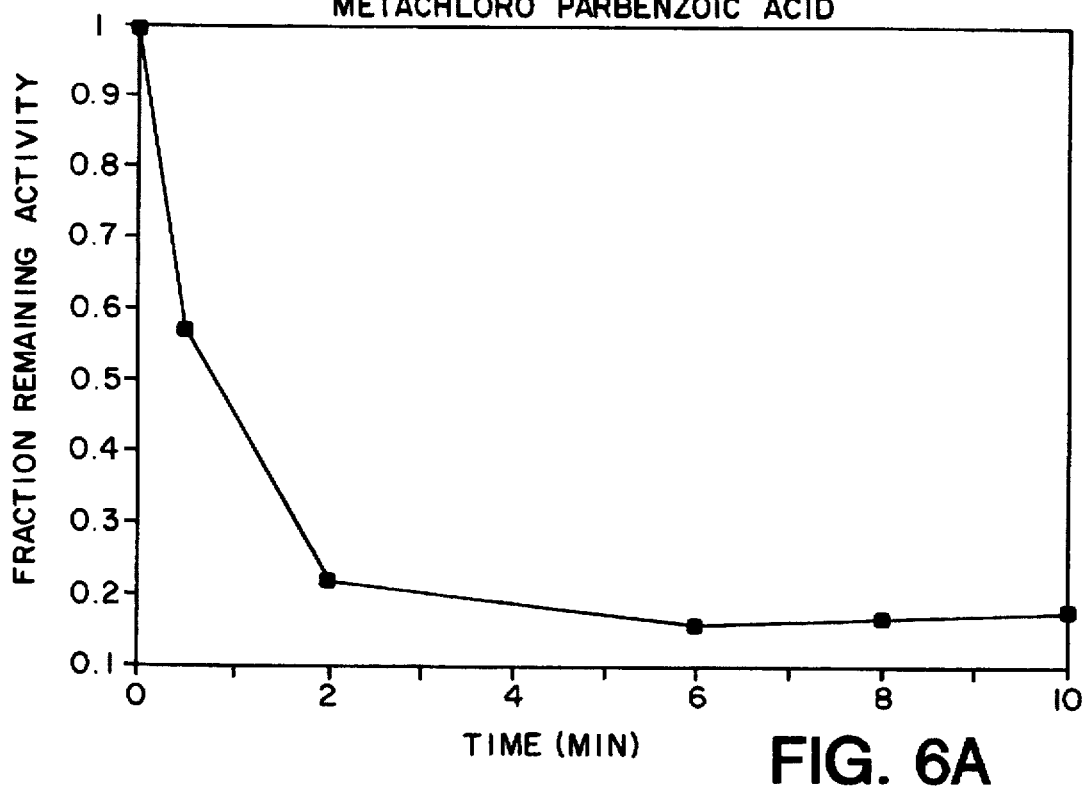
FIGS. 6A and 6B depict the inactivation of the mutants Met222L and Met222Q when exposed to various organic oxidants.
Figure 6B:
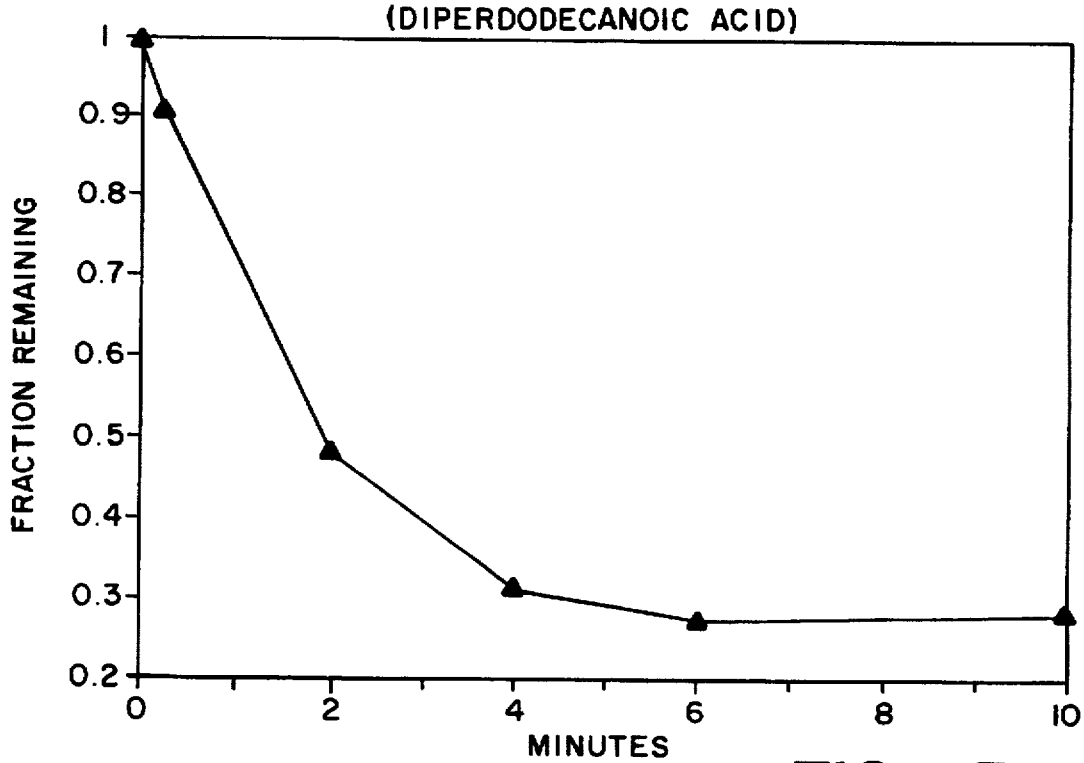

The activity of naturally-occurring subtilisin is rapidly reduced up to 85% by a series of oxidants. One of the most characterized modification is the conversion of Met222 to met-sulfoxide in the presence of hydrogen peroxide. Stauffer, C. E., et al. (1969) *J. Biol. Chem.* 244, 5333–5338. This defect has been eliminated by substituting a variety of non-oxidizable amino acids into this position by site-directed mutagenesis of the *B. amyloliquefaciens* enzyme, thereby confering enhanced stability to hydrogen peroxide. See EPO Publication No. 0130756 and Estell, D. A., et al. (1985) *J. Biol. Chem.* 260, 6518. However, as shown in FIGS. 6A and 6B, organic peracid oxidants can still inactivate the mutant enzymes Met222L and Met222Q (L222 and Q222). This example describes the identification of peracid oxidizable sites in 222 substituted mutant subtilisins.

Figure 7A:
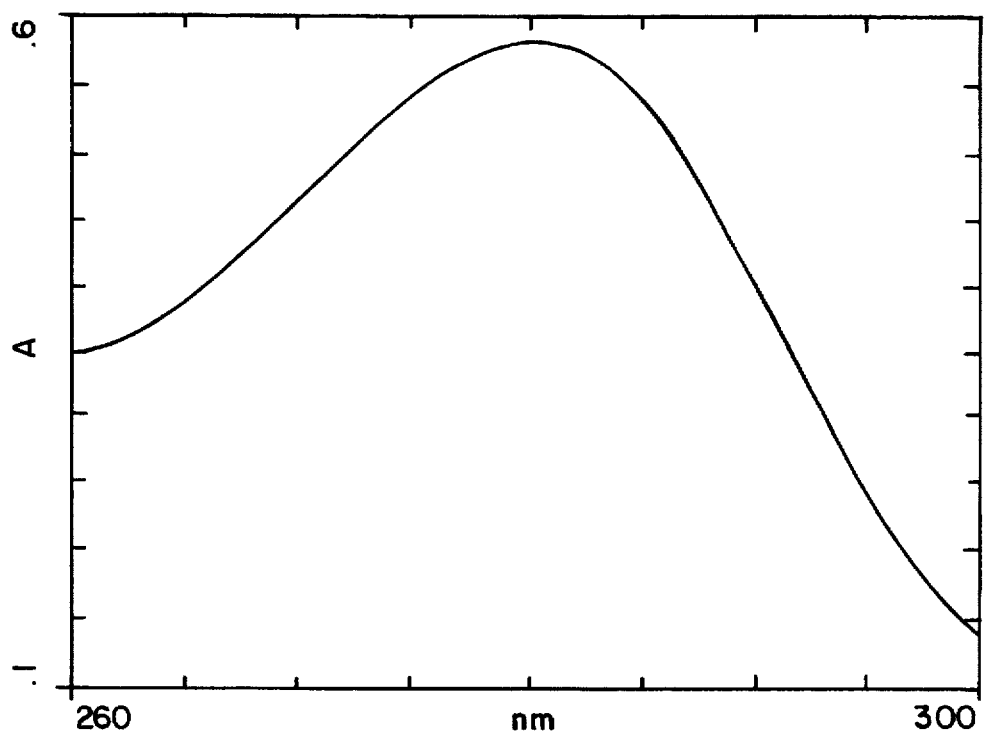
FIGS. 7A and 7B depicts the ultraviolet spectrum of Met222F subtilisin and the difference spectrum generated after inactivation by diperdodecanoic acid (DPDA).
Figure 7B:
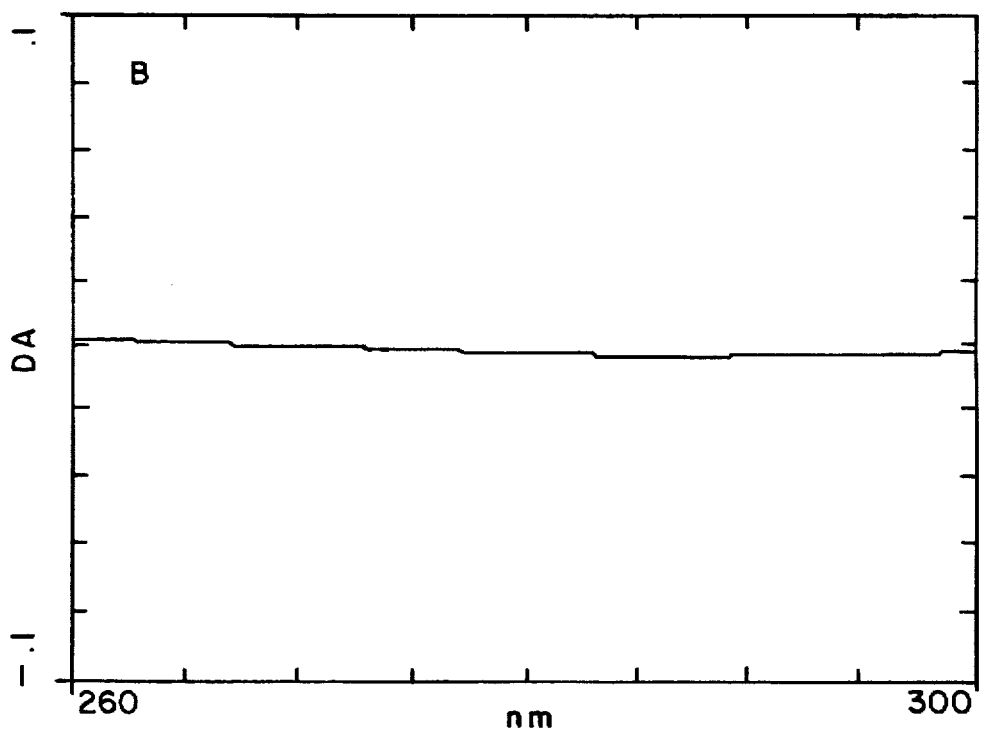

The first step was to determine the type of amino acid involved in peracid oxidation. Except under drastic conditions (Means, G. E., et al. (1971) *Chemical Modifications of Proteins*, Holden-Day, San Francisco, Calif., pp. 160–162), organic peracids modify only methionine and tryptophan in subtilisin. In order to rule out tryptophan as a candidate, difference spectra of the enzyme over the 250 nm to 350 nm range were determined during an inactivation titration employing the reagent, diperdodecanoic acid (DPDA) as the oxidant. Despite quantitative inactivation of the enzyme, no change in absorbance over this wavelength range was noted as shown in FIGS. 7A and 7B. Oxidation of tryptophan would be expected to result in marked changes over this region. Fontana, A., et al. (1980) *Methods in Peptide and Protein Sequence Analysis* (C. Birr ed.) Elsevier, N.Y., p.

309. The absence of tryptophan modification implied oxidation of one or more of the remaining methionines of *B. amyloliquefaciens* subtilisin. See FIGS. 1A and 1B.

To confirm this result the recombinant subtilisin Met222F was cleaved with cyanogen bromide (CNBr) both before and after oxidation by DPDA. The peptides produced by CNBr cleavage were analyzed on high resolution SDS-pyridine peptide gels (SPG).

Subtilisin Met222F (F222) was oxidized in the following manner. Purified F222 was resuspended in 0.1M sodium borate pH 9.5 at 10 mg/ml and was added to a final concentration of 26 diperdodecanoic acid (DPDA) at 26 mg/ml was added to produce an effective active oxygen concentration of 30 ppm. The sample was incubated for at least 30 minutes at room temperature and then quenched with 0.1 volume of 1M Tris pH 8.6 buffer to produce a final concentration of 0.1M Tris pH 8.6). 3 mM phenylmethylsulfonyl fluoride (PMSF) was added and 2.5 ml of the sample was applied to a Pharmacia PD10 column equilibrated in 10 mM sodium phosphate pH 6.2, 1 mM PMSF. 3.5 ml of 10 mM sodium phosphate pH6.2, 1 mM PMSF was applied and the eluant collected. The sample was assumed to be at 7 mg/ml based on the observation that a 2.5 ml sample of untreated F222 at 10 mg/ml in phosphate buffer when treated with PMSF and desalted in the same manner on a Pharmacia PD10 column produced a concentration of about 7 mg/ml.

F222 and DPDA oxidized F222 were precipitated with 9 volumes of acetone at −20° C. For 100 ug of protein, the acetone mixture was vortexed and centrifuged in a Fischer tabletop centrifuge for 10 minutes. The pellets were washed once with 0.5 ml acetone and then dried. The sample was carefully resuspended at 10 mg/ml in 8M urea in 88% formic acid and allowed to sit for 5 minutes. An equal volume of 200 mg/ml CNBr in 88% formic acid was added (5 mg/ml protein) and the samples incubated for 2 hours at room temperature in the dark. Prior to gel electrophoresis, the samples were lyophilized for 3–4 hours in a Spin Vac (Savant Instruments) and the pellets were resuspended at 2–5 mg/ml in sample buffer (1% pyridine, 5% NaDodSO$_4$, 5% glycerol and bromophenol blue) and disassociated at 95° C. for 3 minutes.

The samples were electrophoresed on discontinuous polyacrylamide gels as described by Kyte and Rodriguez (Kyte, J., et al. (1983) *Anal. Bioch.* 133, 515–522).

The gels were stained using the Pharmacia silver staining technique (Sammons, D. W., et al. (1981) *Electrophoresis* 2 135–141).

Figure 8:
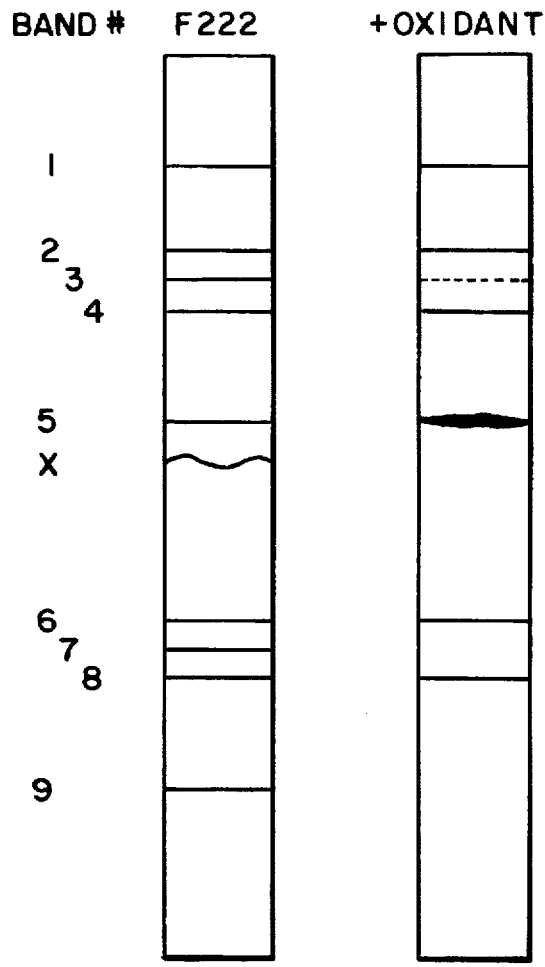
FIG. 8 shows the pattern of cyanogen bromide digests of untreated and DPDA oxidized subtilisin Met222F on high resolution SDS-pyridine peptide gels.

The results of this experiment are shown in FIG. 8. As can be seen, F222 treated with CNBr only gives nine resolved bands on SPG. However, when F222 is also treated with DPDA prior to cleavage, bands X, 7 and 9 disappear whereas bands 5 and 6 are greatly increased in intensity.

In order to determine which of the methionines were effected, each of the CNBr peptides was isolated by reversed phase HPLC and further characterized. The buffer system in both Solvent A (aqueous) and Solvent B (organic) for all HPLC separations was 0.05% TEA-TFA. Solutions were prepared by adding equal volumes of neat triethylamine and neat trifloroacetic acid to the solvent. Programs for the gradients were generated on a Waters Systems Controller. In all cases unless noted, solvent A consisted of 0.05% TEA-TFA in H20, solvent B was 0.05% TEA-TFA in 1-propanol, and the flow rate was 0.5 ml/minute.

For HPLC analysis, two injections of 1 mg enzyme digest were used. Three samples were acetone precipitated, washed and dried as above. The dried 1 mg samples were resuspended at 10 mg/ml in 8M urea, 88% formic acid; an equal volume of 200 mg/ml CNBr in 88% formic acid was added (5 mg/ml protein). After incubation for 2 hours in the dark at room temperature, the samples were desalted on a 0.8 cm×7 cm column of Tris Acryl GF05 coarse resin (IBF, Paris, France) equilibrated with 40% solvent B, 60% solvent A. 200 ul samples were applied at a flow rate of 1 ml a minute and 1.0–1.2 ml collected by monitoring the absorbance at 280 nm. Prior to injection on the HPLC, each desalted sample was diluted with 3 volumes of solvent A. The samples were injected at 1.0 ml/min (2 minutes) and the flow then adjusted to 0.5 ml/min (100% A). After 2 minutes, a linear gradient to 60% B at 1.0% B/min was initiated. From each 1 mg run, the pooled peaks were sampled (50 ul) and analyzed by gel electrophoresis as described above.

Each polypeptide isolated by reversed phase HPLC was further analyzed for homogeneity by SPG. The position of each peptide on the known gene sequence (Wells, J. A., et al. (1983) *Nucleic Acids Res.* 11 7911–7924) was obtained through a combination of amino acid compositional analysis and, where needed, amino terminal sequencing.

Prior to such analysis the following peptides were to rechromatographed.

1. CNBr peptides from F222 not treated with DPDA

Peptide 5 was subjected to two additional reversed phase separations. The 10 cm C4 column was equilibrated to 80% A/20% B and the pooled sample applied and washed for 2 minutes. Next an 0.5% ml B/min gradient was initiated. Fractions from this separation were again rerun, this time on the 25 cm C4 column, and employing 0.05% TEA-TFA in acetonitrile/1-propanol (1:1) for solvent B. The gradient was identical to the one just described.

Peptide "X" was subjected to one additional separation after the initial chromatography. The sample was applied and washed for 2 minutes at 0.5 ml/min (100% A), and a 0.5% ml B/min gradient was initiated.

Peptides 7 and 9 were rechromatographed in a similar manner to the first rerun of peptide 5.

Peptide 8 was purified to homogeneity after the initial separation.

2. CNBr Peptides from DPDA Oxidized F222

Peptides 5 and 6 from a CNBr digest of the oxidized F222 were purified in the same manner as peptide 5 from the untreated enzyme.

Amino acid compositional analysis was obtained as follows. Samples (~nM each amino acid) were dried, hydrolyzed in vacuo with 100 ul 6N HCl at 106° C. for 24 hours and then dried in a Speed Vac. The samples were analyzed on a Beckmann 6300 AA analyzer employing ninhydrin detection.

Amino terminal sequence data was obtained as previously described (Rodriguez, H., et al. (1984) *Anal. Biochem.* 134, 538–547).

Figure 9:
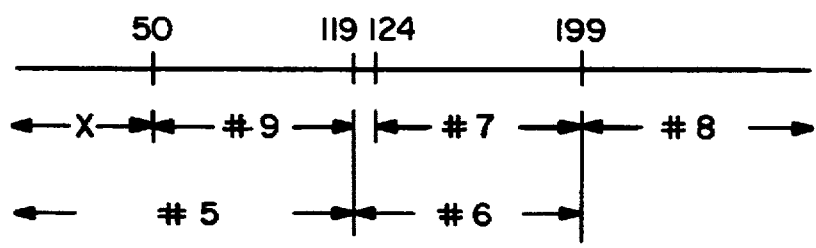
FIG. 9 depicts a map of the cyanogen bromide fragments of FIG. 8 and their alignment with the sequence of subtilisin Met222F.

The results are shown in Table VII and FIG. 9.

TABLE VII

Amino and COOH terminii of CNBr fragments
Terminus and Method

| Fragment | amino, method | COOH, method |
| --- | --- | --- |
| X | 1, sequence | 50, composition |
| 9 | 51, sequence | 119, composition |
| 7 | 125, sequence | 199, composition |
| 8 | 200, sequence | 275, composition |

TABLE VII-continued

| Amino and COOH terminii of CNBr fragments Terminus and Method | | |
|---|---|---|
| Fragment | amino, method | COOH, method |
| 5ox | 1, sequence | 119, composition |
| 6ox | 120, composition | 199, composition |

Peptides 5ox and 6ox refer to peptides 5 and 6 isolated from CNBr digests of the oxidized protein where their respective levels are enhanced.

From the data in Table VII and the comparison of SPG tracks for the oxidized and native protein digests in FIG. 8, it is apparent that (1) Met50 is oxidized leading to the loss of peptides X and 9 and the appearance of 5; and (2) Met124 is also oxidized leading to the loss of peptide 7 and the accumulation of peptide 6. Thus oxidation of *B. amyloliquefaciens* subtilisin with the peracid, diperdocecanoic acid leads to the specific oxidation of methionines 50 and 124.

EXAMPLE 2
Substitution at Met50 and Met124 in Subtilisin Met2220

The choice of amino acid for substitution at Met50 was based on the available sequence data for subtilisins from *B. licheniformis* (Smith, E. C., et al. (1968) *J. Biol. Chem.* 243, 2184–2191), B.DY (Nedkov, P., et al. (1983)*Hoppe Sayler's Z. Physiol. Chem.* 364 1537–1540), *B. amylosacchariticus* (Markland, F. S., et al. (1967) *J. Biol. Chem.* 242 5198–5211) and *B. subtilis* (Stahl, M. L., et al. (1984) *J. Bacteriol.* 158, 411–418). In all cases, position 50 is a phenylalanine. See FIGS. 5A-1, 5A-2, 5B-1, 5B-2 and 5C. Therefore, Phe50 was chosen for construction.

At position 124, all known subtilisins possess a methionine. See FIGS. 5A-1, 5A-2, 5B-1, 5B-2 and 5C. Molecular modelling of the x-ray derived protein structure was therefore required to determine the most probable candidates for substitution. From all 19 candidates, isoleucine and leucine were chosen as the best residues to employ. In order to test whether or not modification at one site but not both was sufficient to increase oxidative stability, all possible combinations were built on the Q222 backbone (F50/Q222, I124/Q222, F50/I124/Q222).

A. Construction of Mutations Between Codons 45 and 50

All manipulations for cassette mutagenesis were carried out on pS4.5 using methods disclosed in EPO Publication No. 0130756 and Wells, J. A., et al, (1985) *Gene* 34, 315–323. The pΔ50 in FIG. 10, line 4, mutations was produced using the mutagenesis primer shown in FIG. 10, line 6, and employed an approach designated as restriction-purification which is described below. Wells, J. A., et al. (1986) *Phil. Trans. R. Soc. Lond. A* (in press). Briefly, a M13 template containing the subtilisin gene, M13mp11-SUBT was used for heteroduplex synthesis (Adelman, et al (1983), *DNA* 2, 183–193). Following transfection of JM101 (ATCC 33876), the 1.5 kb EcoRI-BamHI fragment containing the subtilisin gene was subcloned from M13mp11 SUBT rf into a recipient vector fragment of pBS42 the construction of which is described in EPO Publication No. 0130756. To enrich for the mutant sequence (pΔ50, line 4), the resulting plasmid pool was digested with KpnI, and linear molecules were purified by polyacrylamide gel electrophoresis. Linear molecules were ligated back to a circular form, and transformed into *E. coli* MM294 cells (ATCC 31446). Isolated plasmids were screened by restriction analysis for the KpnI site. KpnI⁺ plasmids were sequenced and confirmed the pΔ50 sequence. Asterisks in FIG. 11 indicate the bases that are mutated from the wid type sequence (line 4). pΔ50 (line 4) was cut with StuI and EcoRI and the 0.5 Kb fragment containing the 5' half of the subtilisin gene was purified (fragment 1). pΔ50 (line 4) was digested with KpnI and EcoRI and the 4.0 Kb fragment containing the 3' half of the subtilisin gene and vector sequences was purified (fragment 2). Fragments 1 and 2 (line 5), and duplex DNA cassettes coding for mutations desired (shaded sequence, line 6) were mixed in a molar ratio of 1:1:10, respectively. For the particular construction of this example the DNA cassette contained the triplet TTT for codon 50 which encodes Phe. This plasmid was designated pF-50. The mutant subtilisin was designated F-50.

B. Construction of Mutation Between Codons 122 and 127

The procedure of Example 2A was followed in substantial detail except that the mutagenesis primer of FIG. 11, line 7 was used and restriction-purification for the EcoRV site in pΔ124 was used. In addition, the DNA cassette (shaded sequence, FIG. 11, line 6) contained the triplet ATT for codon 124 which encodes Ile and CTT for Leu. Those plasmids which contained the substitution of Ile for Met124 were designeated pI124. The mutant subtilisin was designated I124.

C. Construction of Various F50/I124/Q222 Multiple Mutants

The triple mutant, F50/I124/Q222, was constructed from a three-way ligation in which each fragment contained one of the three mutations. The single mutant Q222 (pQ222) was prepared by cassette mutagenesis as described in EPO Publication No. 0130756. The F50 mutation was contained on a 2.2 kb AvaII to PvuII fragment from pF50; the I124 mutation was contained on a 260 bp PvuII to AvaII fragment from pI124; and the Q222 mutation was contained on 2.7 kb AvaII to AvaII fragment from pQ222. The three fragments were ligated together and transformed into *E. coli* MM294 cells. Restriction analysis of plasmids from isolated transformants confirmed the construction. To analyze the final construction it was convenient that the AvaII site at position 798 in the wild-type subtilisin gene was eliminated by the I124 construction.

The F50/Q222 and I124/Q222 mutants were constructed in a similar manner except that the appropriate fragment from pS4.5 was used for the final construction.

D. Oxidative Stability of Q222 Mutants

Figure 12:
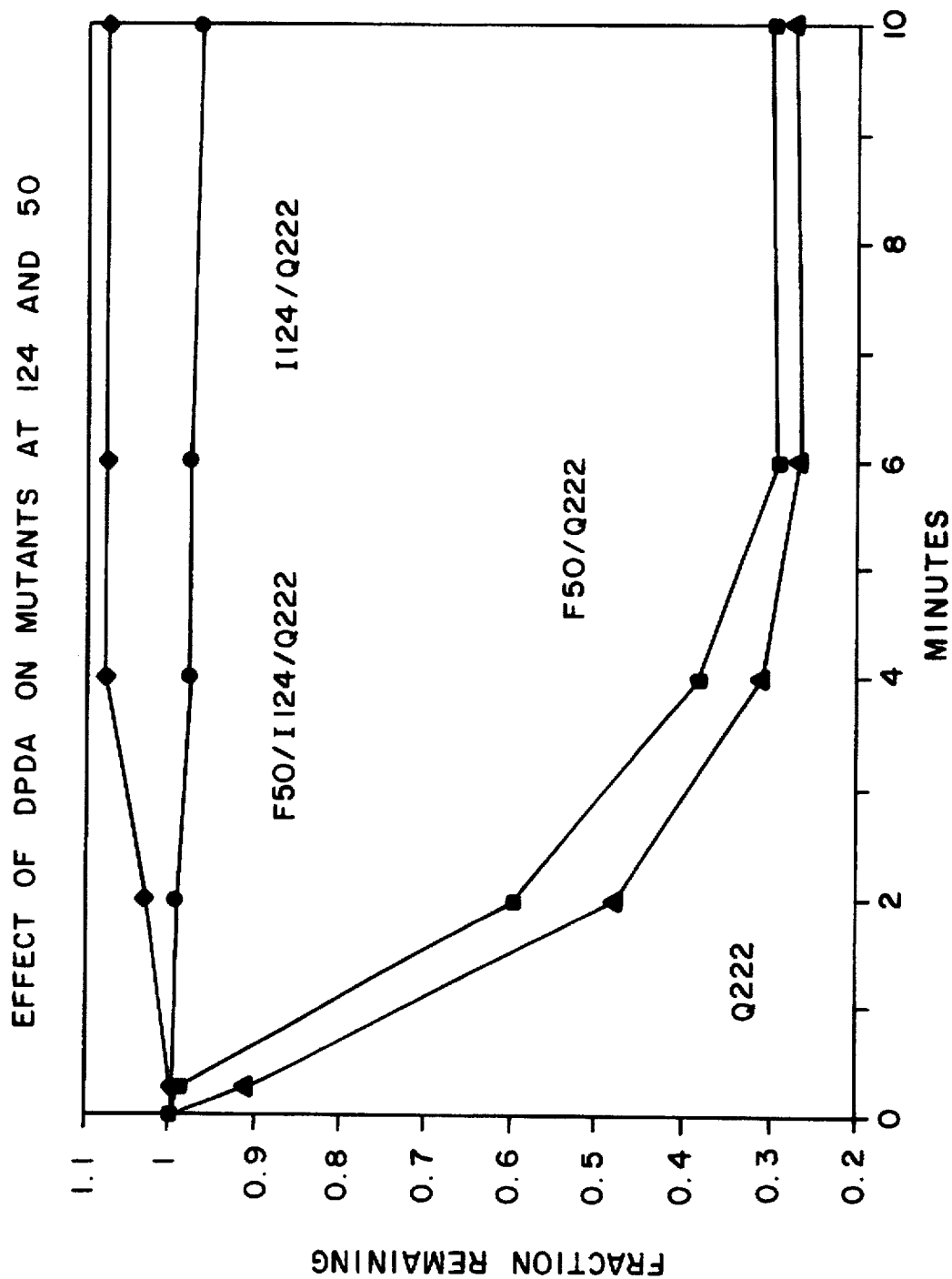
FIG. 12 depicts the effect of DPDA on the activity of subtilisin mutants at positions 50 and 124 in subtilisin Met222F.

The above mutants were analyzed for stability to peracid oxidation. As shown in FIG. 12, upon incubation with diperdodecanoic acid (protein 2 mg/mL, oxidant 75 ppm[O]), both the I124/Q222 and the F50/I124/Q222 are completely stable whereas the F50/Q222 and the Q222 are inactivated. This indicates that conversion of M124 to I124 in subtilisin Q222 is sufficient to confer resistance to organic peracid oxidants.

EXAMPLE 3
Subtilisin Mutants Having Altered Substrate Specificity-Hydrophobic Substitutions at Residues 166

Subtilisin contains an extended binding cleft which is hydrophobic in character. A conserved glycine at residue 166 was replaced with twelve non-ionic amino acids which can project their side-chains into the S-1 subsite. These mutants were constructed to determine the effect of changes in size and hydrophobicity on the binding of various substrates.

A. Kinetics for Hydrolysis of Substrates Having Altered P-1 Amino Acids by Subtilisin BPN' from *B. Amyloliquefaciens*

Wild-type subtilisin was purified from *B. subtilis* culture supernatants expressing the *B. amyloliquefaciens* subtilisin gene (Wells, J. A., et al. (1983) *Nucleic Acids Res.* 11, 7911–7925) as previously described (Estell, D. A., et al. (1985) *J. Biol. Chem.* 260, 6518–6521). Details of the synthesis of tetrapeptide substrates having the form succinyl-L-AlaL-AlaL-ProL-[X]-p-nitroanilide (where X is the P1 amino acid) are described by DelMar, E. G., et al. (1979) *Anal. Biochem.* 99, 316–320. Kinetic parameters, Km(M) and kcat($s^{-1}$) were measured using a modified progress curve analysis (Estell, D. A., et al. (1985) *J. Biol. Chem.* 260, 6518–6521). Briefly, plots of rate versus product concentration were fit to the differential form of the rate equation using a non-linear regression algorithm. Errors in kcat and Km for all values reported are less than five percent. The various substrates in Table VIII are ranged in order of decreasing hydrophobicity. Nozaki, Y. (1971), *J. Biol. Chem.* 246, 2211–2217; Tanford C. (1978) *Science* 200, 1012).

TABLE VIII

| P1 substrate Amino Acid | kcat ($S^{-1}$) | 1/Km ($M^{-1}$) | kcat/Km ($s^{-1}M$-1) |
|---|---|---|---|
| Phe | 50 | 7,100 | 360,000 |
| Tyr | 28 | 40,000 | 1,100,000 |
| Leu | 24 | 3,100 | 75,000 |
| Met | 13 | 9,400 | 120,000 |
| His | 7.9 | 1,600 | 13,000 |
| Ala | 1.9 | 5,500 | 11,000 |
| Gly | 0.003 | 8,300 | 21 |
| Gln | 3.2 | 2,200 | 7,100 |
| Ser | 2.8 | 1,500 | 4,200 |
| Glu | 0.54 | 32 | 16 |

Figure 14:
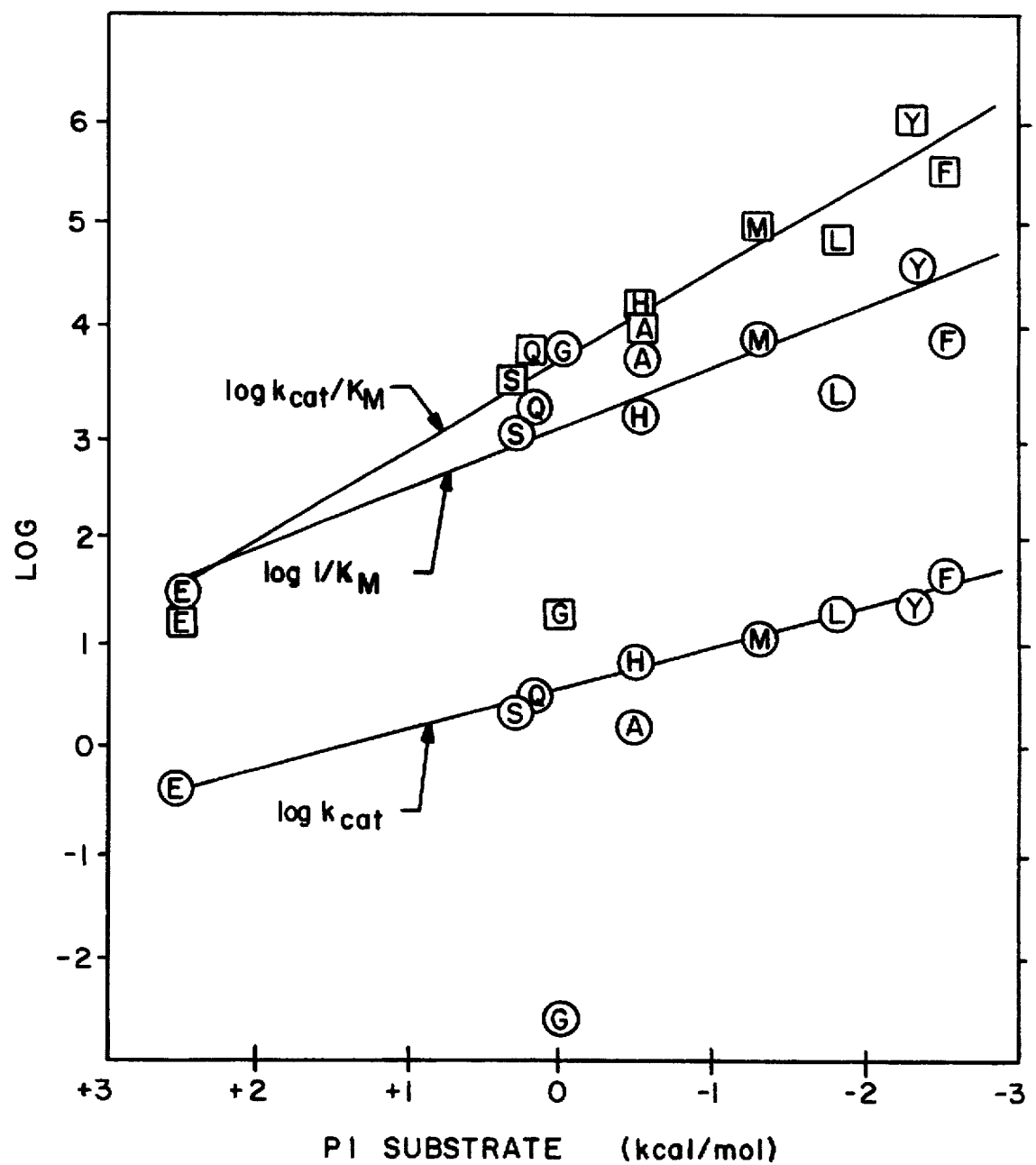
FIG. 14 depicts the effect of hydrophobicity of the P-1 substrate side-chain on the kinetic parameters of wild-type *B. amyloliquefaciens* subtilisin.

The ratio of kcat/Km (also referred to as catalytic efficienty) is the apparent second order rate constant for the conversion of free enzyme plus substrate (E+S) to enzyme plus products (E+P) (Jencks, W. P., *Catalysis in Chemistry and Enzymology* (McGraw-Hill, 1969) pp. 321–436; Fersht, A., *Enzyme Structure and Mechanism* (Freeman, San Francisco, 1977) pp. 226–287). The log (kcat/Km) is proportional to transition state binding energy, $\Delta G_T^{\neq}$. A plot of the log kcat/Km versus the hydrophobicity of the P1 side-chain (FIG. 14) shows a strong correlation (r=0.98), with the exception of the glycine substrate which shows evidence for non-productive binding. These data show that relative differences between transition-state binding energies can be accounted for by differences in P-1 side-chain hydrophobicity. When the transition-state binding energies are calculated for these substrates and plotted versus their respective side-chain hydrophobicities, the line slope is 1.2 (not shown). A slope greater than unity, as is also the case for chymotrypsin (Fersht, A., *Enzyme Structure and Mechanism* (Freeman, San Francisco, 1977) pp. 226–287; Harper, J. W., et al. (1984) *Biochemistry*, 23, 2995–3002), suggests that the P1 binding cleft is more hydrophobic than ethanol or dioxane solvents that were used to empirically determine the hydrophobicity of amino acids (Nozaki, Y., et al. *J. Biol. Chem.* (1971) 246, 2211–2217; Tanford, C. (1978) *Science* 200, 1012).

For amide hydrolysis by subtilisin BPN', kcat can be interpreted as the acylation rate constant and Km as the dissociation constant, for the Michaelis complex (E·S), Ks. Gutfreund, H., et al (1956) *Biochem. J.* 63, 656. The fact that the log kcat, as well as log 1/Km, correlates with substrate hydrophobicity is consistent with proposals (Robertus, J. D., et al. (1972) *Biochemistry* 11, 2439–2449; Robertus, J. D., et al. (1972) *Biochemistry* 11, 4293–4303) that during the acylation step the P-1 side-chain moves deeper into the hydrophobic cleft as the substrate advances from the Michaelis complex (E·S) to the tetrahedral transition-state complex (E·S$^{\neq}$). However, these data can also be interpreted as the hydrophobicity of the P1 side-chain effecting the orientation, and thus the susceptibility of the scissile peptide bond to nucleophilic attack by the hydroxyl group of the catalytic Ser221.

The dependence of kcat/Km on P-1 side chain hydrophobicity suggested that the kcat/Km for hydrophobic substrates may be increased by increasing the hydrophobicity of the S-1 binding subsite. To test this hypothesis, hydrophobic amino acid substitutions of Gly166 were produced.

Since hydrophobicity of aliphatic side-chains is directly proportional to side-chain surface area (Rose, G. D., et al. (1985) *Science* 229, 834–838; Reynolds, J. A., et al. (1974) *Proc. Natl. Acad. Sci. USA* 71, 2825–2927), increasing the hydrophobicity in the S-1 subsite may also sterically hinder binding of larger substrates. Because of difficulties in predicting the relative importance of these two opposing effects, we elected to generate twelve non-charged mutations at position 166 to determine the resulting specificities against non-charged substrates of varied size and hydrophobicity.

B. Cassette Mutagenesis of the P1 Binding Cleft

The preparation of mutant subtilisins containing the substitution of the hydrophobic amino acids Ala, Val and Phe into residue 166, has been described in EPO Publication No. 0130756. The same method was used to produce the remaining hydrophobic mutants at residue 166. In applying this method, two unique and silent restriction sites were introduced in the subtilisin genes to closely flank the target codon 166. As can be seen in FIG. 13, the wild type sequence (line 1) was altered by site-directed mutagenesis in M13 using the indicated 37mer mutagenesis primer, to introduce a 13 bp deletion (dashedline) and unique SacI and XmaI sites (underlined sequences) that closely flank codon 166. The subtilisin gene fragment was subcloned back into the *E. coli—B. subtilis* shuttle plasmid, pBS42, giving the plasmid pΔ166 (FIG. 13, line 2). pΔ166 was cut open with SacI and XmaI, and gapped linear molecules were purified (FIG. 13, line 3). Pools of synthetic oligonucleotides containing the mutation of interest were annealed to give duplex DNA cassettes that were ligated into gapped pΔ166 (underlined and overlined sequences in FIG. 13, line 4). This construction restored the coding sequence except over position 166(NNN; line 4). Mutant sequences were confirmed by dideoxy sequencing. Asterisks denote sequence changes from the wild type sequence. Plasmids containing each mutant *B. amyloliquefaciens* subtilisin gene were expressed at roughly equivalent levels in a protease deficient strain of *B. subtilis*, BG2036 as previously described. EPO Publication No. 0130756; Yang, M., et al. (1984) *J. Bacteriol.* 160, 15–21; Estell, D. A., et al (1985) *J. Biol. Chem.* 260, 6518–6521.

C. Narrowing Substrate Specificity by Steric Hindrance

To probe the change in substrate specificity caused by steric alterations in the S-1 subsite, position 166 mutants were kinetically analyzed versus P1 substrates of increasing size (i.e., Ala, Met, Phe and Tyr). Ratios of kcat/Km are presented in log form in FIGS. 15A–15B to allow direct comparisons of transition-state binding energies between various enzyme-substrate pairs.

According to transition state theory, the free enery difference between the free enzyme plus substrate (E+S) and the transition state complex (E·S$^{\neq}$) can be calculated from equation (1), $$\Delta_{OT}^{\neq} = -RT \ln kcat/Km + RT \ln kT/h \qquad (1)$$

in which kcat is the turnover number, Km is the Michaelis constant, R is the gas constant, T is the temperature, k is Boltzmann's constant, and h is Planck's constant. Specificity differences are expressed quantitatively as differences between transition state binding energies (i.e., $\Delta\Delta G_T^*$), and can be calculated from equation (2).

$$\Delta\Delta G_T^* = -RT \ln (kcat/Km)_A/(kcat/KM)_B \quad (2)$$

A and B represent either two different substrates assayed against the same enzyme, or two mutant enzymes assayed against the same substrate.

Figure 15A:
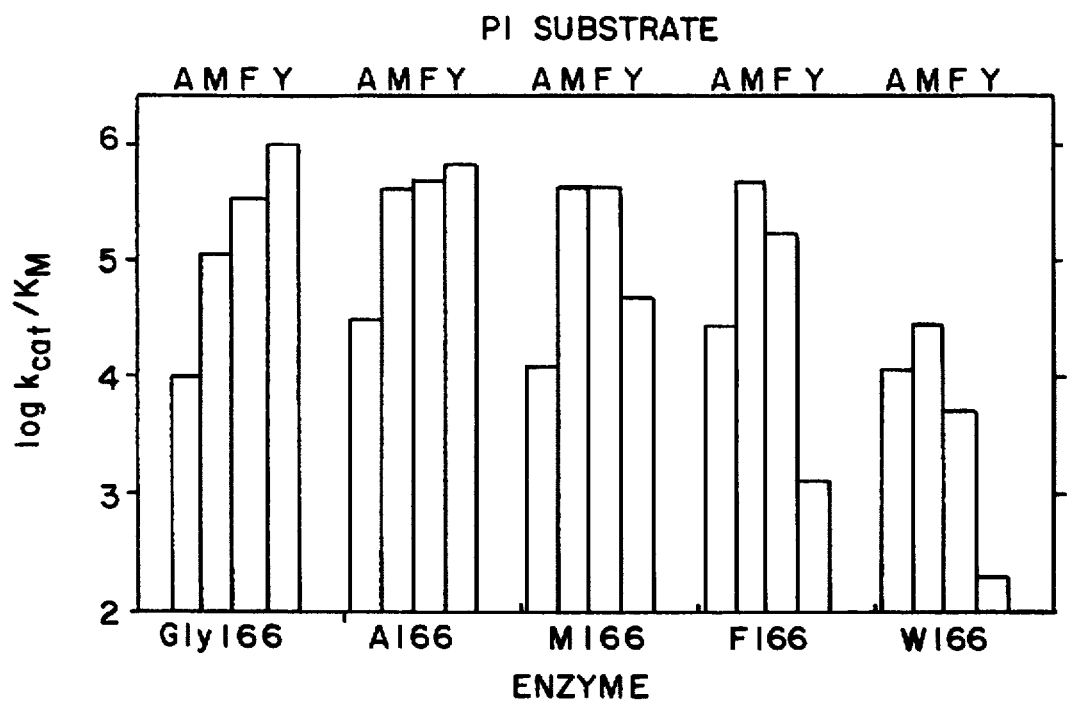
FIGS. 15A and 15B depicts the effect of position 166 side-chain substitutions on P-1 substrate specificity.
Figure 15B:
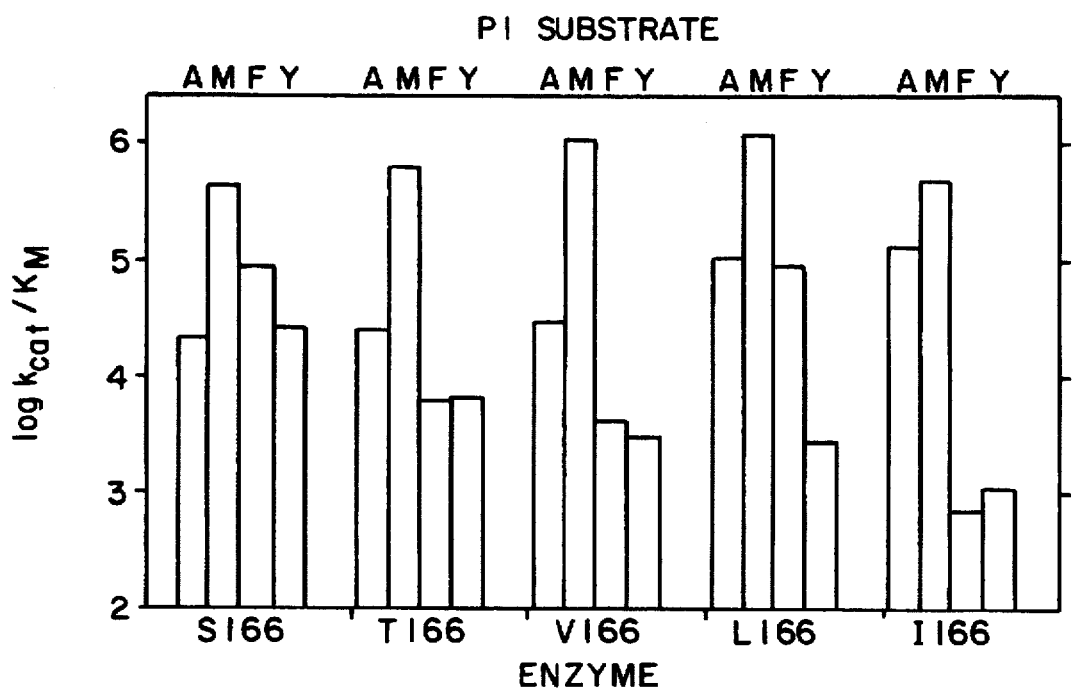
Figure 16A:
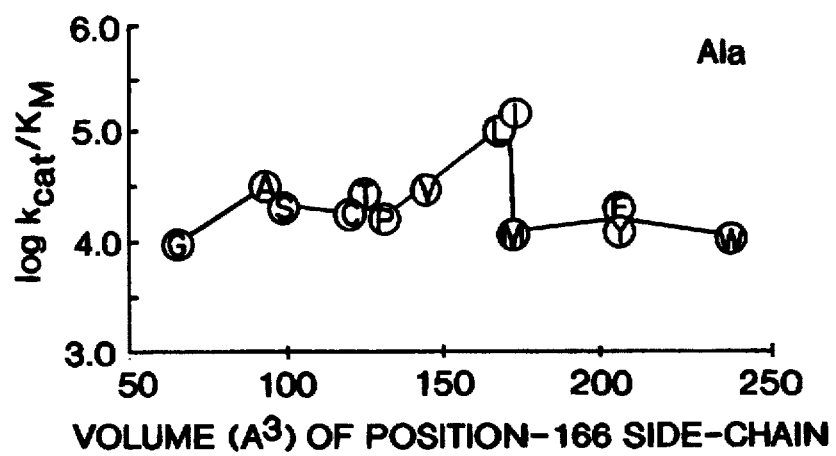
FIGS. 16A, 16B, 16C and 16D depicts the effect of position 166 side-chain volumn on log kcat/Km for various P-1 substrates.
Figure 16B:
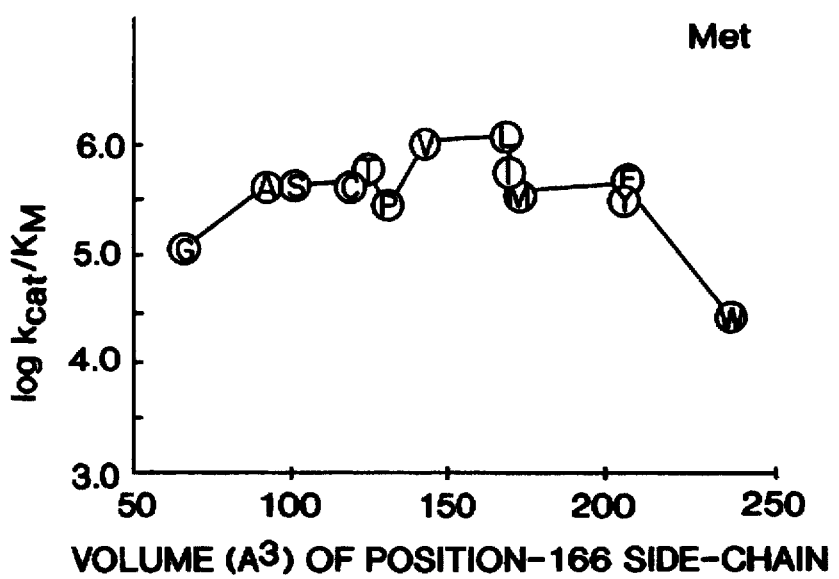
Figure 16C:
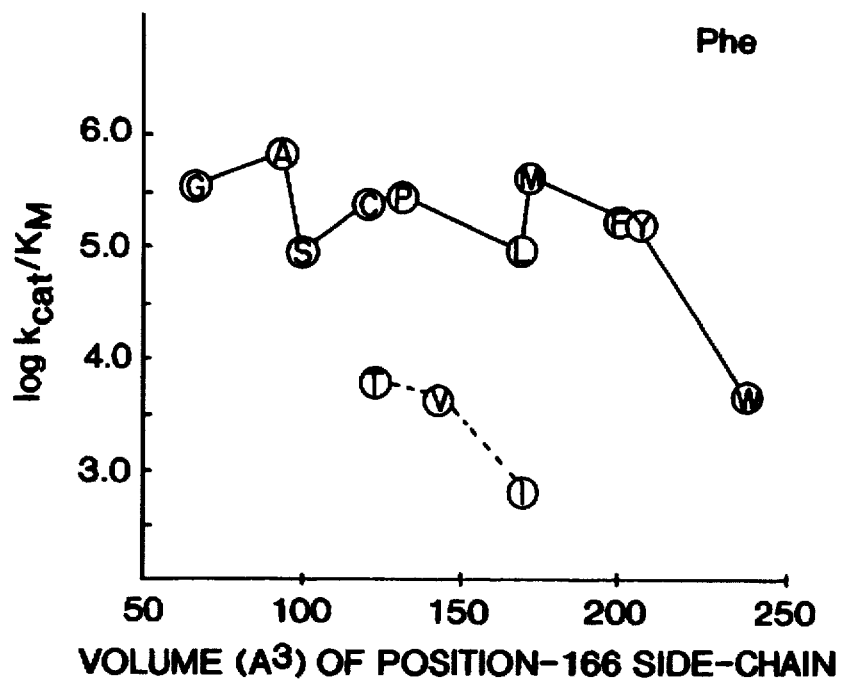
Figure 16D:
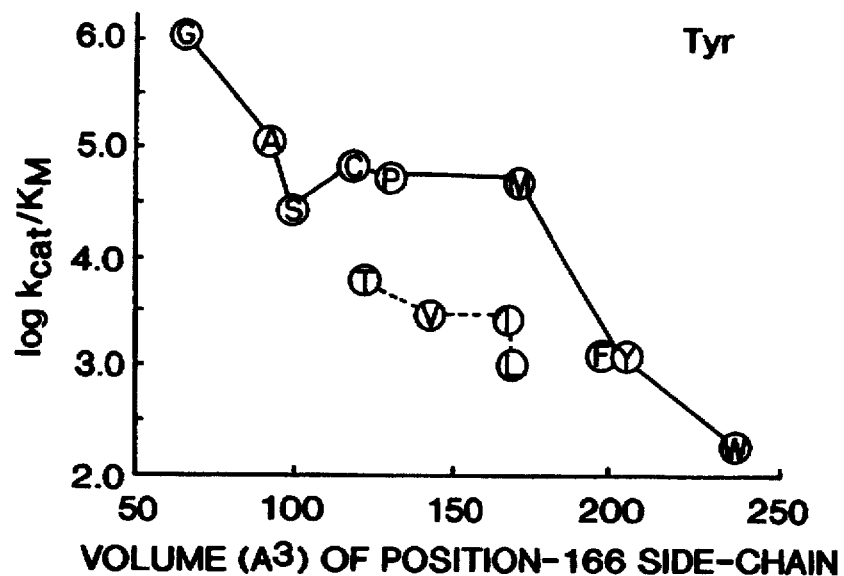

As can be seen from FIG. 15A, as the size of the side-chain at position 166 increases the substrate preference shifts from large to small P-1 side-chains. Enlarging the side-chain at position 166 causes kcat/Km to decrease in proportion to the size of the P-1 substrate side-chain (e.g., from Gly166 (wild-type) through W166, the kcat/Km for the Tyr substrate is decreased most followed in order by the Phe, Met and Ala P-1 substrates).

Specific steric changes in the position 166 side-chain, such as he presence of a β-hydroxyl group, β- or γ-aliphatic branching, cause large decreases in kcat/Km for larger P1 substrates. Introducing a β-hydroxyl group in going from A166 (FIGS. 15A and 15B) to S166 (FIG. 15B), causes an 8 fold and 4 fold reduction in kcat/Km for Phe and Tyr substrates, respectively, while the values for Ala and Met substrates are unchanged. Producing a β-branched structure, in going from S166 to T166, results in a drop of 14 and 4 fold in kcat/Km for Phe and Tyr, respectively. These differences are slightly magnified for V166 which is slightly larger and isosteric with T166. Enlarging the β-branched substituents from V166 to I166 causes a lowering of kcat/Km between two and six fold toward Met, Phe and Tyr substrates. Inserting a γ-branched structure, by replacing M166 (FIG. 15A) with L166 (FIG. 15B), produces a 5 fold and 18 fold decrease in kcat/Km for Phe and Tyr substrates, respectively. Aliphatic γ-branched appears to induce less steric hindrance toward the Phe P-1 substrate than β-branching, as evidenced by the 100 fold decrease in kcat/Km for the Phe substrate in going from L166 to I166.

Reductions in kcat/Km resulting from increases in side chain size in the S-1 subsite, or specific structural features such as β- and γ-branching, are quantitatively illustrated in FIGS. 16A, 16B, 16C and 16D. The kcat/Km values for the position 166 mutants determined for the Ala, Met, Phe, and Tyr P-1 substrates (top panel through bottom panel, respectively), are plotted versus the position 166 side-chain volumes (Chothia, C. (1984) Ann. Rev. Biochem. 53, 537–572). Catalytic efficiency for the Ala substrate reaches a maximum for I166, and for the Met substrate it reaches a maximum between V166 and L166. The Phe substrate shows a broad kcat/Km peak but is optimal with A166. Here, the β-branched position 166 substitutions form a line that is parallel to, but roughly 50 fold lower in kcat/Km than side-chains of similar size [i.e., C166 versus T166, L166 versus I166]. The Tyr substrate is most efficiently utilized by wild type enzyme (Gly166), and there is a steady decrease as one proceeds to large position 166 side-chains. The β-branched and γ-branched substitutions form a parallel line below the other non-charged substitutions of similar molecular volume.

The optimal substitution at position 166 decreases in volume with increasing volume of the P1 substrate [i.e., I166/Ala substrate, L166/Met substrate, A166/Phe substrate, Gly166/Tyr substrate]. The combined volumes for these optimal pairs may approximate the volume for productive binding in the S-1 subsite. For the optimal pairs, Gly166/Tyr substrate, A166/Phe substrate, L166/Met substrate, V166/Met substrate, and I166/Ala substrate, the combined volumes are 266,295,313,339 and 261 $A^3$, respectively. Subtracting the volume of the peptide backbone from each pair (i.e., two times the volume of glycine), an average side-chain volume of $160 \pm 32 A^3$ for productive binding can be calculated.

The effect of volume, in excess to the productive binding volume, on the drop in transition-state binding energy can be estimated from the Tyr substrate curve (bottom panel, FIGS. 16A, 16B, 16C and 16D), because these data, and modeling studies (FIG. 2), suggest that any substitution beyond glycine causes steric repulsion. A best-fit line drawn to all the data (r=0.87) gives a slope indicating a loss of roughly 3 kcal/mol in transition state binding energy per $100 A^3$ of excess volume. ($100 A^3$ is approximately the size of a leucyl side-chain.)

D. Enhanced Catalytic Efficiency Correlates with Increasing Hydrophobicity of the Position 166 Substitution Substantial increases in kcat/Km occur with enlargement of the position 166 side-chain, except for the Tyr P-1 substrate (FIGS. 16A, 16B, 16C and 16D). For example, kcat/Km increases in progressing from Gly166 to I166 for the Ala substrate (net of ten-fold), from Gly166 to L166 for the Met substrate (net of ten-fold) and from Gly166 to A166 for the Phe substrate (net of two-fold). The increases in kcat/Km cannot be entirely explained by the attractive terms in the van der Waals potential energy function because of their strong distance dependence ($1/r^6$) and because of the weak nature of these attractive forces (Jencks, W. P., Catalysis in Chemistry and Enzymology (McGraw-Hill, 1969) pp. 321–436; Fersht, A., Enzyme Structure and Mechanism (Freeman, San Francisco, 1977) pp. 226–287; Levitt, M. (1976) J. Mol. Biol. 104, 59–107). For example, Levitt (Levitt, M. (1976) J. Mol. Biol. 104, 59–107) has calculated that the van der Waals attraction between two methionyl residues would produce a maximal interaction energy of roughly –0.2 kcal/mol. This energy would translate to only 1.4 fold increase in kcat/Km.

The increases of catalytic efficiency caused by side-chain substitutions at position 166 are better accounted for by increases in the hydrophobicity of the S-1 subsite. The increase kcat/Km observed for the Ala and Met substrates with increasing position 166 side-chain size would be expected, because hydrophobicity is roughly proportional to side-chain surface area (Rose, G. D., et al. (1985) Science 229, 834–838; Reynolds, J. A., et al. (1974) Proc. Natl. Acad. Sci. USA 71, 2825–2927).

Another example that can be interpreted as a hydrophobic effect is seen when comparing kcat/Km for isosteric substitutions that differ in hydrophobicity such as S166 and C166 (FIGS. 16A, 16B, 16C and 16D). Cysteine is considerably more hydrophobic than serine (–1.0 versus +0.3 kcal/mol) (Nozaki, Y., et al. (1971) J. Biol. Chem. 246, 2211–2217; Tanford, C. (1978) Science 200, 1012). The difference in hydrophobicity correlates with the observation that C166 becomes more efficient relative to Ser166 as the hydrophobicity of the substrates increases (i.e., Ala<Met<Tye<Phe). Steric hindrance cannot explain these differences because serine is considerably smaller than cysteine (99 versus $118 A^3$). Paul, I. C., Chemistry of the –SH Group (ed. S. Patai, Wiley Interscience, New York, 1974) pp. 111–149.

E. Production of an Elastase-Like Specificity in Subtilisin

Figure 17:
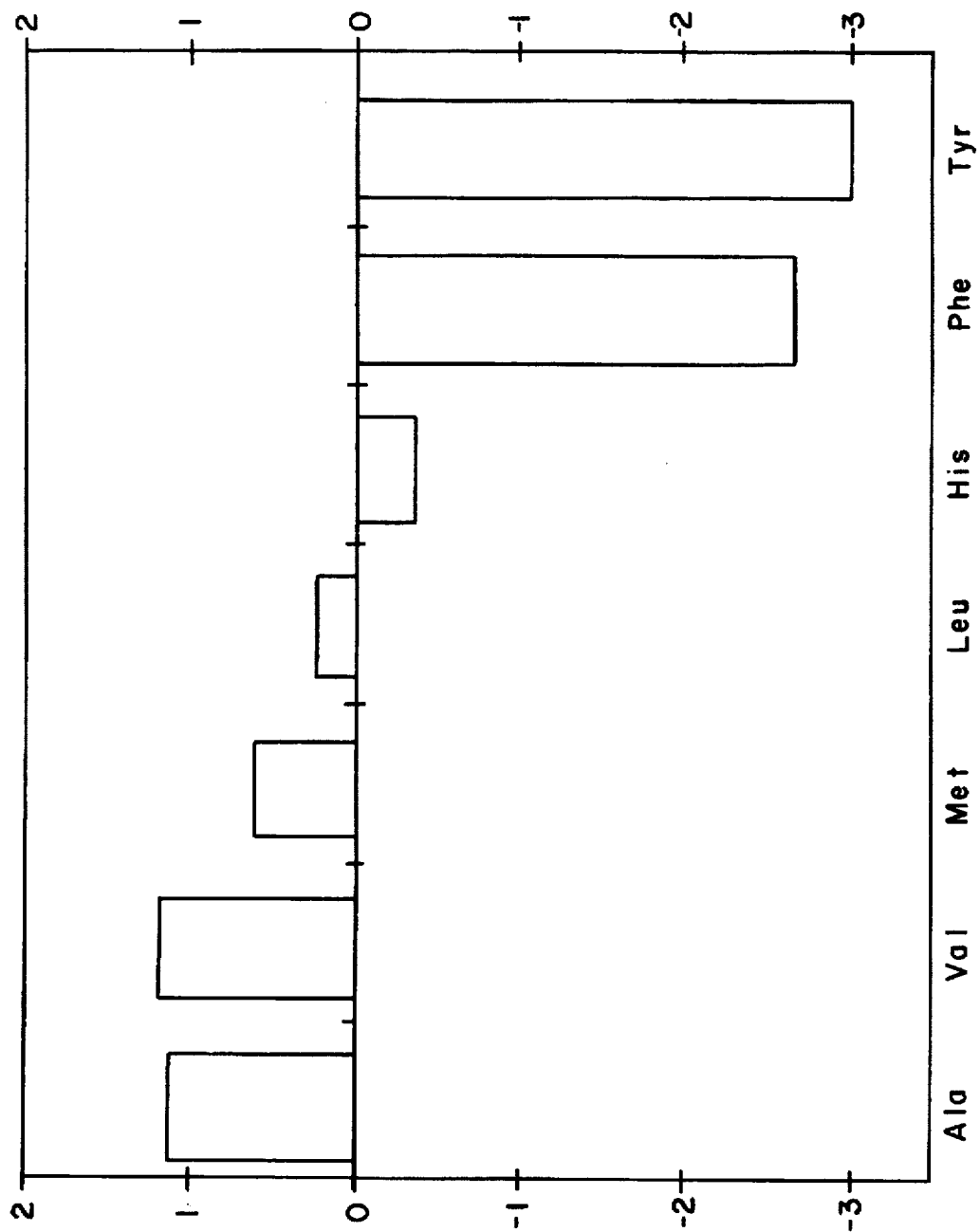
FIG. 17 shows the substrate specificity differences between Ile166 and wild-type (Gly166) *B. amyloliquefaciens* subtilisin against a series of alphatic and aromatic substrates. Each bar represents the difference in log kcat/Km for Ile166 minus wild-type (Gly166) subtilisin.

The I166 mutation illustrates particularly well that large changes in specificity can be produced by altering the structure and hydrophobicity of the S-1 subsite by a single mutation (FIG. 17). Progressing through the small hydrophobic substrates, a maximal specificity improvement over wild type occurs for the Val substrate (16 fold in kcat/Km).

As the substrate side chain size increases, these enhancements shrink to near unity (i.e., Leu and His substrates). The I166 enzyme becomes poorer against larger aromatic substrates of increasing size (e.g., I166 is over 1,000 fold worse against the Tyr substrate than is Gly166). We interpret the increase in catalytic efficiency toward the small hydrophobic substrates for I166 compared to Gly166to the greater hydrophobicity of isoluecine (i.e., −1.8 kcal/mol versus 0). Nozaki, Y., et al. (1971) *J. Biol. Chem.* 246, 2211–2217; Tanford, C. (1978) *Science* 200, 1012. The decrease in catalytic efficiency toward the very large substrates for I166 versus Gly166is attributed to steric repulsion.

The specificity differences between Gly166and I166 are similar to the specificity differences between chymotrypsin and the evolutionary relative, elastase (Harper, J. W., et al (1984) *Biochemistry* 23, 2995–3002). In elastase, the bulky amino acids, Thr and Val, block access to the P-1 binding site for large hydrophobic substrates that are preferred by chymotrypsin. In addition, the catalytic efficiencies toward small hydrophobic substrates are greater for elastase than for chymotrypsin as we obeseve for I166 versus Gly166in subtilisin.

EXAMPLE 4
Substitution of Ionic Amino Acids for Gly166

The construction of subtilisin mutants containing the substitution of the ionic amino acids Asp, Asn, Gln, Lys and Ang are disclosed in EPO Publication No. 0130756. In addition, a limited analysis of substrate specificity was presented therein. The present example describes the construction of the mutant subtilisin containing Glu at position 166 (E166) and presents some of the specificity data on these mutants. Further data on position 166 and 156 single and double mutants will be presented infra.

pΔ166, described in Example 3, was digested with SacI and XmaI. The double strand DNA cassette (underlined and overlined) of line 4 in FIG. 13 contained the triplet GAA for the codon 166 to encode the replacement of Glu for Gly166. This mutant plasmid designated pQ166 was propagated in BG2036 as described. This mutant subtilisin, together with the other mutants containing ionic substituent amino acids at residue 166, were isolated as described and further analyzed for variations in substrate specificity.

Each of these mutants was analyzed with the tetrapeptide substrates, succinyl-L-AlaL-AlaProL-X-p-nitroanilide, where X was Phe, Ala and Glu.

The results of this analysis are shown in Table IX.

TABLE IX

| Position 166 | P-1 Substrate (kcat/Km × 10⁻⁴) | | |
|---|---|---|---|
| | Phe | Ala | Glu |
| Gly (wild type) | 36.0 | 1.4 | 0.002 |
| Asp (D) | 0.5 | 0.4 | <0.001 |
| Glu (E) | 3.5 | 0.4 | <0.001 |
| Asn (N) | 18.0 | 1.2 | 0.004 |
| Gln (Q) | 57.0 | 2.6 | 0.002 |
| Lys (K) | 52.0 | 2.8 | 1.2 |
| Arg (R) | 42.0 | 5.0 | 0.08 |

These results indicate that charged amino acid substitutions at Gly166have improved catalytic efficiencies (kcat/Km) for oppositely charged P-1 substrates (as much as 500 fold) and poorer catalytic efficiency for like charged P-1 substrates.

EXAMPLE 5
Substitution of Glycine at Position 169

The substitution of Gly169 in *B. amyloliquefaciens* subtilisin with Ala and Ser is described in EPO Publication No. 0130756. The same method was used to make the remaining 17 mutants containing all other substituent amino acids for position 169.

The construction protocol is summarized in FIG. 18. The overscored and underscored double stranded DNA cassettes used contained the following triplet encoding the substitution of the indicated amino acid at residue 169.

| | |
|---|---|
| GCT | A |
| TGT | C |
| GAT | D |
| GAA | E |
| TTC | F |
| GGC | G |
| CAC | H |
| ATC | I |
| AAA | K |
| CTT | L |
| ATG | M |
| AAC | N |
| CCT | P |
| CAA | Q |
| AGA | R |
| AGC | S |
| ACA | T |
| GTT | V |
| TGG | W |
| TAC | Y |

Each of the plasmids containing a substituted Gly169 was designated pX169, where X represents the substituent amino acid. The mutant subtilisins were simialrly designated.

Two of the above mutant subtilisins, A169 and S169, were analyzed for substrate specificity against synthetic substrates containing Phe, Leu, Ala and Arg in the P-1 position. The following results are shown in Table X.

TABLE X

Effect of Serine and Alanine Mutations at Position 169 on P-1 Substrate Specificity

| Position 169 | P-1 Substrate (kcat/Km × 10⁻⁴) | | | |
|---|---|---|---|---|
| | Phe | Leu | Ala | Arg |
| Gly (wild type) | 40 | 10 | 1 | 0.4 |
| A169 | 120 | 20 | 1 | 0.9 |
| S169 | 50 | 10 | 1 | 0.6 |

These results indicate that substitutions of Ala and Ser at Gly169 have remarkably similar catalytic efficiencies against a range of P-1 substrates compared to their position 166 counterparts. This is probably because position 169 is at the bottom of the P-1 specificity subsite.

EXAMPLE 6
Substitution at Position 104

Tyr104 has been substituted with Ala, His, Leu, Met and Ser. The method used was a modification of the site directed mutagenesis method. According to the protocol of FIG. 19, a primer (shaded in line 4) introduced a unique HindIII site and a frame shift mutation at codon 104. Restriction-purification for the unique HindIII site facilitated the isolation of the mutant sequence (line 4). Restriction-selection against this HindIII site using pimers in line 5 was used to obtain position 104 mutants.

The following triplets were used in the primers of FIG. 19, line 5 for the 104 codon which substituted the following amino acids.

| GCT | Ala | TTC | Phe |
| ATG | Met | CCT | Pro |
| CTT | Leu | ACA | Thr |
| AGC | Ser | TGG | Trp |
| CAC | His | TAC | Tyr |
| CAA | Gln | GTT | Val |
| GAA | Glu | AGA | Arg |
| GGC | Gly | AAC | Asn |
| ATC | Ile | GAT | Asp |
| AAA | Lys | TGT | Cys |

The following substrates were used to analyze the substrate specificity of these mutants to give the indicated results in Table XI.

TABLE XI

| Substrate | kcat | | Km | | Kcat/Km | |
| --- | --- | --- | --- | --- | --- | --- |
| | WT | H104 | WT | H104 | WT | H104 |
| sAAPFpNA | 50.0 | 22.0 | 1.4e-4 | 7.1e-4 | 3.6e5 | 3.1e4 |
| sAAPApNA | 3.2 | 2.0 | 2.3e-4 | 1.9e-3 | 1.4e4 | 1e3 |
| sFAPFpNA | 26.0 | 38.0 | 1.8e-4 | 4.1e-4 | 1.5e5 | 9.1e4 |
| sFAPApNA | 0.32 | 2.4 | 7.3e-5 | 1.5e-4 | 4.4e3 | 1.6e4 |

From these data it is clear that the substitution of His for Tyr at position 104 produces an enzyme which is more efficient (higher kcat/Km) when Phe is at the P-4 substrate position than when Ala is at the P-4 substrate position.

EXAMPLE 7
Substitution of Ala152

Ala152 has been substituted by Gly and Ser to determine the effect of such substitutions on substrate specificity.

The wild type DNA sequence was mutated by the V152/P153 primer (FIG. 20, line 4) using the above restriction-purification approach for the new KpnI site. Other mutant primers (shaded sequences FIG. 20; S152, line 5 and G152, line 6) mutated the new KpnI site away and such mutants were isolated using the restriction-selection procedure as described above for loss of the KpnI site.

The results of these substitutions for the above synthetic substrates containing the P-1 amino acids Phe, Leu and Ala are shown in Table XII.

TABLE XII

| | P-1 Substrate (kcat/Km × 10⁻⁴) | | |
| --- | --- | --- | --- |
| Position 152 | Phe | Leu | Ala |
| Gly (G) | 0.2 | 0.4 | <0.04 |
| Ala (wild type) | 40.0 | 10.0 | 1.0 |
| Ser (S) | 1.0 | 0.5 | 0.2 |

These results indicate that, in contrast to positions 166 and 169, replacement of Ala152 with Ser or Gly causes a dramatic reduction in catalytic efficiencies across all substrates tested. This suggests Ala152, at the top of the S-1 subsite, may be the optimal amino acid because Ser and Gly are homologous Ala substitutes.

EXAMPLE 8
Substitution at Position 156

Figure 21:
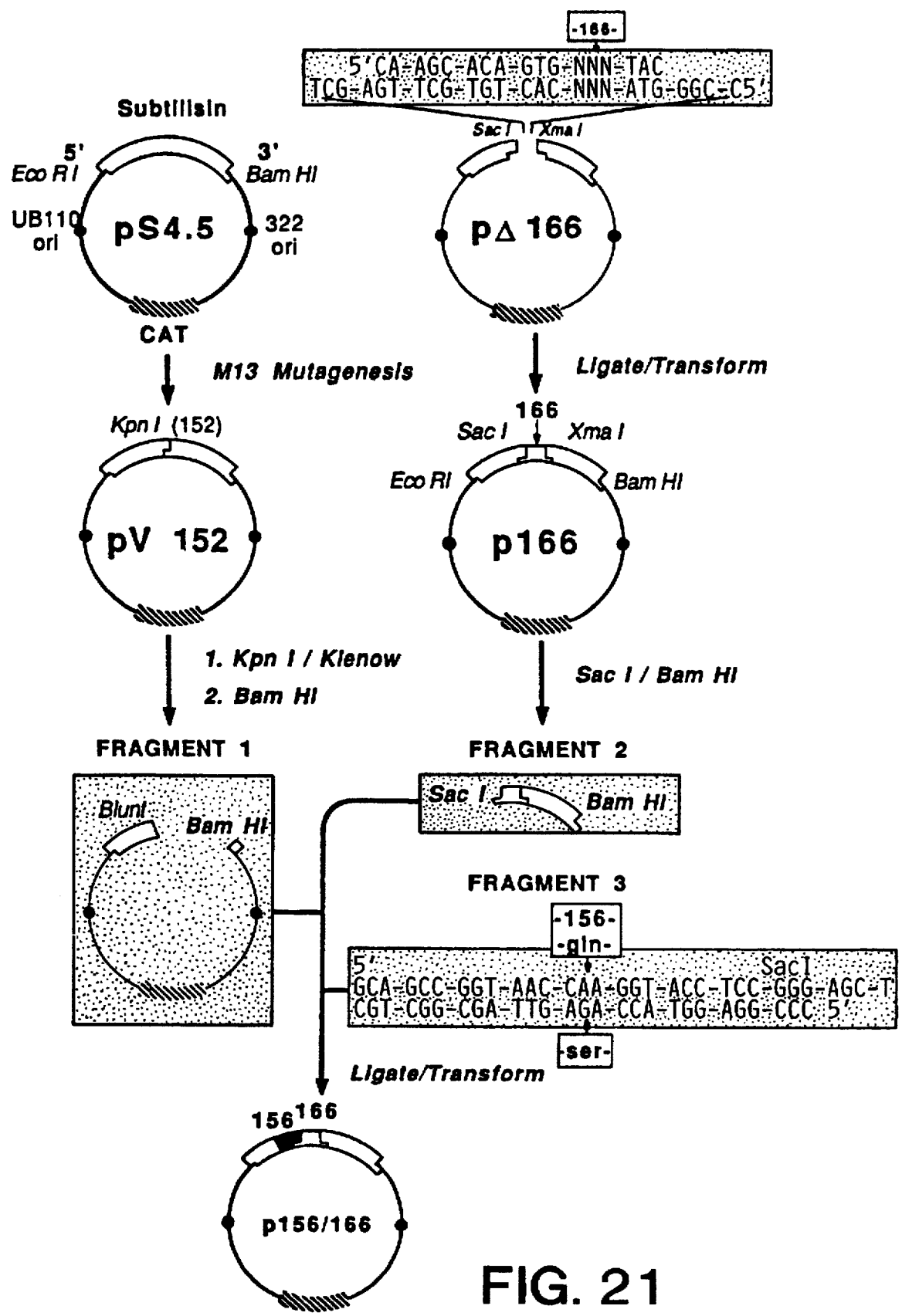
FIG. 21 depicts the construction of single mutations at codon 156 and double mutations at codons 156 and 166 of *B. amyloliquefaciens* subtilisin.

Mutants containing the substitution of Ser and Gln for Glu156 have been constructed according to the overall method depicted in FIG. 21. This method was designed to facilitate the construciton of multiple mutants at position 156 and 166 as will be described hereinafter. However, by regenerating the wild type Gly166, single mutations at Glu156 were obtained.

The plasmid pΔ166 is already depicted in line 2 of FIG. 13. The synthetic oligonucleotides at the top right of FIG. 21 represent the same DNA cassettes depicted in line 4 of FIG. 13. The plasmid p166 in FIG. 21 thus represents the mutant plasmids of Examples 3 and 4. In this particular example, p166 contains the wild type Gly166.

Construction of position 156 single mutants were prepared by ligation of the three fragments (1–3) indicated at the bottom of FIG. 21. Fragment 3, containing the carboxy-terminal portion of the subtilisin gene including the wild type position 166 codon, was isolated as a 610 bp SacI-BamHI fragment. Fragment 1 contained the vector sequences, as well as the amino-terminal sequences of the subtilisin gene through codon 151. To produce fragment 1, a unique KpnI site at codon 152 was introduced into the wild type subtilisin sequence from pS4.5. Site-directed mutagenesis in M13 employed a primer having the sequence 5'-TA-GTC-GTT-GCG-GTA-CCC-GGT-AAC-GAA-3' to produce the mutation. Enrichment for the mutant sequence was accomplished by restriction with KpnI, purification and self ligation. The mutant sequence containing the KpnI site was confirmed by direct plasmid sequencing to give pV-152. pV-152 (~1 μg) was digested with KpnI and treated with 2 units of DNA polymerase I large fragment (Klenow fragment from Boeringer-Mannheim) plus 50 μM deoxynucleotide triphosphates at 37° C. for 30 min. This created a blunt end that terminated with codon 151. The DNA was extracted with 1:1 volumes phenol and CHCl₃, and DNA in the aqueous phase was precipitated by addition of 0.1 volumes 5M ammonium acetate and two volumes ethanol. After centrifugation and washing the DNA pellet with 70% ethanol, the DNA was lyophilized. DNA was digested with BamHI and the 4.6 kb piece (fragment 1) was purified by acrylamide gel electrophoresis followed by electroelution. Fragment 2 was a duplex synthetic DNA cassette which when ligated with fragments 1 and 3 properly restored the coding sequence except at codon 156. The top strand was synthesized to contain a glutamine codon, and the complementary bottom strand coded for serine at 156. Ligation of heterophosphorylated cassettes leads to a large and favorable bias for the phosphorylated over the non-phosphorylated oligonucleotide sequence in the final segrated plasmid product. Therefore, to obtain Q156 the top strand was phosphorylated, and annealed to the non-phosphorylated bottom strand prior to ligation. Similarly, to obtain S156 the bottom strand was phosphorylated and annealed to the non-phosphorylated top strand. Mutant sequences were isolated after ligation and transformation, and were confirmed by restriction analysis and DNA sequencing as before. To express variant subtilisins, plasmids were transformed into a subtilisin-neutral protease deletion mutant of B. subtilis, BG2036, as previously described. Cultures were fermented in shake flasks for 24 h at 37° C. in LB media containing 12.5 mg/mL chlorphenicol and subtilisin was purified from culture supernatants as described. Purity of subtilisin was greater than 95% as judged by SDS PAGE.

These mutant plasmids designated pS156 and pQ156 and mutant subtilisins designated S156 and Q156 were analyzed with the above synthetic substrates where P-1 comprised the amino acids Glu, Gln, Met and Lys. The results of this analyses are presented in Example 9.

EXAMPLE 9
Multiple Mutants With Altered Substrate Specificity—Substitution at Positions 156 and 166

Single substitutions of position 166 are described in Examples 3 and 4. Example 8 describes single substitutions at position 156 as well as the protocol of FIG. 21 whereby various double mutants comprising the substitution of various amino acids at positions 156 and 166 can be made. This example describes the construction and substrate specificity of subtilisin containing substitutions at position 156 and 166 and summarized some of the data for single and double mutants at positions 156 and 166 with various substrates.

K166 is a common replacement amino acid in the 156/166 mutants described herein. The replacement of Lys for Gly166was achieved by using the synthetic DNA cassette at the top right of FIG. 21 which contained the triplet AAA for NNN. This produced fragment 2 with Lys substituting for Gly166.

The 156 substituents were Gln and Ser. The Gln and Ser substitutions at Gly156 are contained within fragment 3 (bottom right FIG. 21).

The multiple mutants were produced by combining fragments 1, 2 and 3 as described in Example 8. The mutants Q156/K166 and S156/K166 were selectively generated by differential phosphorylation as described. Alternatively, the double 156/166 mutants, c.f. Q156/K166 and S156/K166, were prepared by ligation of the 4.6 kb SacI-BamHI fragment from the relevant p156 plasmid containing the 0.6 kb SacI-BamHI fragment from the relevant p166 plasmid.

Figure 23A:
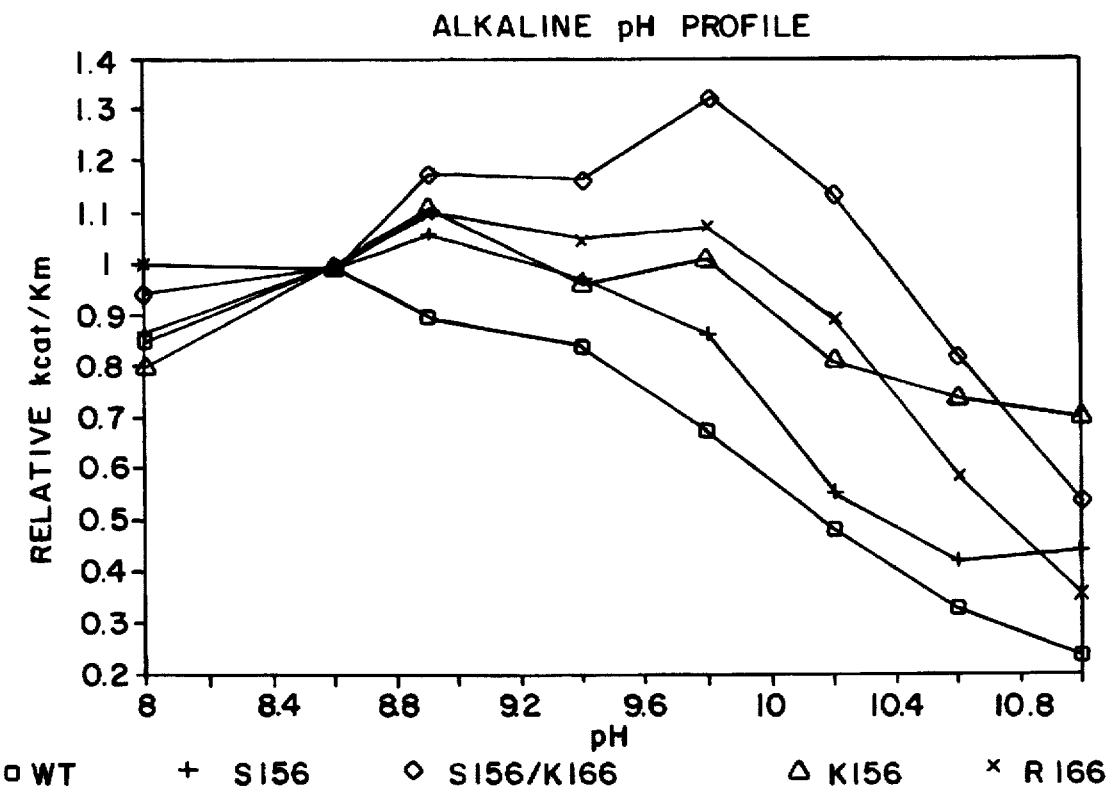
FIG. 23A depicts the kcat/Km versus pH profile for mutations at codon 156 and 166 in *B. amyloliquefaciens* subtilisin.
Figure 23B:
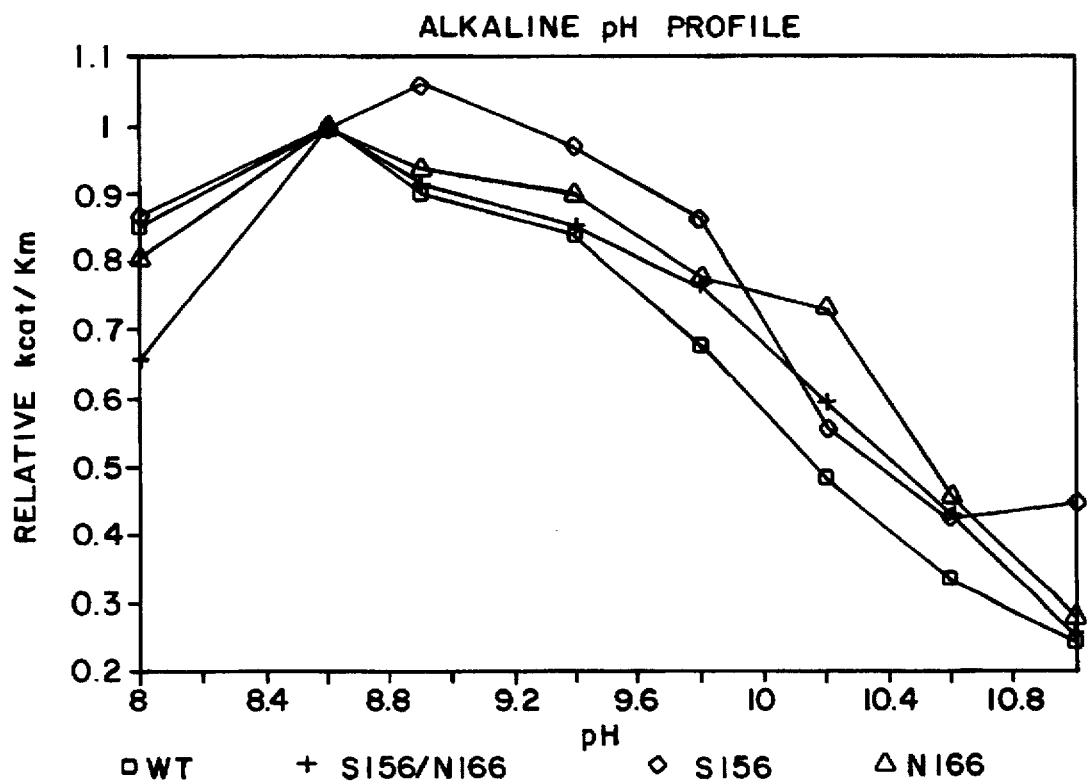
FIG. 23B depicts the kcat/Km versus pH profile for mutations at codon 156 and 166 in *B. amyloliquefaciens* subtilisin.
Figure 24:
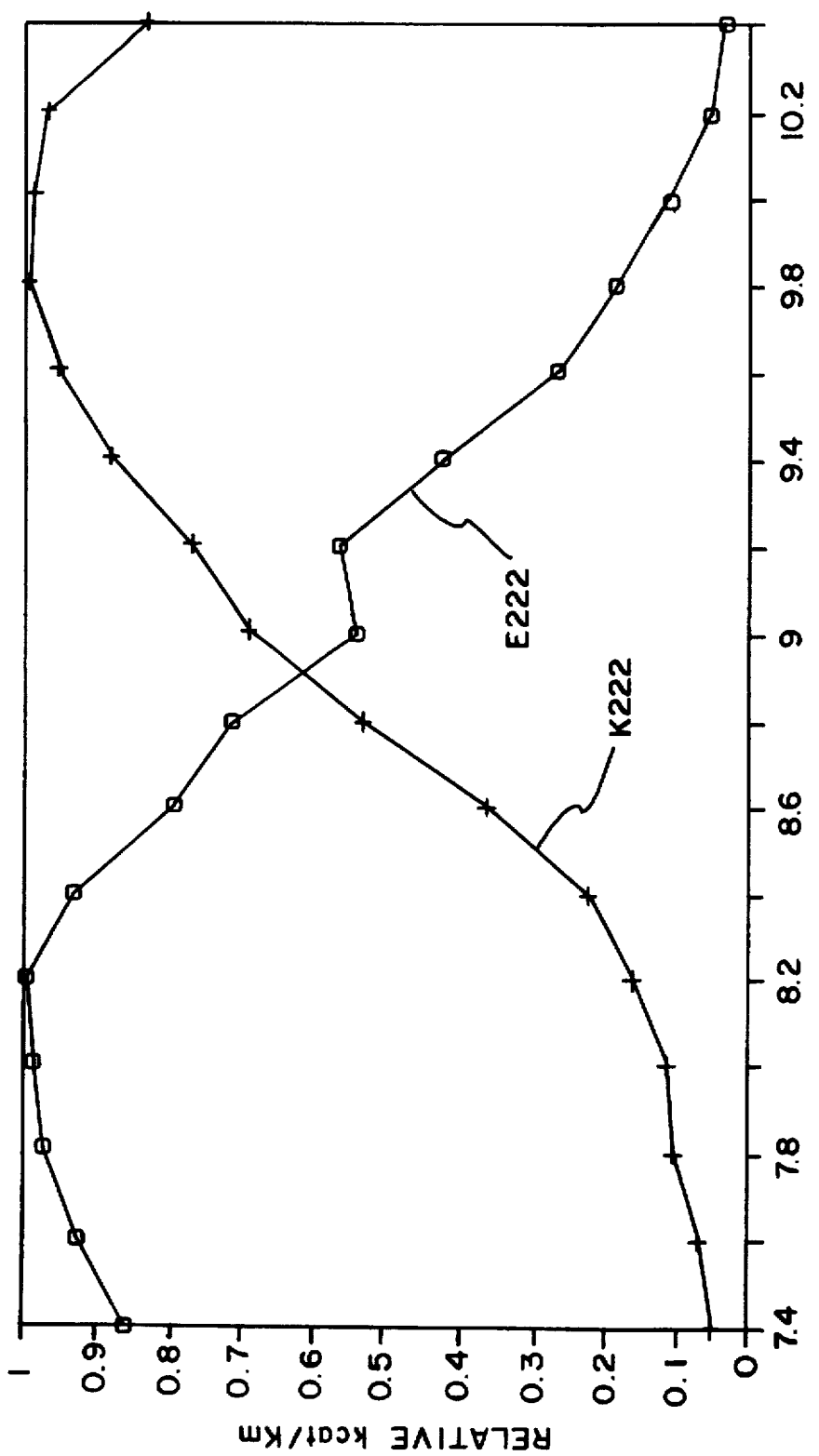
FIG. 24 depicts the kcat/Km versus pH profile for mutations at codon 222 in *B. amyloliquefaciens* subtilisin.

These mutants, the single mutant K166, and the S156 and Q156 mutants of Example 8 were analyzed for substitute specificity against synthetic polypeptides containing Phe or Glu as the P-1 substrate residue. The results are presented in Table XIII.

with glutamate at the P-1 enzyme binding site. When these single mutations were combined, the resulting multiple enzyme mutants are better than either parent. These single or multiple mutations also alter the relative pH activity profiles of the enzymes as shown in FIGS. 23A and 23B.

To isolate the contribution of electrostatics to substrate specificity from other chemical binding forces, these various single and double mutants were analyzed for their ability to bind and cleave synthetic substrates containing Glu, Gln, Met and Lys as the P-1 substrate amino acid. This permitted comparisons between side-chains that were more sterically similar but differed in charge (e.g., Glu versus Gln, Lys versus Met). Similarly, mutant enzymes were assayed against homologous P-1 substrates that were most sterically similar but differed in charge (Table XIV).

TABLE XIII

| Enzymes Compared[b] | Substrate P-1 Residue | kcat | Km | kcat/Km | kcat/Km (mutant) kcat/Km(wt) |
|---|---|---|---|---|---|
| Glu-156/Gly-166 (WT) | Phe | 50.00 | $1.4 \times 10^{-4}$ | $3.6 \times 10^5$ | (1) |
|  | Glu | 0.54 | $3.4 \times 10^{-2}$ | $1.6 \times 10^1$ | (1) |
| Lys-166 | Phe | 20.00 | $4.0 \times 10^{-5}$ | $5.2 \times 10^5$ | 1.4 |
|  | Glu | 0.70 | $5.6 \times 10^{-5}$ | $1.2 \times 10^4$ | 750 |
| Gln-156/Lys-166 | Phe | 30.00 | $1.9 \times 10^{-5}$ | $1.6 \times 10^6$ | 4.4 |
|  | Glu | 1.60 | $3.1 \times 10^{-5}$ | $5.0 \times 10^4$ | 3100 |
| Ser-156/Lys-166 | Phe | 30.00 | $1.8 \times 10^{-5}$ | $1.6 \times 10^6$ | 4.4 |
|  | Glu | 0.60 | $3.9 \times 10^{-5}$ | $1.6 \times 10^4$ | 1000 |
| Ser-156 | Phe | 34.00 | $4.7 \times 10^{-5}$ | $7.3 \times 10^5$ | 2.0 |
|  | Glu | 0.40 | $1.8 \times 10^{-3}$ | $1.1 \times 10^2$ | 6.9 |
| Glu-156 | Phe | 48.00 | $4.5 \times 10^{-5}$ | $1.1 \times 10^6$ | 3.1 |
|  | Glu | 0.90 | $3.3 \times 10^{-3}$ | $2.7 \times 10^2$ | 17 |

As can be seen in Table XIV, either of these single mutations improve enzyme performance upon substrates

TABLE XIV

Kinetics of Position 156/166 Subtilisins Determined for Different P1 Substrates

| Enzyme Position[a] | Net Charge[b] | P-1 Substrate log kcat/Km (log 1/Km)[c] | | | |
|---|---|---|---|---|---|
| | | Glu | Gln | Met | Lys |
| 156 166 | | | | | |
| Glu Asp | −2 | n.d. | 3.02 (2.56) | 3.93 (2.74) | 4.23 (3.00) |
| Glu Glu | −2 | n.d. | 3.06 (2.91) | 3.86 (3.28) | 4.48 (3.69) |
| Glu Asn | −1 | 1.62 (2.22) | 3.85 (3.14) | 4.99 (3.85) | 4.15 (2.88) |
| Glu Gln | −1 | 1.20 (2.12) | 4.36 (3.64) | 5.43 (4.36) | 4.10 (3.15) |
| Gln Asp | −1 | 1.30 (1.79) | 3.40 (3.08) | 4.94 (3.87) | 4.41 (3.22) |
| Ser Asp | −1 | 1.23 (2.13) | 3.41 (3.09) | 4.67 (3.68) | 4.24 (3.07) |
| Glu Met | −1 | 1.20 (2.30) | 3.89 (3.19) | 5.64 (4.83) | 4.70 (3.89) |

TABLE XIV-continued

Kinetics of Position 156/166 Subtilisins Determined for Different P1 Substrates

| Enzyme Position[a] | Net Charge[b] | P-1 Substrate log kcat/Km (log 1/Km)[c] | | | |
|---|---|---|---|---|---|
| | | Glu | Gln | Met | Lys |
| Glu Ala | −1 | n.d. | 4.34 (3.55) | 5.65 (4.46) | 4.90 (3.24) |
| Glu Gly(wt) | −1 | 1.20 (1.47) | 3.85 (3.35) | 5.07 (3.97) | 4.60 (3.13) |
| Gln Gly | 0 | 2.42 (2.48) | 4.53 (3.81) | 5.77 (4.61) | 3.76 (2.82) |
| Ser Gly | 0 | 2.31 (2.73) | 4.09 (3.68) | 5.61 (4.55) | 3.46 (2.74) |
| Gln Asn | 0 | 2.04 (2.72) | 4.51 (3.76) | 5.79 (4.66) | 3.75 (2.74) |
| Ser Asn | 0 | 1.91 (2.78) | 4.57 (3.82) | 5.72 (4.64) | 3.68 (2.80) |
| Glu Arg | 0 | 2.91 (3.30) | 4.26 (3.50) | 5.32 (4.22) | 3.19 (2.80) |
| Glu Lys | 0 | 4.09 (4.25) | 4.70 (3.88) | 6.15 (4.45) | 4.23 (2.93) |
| Gln Lys | +1 | 4.70 (4.50) | 4.64 (3.68) | 5.97 (4.68) | 3.23 (2.75) |
| Ser Lys | +1 | 4.21 (4.40) | 4.84 (3.94) | 6.16 (4.90) | 3.73 (2.84) |
| Maximum difference: | | | | | |
| log kcat/Km (log 1/Km)[d] | | 3.5 (3.0) | 1.8 (1.4) | 2.3 (2.2) | −1.3 (−1.0) |

Footnotes to Table XIV
(a) *B. subtilis*, BG 2036, expressing indicated variant subtilisin were fermented and enzymes purified as previously described (Estell, et al. (1985) *J. Biol. Chem.* 260, 6518–6521). Wild type subtilisin is indicated (wt) containing Glu156 and Gly166.
(b) Net charge in the P-1 binding site is defined as the sum of charges from positions 156 and 166 at pH 8.6.
(c) Values for kcat($s^{-1}$) and Km(M) were measured in 0.1M Tris pH 8.6 at 25° C. as previously described[3] against P-1 substrates having the form succinyl-L-AlaL-AlaL-ProL-[X]-p-nitroanilide, where X is the indicated P-1 amino acid. Values for log 1/Km are shown inside parentheses. All errors in determination of kcat/Km and 1/Km are below 5%.
(d) Because values for Glu156/Asp166(D166) are too small to determine accurately, the maximum difference taken for GluP-1 substrate is limited to a charge range of +1 to −1 charge change.
n.d.=not determined The kcat/Km ratios shown are the second order rate constants for the conversion of substrate to product, and represent the catalytic efficiency of the enzyme. These ratios are presented in logarithmic form to scale the data, and because log kcat/Km is proportional to the lowering of transition-state activation energy ($\Delta G_T$). Mutations at position 156 and 166 produce changes in catalytic efficiency toward Glu, Gln, Met and Lys P-1 substrates of 3100, 60, 200 and 20 fold, respectively. Making the P-1 binding-site more positively charged [e.g., compare Gln156/Lys166 (Q156/K166) versus Glu156/Met166 (Glu156/M166)] dramatically increased kcat/Km toward the Glu P-1 substrate (up to 3100 fold), and decreased the catalytic efficiency toward the Lys P-1 substrate (up to 10 fold). In addition, the results show that the catalytic efficiency of wild type enzyme can be greatly improved toward any of the four P-1 substrates by mutagenesis of the P-1 binding site.

The changes in kcat/Km are caused predominantly by changes in 1/Km. Because 1/Km is approximately equal to 1/Ks, the enzyme-substrate association constant, the mutations primarily cause a change in substrate binding. These mutations produce smaller effects on kcat that run parallel to the effects on 1/Km. The changes in kcat suggest either an alteration in binding in the P-1 binding site in going from the Michaelis-complex E·S) to the transition-state complex (E-S‡) as previously proposed (Robertus, J. D., et al. (1972) *Biochemistry* 11, 2439–2449; Robertus, J. D., et al. (1972) *Biochemistry* 11, 4293–4303), or change in the position of the scissile peptide bond over the catalytic serine in the E·S complex.

Figure 28B:
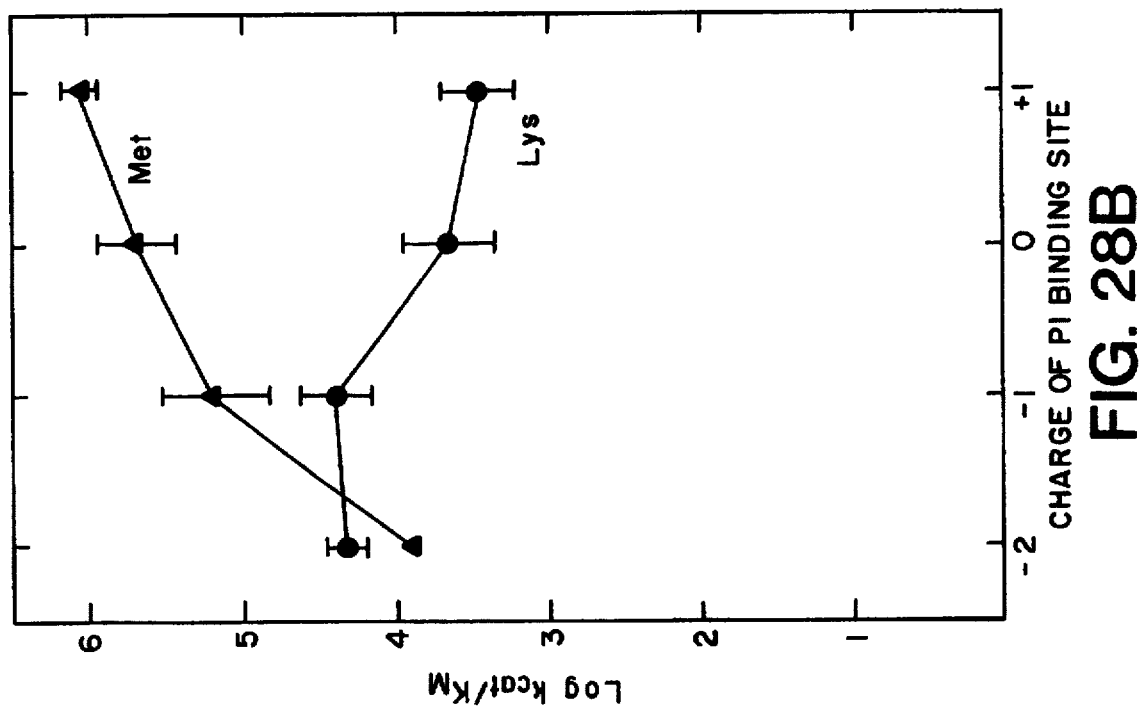
FIGS. 28A, B, C and D depict the effect of charge in the P-1 binding sites due to substitutions at codon 156 and 166.
Figure 28A:
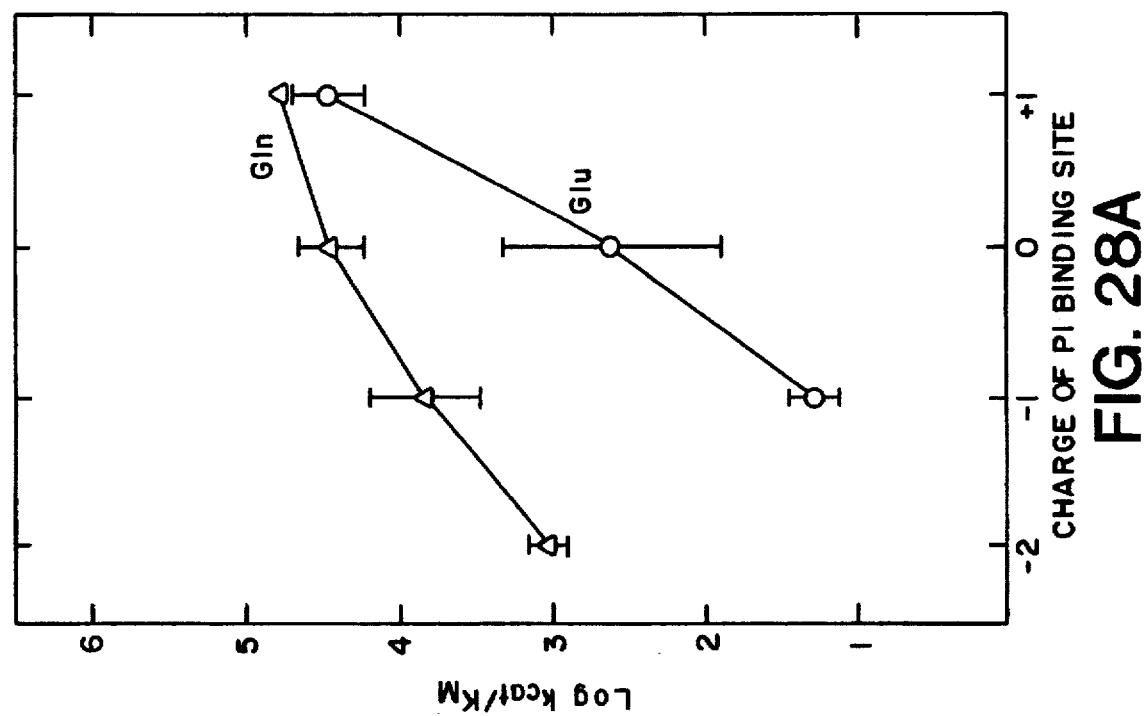

Changes in substrate preference that arise from changes in the net charge in the P-1 binding site show trends that are best accounted for by electrostatic effects (FIG. 28). As the P-1 binding cleft becomes more positively charged, the average catalytic efficiency increases much more for the Glu P-1 substrate than for its neutral and isosteric P-1 homolog, Gln (FIG. 28A). Furthermore, at the positive extreme both substrates have nearly identical catalytic efficiencies.

In contrast, as the P-1 site becomes more positively charged the catalytic efficiency toward the Lys P-1 substrate decreases, and diverges sharply from its neutral and isosteric homolog, Met (FIG. 28B). The similar and parallel upward trend seen with increasing positive charge for the Met and Glu P-1 substrates probably results from the fact that all the substrates are succinylated on their amino-terminal end, and thus carry a formal negative charge.

The trends observed in log kcat/Km are dominated by changes in the Km term (FIGS. 28C and 28D). As the pocket becomes more positively charged, the log 1/Km values converge for Glu and Gln P-1 substrates (FIG. 28C), and diverge for Lys and Met P-1 substrates (FIG. 28D). Although less pronounced effects are seen in log kcat, the effects of P-1 charge on log kcat parallel those seen in log 1/Km and become larger as the P-1 pocket becomes more positively charged. This may result from the fact that the transition-state is a tetrahedral anion, and a net positive charge in the enzyme may serve to provide some added stabilization to the transition-state.

The effect of the change in P-1 binding-site charge on substrate preference can be estimated from the differences in slopes between the charged and neutral isosteric P-1 substrates (FIG. 28B). The average change in substrate preference ($\Delta$log kcat/Km) between charged and neutral isosteric substrates increases roughly 10-fold as the complementary charge or the enzyme increases (Table XV). When comparing Glu versus Lys, this difference is 100-fold and the change in substrate preference appears predominantly in the Km term.

TABLE XV

Differential Effect on Binding Site Charge on log kcat/Km or (log 1/Km) for P-1 Substrates that Differ in Charge[a]

| Change in P-1 Binding Site Charge[b] | Δlog kcat/Km GluGln | Δlog kcat/Km MetLys | (Δlog 1/Km) GluLys |
|---|---|---|---|
| −2 to −1 | n.d. | 1.2 (1.2) | n.d. |
| −1 to 0 | 0.7 (0.6) | 1.3 (0.8) | 2.1 (1.4) |
| 0 to +1 | 1.5 (1.3) | 0.5 (0.3) | 2.0 (1.5) |
| Avg. change in log kcat/Km or (log 1/Km) per unit charge change | 1.1 (1.0) | 1.0 (0.8) | 2.1 (1.5) |

[a] The difference in the slopes of curves were taken between the P-1 substrates over the charge interval given for log (k(cat/Km) (FIG. 3A, B) and (log 1/Km) (FIG. 3D, D). Values represent the differential effect a charge change has in distinguishing the substrates that are compared.
[b] Charge in P-1 binding site is defined as the sum of charges from positions 156 and 166.

Figure 29A:
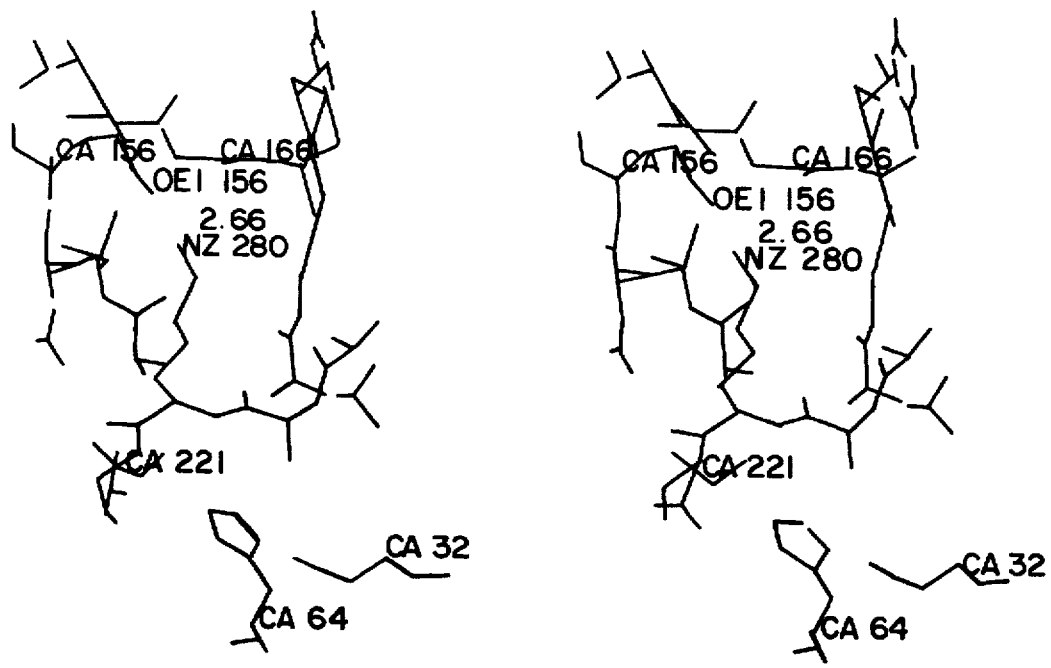
FIGS. 29A and B are a stereoview of the P-1 binding site of subtilisin BPN' showing a lysine P-1 substrate bound in the site in two ways. In 29A, Lysine P-1 substrate is built to form a salt bridge with a Glu at codon 156. In 29B, Lysine P-1 substrate is built to form a salt bridge with Glu at codon 166.
Figure 29B:
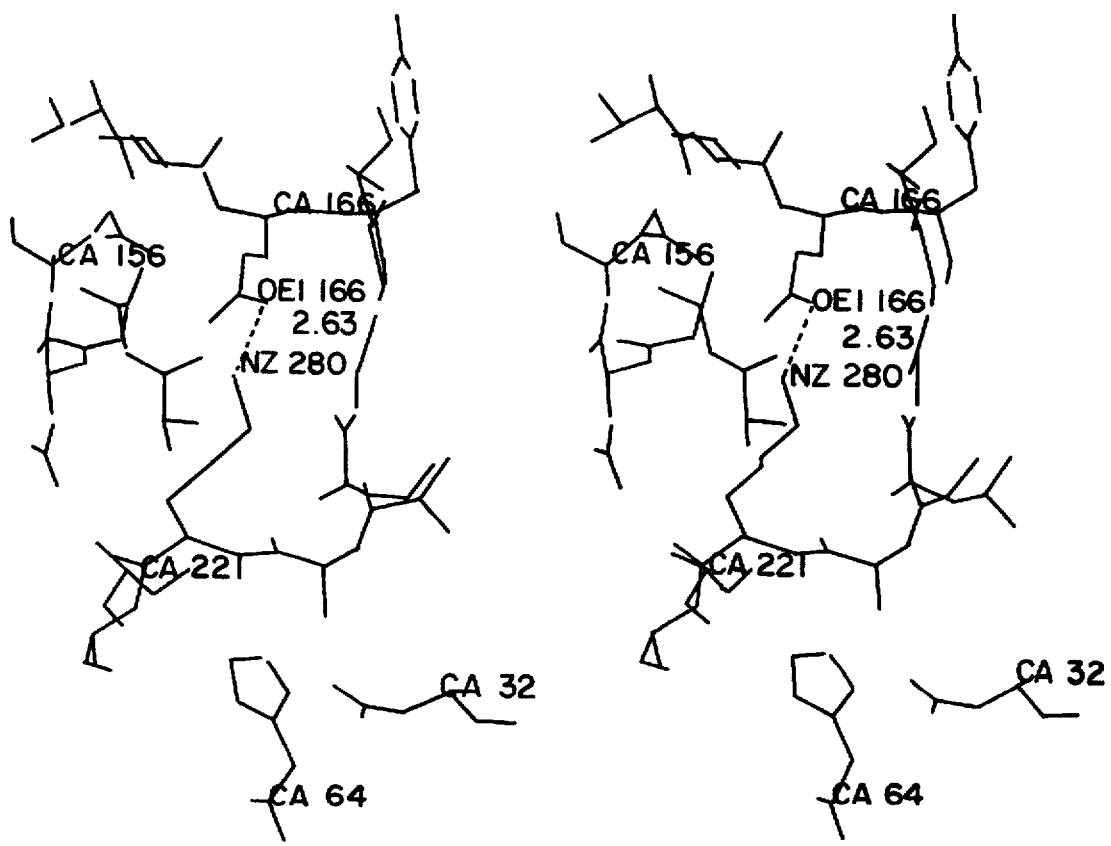

The free energy of electrostatic interactions in the structure and energetics of salt-bridge formation depends on the distance between the charges and the microscopic dielectric of the media. To dissect these structural and microenvironmental effects, the energies involved in specific salt-bridges were evaluated. In addition to the possible salt-bridges shown (FIGS. 29A and 29B), reasonable salt-bridges can be built between a Lys P-1 substrate and Asp at position 166, and between a Glu P-1 substrate and a Lys at position 166 (not shown). Although only one of these structures is confirmed by X-ray crystalography (Poulos, T. L., et al. (1976) *J. Mol. Biol.* 257 1097–1103), all models have favorable torsion angles (Sielecki, A. R., et al. (1979) *J. Mol. Biol.* 134, 781–804), and do not introduce unfavorable van der Waals contacts.

The change in charged P-1 substrate preference brought about by formation of the model salt-bridges above are shown in Table XVI.

(b) Enzymes compared have sterically similar amino acid substitutions that differ in charge at the indicated position.
(c) The P-1 substrates compared are structurally similar but differ in charge. The charged P-1 substrate is complementary to the charge change at the position indicated between enzymes 1 and 2.
(d) Date from Table XIV was used to compute the difference in log (kcat/Km) between the charged and the non-charged P-1 substrate (i.e., the substrate preference). The substrate preference is shown separately for enzyme 1 and 2.
(e) The difference in substrate preference between enzyme 1 (more highly charged) and enzyme 2 (more neutral) represents the rate change accompanying the electrostatic interaction.

The difference between catalytic efficiencies (i.e., Δlog kcat/Km) for the charged and neutral P-1 substrates (e.g., Lys minus Met or Glu minus Gln) give the substrate preference for each enzyme. The change in substrate preference (ΔΔlog kcat/Km) between the charged and more neutral enzyme homologs (e.g., Glu156/Gly166 minus Gln156 (Q156)/Gly166) reflects the change in catalytic efficiency that may be attributed solely to electrostatic effects.

These results show that the average change in substrate preference is considerably greater when electrostatic substitutions are produced at position 166 (50-fold in kcat/Km) versus position 156 (12-fold in kcat/Km). From these ΔΔlog kcat/Km values, an average change in transition-state stabilization energy can be calculated of −1.5 and −2.4 kcal/mol for substitutions at positions 156 and 166, respectively. This should represent the stabilization energy contributed from a favorable electrostatic interaction for the binding of free enzyme and substrate to form the transition-state complex.

At least three factors can contribute to the higher transition-state binding energies for electrostatic interactions at position 166. These include: (i) smaller charge separation for salt-bridges at position 166; (ii) more stable side-chain

TABLE XVI

Effect of Salt Bridge Formation Between Enzyme and Substrate on P1 Substrate Preference[a]

| Enzymes Compared[b] | | Enzyme Position Changed | P-1 Substrates Compared | Substrate[d] Preference Δlog (kcat/Km) | | Change in Substrate Preference ΔΔlog (kcat/Km) |
|---|---|---|---|---|---|---|
| 1 | 2 | | | 1 | 2 | (1−2) |
| Glu156/Asp166 | Gln156/Asp166 | 156 | LysMet | +0.30 | −0.53 | 0.83 |
| Glu156/Asn166 | Gln156/Asn166 | 156 | LysMet | −0.84 | −2.04 | 1.20 |
| Glu156/Gly166 | Gln156/Gly166 | 156 | LysMet | −0.47 | −2.10 | 1.63 |
| Glu156/Lsy-166 | Gln156/Lys166 | 156 | LysMet | −1.92 | −2.74 | 0.82 |
| | | | | | Ave ΔΔlog (kcat/Km) | 1.10 ± 0.3 |
| Glu156/Asp166 | Glu156/Asn166 | 166 | LysMet | +0.30 | −0.84 | 1.14 |
| Glu156/Glu166 | Glu156/Gln166 | 166 | LysMet | +0.62 | −1.33 | 1.95 |
| Gln156/Asp166 | Gln156/Asn166 | 166 | LysMet | −0.53 | −2.04 | 1.51 |
| Ser156/Asp166 | Ser156/Asn166 | 166 | LysMet | −0.43 | −2.04 | 1.61 |
| Glu156/Lys166 | Glu156/Met166 | 166 | GluGln | −0.63 | −2.69 | 2.06 |
| | | | | | Ave ΔΔlog (kcat/Km) | 1.70 ± 0.3 |

Footnotes to Table XVI (a) Molecular modeling shows it is possible to form a salt bridge between the indicated charged P-1 substrate and a complementary charge in the P-1 binding site of the enzyme at the indicated position changed.

geometries for salt-bridges at position 166; and (iii) microscopic dielectric constants at positions 166.

It is unreasonable to expect all of the energy difference to be due to shorter salt bridges at position 166, because these would have to be 1.6 times shorter than at position 156 for which crystalographic data (Mathews, D. A., et al. (1975) *J.*

*Biol. Chem.* 250, 7120–7126) indicate are optimally formed. Furthermore, molecular models of salt-bridges appear as structurally reasonable at 156 as at 166.

The binding energies may be more easily explained as differences in the microscopic dielectric constants at position 156 and 166. Assuming a salt-bridge distance of 3Å, ~2.7Å), the calculated dielectric constant at position 156 would be 72 ($\Delta Ge=Z_1Z_2/rD$ where Z is the charge on particle 1 and 2, r is the charge separation, and D is the dielectric constant). This corresponds closely with the dielectric constant of 78 for water at this temperature, and qualitatively fits with the fact that position 156 is located on the surface of the enzyme, and is freely exposed to solvent. A calculated dielectric constant for a salt-bridge at position 166 is 45, and fits with the fact that position 166 is more buried and less accessible to solvent. Furthermore, our estimate, based on the hydrophobicity, of the P-1 binding site, indicates that P-1 binding site has an overall dielectric constant close to that of ethanol (D=25).

A large number of mutant comparisons is necessary to show a statistically significant difference between saltbridges at positive 156 and 166 because there is considerable variation in $\Delta\Delta$log kcat/Km for different mutant comparisons at the same position. The change in susbtrate preference from putative salt-bridges at position 156 varies from six to 40-fold in kcat/Km, and those at position 166 vary 14 to 120 fold.

In addition to variation produced by factors mentioned above, it is possible that the P-1 side chains are not binding in the same ways between the enzymes compared, even though the comparisons are nearly isosteric in each case. For example, the Lys P-1 substrate side chain may contact Glu156 in Glu156/Asp166 (Glu156/D166) and Asp166 in Gln156/Asp166 (Q156/D166). Thus, one salt-bridge may be substituted for another. It is also possible that complementary charges within the P-1 binding site, e.g., Glu156/Lys166 (Glu156/K166), can form an intramolecular salt-bridge so that the charged side-chains are not free to interact independently with the substrate. Given these caveats it is remarkable that greater variation in substrate preference is not seen by electrostatic substitutions at each position.

EXAMPLE 10
Substitutions at Position 217

Tyr217 has been substituted by all other 19 amino acids. Cassette mutagenesis as described in EPO publication No. 0130756 was used according to the protocol of FIG. 22. The EcoRV restriction site was used for restriction-purification of p^217.

Since this position is involved in substrate binding, mutations here affect kinetic parameters of the enzyme. An example is the substitution of Leu for Tyr at position 217. For the substrate sAAPFpNa, this mutant has a kcat of 277 5' and a Km of $4.7\times10^{-4}$ with a kcat/Km ratio of $6\times10^5$. This represents a 5.5-fold increase in kcat with a 3-fold increase in Km over the wild type enzyme.

In addition, replacement of Tyr217 by Lys, Arg, Phe or Leu results in mutant enzymes which are more stable at pH of about 9–11 than the WT enzyme. Conversely, replacement of Tyr217 by Asp, Glu, Gly or Pro results in enzymes which are less stable at pH of about 9–11 than the WT enzyme.

EXAMPLE 11
Multiple Mutants Having Altered Thermal Stability

*B. amyloliquefacien* subtilisin does not contain any cysteine residues. Thus, any attempt to produce thermal stability by Cys cross-linkage required the substitution of more than one amino acid in subtilisin with Cys. The following subtilisin residues were multiply substituted with cysteine:

Thr22/Ser87

Ser24/Ser87

Mutagenesis of Ser24 to Cys was carried out with a 5' phosphorylated oligonucleotide primer having the sequence $$5'\text{-pC—TAC—ACT—}\underline{\text{GGA}}\text{—}\underline{\text{TGC}}\text{—AAT—GTT—AAA—G-3'}.$$
\* \*

(Asterisks show the location of mismatches and the underlined sequence shows the position of the altered Sau3A site.) The *B. amyloliquefaciens* subtilisin gene on a 1.5 kb EcoRI-BAMHI fragment from pS4.5 was cloned into M13mp11 and single stranded DNA was isolated. This template (M13mp11SUBT) was double primed with the 5' phosphorylated M13 universal sequencing primer and the mutagenesis primer. Adelman, et al. (1983) *DNA* 2, 183–193. The heteroduplex was transfected into competent JM101 cells and plaques were probed for the mutant sequence (Zoller, M. J., et al. (1982) *Nucleic Acid Res.* 10, 6487–6500; Wallace, et al. (1981) *Nucleic Acid Res.* 9, 3647–3656) using a tetramethylammonium chloride hybridization protocol (Wood, et al. (1985) *Proc. Natl. Acad. Sci. USA* 82, 1585–1588). The Ser87 to Cys mutation was prepared in a similar fashion using a 5' phosphorylated primer having the sequence $$5'\text{-pGGC—GTT—GCG—CCA—}\underline{\text{TGC}}\text{—}\underline{\text{GCA}}\text{—TCA—CT-3'}.$$
\*

(The asterisk indicates the position of the mismatch and the underlined sequence shows the position of a new MstI site.) The C24 and C87 mutations were obtained at a frequency of one and two percent, respectively. Mutant sequences were confirmed by dideoxy sequencing in M13.

Mutagenesis of Tyr21/Thr22 to A21/C22 was carried out with a 5' phosphorylated oligonucleotide primer having the sequence $$5'\text{-pAC—TCT—CAA—GGC—GCT—TGT—}\underline{\text{GGC}}\text{—TCA—AAT—GTT-3'}.$$
\*\*\* \*\* \*

(The asterisks show mismatches to the wild type sequence and the underlined sequence shows the position of an altered Sau3A site.) Manipulations for heteroduplex synthesis were identical to those described for C24. Because direct cloning of the heteroduplex DNA fragment can yield increased frequencies of mutagenesis, the EcoRI-BamHI subtilisin fragment was purified and ligated into pBS42. *E. coli* MM 294 cells were transformed with the ligation mixture and plasmid DNA was purified from isolated transformants. Plasmid DNA was screened for the loss of the Sau3A site at codon 23 that was eliminated by the mutagenesis primer. Two out of 16 plasmid preparations had lost the wild type Sau3A site. The mutant sequence was confirmed by dideoxy sequencing in M13.

Figure 30A:
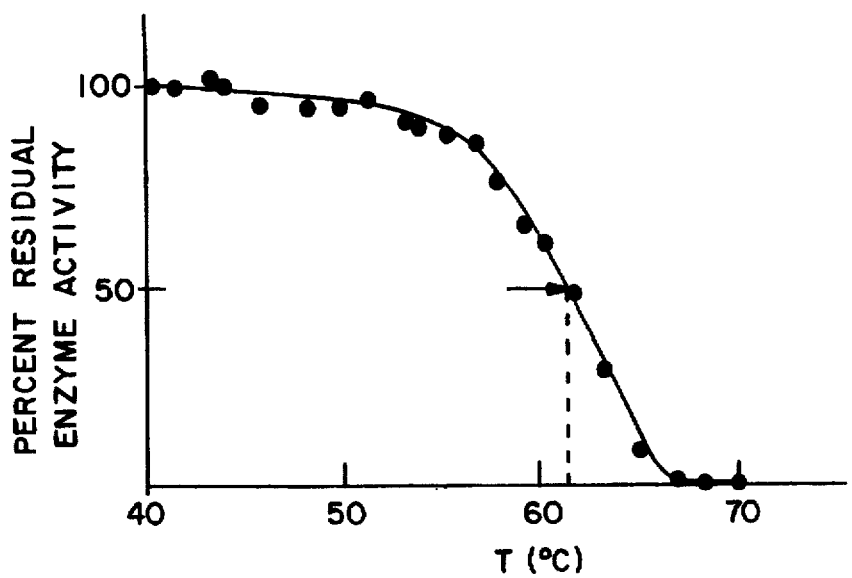
FIGS. 30A, 30B, and 30C demonstrates residual enzyme activity versus temperature curves for purified wild-type (Panel A), C22/C87 (Panel B) and C24/C87 (Panel C).
Figure 30B:
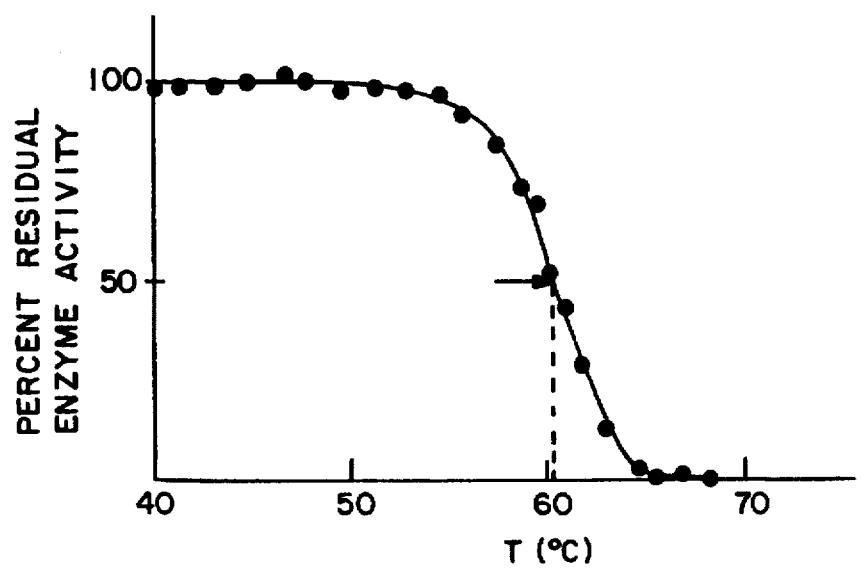
Figure 30C:
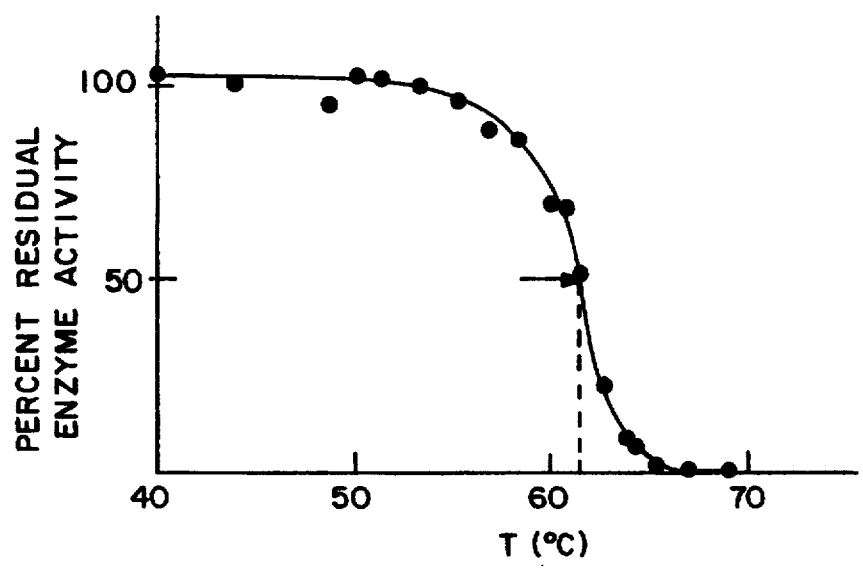

Double mutants, C22/C87 and C24/C87, were constructed by ligating fragments sharing a common ClaI site that separated the single parent cystine codons. Specifically, the 500 bp EcoRI-ClaI fragment containing the 5' portion of the subtilisin gene (including codons 22 and 24) was ligated with the 4.7 kb ClaI-EcoRI fragment that contained the 3' portion of the subtilisin gene (including codon 87) plus pBS42 vector sequence. *E. coli* MM 294 was transformed with ligation mixtures and plasmid DNA was purified from individual transformants. Double-cysteine plasmid constructions were identified by restriction site markers originating from the parent cysteine mutants (i.e., C22 and C24, Sau3A minus; Cys87,MstI plus). Plasmids from *E. coli* were transformed into *B. subtilis* BG2036. The thermal stability of these mutants as compared to wild type subtilisin are presented in FIGS. 30A, 30B and 30C and Tables XVII and XVIII.

TABLE XVII

Effect of DTT on the Half-Time of Autolytic Inactivation of Wild-Type and Disulfide Mutants of Subtilisin*

| Enzyme | $t_{1/2}$ | | |
|---|---|---|---|
| | −DTT min | +DTT | −DTT/+DTT |
| Wild-type | 95 | 85 | 1.1 |
| C22/C87 | 44 | 25 | 1.8 |
| C24/C87 | 92 | 62 | 1.5 |

*Purified enzymes were either treated or not treated with 25 mM DTT and dialyzed with or without 10 mM DTT in 2 mM CaCl₂, 50 mM Tris (pH 7.5) for 14 hr. at 4° C. Enzyme concentrations were adjusted to 80 μl aliquots were quenched on ice and assayed for residual activity. Half-times for autolytic inactivation were determined from semi-log plots of log₁₀ (residual activity) versus time. These plots were linear for over 90% of the inactivation.

TABLE XVIII

Effect of Mutations in Subtilisin on the Half-Time of Autolytic Inactivation at 58° C.*

| Enzyme | $t_{1/2}$ min |
|---|---|
| Wild-type | 120 |
| C22 | 22 |
| C24 | 120 |
| C87 | 104 |
| C22/C87 | 43 |
| C24/C87 | 115 |

*Half-times for autolytic inactivation were determined for wild-type and mutant subtilisins as described in the legend to Table III. Unpurified and non-reduced enzymes were used directly from *B. subtilis* culture supernatants.

It has been demonstrated that double-cysteine mutants of subtilisin are efficiently secreted and that disulfide bonds are formed in vivo in *B. subtilis* (date not shown). The introduction of disulfide bonds in subtilisin extends upon previous work in dihydrofolate reductase and T4 lysozyme (Perry, L. J., et al. (1984) *Science* 226, 555–557), where single cysteines were introduced near pre-existing cysteines and disulfides were oxidized in vitro. Analyses of physical properties of the subtilisin disulfides, unlike the T4 lysozyme disulfide (Perry, L. J., et al. (1986) *Biochemistry*, in press), were not complicated by the presence of free cysteines other than those involved in disulfide formation. Because most naturally occuring disulfides occur in secreted proteins, subtilisin is an excellent model system to identify the structural requirements for in vitro formation of stable disulfide bonds in secreted proteins.

Thermal Stability and Autolytic Stability

The data presented here do not address reverisble thermostability of subtilisin directly because of complications arising from autolysis and aggregation. For example, studies monitoring the change in the circular dichroic eliptcity at 220 nm versus temperature of phenylmethanesulfonyl fluoride-inhibited subtilisin show typical melt profiles that are coincident with the autolysis curves. However, at the end of thermal melt, SDS-PAGE shows that >90% of the subtilisin is autolyzed. Moreover, Brown and Schleich (Brown, M. F., et al. (1975) *Biochemistry* 14, 3069–3074) have shown that diisopropylfluorophosphate-inhibited subtilisin irreversibly aggregates in denaturants, which precludes reversible denaturation studies. Thus, until these problems are overcome, subtilisin is not an ideal system for studying the thermodynamics of protein folding.

Although there appears to be a relationship between autolytic stability and conformational stability, the disulfides introduced into subtilisin did not improve the autolytic stability of the mutant enzymes when compared to the wild-type enzyme. However, the disulfide bonds did provide a margin of autolytic stability when compared to their corresponding reduced double-cysteine enzyme. Inspection of a highly refined x-ray structure of wild-type *B. amyloliquefaciens* subtilisin reveals a hydrogen bond between Thr22 and Ser87. Because cysteine is a poor hydrogen donor or acceptor (Paul, I. C. (1974) in *Chemistry of the —SH Group* (Patai, S., ed.) pp. 111–149, Wiley Interscience, New York) weakening of 22/87 hydrogen bond may explain why the C22 and C87 single-cysteine mutant proteins are less autolytically stable than either C24 or wild-type (Table XVIII). The fact that C22 is less autolytically stable than C87 may be the result of the Tyr21A mutation (Table XVIII). Indeed, recent construction and analysis of Tyr21/C22 shows the mutant protein has an autolytic stability closer to that of C87. In summary, the C22 and C87 of single-cysteine mutations destabilize the protein toward autolysis, and disulfide bond formation increases the stability to a level less than or equal to that of wild-type enzyme.

These data suggest that the stabilizing effect of an engineered disulfide can be lowered when the parent cysteine mutations disrupt pre-existing stabilizing interactions. Similar conclusions have been drawn from reversible thermal unfolding studies of disulfide cross-linked T4 lysozyme mutants that contain destabilizing mutations. Therefore, a strategy to stbilize a protein by introduction of a disulfide bond should consider avoiding the disruption of stabilizing interactions as well as producing a disulfide with good bond geometry.

EXAMPLE 12

Multiple Mutants Containing Substitutions at Position 222 and Position 166 or 169

Double mutants 166/222 and 169/222 were prepared by ligating together (1) the 2.3 kb AcaII fragment from pS4.5 which contains the 5' portion of the subtilisin gene and vector sequences, (2) the 200 bp AvaII fragment which contains the relevant 166 or 169 mutations from the respective 166 or 169 plasmids, and (3) the 2.2 kb AvaII fragment which contains the relevant 222 mutation 3' and of the subtilisin genes and vector sequence from the respective p222 plasmid.

Although mutations at position 222 improve oxidation stability they also tend to increase the Km. An example is shown in Table XIX. In this case the A222 mutation was combined with the K166 mutation to give an enzyme with kcat and Km intermediate between the two parent enzymes.

TABLE XIX substrate sAAPFpNa

| | kcat | Km |
|---|---|---|
| WT | 50 | $1.4 \times 10^{-4}$ |
| A222 | 42 | $9.9 \times 10^{-4}$ |
| K166 | 21 | $3.7 \times 10^{-5}$ |
| K166/A222 | 29 | $2.0 \times 10^{-4}$ |

EXAMPLE 13
Multiple Mutants Containing Substitutions at Positions 50, 156, 166, 217 and Combinations Thereof The double mutant S156/A169 was prepared by ligation of two fragments, each containing one of the relevant mutations. The plasmid pS156 was cut with XmaI and treated with Si nuclease to create a blunt end at codon 167. After removal of the nuclease by phenol/chloroform extraction and ethanol precipitation, the DNA was digested with BamHI and the approximately 4kb fragment containing the vector plus the 5' portion of the subtilisin gene through codon 167 was purified.

The pA169 plasmid was digested with KpnI and treated with DNA polymerase Klenow fragment plus 50 μM dNTPs to create a blunt end codon at codon 168. The Klenow was removed by phenol/chloroform extraction and ethanol precipitation. The DNA was digested with BamHI and the 590 bp fragment including codon 168 through the carboxy terminus of the subtilisin gene was isolated. The two fragments were then ligated to give S156/A169.

Triple and quadruple mutants were prepared by ligating together (1) the 220bp PvuII/HaeII fragment containing the relevant 156, 166 and/or 169 mutations from the respective p156, p166 and/or p169 double of single mutant plasmid, (2) the 550 bp HaeII/BamHI fragment containing the relevant 217 mutant from the respective p217 plasmid, and (3) the 3.9 kb PvuII/BamHI fragment containing the F50 mutation and vector sequences.

Figure 26:
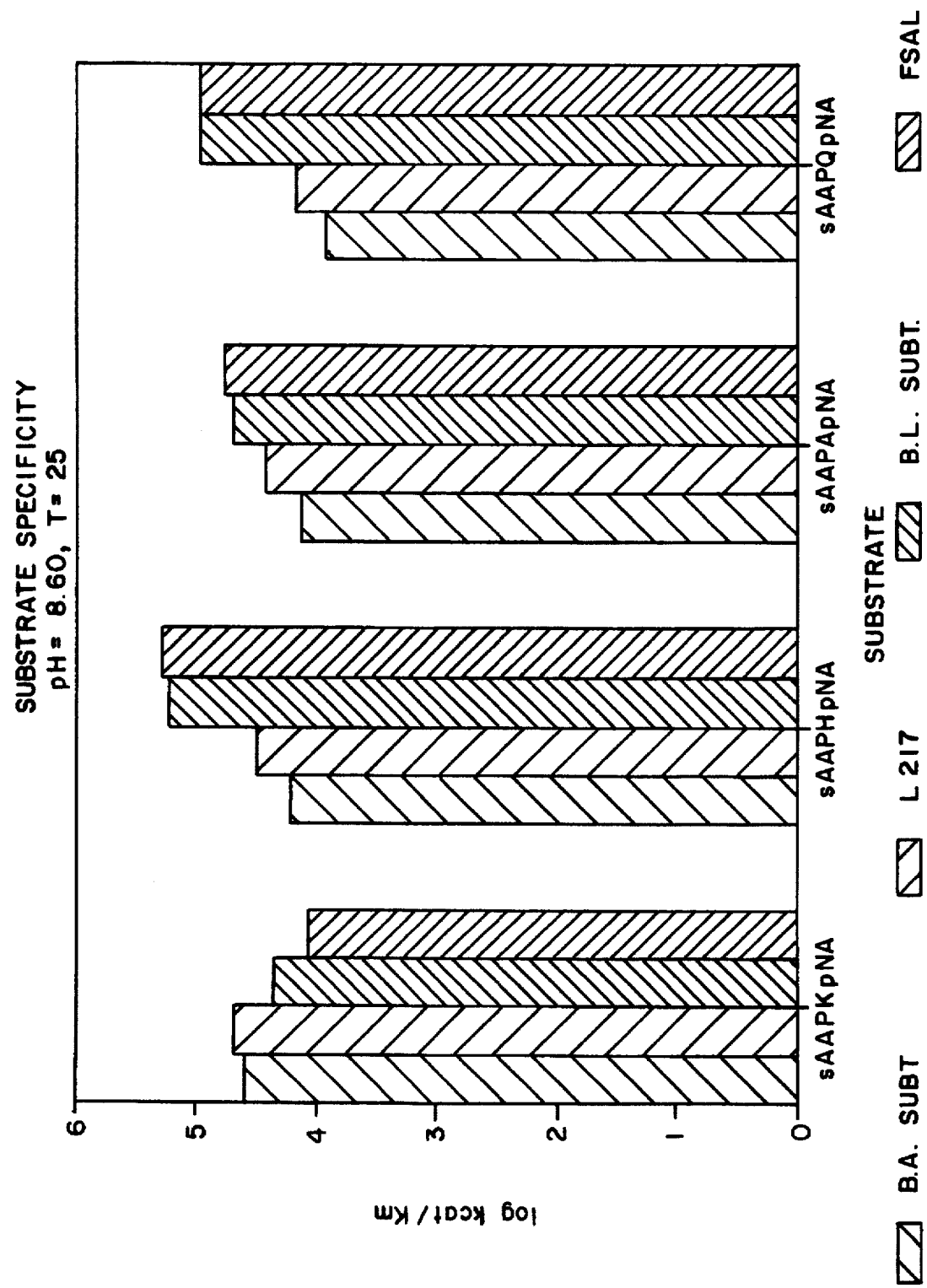
FIGS. 26 and 27 depict substrate specificity of proteins for 4 substrates.
Figure 27:
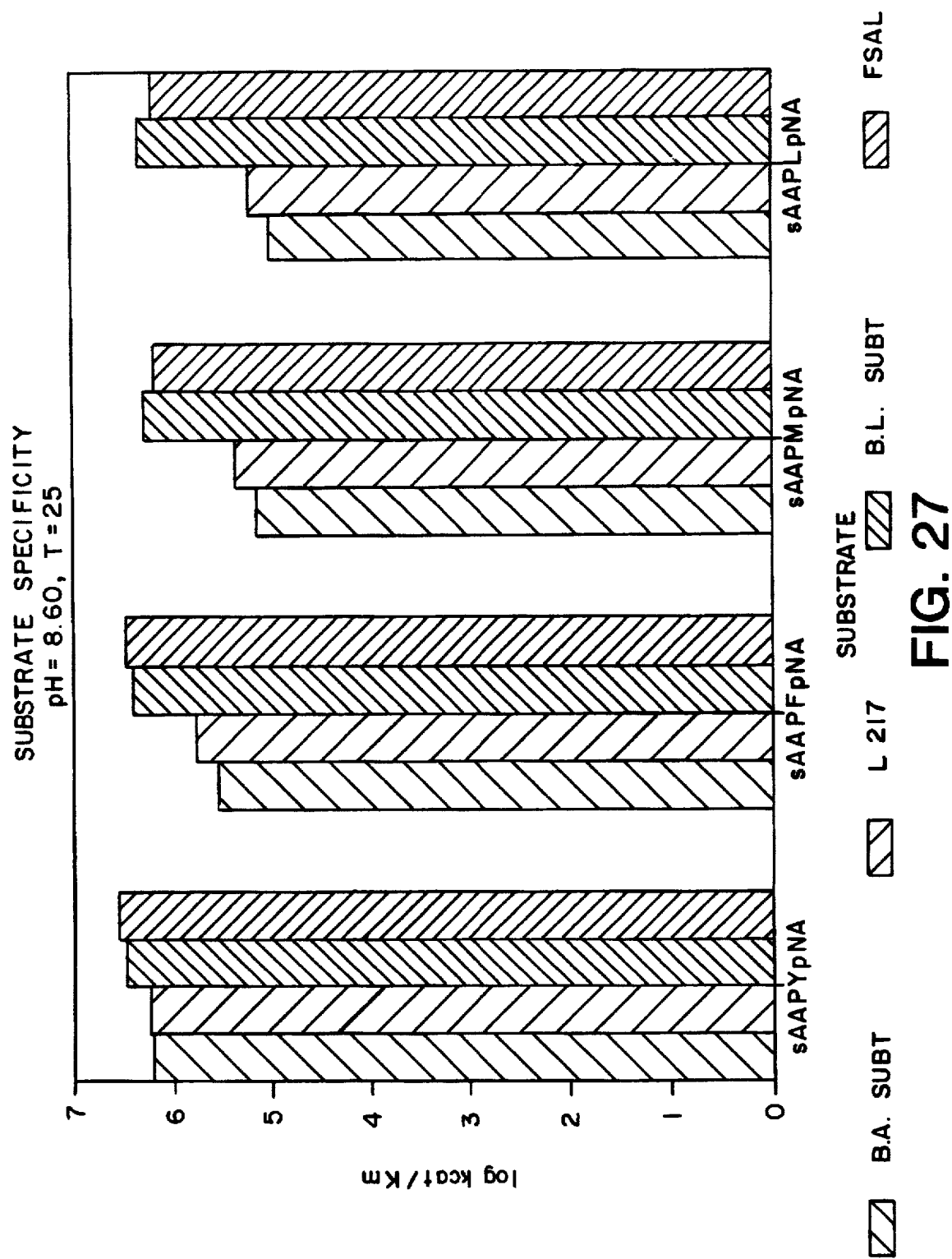

The multiple mutant F50/S156/A169/L217, as well as B. amyloliquefaciens subtilisin, B. lichenformis subtilisin and the single mutant L217 were analyzed with the above synthetic polypeptides where the P-1 amino acid in the substrate was Lys, His, Ala, Gln, Tyr, Phe, Met and Leu. These results are shown in FIGS. 26 and 27.

These results show that the F50/S156/A169/L217 mutant has substrate specificity similar to that of the B. lichenformis enzyme and differs dramatically from the wild type enzyme. Although only data for the L217 mutant are shown, none of the single mutants (e.g., F50, S156 or A169) showed this effect. Although B. licheniformis differs in 88 residue positions from B. amyloliquefaciens, the combination of only these four mutations accounts for most of the differences in substrate specificity between the two enzymes.

EXAMPLE 14
Subtilisin Mutants Having Altered Alkaline Stability

A random mutagenesis technique was used to generate single and multiple mutations within the B. amyloliquefaciens subtilisin gene. Such mutants were screened for altered alkaline stability. Clones having increased (positive) alkaline stability and decreased (negative) alkaline stability were isolated and sequenced to identify the mutations within the subtilisin gene. Among the positive clones, the mutants V107 and R213 were identified. These single mutants were subsequently combined to produce the mutant V107/R213.

One of the negative clones (V50) from the random mutagenesis experiments resulted in a marked decrease in alkaline stability. Another mutant (P50) was analyzed for alkaline stability to determine the effect of a different substitution at position 50. The F50 mutant was found to have a greater alkaline stability than wild type subtilisin and when combined with the double mutant V107/R213 resulted in a mutant having an alkaline stability which reflected the aggregate of the alkaline stabilities for each of the individual mutants.

The single mutant R204 and double mutant C204/R213 were identified by alkaline screening after random cassette mutagenesis over the region from position 197 to 228. The C204/R213 mutant was thereafter modified to produce mutants containing the individual mutations C204 and R213 to determine the contribution of each of the individual mutations. Cassette mutagenesis using pooled oligonucleotides to substitute all amino acids at position 204, was utilized to determine which substitution at position 204 would maximize the increase in alkaline stability. The mutation from Lys213 to Arg was maintained constant for each of these substitutions at position 204.

A. Construction of pBO180, an E. coli-B. subtilis Shuttle Plasmid

The 2.9 kb EcoRI-BamHI fragment from pBR327 (Covarrubias, L., et al. (1981) Gene 13, 25–35) was ligated to the 3.7 kb EcoRI-BamHI fragment of pBD64 (Gryczan, T., et al. (1980) J. Bacteriol., 246–253) to give the recombinant plasmid pBO153. The unique EcoRI recognition sequence in pBD64 was eliminated by digestion with EcoRI followed by treatment with Klenow and deoxynucleotide triphosphates (Maniatis, T., et al. (eds.) (1982) in Molecular Cloning, A Laboratory Manual, Cold Spring Harbor Laboratory, Cold Spring Harbor, N.Y.). Blunt end ligation and transformation yielded pBO154. The unique AvaI recognition sequence in pBO154 was eliminated in a similar manner to yield pBO171. pBO171 was digested with BamHI and PvuII and treated with Klenow and deoxynucleotide triphosphates to create blunt ends. The 6.4 kb fragment was purified, ligated and transformed into LE392 cells (Enquest, L. W., et al. (1977) J. Mol. Biol. 111, 97–120), to yield pBO172 which retains the unique BamHI site. To facilitate subcloning of subtilisin mutants, a unique and silent KpnI site starting at codon 166 was introduced into the subtilisin gene from pS4.5 (Wells, J. A., et al. (1983) Nucleic Acids Res., 11, 7911–7925) by site-directed mutagenesis. The KpnI+ plasmid was digested with EcoRI and treated with Klenow and deoxynucleotide triphosphates to create a blunt end. The Klenow was inactivated by heating for 20 min at 68° C., and the DNA was digested with BamHI. The 1.5 kb blunt EcoRI-BamHI fragment containing the entire subtilisin was ligated with the 5.8 kb NruI-BamHI from pBO172 to yield pBO180. The ligation of the blunt NruI end to the blunt EcoRI end recreated an EcoRI site. Proceeding clockwise around pBO180 from the EcoRI site at the 5' end of the subtilisin gene is the unique BamHI site at the 3' end of the subtilisin gene, the chloramphenicol and neomycin resistance genes and UB110 gram positive replication origin derived from pBD64, the ampicillin resistance gene and gram negative replication origin derived from pBR327.

B. Construction of Random Mutagenesis Library

The 1.5 kb EcoRI-BamHI fragment containing the B. amyloliquefaciens subtilisin gene (Wells et al., 1983) from pBO180 was cloned into M13mp11 to give M13mp11 SUBT essentially as previously described (Wells, J. A., et al. (1986) J. Biol. Chem., 2261,6564–6570). Deoxyuridine containing template DNA was prepared according to Kunkel (Kunkel, T. A. (1985) Proc. Natl. Acad. Sci. USA, 82 488–492). Uridine containing template DNA (Kunkel, 1985)

was purified by CsCl density gradients (Maniatis, T. et al. (eds.) (1982) in *Molecular Cloning, A Laboratory Manual*, Cold Spring Harbor Laboratory, Cold Spring Harbor, N.Y.). A primer (AvaI) having the sequence

Figure 31:
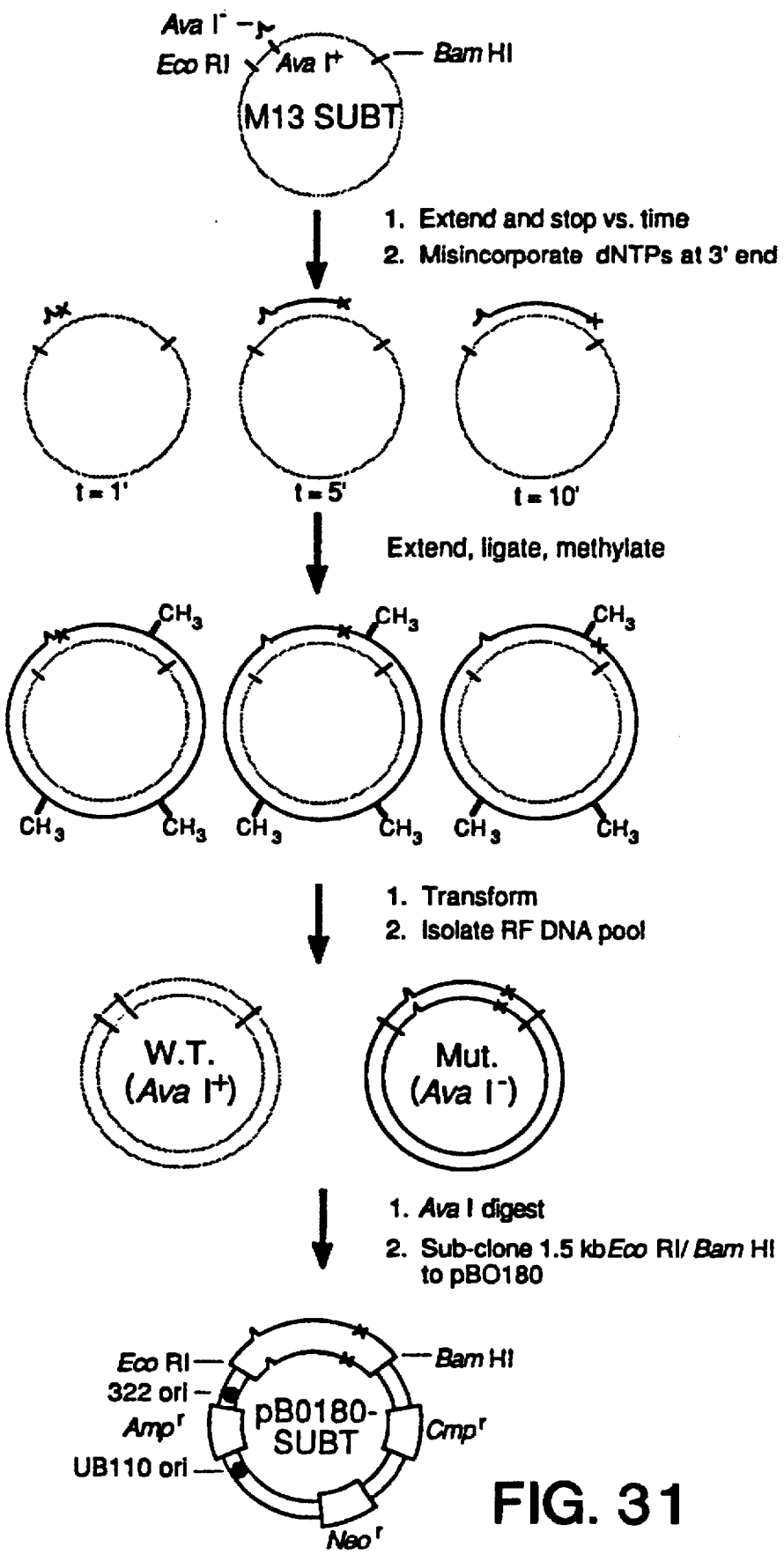
FIG. 31 depicts the strategy for producing point mutations in the subtilisin coding sequence by misin-corporation of α-thioldeoxynucleotide triphosphates.

```
              *
5'GAAAAAAGACCCTAGCGTCGCTTA
``` ending at codon −11, was used to alter the unique AvaI recognition sequence within the subtilisin gene. (The asterisk denotes the mismatches from the wild-type sequence and underlined is the altered AvaI site.) The 5' phosphorylated AvaI primer (~320 pmol) and ~40 pmol (~120 μg) of uridine containing M13mp11 SUBT template in 1.88 ml of 53 mM NaCl, 7.4 mM MgC12 and 7.4 mM Tris.HCl (pH 7.5) were annealed by heating to 90° C. for 2 min. and cooling 15 min at 24° C. (FIG. 31). Primer extension at 24° C. was initiated by addition of 100 μL containing 1 mM in all four deoxynucleotide triphosphates, and 20 μl Klenow fragment (5 units/l). The extension reaction was stopped every 15 seconds over ten min by addition of 10 μl 0.25M EDTA (pH 8) to 50 μl aliquots of the reaction mixture. Samples were pooled, phenol chlorophorm extract and DNA was precipitated twice by addition of 2.5 vol 100% ethanol, and washed twice with 70% ethanol. The pellet was dried, and redissolved in 0.4 ml 1 mM EDTA, 10 mM Tris (pH 8). Misincorporation of α-thiodeoxynucleotides onto the 3' ends of the pool of randomly terminated template was carried out by incubating four 0.2 ml solutions each containing one-fourth of the randomly terminated template mixture (~20 μg), 0.25 mM of a given α-thiodeoxynucleotide triphosphate, 100 units AMV polymerase, 50 mM KCL, 10 mM $MgCl_2$, 0.4 mM dithiothreitol, and 50 mM Tris (pH 8.3) (Champoux, J. J. (1984) *Genetics*, 2, 454–464). After incubation at 37° C. for 90 minutes, misincorporation reactions were sealed by incubation for five minutes at 37° C. with 50 mM all four deoxynucleotide triphosphates (pH 8), and 50 units AMV polymerase. Reactions were stopped by addition of 25 mM EDTA (final), and heated at 68° C. for ten min to inactivate AMV polymerase. After ethanol precipitation and resuspension, synthesis of closed circular heteroduplexes was carried out for two days at 14° C. under the same conditions used for the timed extension reactions above, except the reactions also contained 1000 units T4 DNA ligase, 0.5 mM ATP and 1 mM β-mercaptoethanol. Simultaneous restriction of each heteroduplex pool with KpnI, BamHI, and EcoRI confirmed that the extension reactions were nearly quantitative. Heteroduplex DNA in each reaction mixture was methylated by incubation with 80 μM S-adenosylmethionine and 150 units dam methylase for 1 hour at 37° C. Methylation reactions were stopped by heating at 68° C. for 15 min. One-half of each of the four methylated heteroduplex reactions were transformed into 2.5 ml competent *E. coli* JM101 (Messing, J. (1979) *Recombinant DNA Tech. Bull.*, 2, 43–48). The number of independent transformants from each of the four transformations ranged from 0.4–2.0×10⁵. After growing out phage pools, RF DNA from each of the four transformations was isolated and purified by centrifugation through CsCl density gradients. Approximately 2 μg of RF DNA from each of the four pools was digested with EcoRI, BamHI and AvaI. The 1.5 kb EcoRI-BamHI fragment (i.e., AvaI resistant) was purified on low gel temperature agarose and ligated into the 5.5 kb EcoRI-BamHI vector fragment of pBO180. The total number of independent transformants from each α-thiodeoxynucleotide misincorporation plasmid library ranged from 1.2–2.4×10⁴. The pool of plasmids from each of the four transformations was grown out in 200 ml LB media containing 12.5 μg/ml cmp and plasmid DNA was purified by centrifugation through CsCl density gradients.

C. Expression and Screening of Subtilisin Point Mutants

Plasmid DNA from each of the four misincorporation pools was transformed (Anagnostopoulos, C., et al. (1967, *J. Bacteriol.*, 81, 741–746) into BG2036, a strain of *B. subtilis* deficient in extracellular protease genes (Yang, M. Y. et al. (1984) *J. Bacteriol.*, 160, 15–21). For each transformation, 5 μg of DNA produced approximately 2.5×10⁵ independent BG2036 transformants, and liquid culture aliquots from the four libraries were stored in 10% glycerol at 70° C. Thawed aliquots of frozen cultures were plated on LB/5 μg/ml cmp/1.6% skim milk plates (Wells, J. A., et al. (1983) *Nucleic Acids Res.*, 11, 7911–7925), and fresh colonies were arrayed onto 96-well microtiter plates containing 150 l per well LB media plus 12.5 μg/ml cmp. After 1 h at room temperature, a replica was stamped (using a matched 96 prong stamp) onto a 132 mm BA 85 nitrocellulose filter (Schleicher and Scheull) which was layered on a 140 mm diameter LB/cmp/skim milk plate. Cells were grown about 16 h at 30° C. until halos of proteolysis were roughly 5–7 mm in diameter and filters were transferred directly to a freshly prepared agar plate at 37° C. containing only 1.6% skim milk and 50 mM sodium phosphate pH 11.5. Filters were incubated on plates for 3–6 h at 37° C. to produce halos of about 5 mm for wild-type subtilisin and were discarded. The plates were stained for 10 min at 24° C. with Coomassie blue solution (0.25% Coomassie blue (R-250) 25% ethanol) and destained with 25% ethanol, 10% acetic acid for 20 min. Zones of proteolysis appeared as blue halos on a white background on the underside of the plate and were compared to the original growth plate that was similarly stained and destained as a control. Clones were considered positive that produced proportionately larger zones of proteolysis on the high pH plates relative to the original growth plate. Negative clones gave smaller halos under alkaline conditions. Positive and negative clones were restreaked to colony purify and screened again in triplicate to confirm alkaline pH results.

D. Identification and Analysis of Mutant Subtilisins

Plasmid DNA from 5 ml overnight cultures of more alkaline active *B. subtilis* clones was prepared according to Birnboim and Doly (1979) except that incubation with 2 mg/ml lysozyme proceeded for 5 min at 37° C. to ensure cell lysis and an additional phenol/$CHCl_3$ extraction was employed to remove contaminants. The 1.5 kb EcoRI-BamHI fragment containing the subtilisin gene was ligated into M13mp11 and template DNA was prepared for DNA sequencing (Messing, J., et al. (1982) *Gene*, 19 269–276). Three DNA sequencing primers ending at codon 26, +95, and +155 were synthesized to match the subtilisin coding sequence. For preliminary sequence identification a single track of DNA sequence, corresponding to the dNTPaS misincorporation library from which the mutant came, was applied over the entire mature protein coding sequence (i.e., a single dideoxyguanosine sequence track was applied to identify a mutant from the dGTPas library). A complete four track of DNA sequence was performed 200 bp over the site of mutagenesis to confirm and identify the mutant sequence (Sanger, F., et al., (1980) *J. Mol. Biol.*, 143, 161–178). Confirmed positive and negative bacilli clones were cultured in LB media containing 12.51 μg/mL cmp and purified from culture supernatants as previously described (Estell, D. A., et al. (1985) *J. Biol. Chem.*, 260, 6518–6521). Enzymes were greater than 98% pure as analyzed by SDS-polyacrylamide gel electrophoresis (Laemmli, U. K. (1970), *Nature*, 227, 680–685), and protein concentrations were calculated from the absorbance at 280 nm ($\epsilon_{280}^{0.1\%}=1.17$, Maturbara, H., et al. (1965), *J. Biol. Chem*, 1125–1130).

Enzyme activity was measured with 200 μg/mL succinyl-L-AlaL-AlaL-ProL-Phep-nitroanilide (Sigma) in 0.1M Tris pH 8.6 or 0.1M CAPS pH 10.8 at 25° C. Specific activity (μ moles product/min-mg) was calculated from the change in absorbance at 410 nm from production of p-nitroaniline with time per mg of enzyme (E410=8,480 M-1 cm−1; Del Mar, E. G., et al. (1979), *Anal. Biochem.*, 99, 316–320). Alkaline autolytic stability studies were performed on purified enzymes (200 μg/mL) in 0.1M potassium phosphate (pH 12.0) at 37C. At various times aliquots were assayed for residual enzyme activity (Wells, J. A., et al. (1986) *J. Biol. Chem.*, 261, 6564–6570).

E. Results

1. Optimization and analysis of mutagenesis frequency

A set of primer-template molecules that were randomly 3'-terminated over the subtilisin gene (FIG. 31) was produced by variable extension from a fixed 5'-primer (The primer mutated a unique AvaI site at codon 11 in the subtilisin gene). This was achieved by stopping polymerase reactions with EDTA after various times of extension. The extent and distribution of duplex formation over the 1 kb subtilisin gene fragment was assessed by multiple restriction digestion (not shown). For example, production of new HinfI fragments identified when polymerase extension had proceeded past Ile110, Leu233, and Asp259 in the subtilisin gene.

Misincorporation of each dNTPas at randomly terminated 3' ends by AMV reverse transcriptase (Zakour, R. A., et al. (1982), *Nature*, 295, 708–710; Zakour, R. A., et al. (1984), *Nucleic Acids Res.*, 12, 6615–6628) used conditions previously described (Champoux, J. J., (1984), *Genetics*, 2, 454–464). The efficiency of each misincorporation reaction was estimated to be greater than 80% by the addition of each dNTPαs to the AvaI restriction primer, and analysis by polyacrylamide gel electrophoresis (Champoux, J. J., (1984). Misincorporations were sealed by polymerization with all four dNTP's and closed circular DNA was produced by reaction with DNA ligase.

Several manipulations were employed to maximize the yield of the mutant sequences in the heteroduplex. These included the use of a deoxyuridine containing template (Kunkel, T. A. (1985), *Proc. Natl. Acad. Sci. USA*, 82 488–492; Pukkila, P. J. et al. (1983), *Genetics*, 104, 571–582), invitro methylation of the mutagenic strand (Kramer, W. et al. (1982) *Nucleic Acids Res.*, 10 6475–6485), and the use of AvaI restriction-selection against the wild-type template strand which contained a unique AvaI site. The separate contribution of each of these enrichment procedures to the final mutagenesis frequency was not determined, except that prior to AvaI restriction-selection roughly one-third of the segregated clones in each of the four pools still retained a wild-type AvaI site within the subtilisin gene. After AvaI restriction-selection greater than 98% of the plasmids lacked the wild-type AvaI site.

The 1.5 kb EcoRI-BamHI subtilisin gene fragment that was resistant to AvaI restriction digestion, from each of the four CsCl purified M13 RF pools was isolated on low melting agarose. The fragment was ligated in situ from the agarose with a similarly cut *E. coli-B. subtilis* shuttle vector, pBO180, and transformed directly into *E coli* LE392. Such direct ligation and transformation of DNA isolated from agarose avoided loses and allowed large numbers of recombinants to be obtained (>100,000 per μg equivalent of input M13 pool).

The frequency of mutagenesis for each of the four dNTPαs misincorporation reactions was estimated from the frequency that unique restriction sites were eliminated (Table XX). The unique restriction sites chosen for this analysis, ClaI, PvuII, and KpnI, were distributed over the subtilisin gene starting at codons 35, 104, and 166, respectively. As a control, the mutagenesis frequency was determined at the PstI site located in the β lactamase gene which was outside the window of mutagenesis. Because the absolute mutagenesis frequency was close to the percentage of undigested plasmid DNA, two rounds of restriction-selection were necessary to reduce the background of surviving uncut wild-type plasmid DNA below the mutant plasmid (Table XX). The background of surviving plasmid from wild-type DNA probably represents the sum total of spontaneous mutations, uncut wild-type plasmid, plus the efficiency with which linear DNA can transform *E. coli*. Subtracting the frequency for unmutagenized DNA (background) from the frequency for mutant DNA, and normalizing for the window of mutagenesis sampled by a given restriction analysis (4–6 bp) provides an estimate of the mutagenesis efficiency over the entire coding sequence (_1000 bp).

TABLE XX

| α-thiol dNTP misincor- porated[b] | Restriction Site Selection | % resistant clones[c] 1st round | % resistant clones[c] 2nd round | % resistant clones[c] Total | % resistant clones over Background[d] | % mutants per 1000bp[e] |
|---|---|---|---|---|---|---|
| None | PstI | 0.32 | 0.7 | 0.002 | 0 | — |
| G | PstI | 0.33 | 1.0 | 0.003 | 0.001 | 0.2 |
| T | PstI | 0.32 | <0.5 | <0.002 | 0 | 0 |
| C | PstI | 0.43 | 3.0 | 0.013 | 0.011 | 3 |
| None | ClaI | 0.28 | 5 | 0.014 | 0 | — |
| G | ClaI | 2.26 | 85 | 1.92 | 1.91 | 380 |
| T | ClaI | 0.48 | 31 | 0.15 | 0.14 | 35 |
| C | ClaI | 0.55 | 15 | 0.08 | 0.066 | 17 |
| None | PvuII | 0.08 | 29 | 0.023 | 0 | — |
| G | PvuII | 0.41 | 90 | 0.37 | 0.35 | 88 |
| T | PvuII | 0.10 | 67 | 0.067 | 0.044 | 9 |
| C | PvuII | 0.76 | 53 | 0.40 | 0.38 | 95 |
| None | KpnI | 0.41 | 3 | 0.012 | 0 | — |
| G | KpnI | 0.98 | 35 | 0.34 | 0.33 | 83 |
| T | KpnI | 0.36 | 15 | 0.054 | 0.042 | 8 |
| C | KpnI | 1.47 | 26 | 0.38 | 0.37 | 93 |

[a]Mutagenesis frequency is estimated from the frequency for obtaining mutations that alter unique restriction sites within the mutagenized subtilisin gene (i.e., ClaI, PvuII, or KpnI) compared to mutation frequencies of the PstI site, that is outside the window of mutagenesis.
[b]Plasmid DNA was from wild-type (none) or mutagenized by dNTPαs misincorporation as described.
[c]Percentage of resistant clones was calculated from the fraction of clones obtained after three fold or greater over-digestion of the plasmid with the indicated restriction enzyme compared to a non-digested control. Restriction-resistant plasmid DNA from the first round was subjected to a second round of restriction-selection. The total represents the product of the fractions of resistant clones obtained from both rounds of selection and gives percentage of restriction-site mutant clones in the original starting pool. Frequencies were derived from counting at least 20 colonies and usually greater than 100.
[d]Percent resistant clones was calculated by subtracting the percentage of restriction-resistant clones obtained for wild-type DNA (i.e., none) from that obtained for mutant DNA.
[e]This extrapolates from the frequency of mutation over each restriction site to the entire subtilisin gene (~1 kb). This has been normalized to the number of possible bases (4–6 bp) within each restriction site that can be mutagenized by a given misincorporation event.

From this analysis, the average percentage of subtilisin genes containing mutations that result from dGTPαs, dCTPαs, or dTTPαs misincorporation was estimated to be 90, 70, and 20 percent, respectively. These high mutagenesis frequencies were generally quite variable depending upon the dNTPαs and misincorporation efficiencies at this site.

Misincorporation efficiency has been reported to be both dependent on the kind of mismatch, and the context of primer (Champoux, J. J., (1984); Skinner, J. A., et al. (1986) *Nucleic Acids Res.*, 14, 6945–6964). Biased misincorporation efficiency of dGTPαs and dCTPαs over dTTPαs has been previously observed (Shortle, D., et al. (1985), *Genetics*, 110, 539–555). Unlike the dGTPαs, dCTPαs, and dTTPαs libraries the efficiency of mutagenesis for the dATPαs misincorporation library could not be accurately assessed because 90% of the restriction-resistant plasmids analyzed simply lacked the subtilisin gene insert. This problem probably arose from self-ligation of the vector when the dATPαs mutagenized subtilisin gene was subcloned from M13 into pBO180. Correcting for the vector background, we estimate the mutagenesis frequency around 20 percent in the dATPas misincorporation library. In a separate experiment (not shown), the mutagenesis efficiencies for dGTPαs and dTTPαs misincorporation were estimated to be around 50 and 30 percent, respectively, based on the frequency of reversion of an inactivating mutation at codon 169.

The location and identity of each mutation was determined by a single track of DNA sequencing corresponding to the misincorporated αthiodeoxy-nucleotide over the entire gene followed by a complete four track of DNA sequencing focused over the site of mutation. Of 14 mutants identified, the distribution was similar to that reported by Shortle and Lin (1985), except we did not observe nucleotide insertion or deletion mutations. The proportion of AG mutations was highest in the G misincorporation library, and some unexpected point mutations appeared in the dTTPas and dCTPαs libraries.

2. Screening and Identification of Alkaline Stability Mutants of Subtilisin

It is possible to screen colonies producing subtilisin by halos of casein digestion (Wells, J. A. et al. (1983) *Nucleic Acids Res.*, 11, 7911–7925). However, two problems were posed by screening colonies under high alkaline conditions (>pH 11). First, *B. subtilis* will not grow at high pH, and we have been unable to transform an alkylophilic strain of bacillus. This problem was overcome by adopting a replica plating strategy in which colonies were grown on filters at neutral pH to produce subtilisin and filters subsequently transferred to casein plates at pH 11.5 to assay subtilisin activity. However, at pH 11.5 the casein micells no longer formed a turbid background and thus prevented a clear observation of proteolysis halos. The problem was overcome by briefly staining the plate with Coomassie blue to amplify proteolysis zones and acidifying the plates to develop casein micell turbidity. By comparison of the halo size produced on the reference growth plate (pH 7) to the high pH plate (pH 11.5), it was possible to identify mutant subtilisins that had increased (positives) or decreased (negatives) stability under alkaline conditions.

Roughly 1000 colonies were screened from each of the four misincorporation libraries. The percentage of colonies showing a differential loss of activity at pH 11.5 versus pH 7 represented 1.4, 1.8, 1.4, and 0.6% of the total colonies screened from the thiol dGTPαs, dATPαs, dTTPαs, and dCTPαs libraries, respectively. Several of these negative clones were sequenced and all were found to contain a single base change as expected from the misincorporation library from which they came. Negative mutants included A36, E170 and V50. Two positive mutants were identified as V107 and R213. The ratio of negatives to positives was roughly 50:1.

3. Stability and Activity of Subtilisin Mutants at Alkaline pH

Figure 32:
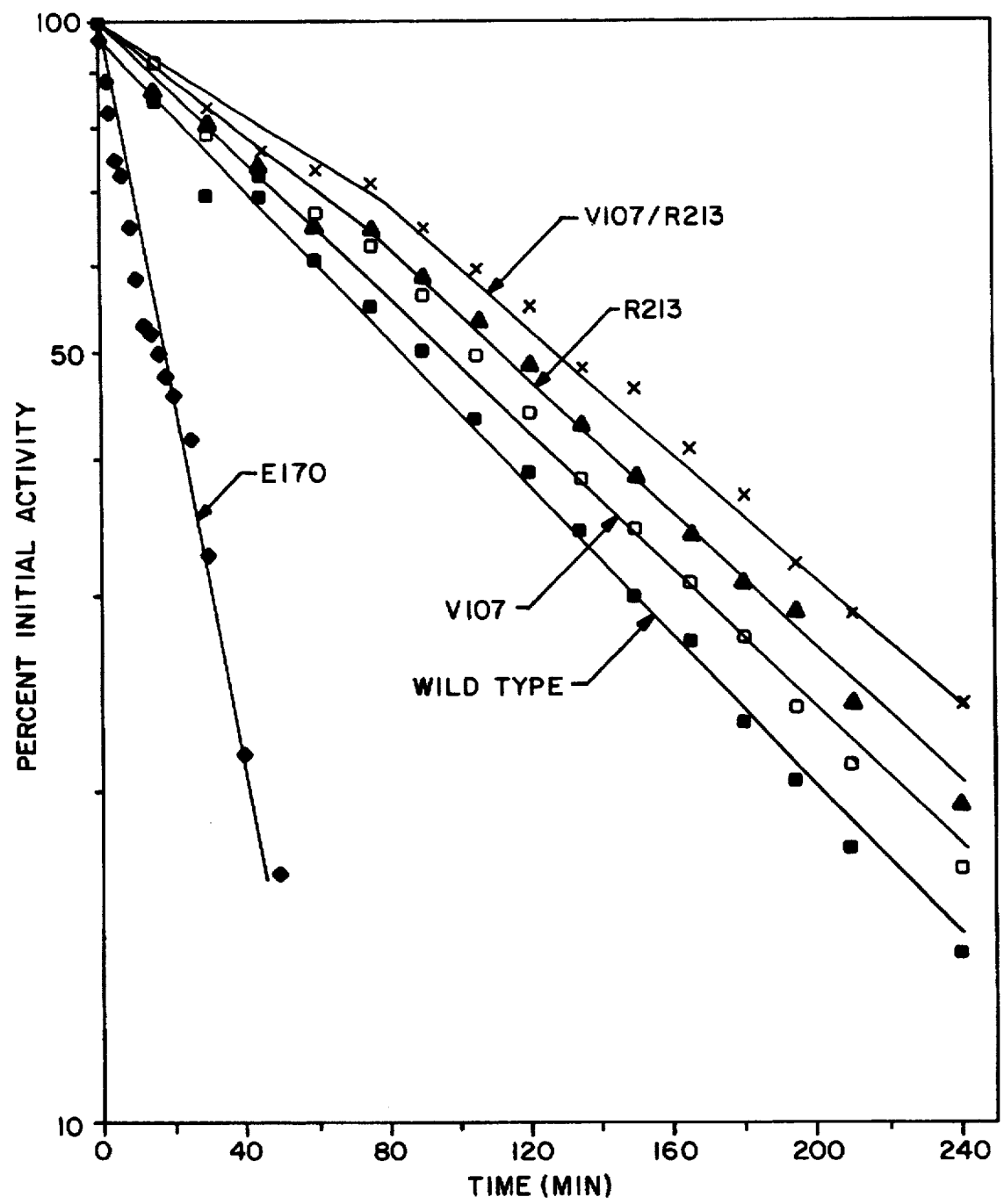
FIG. 32 depicts the autolytic stability of purified wild type and mutant subtilisins 170E, 107V, 213R and 107V/213R at alkaline pH.
Figure 33:
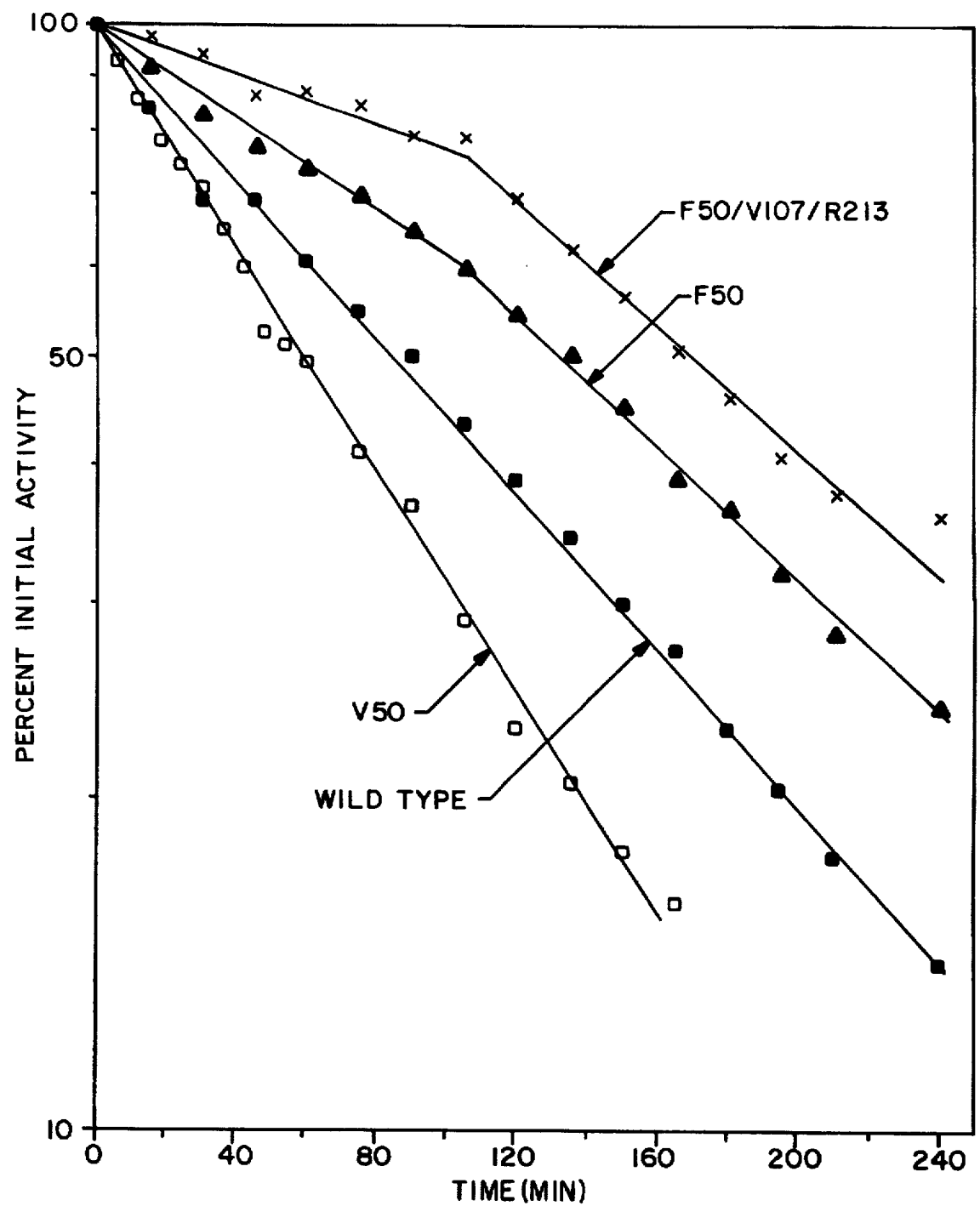
FIG. 33 depicts the autolytic stability of purified wild type and mutant subtilisins V50, F50 and F50/V107/R213 at alkaline pH.

Subtilisin mutants were purified and their autolytic stabilities were measured by the time course of inactivation at pH 12.0 (FIGS. 32 and 33). Positive mutants identified from the screen (i.e., V107 and R213) were more resistant to alkaline induced autolytic inactivation compared to wild-type; negative mutants (i.e., E170 and V50) were less resistant. We had advantageously produced another mutant at position 50 (F50) by site-directed mutagenesis. This mutant was more stable than wild-type enzyme to alkaline autolytic inactivation (FIG. 33) At the termination of the autolysis study, SDS-PAGE analysis confirmed that each subtilisin variant had autolyzed to an extent consistent with the remaining enzyme activity.

The stabilizing effects of V107, R213, and F50 are cumulative. See Table XXI. The double mutant, V107/R213 (made by subcloning the 920 bp EcoRI-KpnI fragment of pBO180V107 into the 6.6 kb EcoRI-KpnI fragment of pBO180R213), is more stable than either single mutant. The triple mutant, F50/V107/R213 (made by subcloning the 735 bp EcoRI-PvuII fragment of pF50 (Example 2) into the 6.8 kb EcoRI-PvuII fragment of pBO180/V107, is more stable than the double mutant V107/R213 or F50. The inactivation curves show a biphasic character that becomes more pronounced the more stable the mutant analyzed. This may result from some destablizing chemical modification(s) (eg., deamidation) during the autolysis study and/or reduced stabilization caused by complete digestion of larger autolysis peptides. These alkaline autolysis studies have been repeated on separately purified enzyme batches with essentially the same results. Rates of autolysis should depend both on the conformational stability as well as the specific activity of the subtilisin variant (Wells, J. A., et al. (1986), *J. Biol. Chem.*, 261, 6564–6570). It was therefore possible that the decreases in autolytic inactivation rates may result from decreases in specific activity of the more stable mutant under alkaline conditions. In general the opposite appears to be the case. The more stable mutants, if anything, have a relatively higher specific activity than wild-type under alkaline conditions and the less stable mutants have a relatively lower specific activity. These subtle effects on specific activity for V107/R213 and F50/V107/R213 are cumulative at both pH 8.6 and 10.8. The changes in specific activity may reflect slight differences in substrate specificity, however, it is noteworthy that only positions 170 and 107 are within 6 Å of a bound model substrate (Robertus, J. D., et al. (1972), *Biochemistry* 11, 2438–2449).

TABLE XXI

Relationship between relative specific activity at pH 8.6 or 10.8 and alkaline autolytic stability

| Enzyme | Relative specific activity | | Alkaline autolysis half-time |
|---|---|---|---|
| | pH 8.6 | pH 10.8 | (min)[b] |
| Wild-type | 100 ± 1 | 100 ± 3 | 86 |
| Q170 | 46 ± 1 | 28 ± 2 | 13 |
| V107 | 126 ± 3 | 99 ± 5 | 102 |
| R213 | 97 ± 1 | 102 ± 1 | 115 |
| V107/R213 | 116 ± 2 | 106 ± 3 | 130 |
| V50 | 66 ± 4 | 61 ± 1 | 58 |
| F50 | 123 ± 3 | 157 ± 7 | 131 |
| F50/V107/R213 | 126 ± 2 | 152 ± 3 | 168 |

TABLE XXI-continued

Relationship between relative specific activity
at pH 8.6 or 10.8 and alkaline autolytic stability

| Enzyme | Relative specific activity | | Alkaline autolysis half-time (min)[b] |
|---|---|---|---|
| | pH 8.6 | pH 10.8 | |

[a] Relative specific activity was the average from triplicate activity determinations divided by the wild-type value at the same pH. The average specific activity of wild-type enzyme at pH 8.6 and 10.8 was 70 μmoles/min-mg and 37 μmoles/min-mg, respectively.
[b] Time to reach 50% activity was taken from FIGS. 32 and 33.

F. Random Cassette Mutagenesis of Residues 197 through 228

Figure 34:
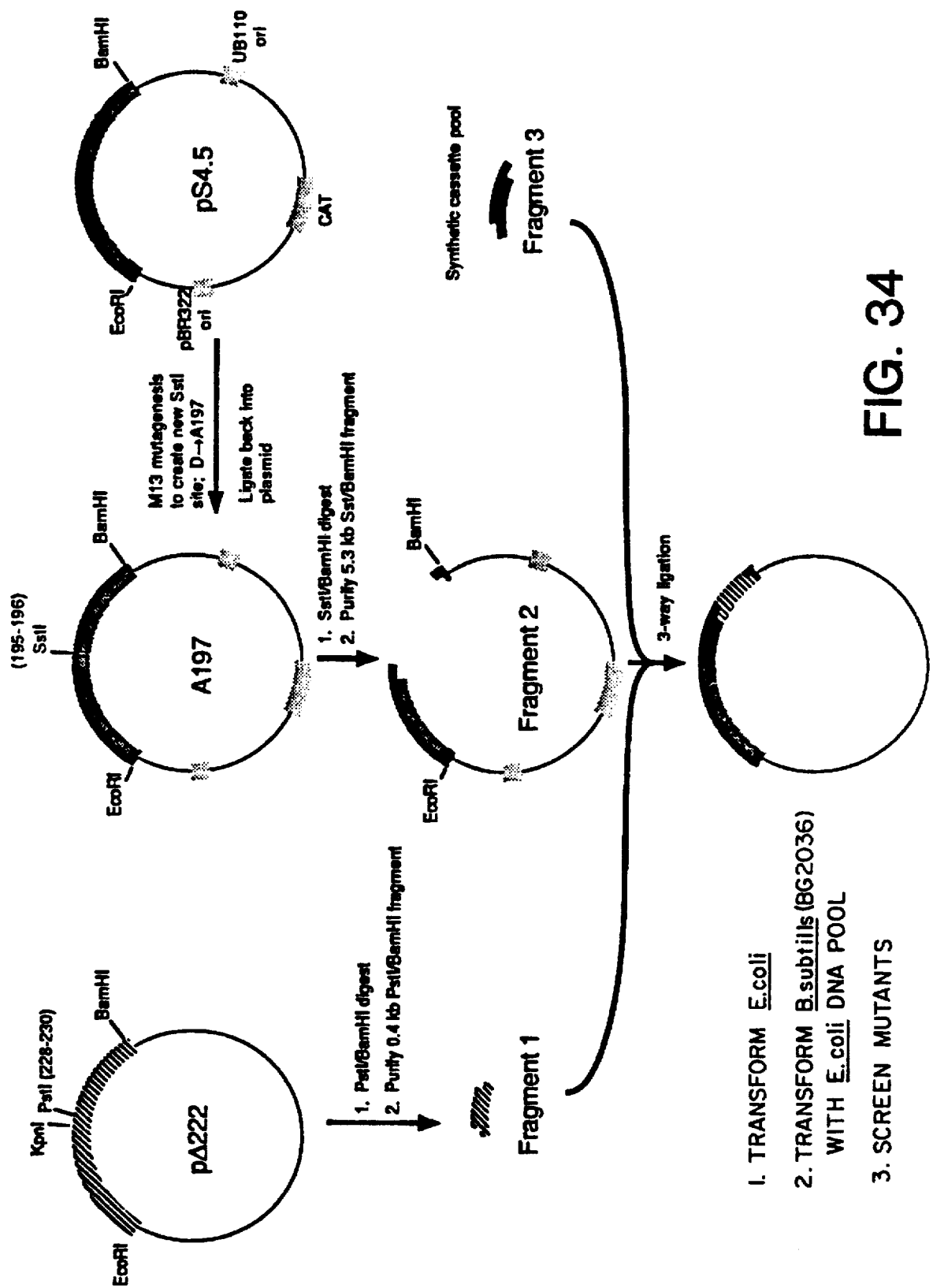
FIG. 34 depicts the strategy for constructing plasmids containing random cassette mutagenesis over residues 197 through 228.

Plasmid pΔ222 (Wells, et al. (1985) *Gene* 34, 315–323) was digested with PstI and BamHI and the 0.4 kb PstI/BamHI fragment (fragment 1, see FIG. 34) purified from a polyacrylamide gel by electroelution (Maniatis, et al. (1982) *Molecular Cloning, A Laboratory Manual.* Cold Spring Harbor Laboratory, Cold Spring Harbor, N.Y.).

The 1.5 kb EcoRI/BamHI fragment from pS4.5 was cloned into M13mp9. Site directed mutagenesis was performed to create the A197 mutant and simultaneously insert a silent SstI site over codons 195-196. The mutant EcoRI/BamHI fragment was cloned back into pBS42. The A197 plasmid was digested with BamHI and SstI and the 5.3 kb BamHI/SstI fragment (fragment 2) was purified from low melting agarose.

Complimentary oligonucleotides were synthesized to span the region from SstI (codons 195-196) to PstI (codons 228-230). These oligodeoxynucleotides were designed to (1) restore codon 197 to the wild type, (2) re-create a silent KpnI site present in pΔ222 at codons 219-220, (3) create a silent SmaI site over codons 210-211, and (4) eliminate the PstI site over codons 228-230 (see FIG. 35). Oligodeoxynucleotides were synthesized with 2% contaminating nucleotides at each cycle of synthesis, e.g., dATP reagent was spiked with 2% dCTP, 2% dGTP, and 2% dTTP. For 97-mers, this 2% poisoning should give the following percentages of non-mutant, single mutants and double or higher mutants per strand with two or more misincorporations per complimentary strand: 14% non-mutant, 28% single mutant, and 57% with ≥2 mutations, according to the general formula $$f = \frac{\mu^n}{n!} e^{-\mu}$$

where μ is the average number of mutations and n is a number class of mutations and f is the fraction of the total having that number of mutations. Complimentary oligodeoxynucleotide pools were phosphorylated and annealed (fragment 3) and then ligated at 2-fold molar excess over fragments 1 and 2 in a three-way ligation.

*E. coli* MM294 was transformed with the ligation reaction, the transformation pool grown up over night and the pooled plasmid DNA was isolated. This pool represented 3.4×10[4] independent transformants. This plasmid pool was digested with PstI and then used to retransform *E. coli*. A second plasmid pool was prepared and used to transform *B. subtilis* (BG2036). Approximately 40% of the BG2036 transformants actively expressed subtilisin as judged by halo-clearing on casein plates. Several of the non-expressing transformants were sequenced and found to have insertions or deletions in the synthetic cassettes. Expressing BG2036 mutants were arrayed in microtiter dishes with 150 μl of LB/12.5 μg/mL chloramphenicol (cmp) per well, incubated at 37° C. for 3–4 hours and then stamped in duplicate onto nitrocellulose filters laid on LB 1.5% skim milk/5 μg/mL cmp plates and incubated overnight at 33° C. (until halos were approximately 4–8 mm in diameter). Filters were then lifted to stacks of filter paper saturated with 1×Tide commercial grade detergent, 50 mM $Na_2CO_3$, pH 11.5 and incubated at 65° C. for 90 min. Overnight growth plates were Commassie stained and destained to establish basal levels of expression. After this treatment, filters were returned to pH7/skim milk/20 μg/mL tetracycline plates and incubated at 37° C. for 4 hours to overnight.

Mutants identified by the high pH stability screen to be more alkaline stable were purified and analyzed for autolytic stability at high pH or high temperature. The double mutant C204/R213 was more stable than wild type at either high pH or high temperature (Table XXII).

This mutant was dissected into single mutant parents (C204 and R213) by cutting at the unique SmaI restriction site (FIG. 35) and either ligating wild type sequence 3' to the SmaI site to create the single C204 mutant or ligating wild type sequence 5' to the SmaI site to create the single R213 mutant. Of the two single parents, C204 was nearly as alkaline stable as the parent double mutant (C204/R213) and slightly more thermally stable. See Table XXII. The R213 mutant was only slightly more stable than wild type under both conditions (not shown).

Another mutant identified from the screen of the 197 to 228 random cassette mutagenesis was R204. This mutant was more stable than wild type at both high pH and high temperature but less stable than C204.

TABLE XXII

Stability of subtilisin variants

Purified enzymes (200 μg/mL) were incubated in 0.1M phosphate, pH 12 at 30° C. for alkaline autolysis, or in 2 mM $CaCl_2$, 50 mM MOPS, pH 7.0 at 62° C. for thermal autolysis. At various times samples were assayed for residual enzyme activity. Inactivations were roughly pseudo-first order, and t ½ gives the time it took to reach 50% of the starting activity in two separate experiments.

| Subtilisin variant | t ½ (alkaline autolysis) | | t ½ (thermal autolysis) | |
|---|---|---|---|---|
| | Exp. #1 | Exp. #2 | Exp. #1 | Exp. #2 |
| wild type | 30 | 25 | 20 | 23 |
| F50/V107/R213 | 49 | 41 | 18 | 23 |
| R204 | 35 | 32 | 24 | 27 |
| C204 | 43 | 46 | 38 | 40 |
| C204/R213 | 50 | 52 | 32 | 36 |
| L204/R213 | 32 | 30 | 20 | 21 |

G. Random Mutagenesis at Codon 204

Based on the above results, codon 204 was targeted for random mutagenesis. Mutagenic DNA cassettes (for codon at 204) all contained a fixed R213 mutation which was found to slightly augment the stability of the C204 mutant.

Plasmid DNA encoding the subtilisin mutant C204/R213 was digested with SstI and EcoRI and a 1.0 kb EcoRI/SstI fragment was isolated by electro-elution from polyacrylamide gel (fragment 1, see FIG. 35).

Figure 36:
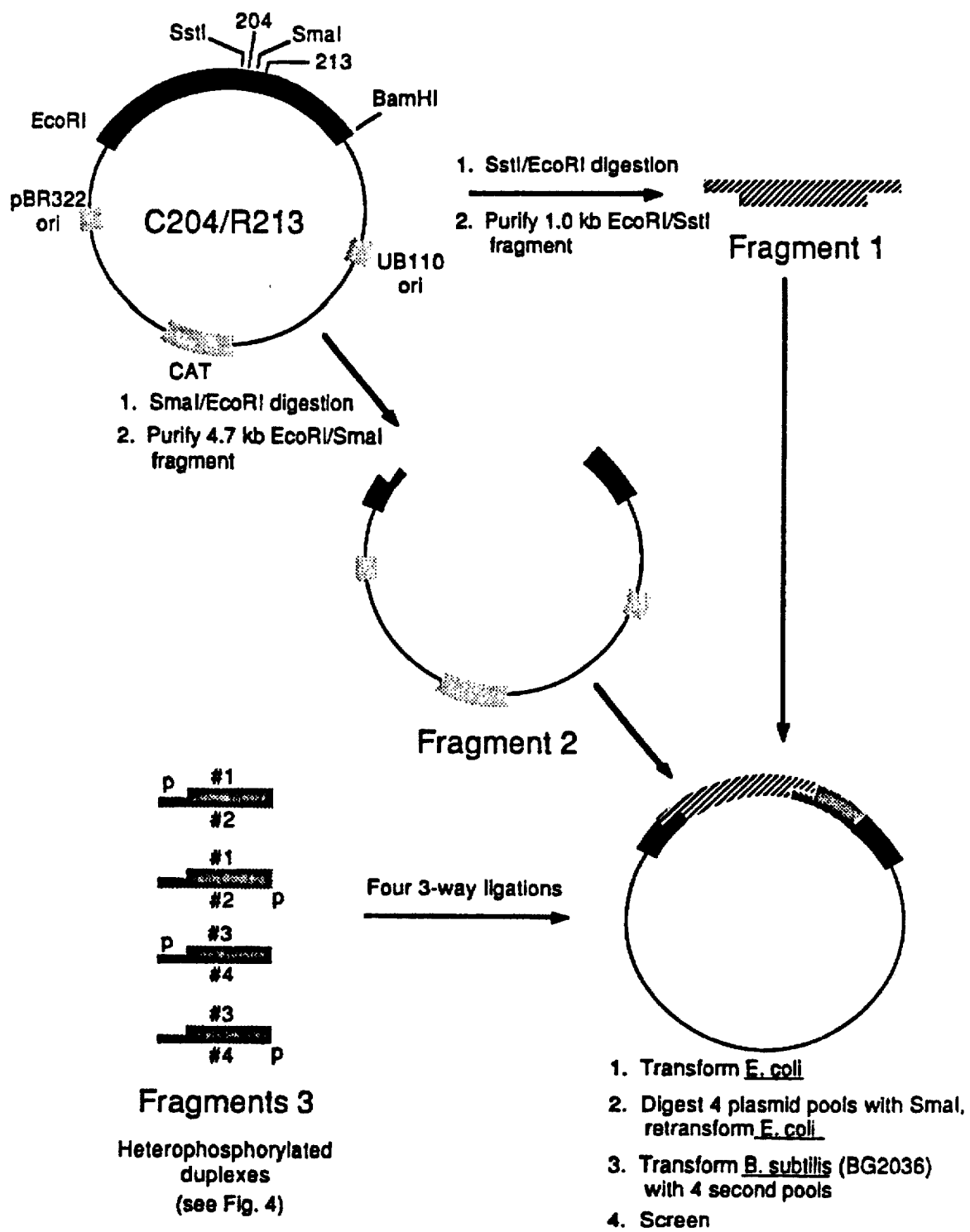
FIG. 36 depicts the construction of mutants at codon 204.

C204/R213 was also digested with SmaI and EcoRI and the large 4.7 kb fragment, including vector sequences and the 3' portion of coding region, was isolated from low melting agarose (fragment 2, see FIG. 36).

Figure 37:
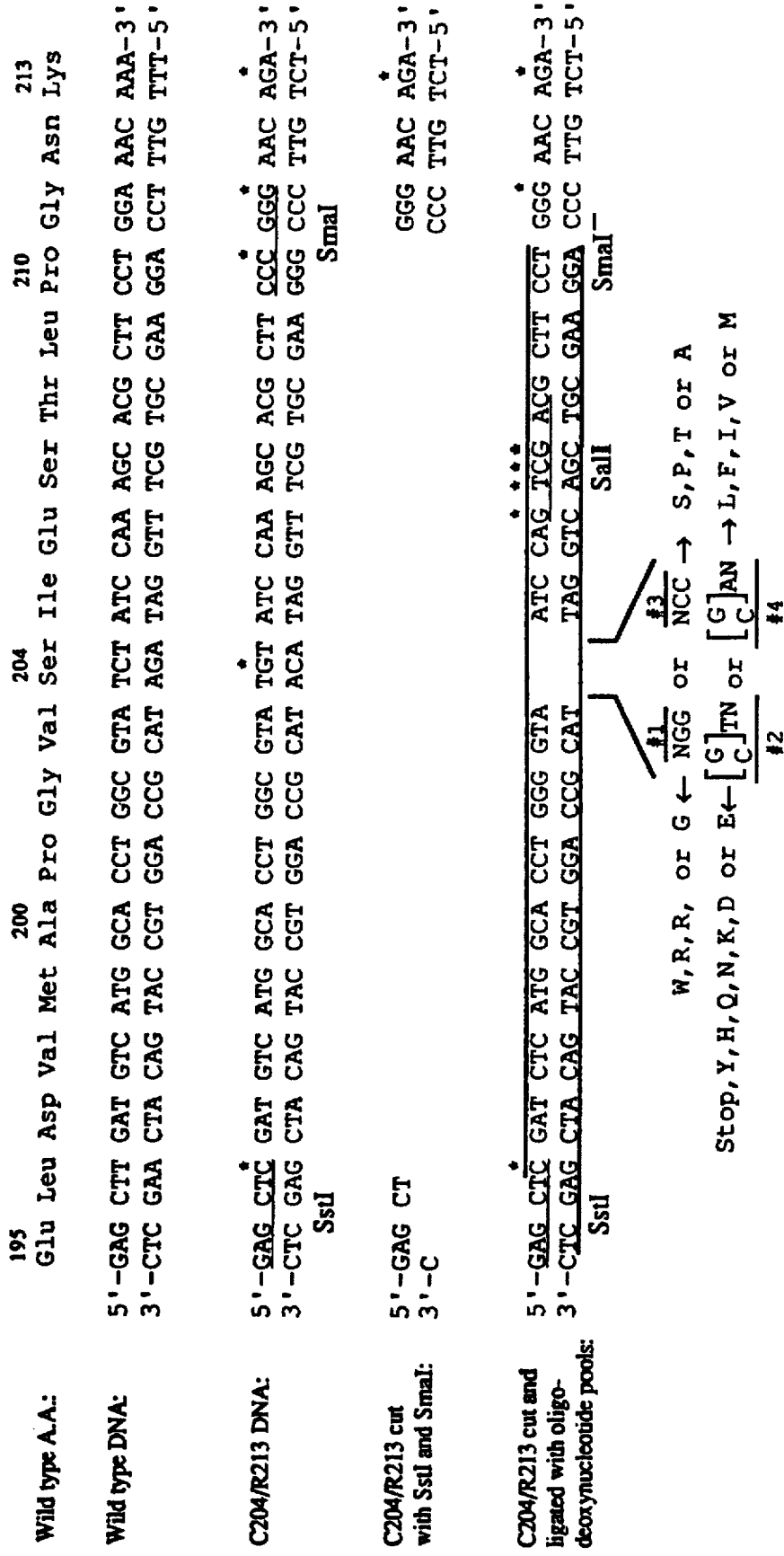
FIG. 37 depicts the oligodeoxynucleotides used for synthesizing mutants at codon 204.

Fragments 1 and 2 were combined in four separate three-way ligations with heterophosphorylated fragments 3 (see FIGS. 36 and 37). This heterophosphrylation of synthetic duplexes should preferentially drive the phosphorylated strand into the plasmid ligation product. Four plasmid pools, corresponding to the four ligations, were restricted with SmaI in order to linearize any single cut C204/R213 present from fragment 2 isolation, thus reducing the background of C204/R213. *E. coli* was then re-transformed with SmaI-restricted plasmid pools to yield a second set of plasmid pools which are essentially free of C204/R213 and any non-segregated heterduplex material.

These second enriched plasmid pools were then used to transform *B. subtilis* (BG2036) and the resulting four mutant pools were screened for clones expressing subtilisin resistant to high pH/temperature inactivation. Mutants found positive by such a screen were further characterized and identified by sequencing.

The mutant L204/R213 was found to be slightly more stable than the wild type subtilisin. See Table XXII.

Having described the preferred embodiments of the present invention, it will appear to those ordinarily skilled in the art that various modifications may be made to the disclosed embodiments, and that such modifications are intended to be within the scope of the present invention.

What is claimed is:

1. A substantially pure subtilisin modified by a substitution of an amino acid at the residue position equivalent to Met50 of the *Bacillus amyloliquefaciens* subtilisin with a different naturally occurring amino acid, wherein the subtilisin which is modified is selected from the group consisting of subtilisins derived from procaryotes, yeast and fungi.

2. A modified subtilisin according to claim 1, wherein said different naturally occurring amino acid is selected from the group consisting of leucine, lysine, isoleucine and valine.

3. A modified subtilisin according to claim 1, wherein said modified subtilisin has altered oxidative stability as compared to the same subtilisin having the amino acid naturally occurring at the residue position equivalent to Met50.

4. A modified subtilisin according to claim 1 wherein Met50 is substituted with Phe, Met124 is substituted with Ile or Leu and Met222 is substituted with Gln.

5. A substantially pure subtilisin modified by a substitution of an amino acid at the residue position equivalent to Met124 of the *Bacillus amyloliquefaciens* subtilisin with a different naturally occurring amino acid, wherein the subtilisin which is modified is selected from the group consisting of subtilisins derived from procaryotes, yeast and fungi.

6. A modified subtilisin according to claim 5, wherein said different naturally occurring amino acid is selected from the group consisting of lysine and alanine.

7. A modified subtilisin according to claim 5, wherein said modified subtilisin has altered oxidative stability as compared to the same subtilisin having the amino acid naturally occurring at the residue position equivalent to Met124.

8. A modified subtilisin according to claim 1 or 5, further comprising a substitution of a naturally occurring amino acid at a residue position selected from the group of equivalent amino acid residues of subtilisin naturally produced by *Bacillus amyloliquefaciens* consisting of Asp32, Ser33, His64, Tyr104, Ala152, Asn155, Glu156, Gly166, Gly169, Phe189, Tyr217 and Met222.

9. A substantially pure subtilisin modified by a substitution of a naturally-occuring amino acid at each residue position of a combination of equivalent residue positions of *B. amyloliquifaciens* subtilisin wherein said combination of equivalent residue positions are selected from the group consisting of Met50/Met124, Met50/Met222, Met124/Met222 and Met50/Met124/Met222, and wherein the subtilisin which is modified is selected from the group consisting of subtilisins derived from procaryotes, yeast and fungi.

10. A substantially pure subtilisin modified by a substitution of a naturally-occuring amino acid at each residue position of a combination of equivalent residue positions of *B. amyloliquifaciens* subtilisin wherein said combination of equivalent residue positions are selected from the group consisting of Gly166/Met222 and Gly169/Met222, wherein the subtilisin which is modified is selected from the group consisting of subtilisins derived from procaryotes, yeast and fungi.

11. A modified subtilisin according to claim 10 wherein said Gly166 is substituted with Ala, Phe, Lys or Val, and said Met222 is substituted with Ala or Cys.

12. A substantially pure subtilisin modified by a substitution of a naturally-occuring amino acid at each residue position of a combination of equivalent residue positions of *B. amyloliquifaciens* subtilisin wherein said combination of equivalent residue positions are selected from the group consisting of Met50/Glu156/Gly169/Tyr217, Met50/Gly156/Gly166/Tyr217 and Met50/Glu156/Tyr217, wherein the subtilisin which is modified is selected from the group consisting of subtilisins derived from procaryotes, yeast and fungi.

13. A modified subtilisin according to claim 12 wherein Glu156 is substituted with Ser or Gln, Gly169 is substituted with Ala and Tyr217 is substituted with Leu.

14. A substantially pure subtilisin modified by a substitution of a naturally-occuring amino acid at each residue position of a combination of equivalent residue positions of *B. amyloliquifaciens* subtilisin wherein said combination of equivalent residue positions are selected from the group consisting of Met50/Val95, Met50/Gly110, Met50/Met124, Met50/Met222, Met124/Met222, Gly166/Met222, Gly169/Met222, Met50/Met124/Met222, Met50/Glu156/Gly166/Tyr217, Met50/Glu156/Tyr217, Met50/Glu156/Gly169/Tyr217 and Met50/Ile107/Lys213, and wherein the subtilisin which is modified is selected from the group consisting of subtilisins derived from procaryotes, yeast and fungi.

15. A modified subtilisin according to claim 1, 5, 9, 10, 12, and 14 derived from a *Bacillus subtilisin*.

16. A composition comprising an enzyme according to claim 1, 5, 9, 10, 12, and 14 in combination with a detergent.

* * * * *